US006969598B2

(12) United States Patent
Olsen et al.

(10) Patent No.: US 6,969,598 B2
(45) Date of Patent: Nov. 29, 2005

(54) METHODS FOR PRODUCING HIGH TITRE VECTORS AND COMPOSITIONS USED IN SUCH METHODS

(75) Inventors: John C. Olsen, Chapel Hill, NC (US); Kyriacos Andreou Mitrophanous, Oxford (GB); Jonathan Rohll, San Diego, CA (US); Alan John Kingsman, Oxford (GB); Fiona Margaret Ellard, Berkshire (GB)

(73) Assignees: Oxford Biomedica (UK) Limited, Oxford (GB); The University of North Carolina at Chapel Hill, Chapel Hill, NC (US)

(*) Notice: Subject to any disclaimer, the term of this patent is extended or adjusted under 35 U.S.C. 154(b) by 352 days.

(21) Appl. No.: 10/134,643

(22) Filed: Apr. 30, 2002

(65) Prior Publication Data

US 2003/0113898 A1 Jun. 19, 2003

Related U.S. Application Data

(60) Provisional application No. 60/287,048, filed on Apr. 30, 2001.

(30) Foreign Application Priority Data

Apr. 30, 2001 (CA) ............................................ 2344208

(51) Int. Cl.[7] .......................... C12P 21/06; C12Q 1/70; C12N 5/00; C12N 15/00; C07H 21/02

(52) U.S. Cl. .......................... 435/69.1; 435/5; 435/325; 435/320; 536/23.1

(58) Field of Search .......................... 435/5, 69.1, 325, 435/320.1, 6; 536/23.1; 424/204.1

(56) References Cited

FOREIGN PATENT DOCUMENTS

EP 0 445 625 A1 2/1991
WO WO 91/00047 A1 1/1991
WO WO 92/05266 A2 4/1992

(Continued)

OTHER PUBLICATIONS

Abe et al., "In Vitro Cell–Free Conversion of Noninfectious Moloney Retrovirus Particles to an Infectious Form by the Addition of the Vesicular Stomatitis Virus Surrogate Envelope G Protein," *Journal of Virology,* 72(8):6356–6361, Aug. 1998, American Society for Microbiology.

Akkina et al., "High–Efficiency Gene Transfer into CD34+ Cells with a Human Immunodeficiency Virus Type 1–Based Retroviral Vector Pseudotyped with Vesicular Stomatitis Virus Envelope Glycoprotein G," *Journal of Virology,* 70(4):2581–2585, Apr. 1996, American Society for Microbiology.

Arai et al., "A New System for Stringent, High–Titer Vesicular Stomatitis Virus G Protein–Pseudotyped Retrovirus Vector Induction by Introduction of Cre Recombinase into Stable Prepacking Cell Lines," *Journal of Virology,* 72(2):1115–1121, Feb. 1998, American Society for Microbiology.

(Continued)

*Primary Examiner*—Hankyel T. Park
(74) *Attorney, Agent, or Firm*—Townsend and Townsend and Crew, LLP

(57) ABSTRACT

A method for producing viral vectors is described using packaging and producer cell lines is described. The producer cell comprises: (i) a first nucleotide sequence (NS) encoding a toxic viral envelope protein operably linked to a promoter; wherein the promoter is operably linked to at least one copy of a TRE; (ii) a second NS wherein the second NS comprises a sequence encoding a tetracycline modulator; (iii) a third NS encoding a retrovirus nucleocapsid protein; and (iv) a fourth NS comprising a retroviral sequence capable of being encapsidated in the nucleocapsid protein such that the retroviral vector particle titre obtainable from the producer cell is regulatable by tetracycline and an initial stimulus with sodium butyrate or functional analogues thereof.

39 Claims, 60 Drawing Sheets

FOREIGN PATENT DOCUMENTS

Figure 1A:
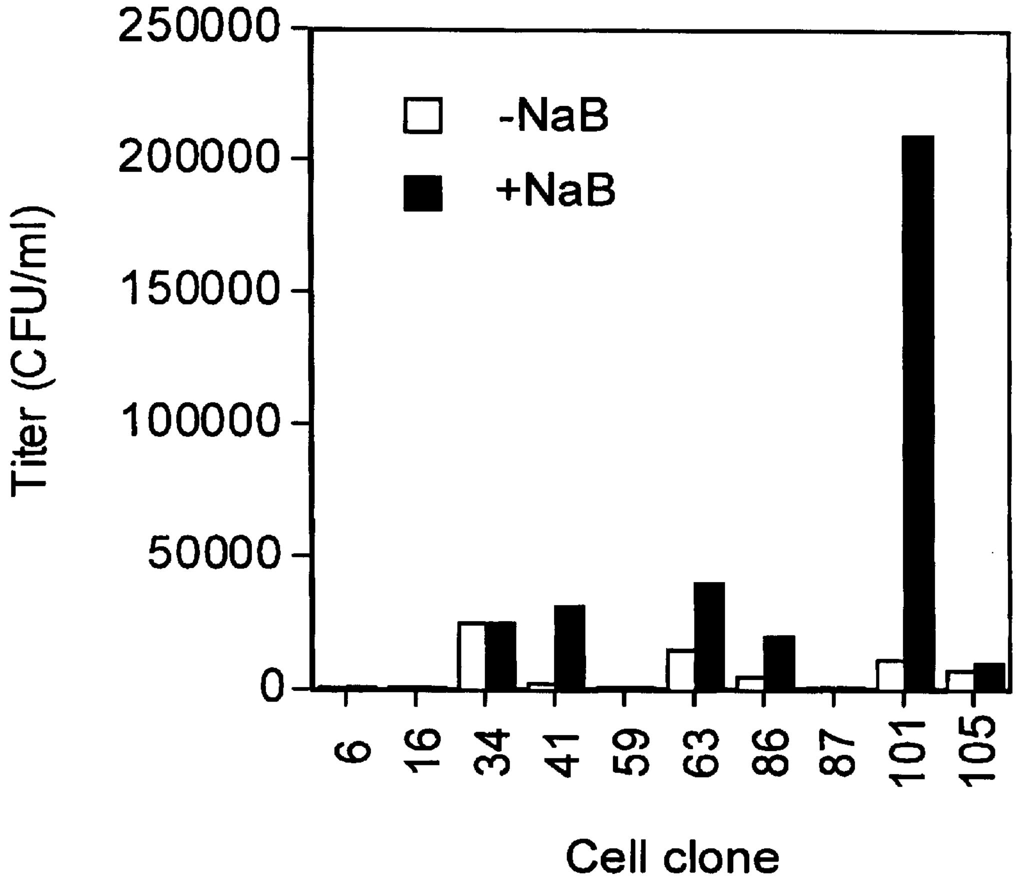

| | | | |
|---|---|---|---|
| WO | WO 94/29438 | A1 | 12/1994 |
| WO | WO 94/29440 | A1 | 12/1994 |
| WO | WO 95/21927 | A2 | 8/1995 |
| WO | WO 95/30018 | A2 | 11/1995 |
| WO | WO 96/09400 | A1 | 3/1996 |
| WO | WO 96/35454 | A1 | 11/1996 |
| WO | WO 97/17457 | A2 | 5/1997 |
| WO | WO 97/27310 | A1 | 7/1997 |
| WO | WO 97/38117 | A1 | 10/1997 |
| WO | WO 98/05635 | A1 | 2/1998 |
| WO | WO 98/05754 | A2 | 2/1998 |
| WO | WO 98/05759 | A1 | 2/1998 |
| WO | WO 98/07859 | A2 | 2/1998 |
| WO | WO 98/09985 | A2 | 3/1998 |
| WO | WO 98/17815 | A1 | 4/1998 |
| WO | WO 98/51810 | A1 | 11/1998 |
| WO | WO 99/15683 | A1 | 4/1999 |
| WO | WO 99/32646 | A1 | 7/1999 |
| WO | WO 99/41397 | A1 | 8/1999 |
| WO | WO 99/58155 | A1 | 11/1999 |
| WO | WO 99/61639 | A2 | 12/1999 |
| WO | WO 00/29428 | A2 | 5/2000 |
| WO | WO 00/31200 | A1 | 6/2000 |
| WO | WO 00/52188 | A1 | 9/2000 |
| WO | WO 01/25466 | A1 | 4/2001 |
| WO | WO 01/79518 | A2 | 10/2001 |

OTHER PUBLICATIONS

Attenello & Lee, "Regulation of a Hybrid Gene by Glucose and Temperature in Hamster Fibroblasts," *Science,* 226:187–190, Oct. 1984.

Benmansour et al., "Antigenicity of Rabies Virus Glycoprotein," *Journal of Virology,* 65(8):4198–4203, Aug. 1991, American Society for Microbiology.

Binns et al., "Companion of a Conserved Region in Fowlpox Virus and Vaccinia Virus Genomes and the Translocation of the Fowlpox Virus Thymidine Kinase Gene," *J. gen. Virol.,* 69:1275–1283, 1988, SGM, Great Britain.

Borrelli et al., "Targeting of an inducible toxic phenotype in animal cells," *Proc. Natl. Acad. Sci. USA,* 85:7572–7576, Oct. 1988.

Boyle et al., "Fowlpox Virus Thymideine Kinase: Nucleotide Sequence and Relationships to Other Thymidine Kinases," *Virology,* 156:355–365, 1987, Academic Press, Inc.

Burger et al., "Stable expression of rabies virus glycoprotein in Chinese hamster ovary cells," *Journal of General Virology,* 72:359–367, 1991, SGM, Great Britain.

Burns et al., "Vesicular stomatitis virus G glycoprotein pseudotypes retroviral vectors: Concentration to very high titer and efficient gene transfer into mammalian and nonmammalian cells," *Proc. Natl. Acad. Sci. USA,* 90:8033–8037, Sep. 1993.

Chen et al., "Generation of packaging cell lines for pseudotyped retroviral vectors of the G protein of vesicular stomatitis virus by using a modified tetracycline inducible system," *Proc. Natl. Acad. Sci. USA,* 93:10057–10062, Sep. 1996.

Chen et al., "Sensitization of Human Breast Cancer Cells to Cyclophosphamide and Ifosfamide by Transfer of a Liver Cytochrome P450 Gene," *Cancer Research,* 56:1331–1340, 1996.

Chung et al., "A 5' Element of the Chicken β–Globin Domain Serves as an Insulator in Human Erythroid Cells and Protects against Effect in Drosophila," *Cell,* 74:505–514, Aug. 1993, Cell Press.

Coffin et al., "Retroviruses," p. 449, JM Coffin et al., eds., Cold Spring Harbour Laboratory Press, 1997.

Coffin et al., "Retroviruses," pp. 758–763, JM Coffin et al., eds., Cold Spring Harbor Laboratory Press, 1997.

Coll, "Synthetic peptides from the heptad repeats of the glycoproteins of rabies, vesicular stomatitis and fish rhabdoviruses bind phosphatidylserine," *Archives of Virology,* 142:2089–2097, 1997, Springer–Verlag, Austria.

Coll, "The glycoprotein G of rhabdoviruses," *Archives of Virology,* 140:827–851, 1995, Springer–Verlag, Austria.

Cosset et al., "High–Titer Packaging Cells Producing Recombinant Retroviruses Resistant to Human Serum," *Journal of Virology,* 69(12):7430–7436, Dec. 1995, American Society for Microbiology.

Cosson, "Direct interaction between the envelope and matrix proteins of HIV–1," *The EMBO Journal,* 15(21):5783–5788, 1996, Oxford University Press.

Coulon et al., "An Avirulent Mutant of Rabies Virus Is Unable to Infect Motoneurons In Vivo and In Vitro," *Journal of Virology,* 72(3):273–278, Jan. 1998, American Society for Microbiology.

Coulon et al., "Invasion of the Peripheral Nervous Systems of Adult Mice by the CVS Strain of Rabies Virus and Its Avirulent Derivative AvO1," *Journal of Virology,* 63(8):3550–3554, Aug. 1989, American Society for Microbiology.

Dachs et al., "Targeting gene expression to hypoxic tumor cells," *Nature Medicine,* 3(5):515–520, May 1997.

Dietzschold et al., "Characterization of an antigenic determinant of the glycoprotein that correlates with pathogenicity of rabies virus," *Proc. Natl. Acad. Sci. USA,* 80:70–74, Jan. 1983.

Dietzschold et al., "Isolation and Purification of a Polymeric Form of the Glycoprotein of Rabies Virus," *J. gen. Virol.,* 40:131–139, Great Britain.

Dietzschold et al., "Structure and Function of Rabies Virus Glycoprotein," *Develop. Biol. Standard,* 40:45–55, 1978, S. Karger, Basel.

Dietzschold, "Oligosaccharides of the Glycoprotein of Rabies Virus," *Journal of Virology,* 23(2):286–293, Aug. 1977, American Society for Microbiology, USA.

Dorfman et al., "Role of the Matrix Protein in the Virion Association of the Human Immunodeficiency Virus Type 1 Envelope Glycoprotein," *Journal of Virology,* 63(3):1689–1696, Mar. 1994, American Society for Microbiology.

Dougherty & Temin, "A promoterless retroviral vector indicates that there are sequences in U3 required for 3' RNA processing," *Proc. Natl. Acad. Sci. USA,* 84:1197–1201, Mar. 1987.

Einfeld, "Maturation and Assembly of Retroviral Glycoproteins," pp. 133–176.

Emerman & Temin, "Genes with Promoters in Retrovirus Vectors Can Be Independently Suppressed by an Epigenetic Mechanism," *Cell,* 39:459–467, Dec. 1984 (Part 2), MIT.

Emery et al., "A chromatin insulator protects retrovirus vectors from chromosomal position effects," *PNAS,* 97(16):9150–9155, Aug. 2000.

EMI et al., "Pseudotype Formation of Murine Leukemia Virus with the G Protein Vesicular Stomatitis Virus," *Journal of Virology,* 65(3):1202–1207, Mar. 1991, American Society for Microbiology.

Esposito & Knight, "Nucleotide Sequence of the Thymidine Kinase Gene Region of Monkeypox and Variola Viruses," *Virology,* 135:561–567, 1984, Academic Press, Inc.

Firth et al., "Oxygen–regulated control elements in the phosphoglycerate kinase 1 and lactate dehydrogenase A genes: Similarities with the erythropoietin 3' enhancer," *Proc. Natl. Acad. Sci. USA,* 91:6496–6500, Jul. 1994.

Friedlos et al., "Mustard Prodrugs for Activation by *Escherichia coli* Nitroreductase in Gene–Directed Enzyme Prodrug Therapy," *J. Med. Chem.,* 40:1270–1275, 1997, American Chemical Society.

Fries et al., "Human safety immunogenicity of a canarypox–rabies glycoprotein recombinant vaccine: an alternative poxvirus vector system," *Vaccine,* 14(5):428–434, 1996, Elsevier Science Ltd., Great Britain.

Gaudin et al., "Biological Function of the Low–pH, Fusion–Inactive Conformation of Rabies Virus Glycoprotein (G): G Is transported in a Fusion–Inactive State–Like Conformation," *Journal of Virology,* 69(9):5528–5534, Sep. 1995, American Society for Microbiology.

Gaudin et al., "Rabies Virus Glycoprotein is a Trimer," *Virology,* 187:627–632, 1992, Academic Press, Inc.

Gazit et al., "Use of the Stress–inducible grp78/BiP Promoter in Targeting High Level Gene Expression in Fibrosarcoma in Vivo," *Cancer Research,* 55:1660–1663, Apr. 1995.

Gentz et al., "Bioassay for trans–activation using purified human immunodeficiency virus tat–encoded protein: Trans–activation requires mRNA synthesis," *Proc. Natl. Acad. Sci. USA,* 86:821–824, Feb. 1989.

Gershon & Black, "The Nucleotide Sequence around the Capripoxvirus Thymidine Kinase Gene Reveals a Gene Shared Specifically with Leporipoxvirus," *J. gen. Virol.,* 70:525–533, 1989, SGM, Great Britain.

Gossen & Bujard, "Tight control of gene expression in mammalian cells by tetracycline–responsive promoters," *Proc. Natl. Acad. Sci. USA,* 89:5547–5551, Jun. 1992.

Hanham et al., "Evidence from the Anti–Idiotypic Network that the Acetylcholine Receptor Is a Rabies Virus Receptor," *Journal of Virology,* 67(1):530–542, Jan. 1993, American Society for Microbiology.

Hawley et al., "Handicapped retroviral vectors efficiently transduce foreign genes into hematopoietic stem cells," *Proc. Natl. Acad. Sci. USA,* 84:2406–2410, Apr. 1987.

Herman & Coffin, "Efficient Packaging of Readthrough RNA in ALV: Implications for Oncogene Transduction," *Science,* 236:845–848, May 1987.

Hong et al., "Adenovirus type 5 fiber knob binds to MHC class I $\alpha2$ domain at the surface of human epithelial and B lymphoblastoid cells," *The EMBO Journal,* 16(9):2294–2306, 1997, Oxford University Press.

Hruby et al., "Fine structure analysis and nucleotide sequence of the vaccinia virus thymidine kinase gene," *Proc. Natl. Acad. Sci. USA,* 80:3411–3415, Jun. 1983.

Hunter, "Macromolecular interactions in the assembly of HIV and other retroviruses," *seminars in Virology,* 5:71–83, 1994.

Inoue et al., "The Human Preproendothelin–1 Gene," *The Journal of Biological Chemistry,* 264(25):14954–14959, Sep. 5, 1989, The American Society for Biochemistry and Molecular Biology, Inc., USA.

Januszeski et al., "Functional Analysis of the Cytoplasmic Tail of Moloney Murine Leukemia Virus Envelope Protein," *Journal of Virology,* 71(5):3613–3619, May 1997, American Society for Microbiology.

Johnson et al., "Effect of Host Modification and Age on Airway Epithelial Gene Transfer Meidated by a Murine Leukemia Virus–Derived Vector," *Journal of Virology,* 72(11):8861–8872, Nov. 1998, American Society for Microbiology.

Jolly et al., "Elements in the long terminal repeat of murine retroviruses enhance stable transformation by thymidine kinase gene," *Nucleic Acids Research,* 11(6):1855–1872, 1983, IRL Press Limited, Oxford, England.

Kafri et al., "A Packaging Cell Line for Lentivirus Vectors," *Journal of Virology,* 73(1):576–584, Jan. 1999. American Society for Microbiology.

Karreman et al., "On the use of double FLP recognition targets (FRTs) in the LTR of retroviruses for the construction of high producer cell lines," *Nucleic Acids Research,* 24(9):1616–1624, 1996, Oxford University Press.

Kerr et al., "Antibody–penicillin–V–amidase conjugates kill antigen–positive tumor cells when combined with doxorubicin phenoxyacetamide," *Cancer Immunol. Immunother,* 31:202–206, 1990, Springer–Verlag.

Kestler et al., "cis Requirements for the Efficient Production of Recombinant DNA Vectors Based on Autonomous Parvoviruses," *Human Gene Therapy,* 10:1619–1632, Jul. 1, 1999, Mary Ann Liebert, Inc.

Kilpatrick & Rouhandeh, "Cloning and Physical Mapping of the Yaba Monkey Tumor Virus DNA," *Virology,* 143:399–406, 1985, Academic Press, Inc.

Klages et al., "A Stable System for the High–Titer Production of Multiply Attenuated Lentiviral Vectors," *Molecular Therapy,* 2(2):170–176, Aug. 2000, The American Society of Gene Therapy.

Krässlich & Welker, "Intracellular Transport of Retroviral Capsid Components," *Curr. Top. Microbiol. Immunol.,* 214:133–176, 1996.

Kroll et al., "A Multifunctional Prokaryotic Protein Expression System: Overproduction, Affinity Purification, and Selective Detection," *DNA And Cell Biology,* 12(5):441–453, 1993, Mary Ann Liebert, Inc. Publishers.

Kučera et al., "Pathways of the Early Propagation of Virulent and Avirulent Rabies Strains from the Eye to the Brain," *Journal of Virology,* 55(1):158–162, Jul. 1985, American Society for Microbiology.

Lefkowitz et al., "Complementation of Vesicular Stomatitis Virus Glycoprotein G Mutant with Wild–Type Protein Expressed from either a Bovine Papilloma Virus or a Vaccinia Virus Vector System," *Virology,* 178:373–383, 1990, Academic Press, Inc.

Lewis & Emerman, "Passage through Mitosis is Required for Oncoretroviruses but Not for the Human Immunodeficiency Virus," *Journal of Virology,* 68(1):510–516, Jan. 1994, American Society for Microbiology.

Lewis et al., "Human immunodeficiency virus infection of cells arrested in the cell cycle," *The EMBO Journal,* 11(8):3053–3058, 1992, Oxford University Press.

Lindemann et al., "Efficient Pseudotyping of Murine Leukemia Virus Particles with Chimeric Human Foamy Virus Envelope Proteins," *Journal of Virology,* 71(6):4815–4820, Jun. 1997, American Society for Microbiology.

Luo et al., "A virus–neutralizing epitope on the glycoprotein of rabies virus that contain Trp251 is a linear epitope," *Virus Research,* 51:35–41, 1997, Elsevier Science B.V.

Luo et al., "Antigenic and Functional Analyses of Glycoprotein of Rabies Virus Using Monoclonal Antibodies," *Microbiol. Immunol.,* 42(3):187–193, 1988.

Lytvyn et al., "Comparison of the thymidine kinase genes from three entomopoxviruses," *Journal of General Virology,* 73:3235–3240, 1992, SGM, Great Britain.

Madan & Curtin, "A 24–base–pair sequence 3' to the human erythropoietin gene contains a hypoxia–responsive transcriptional enhancer," *Proc. Natl. Acad. Sci. USA,* 90:3928–3932, May 1993.

Mammano et al., "Truncation of the Human Immunodeficiency Virus Type 1 Envelope Glycoprotein Allows Efficient Pseudotyping of Moloney Murine Leukemia Virus Particles and Gene Transfer into $CD4^+$ Cells," *Journal of Virology,* Apr. 1997, American Society for Microbiology.

Mann et al., "Construction of a Retrovirus Packagin Mutant and its Use to Produce Helper–Free Defective Retrovirus," *Cell,* 33:153–159, May 1983, MIT.

Martarano et al., "Equine Infectious Anemia Virus trans–Regulatory Protein Rev Controls Viral mRNA Stability, Accumulation, and Alternative Splicing," *Journal of Virology,* 68(5):3102–3111, May 1994, American Society for Microbiology.

Mebatsion et al., "A CXCR4/CD4 Pseudotye Rhabdovirus That Selectively Infects HIV–1 Envelope Protein–Expressing Cells," *Cell,* 90:841–847, Sep. 1997, Cell Press.

Meyer et al., "Mapping of deletions in the genome of the highly attenuated vaccina virus MVA and their influence on virulence," *Journal of General Virology,* 72:1031–1038, 1991, SGM, Great Britain.

Miletic et al., "Retroviral Vectors Pseudotyped with Lymphocytic Choriomeningitis Virus," *Journal of Virology,* 73(7):6114–6116, Jul. 1999, American Society for Microbiology.

Mitchell et al., "Vectors for the Inducible Overexpression of Glutathione S–Transferase Fusion Proteins in Yeast," *Yeast,* 9:715–723, 1993.

Morimoto et al., "Syncytium Formation Is Induced in the Murine Neuroblastoma Cell Culture Which Produce Pathogenic Type G Proteins of the Rabies Virus," *Virology,* 189:203–216, 1992, Academic Press.

Moss, "Vaccinia Virus: A Tool for Research and Vaccine Development," *Science,* 252:1662–1667, Jun. 1991.

Mullen et al., "Tumors Expressing the Cytosine Deaminase Suicide Gene Can Be Eliminated in Vivo with 5–Fluorocytosine and Induce Protective Immunity to Wild Type Tumor," *Cancer Research,* 54:1503–1506, Mar. 1994.

*Nature Biotechnology,* 14:556, May 1996.

Olsen & Sechelski, "Use of Sodium Butyrate to Enhance Production of Retroviral Vectors Expressing CFTR cDNA," *Human Gene Therapy,* 6:1195–1202, Sep. 1995, Mary Ann Liebert, Inc.

Olsen et al., "882. An Inducible First Generation Stable Packaging Cell Line for Equine Levinthal Vectors," *Molecular Therapy,* vol. 1, No. 5, May 2000, Part 2 of 2 parts.

Olsen, "Gene transfer vectors derived from equine infectious anemia virus," *Gene Therapy,* 5:1481–1487, 1998, Stockton Press, United Kingdom.

Ory et al., "A stable human–derived packaging cell line for production of high titer retrovirus/vesicular stomatitis virus G pseudotypes," *Proc. Natl. Acad. Sci. USA,* 93:11400–11406, Oct. 1996.

Otvos et al., "Glycosylation of synthetic T helper cell epitopic peptides and their antigenic potency and conformation in a sugar location–specific manner," *Biochimica et Biophysica Acta,* 1224:68–76, 1994.

Pear et al., "Production of high–titer helper–free retroviruses by transient transfection," *Proc. Natl. Acad. Sci. USA,* 90:8392–8396, Sep. 1993.

Peshavaria & Day, "Molecular structure of the human muscle–specific enolase gene (ENO3)," *Biochem. J.,* 275:427–433, Great Britain.

Porath, "Immobilized Metal Ion Affinity Chromatography," *Protein Expression and Purification,* 3(4):263–281, 1992, Academic Press, Inc.

Rice et al., "Synthesis and Processing of the Transmembrane Envelope Protein of Equine Infectious Anemia Virus," *Journal of Virology,* 64(8):3770–3778, Aug. 1990, American Society for Microbiology.

Rivella et al., "The cHS4 Insulator Increases the Probability of Retroviral Expression at Random Chromosomal Integration Sites," *Journal of Virology,* 74(10):4679–4687, American Society for Microbiology.

Roitt et al., "Immunology," $4^{th}$ Edition, p. 14.7, Mosby.

Rose et al., "Homology Between the Glycoproteins of Vesicular Stomatitis Virus and Rabies Virus," *Journal of Virology,* 43(1):361–364, Jul. 1982.

Schnitzlein et al., "A rapid method for identifying the thymidine kinase genes of avipoxviruses," *Journal of Virological Methods,* 29:341–352, 1988, Elsevier Science Publishers B.V. (Biomedical Division).

Seganti et al., "Susceptibility of Mammalian, Avian, Fish, and Mosquito Cell Lines to Rabies Virus Infection," *Acta virol.,* 34:155–163, 1990.

Seif et al., "Rabies Virulence: Effect on Pathogenicity and Sequence Characterization of Rabies Virus Mutations Affecting Antigenic Sit III of the Glycoprotein," *Journal of Virology,* 53(3):926–934, Mar. 1985, American Society for Microbiology.

Semenza & Wang, "A Nuclear Factor Induced by Hypoxia via De Novo Protein Synthesis Binds to the Human Erythropoietin Gene Enhancer at a Site Required for Transcriptional Activation," *Molecular and Cellular Biology,* 12(12):5447–5454, Dec. 1992, American Society for Microbiology.

Senter et al., "Anti–tumor effects of antibody–alkaline phosphatase conjugates in combination with etoposide phosphate," *Proc. Natl. Acad. Sci. USA,* 85:4842–4846, Jul. 1998.

Sheridan et al., "Generation of Retroviral Packaging and Producer Cell Lines for Large–Scale Vector Production and Clinical Application: Improved Safety and High Titer," *Molecular Therapy,* 2(3):262–275, Sep. 2000, The American Society of Gene Therapy.

Smith & Moss, "Infectious poxvirus vectors have capacity for at least 25 000 base pairs of foreign DNA," *Gene,* 25:21–28, 1983, Elsevier Science Publishers.

Soneoka et al., "A transient three–plasmid expression system for the production of high titer retroviral vectors," *Nucleic Acids Research,* 23(4):628–633, 1995, Oxford University Press.

Takenaka et al., "Rat Pyruvate Kinase M Gene," *The Journal of Biological Chemistry,* 264(4):2363–2367, Feb. 1989, The American Society for Biochemistry and Molecular Biology, Inc., USA.

Thoulouze et al., "The Neural Cell Adhesion Molecule is a Receptor for Rabies Virus," *Journal of Virology,* 72(9):7181–1790, Sep. 1998, American Society for Microbiology.

Tomko et al., "HCAR and MCAR: The human and mouse cellular receptors for subgroup C adenoviruses and group B coxsackieviruses," *Proc. Natl. Acad. Sci. USA,* 94:3352–3356, Apr. 1997.

Tuchiya et al., "Characterization of rabies virus glycoprotein expressed by recombinant baculovirus," *Virus Research,* 25:1–13, 1992, Elsevier Science Publishers, B.V.

Tuffereau et al., "Low–affinity nerve–growth factor receptor (P75NTR) can serve as a receptor for rabies virus," *The EMBO Journal,* 17(24):7250–7259, 1998, Oxford University Press.

Tuffereau et al.,"Neuronal Cell Surface Molecules Mediate Specific Binding to Rabies Virus Glycoprotein Expressed by a Recombinant Baculovirus on the Surfaces of Lepidopteran Cells," *Journal of Virology,* 72(2):1085–1091, Feb. 1998, American Society for Microbiology.

Upton & McFadden, "Identification and Nucleotide Sequences of the Thymidine Kinase Gene of Shope Fibroma Virus," *Journal of Virology,* 60(3):920–927, Dec. 1986, American Society for Microbiology.

Vanin et al., "Development of High–Titer Retroviral Producer Cell Lines by Using Cre–Mediated Recombination," *Journal of Virology,* 71(10):7820–7826, Oct. 1997, American Society for Microbiology.

Wang & Semenza, "General involvement of hypoxia–inducible factor 1 in transcriptional response to hypoxia," *Proc. Natl. Acad. Sci. USA,* 90:4304–4308, May 1993.

Weir & Moss, "Nucleoside Sequence of the Vaccinia Virus Thymidine Kinase Gene of the Nature of Spontaneous Frameshift Mutations," *Journal of Virology,* 46(2):530–537, May 1993, American Society for Microbiology.

Whitt et al., "Membrane Fusion Activity, Oligomerization and Assembly of the Rabies Virus Glycoprotein," *Virology,* 185:681–688, 1991, Academic Press, Inc.

Wickham et al., "Integrin αvβ5 Selectivity Promotes Adenovirus Mediated Cell Membrane Permeabilization," *The Journal of Cell Biology,* 127:257–265, 1994, The Rockefeller University Press.

Wickham et al., "Integrins $\alpha_v\beta_3$ and $\alpha_v\beta_5$ Promote Adenovirus Internalization but Not Virus Attachment," *Cell,* 73:309–319, Apr. 1993, Cell Press.

Wilcox et al., "Integrin αIIb promoter–targeted expression of gene products in megakaryocytes derived from retrovirus–transduced human hematopoietic cells," *Proc. Natl. Acad. Sci. USA,* 96:9654–9659, Aug. 1999.

Wolff & Trubetskoy, "The Cambrian period of nonviral gene delivery," *Nature Biotechnology,* 16:421–422, May 1998.

Xu et al., "Generation of a Stable Cell Line Producing High–Titer Self–Inactivating Lentiviral Vectors," *Molecular Therapy,* 3(1):97–104, Jan. 2001, The American Society for Gene Therapy.

Yang et al.,"Inducible, High–Level Production of Infectious Murine Leukemia Retroviral Vector Particles Pseudotyped with Vesicular Stomatitis Virus G Envelope Protein," *Human Gene Therapy,* 6:1203–1213, Sep. 1995, Mary Ann Liebert, Inc.

Yee et al., "A general method for the generation of high–titer, pantropic retroviral vectors: Highly efficient infection of primary hepatocytes," *Proc. Natl. Acad. Sci. USA,* 91:9564–9568, Sep. 1994.

Yoshida et al., "VSV–G–Pseudotyped Retroviral Packaging through Adenovirus–Mediated Inducible Gene Expression," *Biochemical and Biophysical Research Communications,* 232:379–382, 1997, Academic Press.

Yu et al., "Self–activating retroviral vectors designed for transfer of whole genes into mammalian cells," *Proc. Natl. Acad. Sci. USA,* 83:3194–3198, May 1986.

Zufferey et al., "Woodchuck Hepatitis Virus Posttranscriptional Regulatory Element Enhances Expression of Transgenes Delivered by Retroviral Vectors," *Journal of Virology,* 73(4):2886–2892, American Society for Microbiology.

http://hiv–web.lanl.gov/content/index, Nov. 25, 2002.

http://www.ncbi.nlm.mih.gov/, Nov. 25, 2002.

Sequence of pEV53B

GACGGATCGGGAGATCTCCCGATCCCCTATGGTCGACTCTCAGTACAATCTGCTCTGATG
CCGCATAGTTAAGCCAGTATCTGCTCCCTGCTTGTGTGTTGGAGGTCGCTGAGTAGTGCG
CGAGCAAAATTTAAGCTACAACAAGGCAAGGCTTGACCGACAATTGCATGAAGAATCTGC
TTAGGGTTAGGCGTTTTGCGCTGCTTCGCGATGTACGGGCCAGATATACGCGTTGACATT
GATTATTGACTAGTTATTAATAGTAATCAATTACGGGGTCATTAGTTCATAGCCCATATA
TGGAGTTCCGCGTTACATAACTTACGGTAAATGGCCCGCCTGGCTGACCGCCCAACGACC
CCCGCCCATTGACGTCAATAATGACGTATGTTCCCATAGTAACGCCAATAGGGACTTTCC
ATTGACGTCAATGGGTGGACTATTTACGGTAAACTGCCCACTTGGCAGTACATCAAGTGT
ATCATATGCCAAGTACGCCCCCTATTGACGTCAATGACGGTAAATGGCCCGCCTGGCATT
ATGCCCAGTACATGACCTTATGGGACTTTCCTACTTGGCAGTACATCTACGTATTAGTCA
TCGCTATTACCATGGTGATGCGGTTTTGGCAGTACATCAATGGGCGTGGATAGCGGTTTG
ACTCACGGGGATTTCCAAGTCTCCACCCCATTGACGTCAATGGGAGTTTGTTTTGGCACC
AAAATCAACGGGACTTTCCAAAATGTCGTAACAACTCCGCCCCATTGACGCAAATGGGCG
GTAGGCGTGTACGGTGGGAGGTCTATATAAGCAGAGCTCTCTGGCTAACTAGAGAACCCA
CTGCTTACTGGCTTATCGAAATTAATACGACTCACTATAGGGAGACCCAAGCTGGCTAGC
CGCGGGCGCGCCAGGTAAGATGGGAGACCCTTTGACATGGAGCAAGGCGCTCAAGAAGTT
AGAGAAGGTGACGGTACAAGGGTCTCAGAAATTAACTACTGGTAACTGTAATTGGGCGCT
AAGTCTAGTAGACTTATTTCATGATACCAACTTTGTAAAAGAAAAGGACTGGCAGCTGAG
GGATGTCATTCCATTGCTGGAAGATGTAACTCAGACGCTGTCAGGACAAGAAAGAGAGGC
CTTTGAAAGAACATGGTGGGCAATTTCTGCTGTAAAGATGGGCCTCCAGATTAATAATGT
AGTAGATGGAAAGGCATCATTCCAGCTCCTAAGAGCGAAATATGAAAAGAAGACTGCTAA
TAAAAAGCAGTCTGAGCCCTCTGAAGAATATCCAATCATGATAGATGGGGCTGGAAACAG
AAATTTTAGACCTCTAACACCTAGAGGATATACTACTTGGGTGAATACCATACAGACAAA
TGGTCTATTAAATGAAGCTAGTCAAAACTTATTTGGGATATTATCAGTAGACTGTACTTC
TGAAGAAATGAATGCATTTTTGGATGTGGTACCTGGCCAGGCAGGACAAAAGCAGATATT
ACTTGATGCAATTGATAAAATAGCAGATGATTGGGATAATAGACATCCATTACCGAATGC
TCCACTGGTGGCACCACCACAAGGGCCTATTCCCATGACAGCAAGGTTTATTAGAGGTTT
AGGAGTACCTAGAGAAAGACAGATGGAGCCTGCTTTTGATCAGTTTAGGCAGACATATAG
ACAATGGATAATAGAAGCCATGTCAGAAGGCATCAAAGTGATGATTGGAAAACCTAAAGC
TCAAAATATTAGGCAAGGAGCTAAGGAACCTTACCCAGAATTTGTAGACAGACTATTATC
CCAAATAAAAAGTGAGGGACATCCACAAGAGATTTCAAAATTCTTGACTGATACACTGAC
TATTCAGAACGCAAATGAGGAATGTAGAAATGCTATGAGACATTTAAGACCAGAGGATAC
ATTAGAAGAGAAAATGTATGCTTGCAGAGACATTGGAACTACAAAACAAAAGATGATGTT
ATTGGCAAAAGCACTTCAGACTGGTCTTGCGGGCCCATTTAAAGGTGGAGCCTTAAAAGG
AGGGCCACTAAAGGCAGCACAAACATGTTATAACTGTGGGAAGCCAGGACATTTATCTAG
TCAATGTAGAGCACCTAAAGTCTGTTTTAAATGTAAACAGCCTGGACATTTCTCAAAGCA
ATGCAGAAGTGTTCCAAAAAACGGGAAGCAAGGGGCTCAAGGGAGGCCCCAGAAACAAAC
TTTCCCGATACAACAGAAGAGTCAGCACAACAAATCTGTTGTACAAGAGACTCCTCAGAC
TCAAAATCTGTACCCAGATCTGAGCGAAATAAAAAAGGAATACAATGTCAAGGAGAAGGA
TCAAGTAGAGGATCTCAACCTGGACAGTTTGTGGGAGTAACATATAATCTAGAGAAAAGG
CCTACTACAATAGTATTAATTAATGATACTCCCTTAAATGTACTGTTAGACACAGGAGCA
GATACTTCAGTGTTGACTACTGCACATTATAATAGGTTAAAATATAGAGGGAGAAAATAT
CAAGGGACGGGAATAATAGGAGTGGGAGGAAATGTGGAAACATTTTCTACGCCTGTGACT
ATAAAGGAAAAGGGTAGACACATTAAGACAAGAATGCTAGTGGCAGATATTCCAGTGACT
ATTTTGGGACGAGATATTCTTCAGGACTTAGGTGCAAAATTGGTTTTGGCACAGCTCTCC
AAGGAAATAAAATTTAGAAAAATAGAGTTAAAAGAGGGCACAATGGGGCCAAAAATTCCT
CAATGGCCACTCACTAAGGAGAAACTAGAAGGGGCTAAAGAGATAGTCCAAAGACTATTG
TCAGAGGGAAAAATATCAGAAGCTAGTGACAATAATCCTTATAATTCACCCATATTTGTA
ATAAAAAAGAGGTCTGGCAAATGGAGGTTATTACAAGATCTGAGAGAATTAAACAAAACA
GTACAAGTAGGAACGGAAATATCCAGAGGATTGCCTCACCCGGGAGGATTAATTAAATGT
AAACACATGACTGTATTAGATATTGGAGATGCATATTTCACTATACCCTTAGATCCAGAG
TTTAGACCATATACAGCTTTCACTATTCCCTCCATTAATCATCAAGAACCAGATAAAAGA
TATGTGTGGAATTGTTTACCACAAGGATTCGTGTTGAGCCCATATATATATCAGAAAACA
TTACAGGAAATTTTACAACCTTTTAGGGAAAGATATCCTGAAGTACAATTGTATCAATAT
ATGGATGATTTGTTCGTGGGAAGTAATGGTTCTAAAAAACAACACAAAGAGTTAATCATA

*FIG. 3A*

GAATTAAGGGCAATCTTACTGGAAAAGGGTTTTGAGACACCAGATGATAAATTACAAGAA
GTGCCACCTTATAGCTGGCTAGGTTATCAACTTTGTCCTGAAAATTGGAAAGTACAAAAA
ATGCAATTAGACATGGTAAAGAATCCAACCCTTAATGATGTGCAAAAATTAATGGGGAAT
ATAACATGGATGAGCTCAGGGGTCCCAGGGTTGACAGTAAAACACATAGCAGCTACTACT
AAGGGATGTTTAGAGTTGAATCAAAAAGTAATTTGGACGGAAGAGGCACAAAAAGAGTTA
GAAGAAAAATAATGAGAAGATTAAAAATGCTCAAGGGTTACAATATTATAATCCAGAAGAA
GAAATGTTATGTGAGGTTGAAATTACAAAAAATTATGAGGCAACTTATGTTATAAAACAA
TCACAAGGAATCCTATGGGCAGGTAAAAAGATTATGAAGGCTAATAAGGGATGGTCAACA
GTAAAAAATTTAATGTTACTGTTGCAACATGTGGCAACAGAAAGTATTACTAGAGTAGGA
AAATGTCCAACGTTTAAGGTACCATTTACCAAAGAGCAAGTAATGTGGGAAATGCAAAAA
GGATGGTATTATTCTTGGCTCCCAGAAATAGTATATACACATCAAGTAGTTCATGATGAT
TGGAGAATGAAATTGGTAGAAGAACCTACATCAGGAATAACAATATACACTGATGGGGGA
AAACAAAATGGAGAAGGAATAGCAGCTTATGTGACCAGTAATGGGAGAACTAAACAGAAA
AGGTTAGGACCTGTCACTCATCAAGTTGCTGAAAGAATGGCAATACAAATGGCATTAGAG
GATACCAGAGATAAACAAGTAAATATAGTAACTGATAGTTATTATTGTTGGAAAAATATT
ACAGAAGGATTAGGTTTAGAAGGACCACAAAGTCCTTGGTGGCCTATAATACAAAATATA
CGAGAAAAAGAGATAGTTTATTTTGCTTGGGTACCTGGTCACAAAGGGATATGTGGTAAT
CAATTGGCAGATGAAGCCGCAAAAATAAAAGAAGAAATCATGCTAGCATACCAAGGCACA
CAAATTAAAGAGAAAAGAGATGAAGATGCAGGGTTTGACTTATGTGTTCCTTATGACATC
ATGATACCTGTATCTGACACAAAAATCATACCCACAGATGTAAAAATTCAAGTTCCTCCT
AATAGCTTTGGATGGGTCACTGGGAAATCATCAATGGCAAAACAGGGGTTATTAATTAAT
GGAGGAATAATTGATGAAGGATATACAGGAGAAATACAAGTGATATGTACTAATATTGGA
AAAAGTAATATTAAATTAATAGAGGGACAAAAATTTGCACAATTAATTATACTACAGCAT
CACTCAAATTCCAGACAGCCTTGGGATGAAAATAAAATATCTCAGAGAGGGGATAAAGGA
TTTGGAAGTACAGGAGTATTCTGGGTAGAAAATATTCAGGAAGCACAAGATGAACATGAG
AATTGGCATACATCACCAAAGATATTGGCAAGAAATTATAAGATACCATTGACTGTAGCA
AAACAGATAACTCAAGAATGTCCTCATTGCACTAAGCAAGGATCAGGACCTGCAGGTTGT
GTCATGAGATCTCCTAATCATTGGCAGGCAGATTGCACACATTTGGACAATAAGATAATA
TTGACTTTTGTAGAGTCAAATTCAGGATACATACATGCTACATTATTGTCAAAAGAAAAT
GCATTATGTACTTCATTGGCTATTTTAGAATGGGCAAGATTGTTTTCACCAAAGTCCTTA
CACACAGATAACGGCACTAATTTTGTGGCAGAACCAGTTGTAAATTTGTTGAAGTTCCTA
AAGATAGCACATACCACAGGAATACCATATCATCCAGAAAGTCAGGGTATTGTAGAAAGG
GCAAATAGGACCTTGAAAGAGAAGATTCAAAGTCATAGAGACAACACTCAAACACTGGAG
GCAGCTTTACAACTTGCTCTCATTACTTGTAACAAAGGGAGGGAAAGTATGGGAGGACAG
ACACCATGGGAAGTATTTATCACTAATCAAGCACAAGTAATACATGAGAAACTTTTACTA
CAGCAAGCACAATCCTCCAAAAAATTTTGTTTTTACAAAATCCCTGGTGAACATGATTGG
AAGGGACCTACTAGGGTGCTGTGGAAGGGTGATGGTGCAGTAGTAGTTAATGATGAAGGA
AAGGGAATAATTGCTGTACCATTAACCAGGACTAAGTTACTAATAAAGCCAAATTGAGTA
TTGTTGCAGGAAGCAAGACCCAACTACCATTGTCAGCTGTGTTTCCTGAGGTCTCTAGGA
ATTGATTACCTCGATGCTTCATTAAGGAAGAAGAATAAACAAAGACTGAAGGCAATCCAA
CAAGGAAGACAACCTCAATATTTGTTATAAGGTTTGATATATGGGATTATTTGGTAAAGG
GGTAACATGGTCAGCATCGCATTCTATGGGGGGATCCCAGGGGGAATCTCAACCCCTATT
ACCCAACAGTCAGAAAAATCTAAGTGTGAGGAGAACACAATGTTTCAACCTTATTGTTAT
AATAATGACAGTAAGAACAGCATGGCAGAATCGAAGGAAGCAAGAGACCAAGAAATGAAC
CTGAAAGAAGAATCTAAAGAAGAAAAAAGAAGAAATGACTGGTGGAAAAAAGGTATGTTT
CTGTTATGCTTAGCAGGAACTACTGGAGGAATACTTTGGTGGTATGAAGGACTCCCACAG
CAACATTATATAGGGTTGGTGGCGATAGGGGGAAGATTAAACGGATCTGGCCAATCAAAT
GCTATAGAATGCTGGGGTTCCTTCCCGGGGTGTAGACCATTTCAAAATTACTTCAGTTAT
GAGACCAATAGAAGCATGCATATGGATAATAATACTGCTACATTATTAGAAGCTTTAACC
AATATAACTGCTCTATAAATAACAAAACAGAATTAGAAACATGGAAGTTAGTAAAGACTT
CTGGCGTAACTCCTTTACCTATTTCTTCTGAAGCTAACACTGGACTAATTAGACATAAGA
GAGATTTTGGTATAAGTGCAATAGTGGCAGCTATTGTAGCCGCTACTGCTATTGCTGCTA
GCGCTACTATGTCTTATGTTGCTCTAACTGAGGTTAACAAAATAATGGAAGTACAAAATC
ATACTTTTGAGGTAGAAAATAGTACTCTAAATGGTATGGATTTAATAGAACGACAAATAA
AGATATTATATGCTATGATTCTTCAAACACATGCAGATGTTCAACTGTTAAAGGAAAGAC
AACAGGTAGAGGAGACATTTAATTTAATTGGATGTATAGAAAGAACACATGTATTTTGTC
ATACTGGTCATCCCTGGAATATGTCATGGGGACATTTAAATGAGTCAACACAATGGGATG

*FIG. 3B*

ACTGGGTAAGCAAAATGGAAGATTTAAATCAAGAGATACTAACTACACTTCATGGAGCTA
GGAACAATTTGGCACAATCCATGATAACATTCAATACACCAGATAGTATAGCTCAATTTG
GAAAAGACCTTTGGAGTCATATTGGAAATTGGATTCCTGGATTGGGAGCTTCCATTATAA
AATATATAGTGATGTTTTTGCTTATTTATTTGTTACTAACCTCTTCGCCTAAGATCCTCA
GGGCCCTCTGGAAAGTGACCAGTGGTGCAGGGTCCTCCGGCAGTCGTTACCTGAAGAAAA
AATTCCATCACAAACATGCATCGCGAGAAGACACCTGGGACCAGGCCCAACACAACATAC
ACCTAGCAGGCGTGACCGGTGGATCAGGGGACAAATACTACAAACAGAAGTACTCCAGGA
ACGACTGGAATGGAGAATCAGAGGAGTACAACAGGCGGCCAAAGAGCTGGGTGAAGTCAA
TCGAGGCATTTGGAGAGAGCTATATTTCCGAGAAGACCAAAGGGGAGATTTCTCAGCCTG
GGGCGGCTATCAACGAGCACAAGAACGGCTCTGGGGGGAACAATCCTCACCAAGGGTCCT
TAGACCTGGAGATTCGAAGCGAAGGAGGAAACATTTATGACTGTTGCATTAAAGCCCAAG
AAGGAACTCTCGCTATCCCTTGCTGTGGATTTCCCTTATGGCTATTTTGGGGACTAGAGG
GCCCGTTTAAACCCGCTGATCAGCCTCGACTGTGCCTTCTAGTTGCCAGCCATCTGTTGT
TTGCCCCTCCCCCGTGCCTTCCTTGACCCTGGAAGGTGCCACTCCCACTGTCCTTTCCTA
ATAAAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCTGGGGATGC
GGTGGGCTCTATGGCTTCTGAGGCGGAAAGAACCAGCTGGGGCTCTAGGGGGTATCCCCA
CGCGCCCTGTAGCGGCGCATTAAGCGCGGCGGGTGTGGTGGTTACGCGCAGCGTGACCGC
TACACTTGCCAGCGCCCTAGCGCCCGCTCCTTTCGCTTTCTTCCCTTCCTTTCTCGCCAC
GTTCGCCGGCTTTCCCCGTCAAGCTCTAAATCGGGGCATCCCTTTAGGGTTCCGATTTAG
TGCTTTACGGCACCTCGACCCCAAAAAACTTGATTAGGGTGATGGTTCACGTAGTGGGCC
ATCGCCCTGATAGACGGTTTTTCGCCCTTTGACGTTGGAGTCCACGTTCTTTAATAGTGG
ACTCTTGTTCCAAACTGGAACAACACTCAACCCTATCTCGGTCTATTCTTTTGATTTATA
AGGGATTTTGGGGATTTCGGCCTATTGGTTAAAAAATGAGCTGATTTAACAAAAATTTAA
CGCGAATTAATTCTGTGGAATGTGTGTCAGTTAGGGTGTGGAAAGTCCCCAGGCTCCCCA
GGCAGGCAGAAGTATGCAAAGCATGCATCTCAATTAGTCAGCAACCAGGTGTGGAAAGTC
CCCAGGCTCCCCAGCAGGCAGAAGTATGCAAAGCATGCATCTCAATTAGTCAGCAACCAT
AGTCCCGCCCCTAACTCCGCCCATCCCGCCCCTAACTCCGCCCAGTTCCGCCCATTCTCC
GCCCCATGGCTGACTAATTTTTTTTATTTATGCAGAGGCCGAGGCCGCCTCTGCCTCTGA
GCTATTCCAGAAGTAGTGAGGAGGCTTTTTTGGAGGCCTAGGCTTTTGCAAAAAGCTCCC
GGGAGCTTGTATATCCATTTTCGGATCTGATCAAGAGACAGGATGAGGATCGTTTCGCAT
GATTGAACAAGATGGATTGCACGCAGGTTCTCCGGCCGCTTGGGTGGAGAGGCTATTCGG
CTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCA
GGACGAGGCAGCGCGGCTATCGTGGCTGGCCACGACGGGCGTTCCTTGCGCAGCTGTGCT
CGACGTTGTCACTGAAGCGGGAAGGGACTGGCTGCTATTGGGCGAAGTGCCGGGGCAGGA
TCTCCTGTCATCTCACCTTGCTCCTGCCGAGAAAGTATCCATCATGGCTGATGCAATGCG
GCGGCTGCATACGCTTGATCCGGCTACCTGCCCATTCGACCACCAAGCGAAACATCGCAT
CGAGCGAGCACGTACTCGGATGGAAGCCGGTCTTGTCGATCAGGATGATCTGGACGAAGA
GCATCAGGGGCTCGCGCCAGCCGAACTGTTCGCCAGGCTCAAGGCGCGCATGCCCGACGG
CGAGGATCTCGTCGTGACCCATGGCGATGCCTGCTTGCCGAATATCATGGTGGAAAATGG
CCGCTTTTCTGGATTCATCGACTGTGGCCGGCTGGGTGTGGCGGACCGCTATCAGGACAT
AGCGTTGGCTACCCGTGATATTGCTGAAGAGCTTGGCGGCGAATGGGCTGACCGCTTCCT
CGTGCTTTACGGTATCGCCGCTCCCGATTCGCAGCGCATCGCCTTCTATCGCCTTCTTGA
CGAGTTCTTCTGAGCGGGACTCTGGGGTTCGAAATGACCGACCAAGCGACGCCCAACCTG
CCATCACGAGATTTCGATTCCACCGCCGCCTTCTATGAAAGGTTGGGCTTCGGAATCGTT
TTCCGGGACGCCGGCTGGATGATCCTCCAGCGCGGGGATCTCATGCTGGAGTTCTTCGCC
CACCCCAACTTGTTTATTGCAGCTTATAATGGTTACAAATAAAGCAATAGCATCACAAAT
TTCACAAATAAAGCATTTTTTTCACTGCATTCTAGTTGTGGTTTGTCCAAACTCATCAAT
GTATCTTATCATGTCTGTATACCGTCGACCTCTAGCTAGAGCTTGGCGTAATCATGGTCA
TAGCTGTTTCCTGTGTGAAATTGTTATCCGCTCACAATTCCACACAACATACGAGCCGGA
AGCATAAAGTGTAAAGCCTGGGGTGCCTAATGAGTGAGCTAACTCACATTAATTGCGTTG
CGCTCACTGCCCGCTTTCCAGTCGGGAAACCTGTCGTGCCAGCTGCATTAATGAATCGGC
CAACGCGCGGGGAGAGGCGGTTTGCGTATTGGGCGCTCTTCCGCTTCCTCGCTCACTGAC
TCGCTGCGCTCGGTCGTTCGGCTGCGGCGAGCGGTATCAGCTCACTCAAAGGCGGTAATA
CGGTTATCCACAGAATCAGGGGATAACGCAGGAAAGAACATGTGAGCAAAAGGCCAGCAA
AAGGCCAGGAACCGTAAAAAGGCCGCGTTGCTGGCGTTTTTCCATAGGCTCCGCCCCCCT

FIG. 3C

GACGAGCATCACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCCGACCCTGCCG
CTTACCGGATACCTGTCCGCCTTTCTCCCTTCGGGAAGCGTGGCGCTTTCTCAATGCTCA
CGCTGTAGGTATCTCAGTTCGGTGTAGGTCGTTCGCTCCAAGCTGGGCTGTGTGCACGAA
CCCCCCGTTCAGCCCGACCGCTGCGCCTTATCCGGTAACTATCGTCTTGAGTCCAACCCG
GTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGG
ACAGTATTTGGTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGAC
GCTCAGTGGAACGAAAACTCACGTTAAGGGATTTTGGTCATGAGATTATCAAAAAGGATC
TTCACCTAGATCCTTTTAAATTAAAAATGAAGTTTTAAATCAATCTAAAGTATATATGAG
TAAACTTGGTCTGACAGTTACCAATGCTTAATCAGTGAGGCACCTATCTCAGCGATCTGT
CTATTTCGTTCATCCATAGTTGCCTGACTCCCCGTCGTGTAGATAACTACGATACGGGAG
GGCTTACCATCTGGCCCCAGTGCTGCAATGATACCGCGAGACCCACGCTCACCGGCTCCA
GATTTATCAGCAATAAACCAGCCAGCCGGAAGGGCCGAGCGCAGAAGTGGTCCTGCAACT
TTATCCGCCTCCATCCAGTCTATTAATTGTTGCCGGGAAGCTAGAGTAAGTAGTTCGCCA
GTTAATAGTTTGCGCAACGTTGTTGCCATTGCTACAGGCATCGTGGTGTCACGCTCGTCG
TTTGGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGCCA
TCCGTAAGATGCTTTTCTGTGACTGGTGAGTACTCAACCAAGTCATTCTGAGAATAGTGT
ATGCGGCGACCGAGTTGCTCTTGCCCGGCGTCAATACGGGATAATACCGCGCCACATAGC
AGAACTTTAAAAGTGCTCATCATTGGAAAACGTTCTTCGGGGCGAAAACTCTCAAGGATC
TTACCGCTGTTGAGATCCAGTTCGATGTAACCCACTCGTGCACCCAACTGATCTTCAGCA
TCTTTTACTTTCACCAGCGTTTCTGGGTGAGCAAAAACAGGAAGGCAAAATGCCGCAAAA
AAGGGAATAAGGGCGACACGGAAATGTTGAATACTCATACTCTTCCTTTTTCAATATTAT
TGAAGCATTTATCAGGGTTATTGTCTCATGAGCGGATACATATTTGAATGTATTTAGAAA
AATAAACAAATAGGGGTTCCGCGCACATTTCCCCGAAAAGTGCCACCTGACGTC

*FIG. 3D* pECG3-CZR, vector genome plasmid.

TCAATATTGGCCATTAGCCATATTATTCATTGGTTATATAGCATAAATCAATATTGGCTA
TTGGCCATTGCATACGTTGTATCTATATCATAATATGTACATTTATATTGGCTCATGTCC
AATATGACCGCCATGTTGGCATTGATTATTGACTAGTTATTAATAGTAATCAATTACGGG
GTCATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTGC
CCACTTGGCAGTACATCAAGTGTATCATATGCCAAGTCCGCCCCCTATTGACGTCAATGA
CGGTAAATGGCCCGCCTGGCATTATGCCCAGTACATGACCTTACGGGACTTTCCTACTTG
GCAGTACATCTACGTATTAGTCATCGCTATTACCATGGTGATGCGGTTTTGGCAGTACAC
CAATGGGCGTGGATAGCGGTTTGACTCACGGGGATTTCCAAGTCTCCACCCCATTGACGT
CAATGGGAGTTTGTTTTGGCACCAAAATCAACGGGACTTTCCAAAATGTCGTAATAACCC
CGCCCCGTTGACGCAAATGGGCGGTAGGCGTGTACGGTGGGAGGTCTATATAAGCAGAGC
TCGTTTAGTGAACCGGGCACTCAGATTCTGCGGTCTGAGTCCCTTCTCTGCTGGGCTGAA
AAGGCCTTTGTAATAAATATAATTCTCTACTCAGTCCCTGTCTCTAGTTTGTCTGTTCGA
GATCCTACAGTTGGCGCCCGAACAGGGACCTGAGAGGGGCGCAGACCCTACCTGTTGAAC
CTGGCTGATCGTAGGATCCCCGGGACAGCAGAGGAGAACTTACAGAAGTCTTCTGGAGGT
GTTCCTGGCCAGAACACAGGAGGACAGGTAAGTAGGGAGACCCTTTGACATGGAGCAAGG
CGCTCAAGAAGTTAGAGAAGGTGACGGTACAAGGGTCTCAGAAATTAACTACTGGTAACT
GTAATTGGGCGCTAAGTCTAGTAGACTTATTTCATGATACCAACTTTGTAAAAGAAAAGG
ACTGGCAGCTGAGGGATGTCATTCCATTGCTGGAAGATGTAACTCAGACGCTGGAATTCG
AGCTTGCATGCCTGCAGGTCGTTACATAACTTACGGTAAATGGCCCGCCTGGCTGACCGC
CCAACGACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGCAGTAC
ATCAAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTACG
TATTAGTCATCGCTATTACCATGGTGATGCGGTTTTGGCAGTACATCAATGGGCGTGGAT
AGCGGTTTGACTCACGGGGATTTCCAAGTCTCCACCCCATTGACGTCAATGGGAGTTTGT
TTTGGCACCAAAATCAACGGGACTTTCCAAAATGTCGTAACAACTCCGCCCCATTGACGC
AAATGGGCGGTAGGCGTGTACGGTGGGAGGTCTATATAAGCAGAGCTCGTTTAGTGAACC
GTCAGATCGCCTGGAGACGCCATCCACGCTGTTTTGACCTCCATAGAAGACACCGGGACC
GATCCAGCCTCCGGACTCTAGAGTCGACCCGGGCGGCCGCAATTCCCGGGGATCGAAAGA
GCCTGCTAAAGCAAAAAAGAAGTCACCATGTCGTTTACTTTGACCAACAAGAACGTGATT
TTCGTTGCCGGTCTGGGAGGCATTGGTCTGGACACCAGCAAGGAGCTGCTCAAGCGCGAT
CCCGTCGTTTTACAACGTCGTGACTGGGAAAACCCTGGCGTTACCCAACTTAATCGCCTT
GCAGCACATCCCCCTTTCGCCAGCTGGCGTAATAGCGAAGAGGCCCGCACCGATCGCCCT
TCCCAACAGTTGCGCAGCCTGAATGGCGAATGGCGCTTTGCCTGGTTTCCGGCACCAGAA
GCGGTGCCGGAAAGCTGGCTGGAGTGCGATCTTCCTGAGGCCGATACTGTCGTCGTCCCC
TCAAACTGGCAGATGCACGGTTACGATGCGCCCATCTACACCAACGTAACCTATCCCATT
ACGGTCAATCCGCCGTTTGTTCCCACGGAGAATCCGACGGGTTGTTACTCGCTCACATTT
AATGTTGATGAAAGCTGGCTACAGGAAGGCCAGACGCGAATTATTTTTGATGGCGTTAAC
TCGGCGTTTCATCTGTGGTGCAACGGGCGCTGGGTCGGTTACGGCCAGGACAGTCGTTTG
CCGTCTGAATTTGACCTGAGCGCATTTTTACGCGCCGGAGAAAACCGCCTCGCGGTGATG
GTGCTGCGTTGGAGTGACGGCAGTTATCTGGAAGATCAGGATATGTGGCGGATGAGCGGC
ATTTTCCGTGACGTCTCGTTGCTGCATAAACCGACTACACAAATCAGCGATTTCCATGTT
GCCACTCGCTTTAATGATGATTTCAGCCGCGCTGTACTGGAGGCTGAAGTTCAGATGTGC
GGCGAGTTGCGTGACTACCTACGGGTAACAGTTTCTTTATGGCAGGGTGAAACGCAGGTC
GCCAGCGGCACCGCGCCTTTCGGCGGTGAAATTATCGATGAGCGTGGTGGTTATGCCGAT
CGCGTCACACTACGTCTGAACGTCGAAAACCCGAAACTGTGGAGCGCCGAAATCCCGAAT
CTCTATCGTGCGGTGGTTGAACTGCACACCGCCGACGGCACGCTGATTGAAGCAGAAGCC
TGCGATGTCGGTTTCCGCGAGGTGCGGATTGAAAATGGTCTGCTGCTGCTGAACGGCAAG
CCGTTGCTGATTCGAGGCGTTAACCGTCACGAGCATCATCCTCTGCATGGTCAGGTCATG
GATGAGCAGACGATGGTGCAGGATATCCTGCTGATGAAGCAGAACAACTTTAACGCCGTG
CGCTGTTCGCATTATCCGAACCATCCGCTGTGGTACACGCTGTGCGACCGCTACGGCCTG
TATGTGGTGGATGAAGCCAATATTGAAACCCACGGCATGGTGCCAATGAATCGTCTGACC
GATGATCCGCGCTGGCTACCGGCGATGAGCGAACGCGTAACGCGAATGGTGCAGCGCGAT

*FIG. 5A*

CGTAATCACCCGAGTGTGATCATCTGGTCGCTGGGGAATGAATCAGGCCACGGCGCTAAT
CACGACGCGCTGTATCGCTGGATCAAATCTGTCGATCCTTCCCGCCCGGTGCAGTATGAA
GGCGGCGGAGCCGACACCACGGCCACCGATATTATTTGCCCGATGTACGCGCGCGTGGAT
GAAGACCAGCCCTTCCCGGCTGTGCCGAAATGGTCCATCAAAAAATGGCTTTCGCTACCT
GGAGAGACGCGCCCGCTGATCCTTTGCGAATACGCCCACGCGATGGGTAACAGTCTTGGC
GGTTTCGCTAAATACTGGCAGGCGTTTCGTCAGTATCCCCGTTTACAGGGCGGCTTCGTC
TGGGACTGGGTGGATCAGTCGCTGATTAAATATGATGAAAACGGCAACCCGTGGTCGGCT
TACGGCGGTGATTTTGGCGATACGCCGAACGATCGCCAGTTCTGTATGAACGGTCTGGTC
TTTGCCGACCGCACGCCGCATCCAGCGCTGACGGAAGCAAAACACCAGCAGCAGTTTTTC
CAGTTCCGTTTATCCGGGCAAACCATCGAAGTGACCAGCGAATACCTGTTCCGTCATAGC
GATAACGAGCTCCTGCACTGGATGGTGGCGCTGGATGGTAAGCCGCTGGCAAGCGGTGAA
GTGCCTCTGGATGTCGCTCCACAAGGTAAACAGTTGATTGAACTGCCTGAACTACCGCAG
CCGGAGAGCGCCGGGCAACTCTGGCTCACAGTACGCGTAGTGCAACCGAACGCGACCGCA
TGGTCAGAAGCCGGGCACATCAGCGCCTGGCAGCAGTGGCGTCTGGCGGAAAACCTCAGT
GTGACGCTCCCCGCCGCGTCCCACGCCATCCCGCATCTGACCACCAGCGAAATGGATTTT
TGCATCGAGCTGGGTAATAAGCGTTGGCAATTTAACCGCCAGTCAGGCTTTCTTTCACAG
ATGTGGATTGGCGATAAAAAACAACTGCTGACGCCGCTGCGCGATCAGTTCACCCGTGCA
CCGCTGGATAACGACATTGGCGTAAGTGAAGCGACCCGCATTGACCCTAACGCCTGGGTC
GAACGCTGGAAGGCGGCGGGCCATTACCAGGCCGAAGCAGCGTTGTTGCAGTGCACGGCA
GATACACTTGCTGATGCGGTGCTGATTACGACCGCTCACGCGTGGCAGCATCAGGGGAAA
ACCTTATTTATCAGCCGGAAAACCTACCGGATTGATGGTAGTGGTCAAATGGCGATTACC
GTTGATGTTGAAGTGGCGAGCGATACACCGCATCCGGCGCGGATTGGCCTGAACTGCCAG
CTGGCGCAGGTAGCAGAGCGGGTAAACTGGCTCGGATTAGGGCCGCAAGAAAACTATCCC
GACCGCCTTACTGCCGCCTGTTTTGACCGCTGGGATCTGCCATTGTCAGACATGTATACC
CCGTACGTCTTCCCGAGCGAAAACGGTCTGCGCTGCGGGACGCGCGAATTGAATTATGGC
CCACACCAGTGGCGCGGCGACTTCCAGTTCAACATCAGCCGCTACAGTCAACAGCAACTG
ATGGAAACCAGCCATCGCCATCTGCTGCACGCGGAAGAAGGCACATGGCTGAATATCGAC
GGTTTCCATATGGGGATTGGTGGCGACGACTCCTGGAGCCCGTCAGTATCGGCGGAATTA
CAGCTGAGCGCCGGTCGCTACCATTACCAGTTGGTCTGGTGTCAAAAATAATAATAACCG
GGCAGGCCATGTCTGCCCGTATTTCGCGTAAGGAAATCCATTATGTACTATTTAAAAAAC
ACAAACTTTTGGATGTTCGGTTTATTCTTTTTCTTTTACTTTTTTATCATGGGAGCCTAC
TTCCCGTTTTTCCCGATTTGGCTACATGACATCAACCATATCAGCAAAAGTGATACGGGT
ATTATTTTTGCCGCTATTTCTCTGTTCTCGCTATTATTCCAACCGCTGTTTGGTCTGCTT
TCTGACAAACTCGGCCTCGACTCTAGGCGGCCGCTCTAGAACTAGTGGATCCCAGGGGGA
ATCTCAACCCCTATTACCCAACAGTCAGAAAAATCTAAGTGTGAGGAGAACACAATGTTT
CAACCTTATTGTTATAATAATGACAGTAAGAACAGCATGGCAGAATCGAAGGAAGCAAGA
GACCAAGAAATGAACCTGAAAGAAGAATCTAAAGAAGAAAAAAGAAGAAATGACTGGTGG
AAAAAAGGTATGTTTCTGTTATGCTTAGCAGGAACTACTGGAGGAATACTTTGGTGGTAT
GAAGGACTCCCACAGCAACATTATATAGGGTTGGTGGCGATAGGGGGAAGATTAAACGGA
TCTGGCCAATCAAATGCTATAGAATGCTGGGGTTCCTTCCCGGGGTGTAGACCATTTCAA
AATTACTTCAGTTATGAGACCAATAGAAGCATGCATATGGATAATAATACTGCTACATTA
TTAGAAGCTTTAACCAATATAACTGCTCTATAAATAACAAAACAGAATTAGAAACATGGA
AGTTAGTAAAGACTTCTGGCGTAACTCCTTTACCTATTTCTTCTGAAGCTAACACTGGAC
TAATTAGACATAAGAGAGATTTTGGTATAAGTGCAATAGTGGCAGCTATTGTAGCCGCTA
CTGCTATTGCTGCTAGCGCTACTATGTCTTATGTTGCTCTAACTGAGGTTAACAAAATAA
TGGAAGTACAAAATCATACTTTTGAGGTAGAAAATAGTACTCTAAATGGTATGGATTTAA
TAGAACGACAAATAAAGATATTATATGCTATGATTCTTCAAACACATGCAGATGTTCAAC
TGTTAAAGGAAAGACAACAGGTAGAGGAGACATTTAATTTAATTGGATGTATAGAAAGAA
CACATGTATTTTGTCATACTGGTCATCCCTGGAATATGTCATGGGGACATTTAAATGAGT
CAACACAATGGGATGACTGGGTAAGCAAAATGGAAGATTTAAATCAAGAGATACTAACTA
CACTTCATGGAGCTAGGAACAATTTGGCACAATCCATGATAACATTCAATACACCAGATA
GTATAGCTCAATTTGGAAAAGACCTTTGGAGTCATATTGGAAATTGGATTCCTGGATTGG
GAGCTTCCATTATAAAATATATAGTGATGTTTTTGCTTATTTATTTGTTACTAACCTCTT
CGCCTAAGATCCTCAGGGCCCTCTGGAAAGTGACCAGTGGTGCAGGGTCCTCCGGCAGTC
GTTACCTGAAGAAAAAATTCCATCACAAACATGCATCGCGAGAAGACACCTGGGACCAGG
CCCAACACAACATACACCTAGCAGGCGTGACCGGTGGATCAGGGGACAAATACTACAAAC
AGAAGTACTCCAGGAACGACTGGAATGGAGAATCAGAGGAGTACAACAGGCGGCCAAAGA

*FIG. 5B*

GCTGGGTGAAGTCAATCGAGGCATTTGGAGAGAGCTATATTTCCGAGAAGACCAAAGGGG
AGATTTCTCAGCCTGGGGCGGCTATCAACGAGCACAAGAACGGCTCTGGGGGGAACAATC
CTCACCAAGGGTCCTTAGACCTGGAGATTCGAAGCGAAGGAGGAAACATTTATGACTGTT
GCATTAAAGCCCAAGAAGGAACTCTCGCTATCCCTTGCTGTGGATTTCCCTTATGGCTAT
TTTGGGGACTAGAGGGCCCGTTTATCAAGCTTATCGATAGAAAAACAAGGGGGGAACTGT
GGGGTTTTTATGAGGGGTTTTATAAATGATTATAAGAGTAAAAAGAAAGTTGCTGATGCT
CTCATAACCTTGTATAACCCAAAGGACTAGCTCATGTTGCTAGGCAACTAAACCGCAATA
ACCACATTTGTGACGCGAGTTCCGCATTGGTGACGCGTTAAGTTCCTGTTTTTACAGTAT
ATAAGTGCTTGTATTCTGACAATTGGGCACTCAGATTCTGCGGTCTGAGTCCCTTCTCTG
CTGGGCTGAAAAGGCCTTTGTAATAAATATAATTCTCTACTCAGTCCCTGTCTCTAGTTT
GTCTGTTCGAGATCCTACATTAATTAAGGAGATCCGGGCTGGCGTAATAGCGAAGAGGCC
CGCACCGATCGCCCTTCCCAACAGTTGCGCAGCCTGAATGGCGAATGGACGCGCCCTGTA
GCGGCGCATTAAGCGCGGCGGGTGTGGTGGTTACGCGCAGCGTGACCGCTACACTTGCCA
GCGCCCTAGCGCCCGCTCCTTTCGCTTTCTTCCCTTCCTTTCTCGCCACGTTCGCCGGCT
TTCCCCGTCAAGCTCTAAATCGGGGGCTCCCTTTAGGGTTCCGATTTAGAGCTTTACGGC
ACCTCGACCGCAAAAAACTTGATTTGGGTGATGGTTCACGTAGTGGGCCATCGCCCTGAT
AGACGGTTTTTCGCCCTTTGACGTTGGAGTCCACGTTCTTTAATAGTGGACTCTTGTTCC
AAACTGGAACAACACTCAACCCTATCTCGGTCTATTCTTTTGATTTATAAGGGATTTTGC
CGATTTCGGCCTATTGGTTAAAAAATGAGCTGATTTAACAAATATTTAACGCGAATTTTA
ACAAAATATTAACGTTTACAATTTCGCCTGATGCGGTATTTTCTCCTTACGCATCTGTGC
GGTATTTCACACCGCATATGGTGCACTCTCAGTACAATCTGCTCTGATGCCGCATAGTTA
AGCCAGCCCCGACACCCGCCAACACCCGCTGACGCGCCCTGACGGGCTTGTCTGCTCCCG
GCATCCGCTTACAGACAAGCTGTGACCGTCTCCGGGAGCTGCATGTGTCAGAGGTTTTCA
CCGTCATCACCGAAACGCGCGAGACGAAAGGGCCTCGTGATACGCCTATTTTTATAGGTT
AATGTCATGATAATAATGGTTTCTTAGACGTCAGGTGGCACTTTTCGGGGAAATGTGCGC
GGAACCCCTATTTGTTTATTTTTCTAAATACATTCAAATATGTATCCGCTCATGAGACAA
TAACCCTGATAAATGCTTCAATAATATTGAAAAAGGAAGAGTATGAGTATTCAACATTTC
CGTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACATCGAA
CTGGATCTCAACAGCGGTAAGATCCTTGAGAGTTTTCGCCCCGAAGAACGTTTTCCAATG
ATGAGCACTTTTAAAGTTCTGCTATGTGGCGCGGTATTATCCCGTATTGACGCCGGGCAA
GAGCAACTCGGTCGCCGCATACACTATTCTCAGAATGACTTGGTTGAGTACTCACCAGTC
ACAGAAAAGCATCTTACGGATGGCATGACAGTAAGAGAATTATGCAGTGCTGCCATAACC
ATGAGTGATAACACTGCGGCCAACTTACTTCTGACAACGATCGGAGGACCGAAGGAGCTA
ACCGCTTTTTTGCACAACATGGGGGATCATGTAACTCGCCTTGATCGTTGGGAACCGGAG
CTGAATGAAGCCATACCAAACGACGAGCGTGACACCACGATGCCTGTAGCAATGGCAACA
ACGTTGCGCAAACTATTAACTGGCGAACTACTTACTCTAGCTTCCCGGCAACAATTAATA
GACTGGATGGAGGCGGATAAAGTTGCAGGACCACTTCTGCGCTCGGCCCTTCCGGCTGGC
TGGTTTATTGCTGATAAATCTGGAGCCGGTGAGCGTGGGTCTCGCGGTATCATTGCAGCA
CTGGGGCCAGATGGTAAGCCCTCCCGTATCGTAGTTATCTACACGACGGGGAGTCAGGCA
ACTATGGATGAACGAAATAGACAGATCGCTGAGATAGGTGCCTCACTGATTAAGCATTGG
TAACTGTCAGACCAAGTTTACTCATATATACTTTAGATTGATTTAAAACTTCATTTTTAA
TTTAAAAGGATCTAGGTGAAGATCCTTTTTGATAATCTCATGACCAAAATCCCTTAACGT
GAGTTTTCGTTCCACTGAGCGTCAGACCCCGTAGAAAAGATCAAAGGATCTTCTTGAGAT
CCTTTTTTTCTGCGCGTAATCTGCTGCTTGCAAACAAAAAAACCACCGCTACCAGCGGTG
GTTTGTTTGCCGGATCAAGAGCTACCAACTCTTTTTCCGAAGGTAACTGGCTTCAGCAGA
GCGCAGATACCAAATACTGTCCTTCTAGTGTAGCCGTAGTTAGGCCACCACTTCAAGAAC
TCTGTAGCACCGCCTACATACCTCGCTCTGCTAATCCTGTTACCAGTGGCTGCTGCCAGT
GGCGATAAGTCGTGTCTTACCGGGTTGGACTCAAGACGATAGTTACCGGATAAGGCGCAG
CGGTCGGGCTGAACGGGGGGTTCGTGCACACAGCCCAGCTTGGAGCGAACGACCTACACC
GAACTGAGATACCTACAGCGTGAGCTATGAGAAAGCGCCACGCTTCCCGAAGGGAGAAAG
GCGGACAGGTATCCGGTAAGCGGCAGGGTCGGAACAGGAGAGCGCACGAGGGAGCTTCCA
GGGGGAAACGCCTGGTATCTTTATAGTCCTGTCGGGTTTCGCCACCTCTGACTTGAGCGT
CGATTTTTGTGATGCTCGTCAGGGGGGCGGAGCCTATGGAAAAACGCCAGCAACGCGGCC
TTTTTACGGTTCCTGGCCTTTTGCTGGCCTTTTGCTCACATGGCTCGACAGATCT

*FIG. 5C* pONY8.0Z vector genome plasmid

AGATCTTGAATAATAAAATGTGTGTTTGTCCGAAATACGCGTTTTGAGATTTCTGTCGCC
GACTAAATTCATGTCGCGCGATAGTGGTGTTTATCGCCGATAGAGATGGCGATATTGGAA
AAATTGATATTTGAAAATATGGCATATTGAAAATGTCGCCGATGTGAGTTTCTGTGTAAC
TGATATCGCCATTTTTCCAAAAGTGATTTTTGGGCATACGCGATATCTGGCGATAGCGCT
TATATCGTTTACGGGGGATGGCGATAGACGACTTTGGTGACTTGGGCGATTCTGTGTGTC
GCAAATATCGCAGTTTCGATATAGGTGACAGACGATATGAGGCTATATCGCCGATAGAGG
CGACATCAAGCTGGCACATGGCCAATGCATATCGATCTATACATTGAATCAATATTGGCC
ATTAGCCATATTATTCATTGGTTATATAGCATAAATCAATATTGGCTATTGGCCATTGCA
TACGTTGTATCCATATCGTAATATGTACATTTATATTGGCTCATGTCCAACATTACCGCC
ATGTTGACATTGATTATTGACTAGTTATTAATAGTAATCAATTACGGGGTCATTAGTTCA
TAGCCCATATATGGAGTTCCGCGTTACATAACTTACGGTAAATGGCCCGCCTGGCTGACC
GCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGT
ACATCAAGTGTATCATATGCCAAGTCCGCCCCCTATTGACGTCAATGACGGTAAATGGCC
CGCCTGGCATTATGCCCAGTACATGACCTTACGGGACTTTCCTACTTGGCAGTACATCTA
CGTATTAGTCATCGCTATTACCATGGTGATGCGGTTTTGGCAGTACACCAATGGGCGTGG
ATAGCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTGCGATCGCCCGCC
CCGTTGACGCAAATGGGCGGTAGGCGTGTACGGTGGGAGGTCTATATAAGCAGAGCTCGT
TTAGTGAACCGGGCACTCAGATTCTGCGGTCTGAGTCCCTTCTCTGCTGGGCTGAAAAGG
CCTTTGTAATAAATATAATTCTCTACTCAGTCCCTGTCTCTAGTTTGTCTGTTCGAGATC
CTACAGTTGGCGCCCGAACAGGGACCTGAGAGGGGCGCAGACCCTACCTGTTGAACCTGG
CTGATCGTAGGATCCCCGGGACAGCAGAGGAGAACTTACAGAAGTCTTCTGGAGGTGTTC
CTGGCCAGAACACAGGAGGACAGGTAAGATTGGGAGACCCTTTGACATTGGAGCAAGGCG
CTCAAGAAGTTAGAGAAGGTGACGGTACAAGGGTCTCAGAAATTAACTACTGGTAACTGT
AATTGGGCGCTAAGTCTAGTAGACTTATTTCATGATACCAACTTTGTAAAAGAAAAGGAC
TGGCAGCTGAGGGATGTCATTCCATTGCTGGAAGATGTAACTCAGACGCTGTCAGGACAA
GAAAGAGAGGCCTTTGAAAGAACATGGTGGGCAATTTCTGCTGTAAAGATGGGCCTCCAG
ATTAATAATGTAGTAGATGGAAAGGCATCATTCCAGCTCCTAAGAGCGAAATATGAAAAG
AAGACTGCTAATAAAAAGCAGTCTGAGCCCTCTGAAGAATATCTCTAGAACTAGTGGATC
CCCCGGGCTGCAGGAGTGGGGAGGCACGATGGCCGCTTTGGTCGAGGCGGATCCGGCCAT
TAGCCATATTATTCATTGGTTATATAGCATAAATCAATATTGGCTATTGGCCATTGCATA
CGTTGTATCCATATCATAATATGTACATTTATATTGGCTCATGTCCAACATTACCGCCAT
GTTGACATTGATTATTGACTAGTTATTAATAGTAATCAATTACGGGGTCATTAGTTCATA
GCCCATATATGGAGTTCCGCGTTACATAACTTACGGTAAATGGCCCGCCTGGCTGACCGC
CCAACGACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGCAGTAC
ATCAAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTACG
TATTAGTCATCGCTATTACCATGGTGATGCGGTTTTGGCAGTACATCAATGGGCGTGGAT
AGCGGTTTGACTCACGGGGATTTCCAAGTCTCCACCCCATTGACGTCAATGGGAGTTTGT
TTTGGCACCAAAATCAACGGGACTTTCCAAAATGTCGTAACAACTCCGCCCCATTGACGC
AAATGGGCGGTAGGCATGTACGGTGGGAGGTCTATATAAGCAGAGCTCGTTTAGTGAACC
GTCAGATCGCCTGGAGACGCCATCCACGCTGTTTTGACCTCCATAGAAGACACCGGGACC
GATCCAGCCTCCGCGGCCCCAAGCTTCAGCTGCTCGAGGATCTGCGGATCCGGGGAATTC
CCCAGTCTCAGGATCCACCATGGGGGATCCCGTCGTTTTACAACGTCGTGACTGGGAAAA
CCCTGGCGTTACCCAACTTAATCGCCTTGCAGCACATCCCCCTTTCGCCAGCTGGCGTAA
TAGCGAAGAGGCCCGCACCGATCGCCCTTCCCAACAGTTGCGCAGCCTGAATGGCGAATG
GCGCTTTGCCTGGTTTCCGGCACCAGAAGCGGTGCCGGAAAGCTGGCTGGAGTGCGATCT
TCCTGAGGCCGATACTGTCGTCGTCCCCTCAAACTGGCAGATGCACGGTTACGATGCGCC
CATCTACACCAACGTAACCTATCCCATTACGGTCAATCCGCCGTTTGTTCCCACGGAGAA
TCCGACGGGTTGTTACTCGCTCACATTTAATGTTGATGAAAGCTGGCTACAGGAAGGCCA
GACGCGAATTATTTTTGATGGCGTTAACTCGGCGTTTCATCTGTGGTGCAACGGGCGCTG
GGTCGGTTACGGCCAGGACAGTCGTTTGCCGTCTGAATTTGACCTGAGCGCATTTTTACG
CGCCGGAGAAAACCGCCTCGCGGTGATGGTGCTGCGTTGGAGTGACGGCAGTTATCTGGA

*FIG. 7A*

AGATCAGGATATGTGGCGGATGAGCGGCATTTTCCGTGACGTCTCGTTGCTGCATAAACC
GACTACACAAATCAGCGATTTCCATGTTGCCACTCGCTTTAATGATGATTTCAGCCGCGC
TGTACTGGAGGCTGAAGTTCAGATGTGCGGCGAGTTGCGTGACTACCTACGGGTAACAGT
TTCTTTATGGCAGGGTGAAACGCAGGTCGCCAGCGGCACCGCGCCTTTCGGCGGTGAAAT
TATCGATGAGCGTGGTGGTTATGCCGATCGCGTCACACTACGTCTGAACGTCGAAAACCC
GAAACTGTGGAGCGCCGAAATCCCGAATCTCTATCGTGCGGTGGTTGAACTGCACACCGC
CGACGGCACGCTGATTGAAGCAGAAGCCTGCGATGTCGGTTTCCGCGAGGTGCGGATTGA
AAATGGTCTGCTGCTGCTGAACGGCAAGCCGTTGCTGATTCGAGGCGTTAACCGTCACGA
GCATCATCCTCTGCATGGTCAGGTCATGGATGAGCAGACGATGGTGCAGGATATCCTGCT
GATGAAGCAGAACAACTTTAACGCCGTGCGCTGTTCGCATTATCCGAACCATCCGCTGTG
GTACACGCTGTGCGACCGCTACGGCCTGTATGTGGTGGATGAAGCCAATATTGAAACCCA
CGGCATGGTGCCAATGAATCGTCTGACCGATGATCCGCGCTGGCTACCGGCGATGAGCGA
ACGCGTAACGCGAATGGTGCAGCGCGATCGTAATCACCCGAGTGTGATCATCTGGTCGCT
GGGGAATGAATCAGGCCACGGCGCTAATCACGACGCGCTGTATCGCTGGATCAAATCTGT
CGATCCTTCCCGCCCGGTGCAGTATGAAGGCGGCGGAGCCGACACCACGGCCACCGATAT
TATTTGCCCGATGTACGCGCGCGTGGATGAAGACCAGCCCTTCCCGGCTGTGCCGAAATG
GTCCATCAAAAAATGGCTTTCGCTACCTGGAGAGACGCGCCCGCTGATCCTTTGCGAATA
CGCCCACGCGATGGGTAACAGTCTTGGCGGTTTCGCTAAATACTGGCAGGCGTTTCGTCA
GTATCCCCGTTTACAGGGCGGCTTCGTCTGGGACTGGGTGGATCAGTCGCTGATTAAATA
TGATGAAAACGGCAACCCGTGGTCGGCTTACGGCGGTGATTTTGGCGATACGCCGAACGA
TCGCCAGTTCTGTATGAACGGTCTGGTCTTTGCCGACCGCACGCCGCATCCAGCGCTGAC
GGAAGCAAAACACCAGCAGCAGTTTTTCCAGTTCCGTTTATCCGGGCAAACCATCGAAGT
GACCAGCGAATACCTGTTCCGTCATAGCGATAACGAGCTCCTGCACTGGATGGTGGCGCT
GGATGGTAAGCCGCTGGCAAGCGGTGAAGTGCCTCTGGATGTCGCTCCACAAGGTAAACA
GTTGATTGAACTGCCTGAACTACCGCAGCCGGAGAGCGCCGGGCAACTCTGGCTCACAGT
ACGCGTAGTGCAACCGAACGCGACCGCATGGTCAGAAGCCGGGCACATCAGCGCCTGGCA
GCAGTGGCGTCTGGCGGAAAACCTCAGTGTGACGCTCCCCGCCGCGTCCCACGCCATCCC
GCATCTGACCACCAGCGAAATGGATTTTTGCATCGAGCTGGGTAATAAGCGTTGGCAATT
TAACCGCCAGTCAGGCTTTCTTTCACAGATGTGGATTGGCGATAAAAAACAACTGCTGAC
GCCGCTGCGCGATCAGTTCACCCGTGCACCGCTGGATAACGACATTGGCGTAAGTGAAGC
GACCCGCATTGACCCTAACGCCTGGGTCGAACGCTGGAAGGCGGCGGGCCATTACCAGGC
CGAAGCAGCGTTGTTGCAGTGCACGGCAGATACACTTGCTGATGCGGTGCTGATTACGAC
CGCTCACGCGTGGCAGCATCAGGGGAAAACCTTATTTATCAGCCGGAAAACCTACCGGAT
TGATGGTAGTGGTCAAATGGCGATTACCGTTGATGTTGAAGTGGCGAGCGATACACCGCA
TCCGGCGCGGATTGGCCTGAACTGCCAGCTGGCGCAGGTAGCAGAGCGGGTAAACTGGCT
CGGATTAGGGCCGCAAGAAAACTATCCCGACCGCCTTACTGCCGCCTGTTTTGACCGCTG
GGATCTGCCATTGTCAGACATGTATACCCCGTACGTCTTCCCGAGCGAAAACGGTCTGCG
CTGCGGGACGCGCGAATTGAATTATGGCCCACACCAGTGGCGCGGCGACTTCCAGTTCAA
CATCAGCCGCTACAGTCAACAGCAACTGATGGAAACCAGCCATCGCCATCTGCTGCACGC
GGAAGAAGGCACATGGCTGAATATCGACGGTTTCCATATGGGGATTGGTGGCGACGACTC
CTGGAGCCCGTCAGTATCGGCGGAATTCCAGCTGAGCGCCGGTCGCTACCATTACCAGTT
GGTCTGGTGTCAAAAATAATAATAACCGGGCAGGGGGGATCCGCAGATCCGGCTGTGGAA
TGTGTGTCAGTTAGGGTGTGGAAAGTCCCCAGGCTCCCCAGCAGGCAGAAGTATGCAAAG
CATGCCTGCAGGAATTCGATATCAAGCTTATCGATACCGTCGACCTCGAGGGGGGGCCCG
GTACCCAGCTTTTGTTCCCTTTAGTGAGGGTTAATTGCGCGGGAAGTATTTATCACTAAT
CAAGCACAAGTAATACATGAGAAACTTTTACTACAGCAAGCACAATCCTCCAAAAAATTT
TGTTTTTACAAAATCCCTGGTGAACATGATTGGAAGGGACCTACTAGGGTGCTGTGGAAG
GGTGATGGTGCAGTAGTAGTTAATGATGAAGGAAAGGGAATAATTGCTGTACCATTAACC
AGGACTAAGTTACTAATAAAACCAAATTGAGTATTGTTGCAGGAAGCAAGACCCAACTAC
CATTGTCAGCTGTGTTTCCTGACCTCAATATTTGTTATAAGGTTTGATATGAATCCCAGG
GGGAATCTCAACCCCTATTACCCAACAGTCAGAAAAATCTAAGTGTGAGGAGAACACAAT
GTTTCAACCTTATTGTTATAATAATGACAGTAAGAACAGCATGGCAGAATCGAAGGAAGC
AAGAGACCAAGAATGAACCTGAAAGAAGAATCTAAAGAAGAAAAAAGAAGAAATGACTGG
TGGAAAATAGGTATGTTTCTGTTATGCTTAGCAGGAACTACTGGAGGAATACTTTGGTGG
TATGAAGGACTCCCACAGCAACATTATATAGGGTTGGTGGCGATAGGGGGAAGATTAAAC
GGATCTGGCCAATCAAATGCTATAGAATGCTGGGGTTCCTTCCCGGGGTGTAGACCATTT
CAAAATTACTTCAGTTATGAGACCAATAGAAGCATGCATATGGATAATAATACTGCTACA

FIG. 7B

TTATTAGAAGCTTTAACCAATATAACTGCTCTATAAATAACAAAACAGAATTAGAAACAT
GGAAGTTAGTAAAGACTTCTGGCATAACTCCTTTACCTATTTCTTCTGAAGCTAACACTG
GACTAATTAGACATAAGAGAGATTTTGGTATAAGTGCAATAGTGGCAGCTATTGTAGCCG
CTACTGCTATTGCTGCTAGCGCTACTATGTCTTATGTTGCTCTAACTGAGGTTAACAAAA
TAATGGAAGTACAAAATCATACTTTTGAGGTAGAAAATAGTACTCTAAATGGTATGGATT
TAATAGAACGACAAATAAAGATATTATATGCTATGATTCTTCAAACACATGCAGATGTTC
AACTGTTAAAGGAAAGACAACAGGTAGAGGAGACATTTAATTTAATTGGATGTATAGAAA
GAACACATGTATTTTGTCATACTGGTCATCCCTGGAATATGTCATGGGGACATTTAAATG
AGTCAACACAATGGGATGACTGGGTAAGCAAAATGGAAGATTTAAATCAAGAGATACTAA
CTACACTTCATGGAGCCAGGAACAATTTGGCACAATCCATGATAACATTCAATACACCAG
ATAGTATAGCTCAATTTGGAAAAGACCTTTGGAGTCATATTGGAAATTGGATTCCTGGAT
TGGGAGCTTCCATTATAAAATATATAGTGATGTTTTTGCTTATTTATTTGTTACTAACCT
CTTCGCCTAAGATCCTCAGGGCCCTCTGGAAGGTGACCAGTGGTGCAGGGTCCTCCGGCA
GTCGTTACCTGAAGAAAAAATTCCATCACAAACATGCATCGCGAGAAGACACCTGGGACC
AGGCCCAACACAACATACACCTAGCAGGCGTGACCGGTGGATCAGGGGACAAATACTACA
AGCAGAAGTACTCCAGGAACGACTGGAATGGAGAATCAGAGGAGTACAACAGGCGGCCAA
AGAGCTGGGTGAAGTCAATCGAGGCATTTGGAGAGAGCTATATTTCCGAGAAGACCAAAG
GGGAGATTTCTCAGCCTGGGGCGGCTATCAACGAGCACAAGAACGGCTCTGGGGGGAACA
ATCCTCACCAAGGGTCCTTAGACCTGGAGATTCGAAGCGAAGGAGGAAACATTTATGACT
GTTGCATTAAAGCCCAAGAAGGAACTCTCGCTATCCCTTGCTGTGGATTTCCCTTATGGC
TATTTTGGGGACTAGTAATTATAGTAGGACGCATAGCAGGCTATGGATTACGTGGACTCG
CTGTTATAATAAGGATTTGTATTAGAGGCTTAAATTTGATATTTGAAATAATCAGAAAAA
TGCTTGATTATATTGGAAGAGCTTTAAATCCTGGCACATCTCATGTATCAATGCCTCAGT
ATGTTTAGAAAAACAAGGGGGGAACTGTGGGGTTTTTATGAGGGGTTTTATAAATGATTA
TAAGAGTAAAAAGAAAGTTGCTGATGCTCTCATAACCTTGTATAACCCAAAGGACTAGCT
CATGTTGCTAGGCAACTAAACCGCAATAACCGCATTTGTGACGCGAGTTCCCCATTGGTG
ACGCGTTAACTTCCTGTTTTTACAGTATATAAGTGCTTGTATTCTGACAATTGGGCACTC
AGATTCTGCGGTCTGAGTCCCTTCTCTGCTGGGCTGAAAAGGCCTTTGTAATAAATATAA
TTCTCTACTCAGTCCCTGTCTCTAGTTTGTCTGTTCGAGATCCTACAGAGCTCATGCCTT
GGCGTAATCATGGTCATAGCTGTTTCCTGTGTGAAATTGTTATCCGCTCACAATTCCACA
CAACATACGAGCCGGAAGCATAAAGTGTAAAGCCTGGGGTGCCTAATGAGTGAGCTAACT
CACATTAATTGCGTTGCGCTCACTGCCCGCTTTCCAGTCGGGAAACCTGTCGTGCCAGCT
GCATTAATGAATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTTTTTCCA
TAGGCTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTCGCTCCAAGCT
GGGCTGTGTGCACGAACCCCCCGTTCAGCCCGACCGCTGCGCCTTATCCGGTAACTATCG
TCTTGAGTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCCTAACTA
CGGCTACACTAGAAGGACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAG
ATTATCAAAAAGGATCTTCACCTAGATCCTTTTAAATTAAAAATGAAGTTTTAAATCAAT
CTAAAGTATATATGAGTAAACTTGGTCTGACAGTTACCAATGCTTAATCAGTGAGGCACC
TATCTCAGCGATCTGTCTATTTCGTTCATCCATAGTTGCCTGACTCCCCGTCGTGTAGAT
AACTACGATACGGGAGGGCTTACCATCTGGCCCCAGTGCTGCAATGATACCGCGAGACCC
ACGCTCACCGGCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCCGGGAAGCTAG
AGTAAGTAGTTCGCCAGTTAATAGTTTGCGCAACGTTGTTGCCATTGCTACAGGCATCGT
GGTGTCACGCTCGTCGTTTGGTATGGCTTCATTCAGCTCCGGTTCCCAACGATCAAGGCG
AGTTACATGATCCCCCATGTTGTGCAAAAAAGCGGTTAGCTCCTTCGGTCCTCCGATCGT
TGTCAGAAGTAAGTTGGCCGCAGTGTTATCACTCATGGTTATGGCAGCACTGCATAATTC

FIG. 7C

TCTTACTGTCATGCCATCCGTAAGATGCTTTTCTGTGACTGGTGAGTACTCAACCAAGTC
ATTCTGAGAATAGTGTATGCGGCGACCGAGTTGCTCTTGCCCGGCGTCAATACGGGATAA
TACCGCGCCACATAGCAGAACTTTAAAAGTGCTCATCATTGGAAAACGTTCTTCGGGGCG
AAAACTCTCAAGGATCTTACCGCTGTTGAGATCCAGTTCGATGTAACCCACTCGTGCACC
CAACTGATCTTCAGCATCTTTTACTTTCACCAGCGTTTCTGGGTGAGCAAAAACAGGAAG
GCAAAATGCCGCAAAAAAGGGAATAAGGGCGACACGGAAATGTTGAATACTCATACTCTT
CCTTTTTCAATATTATTGAAGCATTTATCAGGGTTATTGTCTCATGAGCGGATACATATT
TGAATGTATTTAGAAAAATAAACAAATAGGGGTTCCGCGCACATTTCCCCGAAAAGTGCC
ACCTAAATTGTAAGCGTTAATATTTTGTTAAAATTCGCGTTAAATTTTTGTTAAATCAGC
TCATTTTTTAACCAATAGGCCGAAATCGGCAAAATCCCTTATAAATCAAAAGAATAGACC
GAGATAGGGTTGAGTGTTGTTCCAGTTTGGAACAAGAGTCCACTATTAAAGAACGTGGAC
TCCAACGTCAAAGGGCGAAAAACCGTCTATCAGGGCGATGGCCCACTACGTGAACCATCA
CCCTAATCAAGTTTTTTGGGGTCGAGGTGCCGTAAAGCACTAAATCGGAACCCTAAAGGG
AGCCCCCGATTTAGAGCTTGACGGGGAAAGCCAACCTGGCTTATCGAAATTAATACGACT
CACTATAGGGAGACCGGC

FIG. 7D pECG3-CZW, vector genome plasmid.

TCAATATTGGCCATTAGCCATATTATTCATTGGTTATATAGCATAAATCAATATTGGCTA
TTGGCCATTGCATACGTTGTATCTATATCATAATATGTACATTTATATTGGCTCATGTCC
AATATGACCGCCATGTTGGCATTGATTATTGACTAGTTATTAATAGTAATCAATTACGGG
GTCATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTGC
CCACTTGGCAGTACATCAAGTGTATCATATGCCAAGTCCGCCCCCTATTGACGTCAATGA
CGGTAAATGGCCCGCCTGGCATTATGCCCAGTACATGACCTTACGGGACTTTCCTACTTG
GCAGTACATCTACGTATTAGTCATCGCTATTACCATGGTGATGCGGTTTTGGCAGTACAC
CAATGGGCGTGGATAGCGGTTTGACTCACGGGGATTTCCAAGTCTCCACCCCATTGACGT
CAATGGGAGTTTGTTTTGGCACCAAAATCAACGGGACTTTCCAAAATGTCGTAATAACCC
CGCCCCGTTGACGCAAATGGGCGGTAGGCGTGTACGGTGGGAGGTCTATATAAGCAGAGC
TCGTTTAGTGAACCGGGCACTCAGATTCTGCGGTCTGAGTCCCTTCTCTGCTGGGCTGAA
AAGGCCTTTGTAATAAATATAATTCTCTACTCAGTCCCTGTCTCTAGTTTGTCTGTTCGA
GATCCTACAGTTGGCGCCCGAACAGGGACCTGAGAGGGGCGCAGACCCTACCTGTTGAAC
CTGGCTGATCGTAGGATCCCCGGGACAGCAGAGGAGAACTTACAGAAGTCTTCTGGAGGT
GTTCCTGGCCAGAACACAGGAGGACAGGTAAGTAGGGAGACCCTTTGACATGGAGCAAGG
CGCTCAAGAAGTTAGAGAAGGTGACGGTACAAGGGTCTCAGAAATTAACTACTGGTAACT
GTAATTGGGCGCTAAGTCTAGTAGACTTATTTCATGATACCAACTTTGTAAAAGAAAAGG
ACTGGCAGCTGAGGGATGTCATTCCATTGCTGGAAGATGTAACTCAGACGCTGGAATTCG
AGCTTGCATGCCTGCAGGTCGTTACATAACTTACGGTAAATGGCCCGCCTGGCTGACCGC
CCAACGACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGCAGTAC
ATCAAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTACG
TATTAGTCATCGCTATTACCATGGTGATGCGGTTTTGGCAGTACATCAATGGGCGTGGAT
AGCGGTTTGACTCACGGGGATTTCCAAGTCTCCACCCCATTGACGTCAATGGGAGTTTGT
TTTGGCACCAAAATCAACGGGACTTTCCAAAATGTCGTAACAACTCCGCCCCATTGACGC
AAATGGGCGGTAGGCGTGTACGGTGGGAGGTCTATATAAGCAGAGCTCGTTTAGTGAACC
GTCAGATCGCCTGGAGACGCCATCCACGCTGTTTTGACCTCCATAGAAGACACCGGGACC
GATCCAGCCTCCGGACTCTAGAGTCGACCCGGGCGGCCGCAATTCCCGGGGATCGAAAGA
GCCTGCTAAAGCAAAAAAGAAGTCACCATGTCGTTTACTTTGACCAACAAGAACGTGATT
TTCGTTGCCGGTCTGGGAGGCATTGGTCTGGACACCAGCAAGGAGCTGCTCAAGCGCGAT
CCCGTCGTTTTACAACGTCGTGACTGGGAAAACCCTGGCGTTACCCAACTTAATCGCCTT
GCAGCACATCCCCCTTTCGCCAGCTGGCGTAATAGCGAAGAGGCCCGCACCGATCGCCCT
TCCCAACAGTTGCGCAGCCTGAATGGCGAATGGCGCTTTGCCTGGTTTCCGGCACCAGAA
GCGGTGCCGGAAAGCTGGCTGGAGTGCGATCTTCCTGAGGCCGATACTGTCGTCGTCCCC
TCAAACTGGCAGATGCACGGTTACGATGCGCCCATCTACACCAACGTAACCTATCCCATT
ACGGTCAATCCGCCGTTTGTTCCCACGGAGAATCCGACGGGTTGTTACTCGCTCACATTT
AATGTTGATGAAAGCTGGCTACAGGAAGGCCAGACGCGAATTATTTTTGATGGCGTTAAC
TCGGCGTTTCATCTGTGGTGCAACGGGCGCTGGGTCGGTTACGGCCAGGACAGTCGTTTG
CCGTCTGAATTTGACCTGAGCGCATTTTTACGCGCCGGAGAAAACCGCCTCGCGGTGATG
GTGCTGCGTTGGAGTGACGGCAGTTATCTGGAAGATCAGGATATGTGGCGGATGAGCGGC
ATTTTCCGTGACGTCTCGTTGCTGCATAAACCGACTACACAAATCAGCGATTTCCATGTT
GCCACTCGCTTTAATGATGATTTCAGCCGCGCTGTACTGGAGGCTGAAGTTCAGATGTGC
GGCGAGTTGCGTGACTACCTACGGGTAACAGTTTCTTTATGGCAGGGTGAAACGCAGGTC
GCCAGCGGCACCGCGCCTTTCGGCGGTGAAATTATCGATGAGCGTGGTGGTTATGCCGAT
CGCGTCACACTACGTCTGAACGTCGAAAACCCGAAACTGTGGAGCGCCGAAATCCCGAAT
CTCTATCGTGCGGTGGTTGAACTGCACACCGCCGACGGCACGCTGATTGAAGCAGAAGCC
TGCGATGTCGGTTTCCGCGAGGTGCGGATTGAAAATGGTCTGCTGCTGCTGAACGGCAAG
CCGTTGCTGATTCGAGGCGTTAACCGTCACGAGCATCATCCTCTGCATGGTCAGGTCATG
GATGAGCAGACGATGGTGCAGGATATCCTGCTGATGAAGCAGAACAACTTTAACGCCGTG
CGCTGTTCGCATTATCCGAACCATCCGCTGTGGTACACGCTGTGCGACCGCTACGGCCTG
TATGTGGTGGATGAAGCCAATATTGAAACCCACGGCATGGTGCCAATGAATCGTCTGACC
GATGATCCGCGCTGGCTACCGGCGATGAGCGAACGCGTAACGCGAATGGTGCAGCGCGAT

*FIG. 9A*

CGTAATCACCCGAGTGTGATCATCTGGTCGCTGGGGAATGAATCAGGCCACGGCGCTAAT
CACGACGCGCTGTATCGCTGGATCAAATCTGTCGATCCTTCCCGCCCGGTGCAGTATGAA
GGCGGCGGAGCCGACACCACGGCCACCGATATTATTTGCCCGATGTACGCGCGCGTGGAT
GAAGACCAGCCCTTCCCGGCTGTGCCGAAATGGTCCATCAAAAAATGGCTTTCGCTACCT
GGAGAGACGCGCCCGCTGATCCTTTGCGAATACGCCCACGCGATGGGTAACAGTCTTGGC
GGTTTCGCTAAATACTGGCAGGCGTTTCGTCAGTATCCCCGTTTACAGGGCGGCTTCGTC
TGGGACTGGGTGGATCAGTCGCTGATTAAATATGATGAAAACGGCAACCCGTGGTCGGCT
TACGGCGGTGATTTTGGCGATACGCCGAACGATCGCCAGTTCTGTATGAACGGTCTGGTC
TTTGCCGACCGCACGCCGCATCCAGCGCTGACGGAAGCAAAACACCAGCAGCAGTTTTTC
CAGTTCCGTTTATCCGGGCAAACCATCGAAGTGACCAGCGAATACCTGTTCCGTCATAGC
GATAACGAGCTCCTGCACTGGATGGTGGCGCTGGATGGTAAGCCGCTGGCAAGCGGTGAA
GTGCCTCTGGATGTCGCTCCACAAGGTAAACAGTTGATTGAACTGCCTGAACTACCGCAG
CCGGAGAGCGCCGGGCAACTCTGGCTCACAGTACGCGTAGTGCAACCGAACGCGACCGCA
TGGTCAGAAGCCGGGCACATCAGCGCCTGGCAGCAGTGGCGTCTGGCGGAAAACCTCAGT
GTGACGCTCCCCGCCGCGTCCCACGCCATCCCGCATCTGACCACCAGCGAAATGGATTTT
TGCATCGAGCTGGGTAATAAGCGTTGGCAATTTAACCGCCAGTCAGGCTTTCTTTCACAG
ATGTGGATTGGCGATAAAAAACAACTGCTGACGCCGCTGCGCGATCAGTTCACCCGTGCA
CCGCTGGATAACGACATTGGCGTAAGTGAAGCGACCCGCATTGACCCTAACGCCTGGGTC
GAACGCTGGAAGGCGGCGGGCCATTACCAGGCCGAAGCAGCGTTGTTGCAGTGCACGGCA
GATACACTTGCTGATGCGGTGCTGATTACGACCGCTCACGCGTGGCAGCATCAGGGGAAA
ACCTTATTTATCAGCCGGAAAACCTACCGGATTGATGGTAGTGGTCAAATGGCGATTACC
GTTGATGTTGAAGTGGCGAGCGATACACCGCATCCGGCGCGGATTGGCCTGAACTGCCAG
CTGGCGCAGGTAGCAGAGCGGGTAAACTGGCTCGGATTAGGGCCGCAAGAAAACTATCCC
GACCGCCTTACTGCCGCCTGTTTTGACCGCTGGGATCTGCCATTGTCAGACATGTATACC
CCGTACGTCTTCCCGAGCGAAAACGGTCTGCGCTGCGGGACGCGCGAATTGAATTATGGC
CCACACCAGTGGCGCGGCGACTTCCAGTTCAACATCAGCCGCTACAGTCAACAGCAACTG
ATGGAAACCAGCCATCGCCATCTGCTGCACGCGGAAGAAGGCACATGGCTGAATATCGAC
GGTTTCCATATGGGGATTGGTGGCGACGACTCCTGGAGCCCGTCAGTATCGGCGGAATTA
CAGCTGAGCGCCGGTCGCTACCATTACCAGTTGGTCTGGTGTCAAAAATAATAATAACCG
GGCAGGCCATGTCTGCCCGTATTTCGCGTAAGGAAATCCATTATGTACTATTTAAAAAAC
ACAAACTTTTGGATGTTCGGTTTATTCTTTTTCTTTTACTTTTTTATCATGGGAGCCTAC
TTCCCGTTTTTCCCGATTTGGCTACATGACATCAACCATATCAGCAAAAGTGATACGGGT
ATTATTTTTGCCGCTATTTCTCTGTTCTCGCTATTATTCCAACCGCTGTTTGGTCTGCTT
TCTGACAAACTCGGCCTCGACTCTAGGCGGCCGCCGAGCATCTTACCGCCATTTATTCCC
ATATTTGTTCTGTTTTTCTTGATTTGGGTATACATTTGAATGTCAATAAAACAAAATGGT
GGGGCAATCATCTACATTTCATGGGATATGTGATTACTAGTTCAGGTGTATTGCCACAAG
ACAAACATGTTAAGAAAATTTCCCGTTATTTGCACTCTGTTCCTGTTAATCAACCTCTGG
ATTACAAAATTTGTGAAAGATTGACTGGTATTCTTAACTATGTTGCTCCTTTTACGCTAT
GTGGATACGCTGCTTTAATGCCTTTGTATCATGCTATTGCTTCCCGTATGGCTTTCATTT
TCTCCTCCTTGTATAAATCCTGGTTGCTGTCTCTTTATGAGGAGTTGTGGCCCGTTGTCA
GGCAACGTGGCGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATTGCCACGGCGG
AACTCATCGCCGCCTGCCTTGCCCGCTGCTGGACAGGGGCTCGGCTGTTGGGCACTGACA
ATTCCGTGGTGTTGTCGGGGAAGCTGACGTCCTTTCCATGGCTGCTCGCCTGTGTTGCCA
CCTGGATTCTGCGCGGGACGTCCTTCTGCTACGTCCCTTCGGCCCTCAATCCAGCGGACC
TTCCTTCCCGCGGCCTGCTGCCGGCTCTGCGGCCTCTTCCGCGTCTTCGCCTTCGCCCTC
AGACGAGTCGGATCTCCCTTTGGGCCGCCTCCCCGCCTGTTTCGCCTCGGCGTCCGGTCC
GTGTTGCTTGGTCTTCACCTGTGCAGACTTGCGAACCATGGATTCCACCGTGAACTTTGT
CTCCTGGCATGCAAATCGTCAACTTGGCATGCCAAATCGATGTCGACATAGAAAAACAAG
GGGGGAACTGTGGGGTTTTTATGAGGGGTTTTATAAATGATTATAAGAGTAAAAAGAAAG
TTGCTGATGCTCTCATAACCTTGTATAACCCAAAGGACTAGCTCATGTTGCTAGGCAACT
AAACCGCAATAACCACATTTGTGACGCGAGTTCCGCATTGGTGACGCGTTAAGTTCCTGT
TTTTACAGTATATAAGTGCTTGTATTCTGACAATTGGGCACTCAGATTCTGCGGTCTGAG
TCCCTTCTCTGCTGGGCTGAAAAGGCCTTTGTAATAAATATAATTCTCTACTCAGTCCCT
GTCTCTAGTTTGTCTGTTCGAGATCCTACATTAATTAAGGAGATCCGGGCTGGCGTAATA
GCGAAGAGGCCCGCACCGATCGCCCTTCCCAACAGTTGCGCAGCCTGAATGGCGAATGGA
CGCGCCCTGTAGCGGCGCATTAAGCGCGGCGGGTGTGGTGGTTACGCGCAGCGTGACCGC

FIG. 9B

TACACTTGCCAGCGCCCTAGCGCCCGCTCCTTTCGCTTTCTTCCCTTCCTTTCTCGCCAC
GTTCGCCGGCTTTCCCCGTCAAGCTCTAAATCGGGGGCTCCCTTTAGGGTTCCGATTTAG
AGCTTTACGGCACCTCGACCGCAAAAAACTTGATTTGGGTGATGGTTCACGTAGTGGGCC
ATCGCCCTGATAGACGGTTTTTCGCCCTTTGACGTTGGAGTCCACGTTCTTTAATAGTGG
ACTCTTGTTCCAAACTGGAACAACACTCAACCCTATCTCGGTCTATTCTTTTGATTTATA
AGGGATTTTGCCGATTTCGGCCTATTGGTTAAAAAATGAGCTGATTTAACAAATATTTAA
CGCGAATTTTAACAAAATATTAACGTTTACAATTTCGCCTGATGCGGTATTTTCTCCTTA
CGCATCTGTGCGGTATTTCACACCGCATATGGTGCACTCTCAGTACAATCTGCTCTGATG
CCGCATAGTTAAGCCAGCCCCGACACCCGCCAACACCCGCTGACGCGCCCTGACGGGCTT
GTCTGCTCCCGGCATCCGCTTACAGACAAGCTGTGACCGTCTCCGGGAGCTGCATGTGTC
AGAGGTTTTCACCGTCATCACCGAAACGCGCGAGACGAAAGGGCCTCGTGATACGCCTAT
TTTTATAGGTTAATGTCATGATAATAATGGTTTCTTAGACGTCAGGTGGCACTTTTCGGG
GAAATGTGCGCGGAACCCCTATTTGTTTATTTTTCTAAATACATTCAAATATGTATCCGC
TCATGAGACAATAACCCTGATAAATGCTTCAATAATATTGAAAAAGGAAGAGTATGAGTA
TTCAACATTTCCGTGTCGCCCTTATTCCCTTTTTTGCGGCATTTTGCCTTCCTGTTTTTG
CTCACCCAGAAACGCTGGTGAAAGTAAAAGATGCTGAAGATCAGTTGGGTGCACGAGTGG
GTTACATCGAACTGGATCTCAACAGCGGTAAGATCCTTGAGAGTTTTCGCCCCGAAGAAC
GTTTTCCAATGATGAGCACTTTTAAAGTTCTGCTATGTGGCGCGGTATTATCCCGTATTG
ACGCCGGGCAAGAGCAACTCGGTCGCCGCATACACTATTCTCAGAATGACTTGGTTGAGT
ACTCACCAGTCACAGAAAAGCATCTTACGGATGGCATGACAGTAAGAGAATTATGCAGTG
CTGCCATAACCATGAGTGATAACACTGCGGCCAACTTACTTCTGACAACGATCGGAGGAC
CGAAGGAGCTAACCGCTTTTTTGCACAACATGGGGGATCATGTAACTCGCCTTGATCGTT
GGGAACCGGAGCTGAATGAAGCCATACCAAACGACGAGCGTGACACCACGATGCCTGTAG
CAATGGCAACAACGTTGCGCAAACTATTAACTGGCGAACTACTTACTCTAGCTTCCCGGC
AACAATTAATAGACTGGATGGAGGCGGATAAAGTTGCAGGACCACTTCTGCGCTCGGCCC
TTCCGGCTGGCTGGTTTATTGCTGATAAATCTGGAGCCGGTGAGCGTGGGTCTCGCGGTA
TCATTGCAGCACTGGGGCCAGATGGTAAGCCCTCCCGTATCGTAGTTATCTACACGACGG
GGAGTCAGGCAACTATGGATGAACGAAATAGACAGATCGCTGAGATAGGTGCCTCACTGA
TTAAGCATTGGTAACTGTCAGACCAAGTTTACTCATATATACTTTAGATTGATTTAAAAC
TTCATTTTTAATTTAAAAGGATCTAGGTGAAGATCCTTTTTGATAATCTCATGACCAAAA
TCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGC
TACCAGCGGTGGTTTGTTTGCCGGATCAAGAGCTACCAACTCTTTTTCCGAAGGTAACTG
GCTTCAGCAGAGCGCAGATACCAAATACTGTCCTTCTAGTGTAGCCGTAGTTAGGCCACC
ACTTCAAGAACTCTGTAGCACCGCCTACATACCTCGCTCTGCTAATCCTGTTACCAGTGG
CTGCTGCCAGTGGCGATAAGTCGTGTCTTACCGGGTTGGACTCAAGACGATAGTTACCGG
ATAAGGCGCAGCGGTCGGGCTGAACGGGGGGTTCGTGCACACAGCCCAGCTTGGAGCGAA
CGACCTACACCGAACTGAGATACCTACAGCGTGAGCTATGAGAAAGCGCCACGCTTCCCG
AAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCT
GACTTGAGCGTCGATTTTTGTGATGCTCGTCAGGGGGGCGGAGCCTATGGAAAAACGCCA
GCAACGCGGCCTTTTTACGGTTCCTGGCCTTTTGCTGGCCTTTTGCTCACATGGCTCGAC
AGATCT

*FIG. 9C* pONY8G, vector genome plasmid

AGATCTTGAATAATAAAATGTGTGTTTGTCCGAAATACGCGTTTTGAGATTTCTGTCGCC
GACTAAATTCATGTCGCGCGATAGTGGTGTTTATCGCCGATAGAGATGGCGATATTGGAA
AAATTGATATTTGAAAATATGGCATATTGAAAATGTCGCCGATGTGAGTTTCTGTGTAAC
TGATATCGCCATTTTTCCAAAAGTGATTTTTGGGCATACGCGATATCTGGCGATAGCGCT
TATATCGTTTACGGGGGATGGCGATAGACGACTTTGGTGACTTGGGCGATTCTGTGTGTC
GCAAATATCGCAGTTTCGATATAGGTGACAGACGATATGAGGCTATATCGCCGATAGAGG
CGACATCAAGCTGGCACATGGCCAATGCATATCGATCTATACATTGAATCAATATTGGCC
ATTAGCCATATTATTCATTGGTTATATAGCATAAATCAATATTGGCTATTGGCCATTGCA
TACGTTGTATCCATATCGTAATATGTACATTTATATTGGCTCATGTCCAACATTACCGCC
ATGTTGACATTGATTATTGACTAGTTATTAATAGTAATCAATTACGGGGTCATTAGTTCA
TAGCCCATATATGGAGTTCCGCGTTACATAACTTACGGTAAATGGCCCGCCTGGCTGACC
GCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGT
ACATCAAGTGTATCATATGCCAAGTCCGCCCCCTATTGACGTCAATGACGGTAAATGGCC
CGCCTGGCATTATGCCCAGTACATGACCTTACGGGACTTTCCTACTTGGCAGTACATCTA
CGTATTAGTCATCGCTATTACCATGGTGATGCGGTTTTGGCAGTACACCAATGGGCGTGG
ATAGCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTGCGATCGCCCGCC
CCGTTGACGCAAATGGGCGGTAGGCGTGTACGGTGGGAGGTCTATATAAGCAGAGCTCGT
TTAGTGAACCGGGCACTCAGATTCTGCGGTCTGAGTCCCTTCTCTGCTGGGCTGAAAAGG
CCTTTGTAATAAATATAATTCTCTACTCAGTCCCTGTCTCTAGTTTGTCTGTTCGAGATC
CTACAGTTGGCGCCCGAACAGGGACCTGAGAGGGGCGCAGACCCTACCTGTTGAACCTGG
CTGATCGTAGGATCCCCGGGACAGCAGAGGAGAACTTACAGAAGTCTTCTGGAGGTGTTC
CTGGCCAGAACACAGGAGGACAGGTAAGATTGGGAGACCCTTTGACATTGGAGCAAGGCG
CTCAAGAAGTTAGAGAAGGTGACGGTACAAGGGTCTCAGAAATTAACTACTGGTAACTGT
AATTGGGCGCTAAGTCTAGTAGACTTATTTCATGATACCAACTTTGTAAAAGAAAAGGAC
TGGCAGCTGAGGGATGTCATTCCATTGCTGGAAGATGTAACTCAGACGCTGTCAGGACAA
GAAAGAGAGGCCTTTGAAAGAACATGGTGGGCAATTTCTGCTGTAAAGATGGGCCTCCAG
ATTAATAATGTAGTAGATGGAAAGGCATCATTCCAGCTCCTAAGAGCGAAATATGAAAAG
AAGACTGCTAATAAAAAGCAGTCTGAGCCCTCTGAAGAATATCTCTAGAACTAGTGGATC
CCCCGGGCTGCAGGAGTGGGGAGGCACGATGGCCGCTTTGGTCGAGGCGGATCCGGCCAT
TAGCCATATTATTCATTGGTTATATAGCATAAATCAATATTGGCTATTGGCCATTGCATA
CGTTGTATCCATATCATAATATGTACATTTATATTGGCTCATGTCCAACATTACCGCCAT
GTTGACATTGATTATTGACTAGTTATTAATAGTAATCAATTACGGGGTCATTAGTTCATA
GCCCATATATGGAGTTCCGCGTTACATAACTTACGGTAAATGGCCCGCCTGGCTGACCGC
CCAACGACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGCAGTAC
ATCAAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTACG
TATTAGTCATCGCTATTACCATGGTGATGCGGTTTTGGCAGTACATCAATGGGCGTGGAT
AGCGGTTTGACTCACGGGGATTTCCAAGTCTCCACCCCATTGACGTCAATGGGAGTTTGT
TTTGGCACCAAAATCAACGGGACTTTCCAAAATGTCGTAACAACTCCGCCCCATTGACGC
AAATGGGCGGTAGGCATGTACGGTGGGAGGTCTATATAAGCAGAGCTCGTTTAGTGAACC
GTCAGATCGCCTGGAGACGCCATCCACGCTGTTTTGACCTCCATAGAAGACACCGGGACC
GATCCAGCCTCCGCGGCCCCAAGCTTGTTGGGATCCACCGGTCGCCACCATGGTGAGCAA
GGGCGAGGAGCTGTTCACCGGGGTGGTGCCCATCCTGGTCGAGCTGGACGGCGACGTAAA
CGGCCACAAGTTCAGCGTGTCCGGCGAGGGCGAGGGCGATGCCACCTACGGCAAGCTGAC
CCTGAAGTTCATCTGCACCACCGGCAAGCTGCCCGTGCCCTGGCCCACCCTCGTGACCAC
CCTGACCTACGGCGTGCAGTGCTTCAGCCGCTACCCCGACCACATGAAGCAGCACGACTT
CTTCAAGTCCGCCATGCCCGAAGGCTACGTCCAGGAGCGCACCATCTTCTTCAAGGACGA
CGGCAACTACAAGACCCGCGCCGAGGTGAAGTTCGAGGGCGACACCCTGGTGAACCGCAT
CGAGCTGAAGGGCATCGACTTCAAGGAGGACGGCAACATCCTGGGGCACAAGCTGGAGTA
CAACTACAACAGCCACAACGTCTATATCATGGCCGACAAGCAGAAGAACGGCATCAAGGT
GAACTTCAAGATCCGCCACAACATCGAGGACGGCAGCGTGCAGCTCGCCGACCACTACCA
GCAGAACACCCCCATCGGCGACGGCCCCGTGCTGCTGCCCGACAACCACTACCTGAGCAC

*FIG. 11A*

CCAGTCCGCCCTGAGCAAAGACCCCAACGAGAAGCGCGATCACATGGTCCTGCTGGAGTT
CGTGACCGCCGCCGGGATCACTCTCGGCATGGACGAGCTGTACAAGTAAAGCGGCCGCGA
CTCTAGAGTCGACCTGCAGGCATGCAAGCTTCAGCTGCTCGAGGGGGGGCCCGGTACCCA
GCTTTTGTTCCCTTTAGTGAGGGTTAATTGCGCGGGAAGTATTTATCACTAATCAAGCAC
AAGTAATACATGAGAAACTTTTACTACAGCAAGCACAATCCTCCAAAAAATTTTGTTTTT
ACAAAATCCCTGGTGAACATGATTGGAAGGGACCTACTAGGGTGCTGTGGAAGGGTGATG
GTGCAGTAGTAGTTAATGATGAAGGAAAGGGAATAATTGCTGTACCATTAACCAGGACTA
AGTTACTAATAAAACCAAATTGAGTATTGTTGCAGGAAGCAAGACCCAACTACCATTGTC
AGCTGTGTTTCCTGACCTCAATATTTGTTATAAGGTTTGATATGAATCCCAGGGGGAATC
TCAACCCCTATTACCCAACAGTCAGAAAAATCTAAGTGTGAGGAGAACACAATGTTTCAA
CCTTATTGTTATAATAATGACAGTAAGAACAGCATGGCAGAATCGAAGGAAGCAAGAGAC
CAAGAATGAACCTGAAAGAAGAATCTAAAGAAGAAAAAAGAAGAAATGACTGGTGGAAAA
TAGGTATGTTTCTGTTATGCTTAGCAGGAACTACTGGAGGAATACTTTGGTGGTATGAAG
GACTCCCACAGCAACATTATATAGGGTTGGTGGCGATAGGGGGAAGATTAAACGGATCTG
GCCAATCAAATGCTATAGAATGCTGGGGTTCCTTCCCGGGGTGTAGACCATTTCAAAATT
ACTTCAGTTATGAGACCAATAGAAGCATGCATATGGATAATAATACTGCTACATTATTAG
AAGCTTTAACCAATATAACTGCTCTATAAATAACAAAACAGAATTAGAAACATGGAAGTT
AGTAAAGACTTCTGGCATAACTCCTTTACCTATTTCTTCTGAAGCTAACACTGGACTAAT
TAGACATAAGAGAGATTTTGGTATAAGTGCAATAGTGGCAGCTATTGTAGCCGCTACTGC
TATTGCTGCTAGCGCTACTATGTCTTATGTTGCTCTAACTGAGGTTAACAAAATAATGGA
AGTACAAAATCATACTTTTGAGGTAGAAAATAGTACTCTAAATGGTATGGATTTAATAGA
ACGACAAATAAAGATATTATATGCTATGATTCTTCAAACACATGCAGATGTTCAACTGTT
AAAGGAAAGACAACAGGTAGAGGAGACATTTAATTTAATTGGATGTATAGAAAGAACACA
TGTATTTTGTCATACTGGTCATCCCTGGAATATGTCATGGGGACATTTAAATGAGTCAAC
ACAATGGGATGACTGGGTAAGCAAAATGGAAGATTTAAATCAAGAGATACTAACTACACT
TCATGGAGCCAGGAACAATTTGGCACAATCCATGATAACATTCAATACACCAGATAGTAT
AGCTCAATTTGGAAAAGACCTTTGGAGTCATATTGGAAATTGGATTCCTGGATTGGGAGC
TTCCATTATAAAATATATAGTGATGTTTTTGCTTATTTATTTGTTACTAACCTCTTCGCC
TAAGATCCTCAGGGCCCCTCTGGAAGGTGACCAGTGGTGCAGGGTCCTCCGGCAGTCGTTA
CCTGAAGAAAAAATTCCATCACAAACATGCATCGCGAGAAGACACCTGGGACCAGGCCCA
ACACAACATACACCTAGCAGGCGTGACCGGTGGATCAGGGGACAAATACTACAAGCAGAA
GTACTCCAGGAACGACTGGAATGGAGAATCAGAGGAGTACAACAGGCGGCCAAAGAGCTG
GGTGAAGTCAATCGAGGCATTTGGAGAGAGCTATATTTCCGAGAAGACCAAAGGGGAGAT
TTCTCAGCCTGGGGCGGCTATCAACGAGCACAAGAACGGCTCTGGGGGGAACAATCCTCA
CCAAGGGTCCTTAGACCTGGAGATTCGAAGCGAAGGAGGAAACATTTATGACTGTTGCAT
TAAAGCCCAAGAAGGAACTCTCGCTATCCCTTGCTGTGGATTTCCCTTATGGCTATTTTG
GGGACTAGTAATTATAGTAGGACGCATAGCAGGCTATGGATTACGTGGACTCGCTGTTAT
AATAAGGATTTGTATTAGAGGCTTAAATTTGATATTTGAAATAATCAGAAAAATGCTTGA
TTATATTGGAAGAGCTTTAAATCCTGGCACATCTCATGTATCAATGCCTCAGTATGTTTA
GAAAAACAAGGGGGGAACTGTGGGGTTTTTATGAGGGGTTTTATAAATGATTATAAGAGT
AAAAAGAAAGTTGCTGATGCTCTCATAACCTTGTATAACCCAAAGGACTAGCTCATGTTG
CTAGGCAACTAAACCGCAATAACCGCATTTGTGACGCGAGTTCCCCATTGGTGACGCGTT
AACTTCCTGTTTTTACAGTATATAAGTGCTTGTATTCTGACAATTGGGCACTCAGATTCT
GCGGTCTGAGTCCCTTCTCTGCTGGGCTGAAAAGGCCTTTGTAATAAATATAATTCTCTA
CTCAGTCCCTGTCTCTAGTTTGTCTGTTCGAGATCCTACAGAGCTCATGCCTTGGCGTAA
TCATGGTCATAGCTGTTTCCTGTGTGAAATTGTTATCCGCTCACAATTCCACACAACATA
CGAGCCGGAAGCATAAAGTGTAAAGCCTGGGGTGCCTAATGAGTGAGCTAACTCACATTA
ATTGCGTTGCGCTCACTGCCCGCTTTCCAGTCGGGAAACCTGTCGTGCCAGCTGCATTAA
TGAATCGGCCAACGCGCGGGGAGAGGCGGTTTGCGTATTGGGCGCTCTTCCGCTTCCTCG
CTCACTGACTCGCTGCGCTCGGTCGTTCGGCTGCGGCGAGCGGTATCAGCTCACTCAAAG
GCGGTAATACGGTTATCCACAGAATCAGGGGATAACGCAGGAAAGAACATGTGAGCAAAA
GGCCAGCAAAAGGCCAGGAACCGTAAAAAGGCCGCGTTGCTGGCGTTTTTCCATAGGCTC
CGCCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGCGCTTTCT
CATAGCTCACGCTGTAGGTATCTCAGTTCGGTGTAGGTCGTTCGCTCCAAGCTGGGCTGT
GTGCACGAACCCCCCGTTCAGCCCGACCGCTGCGCCTTATCCGGTAACTATCGTCTTGAG

*FIG. 11B*

TCCAACCCGGTAAGACACGACTTATCGCCACTGGCAGCAGCCACTGGTAACAGGATTAGC
AGAGCGAGGTATGTAGGCGGTGCTACAGAGTTCTTGAAGTGGTGGCCTAACTACGGCTAC
ACTAGAAGGACAGTATTTGGTATCTGCGCTCTGCTGAAGCCAGTTACCTTCGGAAAAAGA
GTTGGTAGCTCTTGATCCGGCAAACAAACCACCGCTGGTAGCGGTGGTTTTTTTGTTTGC
AAGCAGCAGATTACGCGCAGAAAAAAAGGATCTCAAGAAGATCCTTTGATCTTTTCTACG
GGGTCTGACGCTCAGTGGAACGAAAACTCACGTTAAGGGATTTTGGTCATGAGATTATCA
AAAAGGATCTTCACCTAGATCCTTTTAAATTAAAAATGAAGTTTTAAATCAATCTAAAGT
ATATATGAGTAAACTTGGTCTGACAGTTACCAATGCTTAATCAGTGAGGCACCTATCTCA
GCGATCTGTCTATTTCGTTCATCCATAGTTGCCTGACTCCCCGTCGTGTAGATAACTACG
ATACGGGAGGGCTTACCATCTGGCCCCAGTGCTGCAATGATACCGCGAGACCCACGCTCA
CCGGCTCCAGATTTATCAGCAATAAACCAGCCAGCCGGAAGGGCCGAGCGCAGAAGTGGT
CCTGCAACTTTATCCGCCTCCATCCAGTCTATTAATTGTTGCCGGGAAGCTAGAGTAAGT
AGTTCGCCAGTTAATAGTTTGCGCAACGTTGTTGCCATTGCTACAGGCATCGTGGTGTCA
CGCTCGTCGTTTGGTATGGCTTCATTCAGCTCCGGTTCCCAACGATCAAGGCGAGTTACA
TGATCCCCCATGTTGTGCAAAAAAGCGGTTAGCTCCTTCGGTCCTCCGATCGTTGTCAGA
AGTAAGTTGGCCGCAGTGTTATCACTCATGGTTATGGCAGCACTGCATAATTCTCTTACT
GTCATGCCATCCGTAAGATGCTTTTCTGTGACTGGTGAGTACTCAACCAAGTCATTCTGA
GAATAGTGTATGCGGCGACCGAGTTGCTCTTGCCCGGCGTCAATACGGGATAATACCGCG
CCACATAGCAGAACTTTAAAAGTGCTCATCATTGGAAAACGTTCTTCGGGGCGAAAACTC
TCAAGGATCTTACCGCTGTTGAGATCCAGTTCGATGTAACCCACTCGTGCACCCAACTGA
TCTTCAGCATCTTTTACTTTCACCAGCGTTTCTGGGTGAGCAAAAACAGGAAGGCAAAAT
GCCGCAAAAAAGGGAATAAGGGCGACACGGAAATGTTGAATACTCATACTCTTCCTTTTT
CAATATTATTGAAGCATTTATCAGGGTTATTGTCTCATGAGCGGATACATATTTGAATGT
ATTTAGAAAAATAAACAAATAGGGGTTCCGCGCACATTTCCCCGAAAAGTGCCACCTAAA
TTGTAAGCGTTAATATTTTGTTAAAATTCGCGTTAAATTTTTGTTAAATCAGCTCATTTT
TTAACCAATAGGCCGAAATCGGCAAAATCCCTTATAAATCAAAAGAATAGACCGAGATAG
GGTTGAGTGTTGTTCCAGTTTGGAACAAGAGTCCACTATTAAAGAACGTGGACTCCAACG
TCAAAGGGCGAAAAACCGTCTATCAGGGCGATGGCCCACTACGTGAACCATCACCCTAAT
CAAGTTTTTTGGGGTCGAGGTGCCGTAAAGCACTAAATCGGAACCCTAAAGGGAGCCCCC
GATTTAGAGCTTGACGGGGAAAGCCAACCTGGCTTATCGAAATTAATACGACTCACTATA
GGGAGACCGGC

*FIG. 11C* pESYNGP, codon-optimised EIAV gag/pol expression plasmid

TCAATATTGGCCATTAGCCATATTATTCATTGGTTATATAGCATAAATCAATATTGGCTA
TTGGCCATTGCATACGTTGTATCTATATCATAATATGTACATTTATATTGGCTCATGTCC
AATATGACCGCCATGTTGGCATTGATTATTGACTAGTTATTAATAGTAATCAATTACGGG
GTCATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTGC
CCACTTGGCAGTACATCAAGTGTATCATATGCCAAGTCCGCCCCCTATTGACGTCAATGA
CGGTAAATGGCCCGCCTGGCATTATGCCCAGTACATGACCTTACGGGACTTTCCTACTTG
GCAGTACATCTACGTATTAGTCATCGCTATTACCATGGTGATGCGGTTTTGGCAGTACAC
CAATGGGCGTGGATAGCGGTTTGACTCACGGGGATTTCCAAGTCTCCACCCCATTGACGT
CAATGGGAGTTTGTTTTGGCACCAAAATCAACGGGACTTTCCAAAATGTCGTAACAACTG
CGATCGCCCGCCCCGTTGACGCAAATGGGCGGTAGGCGTGTACGGTGGGAGGTCTATATA
AGCAGAGCTCGTTTAGTGAACCGTCAGATCACTAGAAGCTTTATTGCGGTAGTTTATCAC
AGTTAAATTGCTAACGCAGTCAGTGCTTCTGACACAACAGTCTCGAACTTAAGCTGCAGT
GACTCTCTTAAGGTAGCCTTGCAGAAGTTGGTCGTGAGGCACTGGGCAGGTAAGTATCAA
GGTTACAAGACAGGTTTAAGGAGACCAATAGAAACTGGGCTTGTCGAGACAGAGAAGACT
CTTGCGTTTCTGATAGGCACCTATTGGTCTTACTGACATCCACTTTGCCTTTCTCTCCAC
AGGTGTCCACTCCCAGTTCAATTACAGCTCTTAAGGCTAGAGTACTTAATACGACTCACT
ATAGGCTAGAGAATTCGCCACCATGGGCGATCCCCTCACCTGGTCCAAAGCCCTGAAGAA
ACTGGAAAAAGTCACCGTTCAGGGTAGCCAAAAGCTTACCACAGGCAATTGCAACTGGGC
ATTGTCCCTGGTGGATCTTTTCCACGACACTAATTTCGTTAAGGAGAAAGATTGGCAACT
CAGAGACGTGATCCCCCTCTTGGAGGACGTGACCCAAACATTGTCTGGGCAGGAGCGCGA
AGCTTTCGAGCGCACCTGGTGGGCCATCAGCGCAGTCAAAATGGGGCTGCAAATCAACAA
CGTGGTTGACGGTAAAGCTAGCTTTCAACTGCTCCGCGCTAAGTACGAGAAGAAAACCGC
CAACAAGAAACAATCCGAACCTAGCGAGGAGTACCCAATTATGATCGACGGCGCCGGCAA
TAGGAACTTCCGCCCACTGACTCCCAGGGGCTATACCACCTGGGTCAACACCATCCAGAC
AAACGGACTTTTGAACGAAGCCTCCCAGAACCTGTTCGGCATCCTGTCTGTGGACTGCAC
CTCCGAAGAAATGAATGCTTTTCTCGACGTGGTGCCAGGACAGGCTGGACAGAAACAGAT
CCTGCTCGATGCCATTGACAAGATCGCCGACGACTGGGATAATCGCCACCCCCTGCCAAA
CGCCCCTCTGGTGGCTCCCCCACAGGGGCCTATCCCTATGACCGCTAGGTTCATTAGGGG
ACTGGGGGTGCCCCGCGAACGCCAGATGGAGCCAGCATTTGACCAATTTAGGCAGACCTA
CAGACAGTGGATCATCGAAGCCATGAGCGAGGGGATTAAAGTCATGATCGGAAAGCCCAA
GGCACAGAACATCAGGCAGGGGGCCAAGGAACCATACCCTGAGTTTGTCGACAGGCTTCT
GTCCCAGATTAAATCCGAAGGCCACCCTCAGGAGATCTCCAAGTTCTTGACAGACACACT
GACTATCCAAAATGCAAATGAAGAGTGCAGAAACGCCATGAGGCACCTCAGACCTGAAGA
TACCCTGGAGGAGAAAATGTACGCATGTCGCGACATTGGCACTACCAAGCAAAAGATGAT
GCTGCTCGCCAAGGCTCTGCAAACCGGCCTGGCTGGTCCATTCAAAGGAGGAGCACTGAA
GGGAGGTCCATTGAAAGCTGCACAAACATGTTATAATTGTGGGAAGCCAGGACATTTATC
TAGTCAATGTAGAGCACCTAAAGTCTGTTTTAAATGTAAACAGCCTGGACATTTCTCAAA
GCAATGCAGAAGTGTTCCAAAAAACGGGAAGCAAGGGGCTCAAGGGAGGCCCCAGAAACA
AACTTTCCCGATACAACAGAAGAGTCAGCACAACAAATCTGTTGTACAAGAGACTCCTCA
GACTCAAAATCTGTACCCAGATCTGAGCGAAATAAAAAAGGAATACAATGTCAAGGAGAA
GGATCAAGTAGAGGATCTCAACCTGGACAGTTTGTGGGAGTAACATACAATCTCGAGAAG
AGGCCCACTACCATCGTCCTGATCAATGACACCCCTCTTAATGTGCTGCTGGACACCGGA
GCCGACACCAGCGTTCTCACTACTGCTCACTATAACAGACTGAAATACAGAGGAAGGAAA
TACCAGGGCACAGGCATCATCGGCGTTGGAGGCAACGTCGAAACCTTTTCCACTCCTGTC
ACCATCAAAAAGAAGGGGAGACACATTAAAACCAGAATGCTGGTCGCCGACATCCCCGTC
ACCATCCTTGGCAGAGACATTCTCCAGGACCTGGGCGCTAAACTCGTGCTGGCACAACTG
TCTAAGGAAATCAAGTTCCGCAAGATCGAGCTGAAAGAGGGCACAATGGGTCCAAAAATC
CCCCAGTGGCCCCTGACCAAAGAGAAGCTTGAGGGCGCTAAGGAAATCGTGCAGCGCCTG
CTTTCTGAGGGCAAGATTAGCGAGGCCAGCGACAATAACCCTTACAACAGCCCCATCTTT
GTGATTAAGAAAAGGAGCGGCAAATGGAGACTCCTGCAGGACCTGAGGGAACTCAACAAG
ACCGTCCAGGTCGGAACTGAGATCTCTCGCGGACTGCCTCACCCCGGCGGCCTGATTAAA
TGCAAGCACATGACAGTCCTTGACATTGGAGACGCTTATTTTACCATCCCCCTCGATCCT
GAATTTCGCCCCTATACTGCTTTTACCATCCCCAGCATCAATCACCAGGAGCCCGATAAA

*FIG. 15A*

CGCTATGTGTGGAAGTGCCTCCCCCAGGGATTTGTGCTTAGCCCCTACATTTACCAGAAG
ACACTTCAAGAGATCCTCCAACCTTTCCGCGAAAGATACCCAGAGGTTCAACTCTACCAA
TATATGGACGACCTGTTCATGGGGTCCAACGGGTCTAAGAAGCAGCACAAGGAACTCATC
ATCGAACTGAGGGCAATCCTCCTGGAGAAAGGCTTCGAGACACCCGACGACAAGCTGCAA
GAAGTTCCTCCATATAGCTGGCTGGGCTACCAGCTTTGCCCTGAAAACTGGAAAGTCCAG
AAGATGCAGTTGGATATGGTCAAGAACCCAACACTGAACGACGTCCAGAAGCTCATGGGC
AATATTACCTGGATGAGCTCCGGAATCCCTGGGCTTACCGTTAAGCACATTGCCGCAACT
ACAAAAGGATGCCTGGAGTTGAACCAGAAGGTCATTTGGACAGAGGAAGCTCAGAAGGAA
CTGGAGGAGAATAATGAAAAGATTAAGAATGCTCAAGGGCTCCAATACTACAATCCCGAA
GAAGAAATGTTGTGCGAGGTCGAAATCACTAAGAACTACGAAGCCACCTATGTCATCAAA
CAGTCCCAAGGCATCTTGTGGGCCGGAAAGAAAATCATGAAGGCCAACAAAGGCTGGTCC
ACCGTTAAAAATCTGATGCTCCTGCTCCAGCACGTCGCCACCGAGTCTATCACCCGCGTC
GGCAAGTGCCCCACCTTCAAAGTTCCCTTCACTAAGGAGCAGGTGATGTGGGAGATGCAA
AAAGGCTGGTACTACTCTTGGCTTCCCGAGATCGTCTACACCCACCAAGTGGTGCACGAC
GACTGGAGAATGAAGCTTGTCGAGGAGCCCACTAGCGGAATTACAATCTATACCGACGGC
GGAAAGCAAAACGGAGAGGGAATCGCTGCATACGTCACATCTAACGGCCGCACCAAGCAA
AAGAGGCTCGGCCCTGTCACTCACCAGGTGGCTGAGAGGATGGCTATCCAGATGGCCCTT
GAGGACACTAGAGACAAGCAGGTGAACATTGTGACTGACAGCTACTACTGCTGGAAAAAC
ATCACAGAGGGCCTTGGCCTGGAGGGACCCCAGTCTCCCTGGTGGCCTATCATCCAGAAT
ATCCGCGAAAAGGAAATTGTCTATTTCGCCTGGGTGCCTGGACACAAAGGAATTTACGGC
AACCAACTCGCCGATGAAGCCGCCAAAATTAAAGAGGAAATCATGCTTGCCTACCAGGGC
ACACAGATTAAGGAGAAGAGAGACGAGGACGCTGGCTTTGACCTGTGTGTGCCATACGAC
ATCATGATTCCCGTTAGCGACACAAAGATCATTCCAACCGATGTCAAGATCCAGGTGCCA
CCCAATTCATTTGGTTGGGTGACCGGAAAGTCCAGCATGGCTAAGCAGGGTCTTCTGATT
AACGGGGGAATCATTGATGAAGGATACACCGGCGAAATCCAGGTGATCTGCACAAATATC
GGCAAAAGCAATATTAAGCTTATCGAAGGGCAGAAGTTCGCTCAACTCATCATCCTCCAG
CACCACAGCAATTCAAGACAACCTTGGGACGAAAACAAGATTAGCCAGAGAGGTGACAAG
GGCTTCGGCAGCACAGGTGTGTTCTGGGTGGAGAACATCCAGGAAGCACAGGACGAGCAC
GAGAATTGGCACACCTCCCCTAAGATTTTGGCCCGCAATTACAAGATCCCACTGACTGTG
GCTAAGCAGATCACACAGGAATGCCCCCACTGCACCAAACAAGGTTCTGGCCCCGCCGGC
TGCGTGATGAGGTCCCCCAATCACTGGCAGGCAGATTGCACCCACCTCGACAACAAAATT
ATCCTGACCTTCGTGGAGAGCAATTCCGGCTACATCCACGCAACACTCCTCTCCAAGGAA
AATGCATTGTGCACCTCCCTCGCAATTCTGGAATGGGCCAGGCTGTTCTCTCCAAAATCC
CTGCACACCGACAACGGCACCAACTTTGTGGCTGAACCTGTGGTGAATCTGCTGAAGTTC
CTGAAAATCGCCCACACCACTGGCATTCCCTATCACCCTGAAAGCCAGGGCATTGTCGAG
AGGGCCAACAGAACTCTGAAAGAAAAGATCCAATCTCACAGAGACAATACACAGACATTG
GAGGCCGCACTTCAGCTCGCCCTTATCACCTGCAACAAAGGAAGAGAAAGCATGGGCGGC
CAGACCCCCTGGGAGGTCTTCATCACTAACCAGGCCCAGGTCATCCATGAAAAGCTGCTC
TTGCAGCAGGCCCAGTCCTCCAAAAAGTTCTGCTTTTATAAGATCCCCGGTGAGCACGAC
TGGAAAGGTCCTACAAGAGTTTTGTGGAAAGGAGACGGCGCAGTTGTGGTGAACGATGAG
GGCAAGGGGATCATCGCTGTGCCCCTGACACGCACCAAGCTTCTCATCAAGCCAAACTGA
ACCCGGGGCGGCCGCTTCCCTTTAGTGAGGGTTAATGCTTCGAGCAGACATGATAAGATA
CATTGATGAGTTTGGACAAACCACAACTAGAATGCAGTGAAAAAAATGCTTTATTTGTGA
AATTTGTGATGCTATTGCTTTATTTGTAACCATTATAAGCTGCAATAAACAAGTTAACAA
CAACAATTGCATTCATTTTATGTTTCAGGTTCAGGGGGAGATGTGGGAGGTTTTTTAAAG
CAAGTAAAACCTCTACAAATGTGGTAAAATCCGATAAGGATCGATCCGGGCTGGCGTAAT
AGCGAAGAGGCCCGCACCGATCGCCCTTCCCAACAGTTGCGCAGCCTGAATGGCGAATGG
ACGCGCCCTGTAGCGGCGCATTAAGCGCGGCGGGTGTGGTGGTTACGCGCAGCGTGACCG
CTACACTTGCCAGCGCCCTAGCGCCCGCTCCTTTCGCTTTCTTCCCTTCCTTTCTCGCCA
CGTTCGCCGGCTTTCCCCGTCAAGCTCTAAATCGGGGGCTCCCTTTAGGGTTCCGATTTA
GAGCTTTACGGCACCTCGACCGCAAAAAACTTGATTTGGGTGATGGTTCACGTAGTGGGC
CATCGCCCTGATAGACGGTTTTTCGCCCTTTGACGTTGGAGTCCACGTTCTTTAATAGTG
GACTCTTGTTCCAAACTGGAACAACACTCAACCCTATCTCGGTCTATTCTTTTGATTTAT
AAGGGATTTTGCCGATTTCGGCCTATTGGTTAAAAAATGAGCTGATTTAACAAATATTTA
ACGCGAATTTTAACAAAATATTAACGTTTACAATTTCGCCTGATGCGGTATTTTCTCCTT
ACGCATCTGTGCGGTATTTCACACCGCATACGCGGATCTGCGCAGCACCATGGCCTGAAA
TAACCTCTGAAAGAGGAACTTGGTTAGGTACCTTCTGAGGCGGAAAGAACCAGCTGTGGA

*FIG. 15B*

ATGTGTGTCAGTTAGGGTGTGGAAAGTCCCCAGGCTCCCCAGCAGGCAGAAGTATGCAAA
GCATGCATCTCAATTAGTCAGCAACCAGGTGTGGAAAGTCCCCAGGCTCCCCAGCAGGCA
GAAGTATGCAAAGCATGCATCTCAATTAGTCAGCAACCATAGTCCCGCCCCTAACTCCGC
CCATCCCGCCCCTAACTCCGCCCAGTTCCGCCCATTCTCCGCCCCATGGCTGACTAATTT
TTTTTATTTATGCAGAGGCCGAGGCCGCCTCGGCCTCTGAGCTATTCCAGAAGTAGTGAG
GAGGCTTTTTTGGAGGCCTAGGCTTTTGCAAAAAGCTTGATTCTTCTGACACAACAGTCT
CGAACTTAAGGCTAGAGCCACCATGATTGAACAAGATGGATTGCACGCAGGTTCTCCGGC
CGCTTGGGTGGAGAGGCTATTCGGCTATGACTGGGCACAACAGACAATCGGCTGCTCTGA
TGCCGCCGTGTTCCGGCTGTCAGCGCAGGGGCGCCCGGTTCTTTTTGTCAAGACCGACCT
GTCCGGTGCCCTGAATGAACTGCAGGACGAGGCAGCGCGGCTATCGTGGCTGGCCACGAC
GGGCGTTCCTTGCGCAGCTGTGCTCGACGTTGTCACTGAAGCGGGAAGGGACTGGCTGCT
ATTGGGCGAAGTGCCGGGGCAGGATCTCCTGTCATCTCACCTTGCTCCTGCCGAGAAAGT
ATCCATCATGGCTGATGCAATGCGGCGGCTGCATACGCTTGATCCGGCTACCTGCCCATT
CGACCACCAAGCGAAACATCGCATCGAGCGAGCACGTACTCGGATGGAAGCCGGTCTTGT
CGATCAGGATGATCTGGACGAAGAGCATCAGGGGCTCGCGCCAGCCGAACTGTTCGCCAG
GCTCAAGGCGCGCATGCCCGACGGCGAGGATCTCGTCGTGACCCATGGCGATGCCTGCTT
GCCGAATATCATGGTGGAAAATGGCCGCTTTTCTGGATTCATCGACTGTGGCCGGCTGGG
TGTGGCGGACCGCTATCAGGACATAGCGTTGGCTACCCGTGATATTGCTGAAGAGCTTGG
CGGCGAATGGGCTGACCGCTTCCTCGTGCTTTACGGTATCGCCGCTCCCGATTCGCAGCG
CATCGCCTTCTATCGCCTTCTTGACGAGTTCTTCTGAGCGGGACTCTGGGGTTCGAAATG
ACCGACCAAGCGACGCCCAACCTGCCATCACGATGGCCGCAATAAAATATCTTTATTTTC
ATTACATCTGTGTGTTGGTTTTTTGTGTGAATCGATAGCGATAAGGATCCGCGTATGGTG
CACTCTCAGTACAATCTGCTCTGATGCCGCATAGTTAAGCCAGCCCCGACACCCGCCAAC
ACCCGCTGACGCGCCCTGACGGGCTTGTCTGCTCCCGGCATCCGCTTACAGACAAGCTGT
GACCGTCTCCGGGAGCTGCATGTGTCAGAGGTTTTCACCGTCATCACCGAAACGCGCGAG
ACGAAAGGGCCTCGTGATACGCCTATTTTTATAGGTTAATGTCATGATAATAATGGTTTC
TTAGACGTCAGGTGGCACTTTTCGGGGAAATGTGCGCGGAACCCCTATTTGTTTATTTTT
CTAAATACATTCAAATATGTATCCGCTCATGAGACAATAACCCTGATAAATGCTTCAATA
ATATTGAAAAAGGAAGAGTATGAGTATTCAACATTTCCGTGTCGCCCTTATTCCCTTTTT
TGCGGCATTTTGCCTTCCTGTTTTTGCTCACCCAGAAACGCTGGTGAAAGTAAAAGATGC
TGAAGATCAGTTGGGTGCACGAGTGGGTTACATCGAACTGGATCTCAACAGCGGTAAGAT
CCTTGAGAGTTTTCGCCCCGAAGAACGTTTTCCAATGATGAGCACTTTTAAAGTTCTGCT
ATGTGGCGCGGTATTATCCCGTATTGACGCCGGGCAAGAGCAACTCGGTCGCCGCATACA
CTATTCTCAGAATGACTTGGTTGAGTACTCACCAGTCACAGAAAAGCATCTTACGGATGG
CATGACAGTAAGAGAATTATGCAGTGCTGCCATAACCATGAGTGATAACACTGCGGCCAA
CTTACTTCTGACAACGATCGGAGGACCGAAGGAGCTAACCGCTTTTTTGCACAACATGGG
GGATCATGTAACTCGCCTTGATCGTTGGGAACCGGAGCTGAATGAAGCCATACCAAACGA
CGAGCGTGACACCACGATGCCTGTAGCAATGGCAACAACGTTGCGCAAACTATTAACTGG
CGAACTACTTACTCTAGCTTCCCGGCAACAATTAATAGACTGGATGGAGGCGGATAAAGT
TGCAGGACCACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGGTAAGCCCTC
CCGTATCGTAGTTATCTACACGACGGGGAGTCAGGCAACTATGGATGAACGAAATAGACA
GATCGCTGAGATAGGTGCCTCACTGATTAAGCATTGGTAACTGTCAGACCAAGTTTACTC
ATATATACTTTAGATTGATTTAAAACTTCATTTTTAATTTAAAAGGATCTAGGTGAAGAT
CCTTTTTGATAATCTCATGACCAAAATCCCTTAACGTGAGTTTTCGTTCCACTGAGCGTC
AGACCCCGTAGAAAAGATCAAAGGATCTTCTTGAGATCCTTTTTTTCTGCGCGTAATCTG
CTGCTTGCAAACAAAAAAACCACCGCTACCAGCGGTGGTTTGTTTGCCGGATCAAGAGCT
ACCAACTCTTTTTCCGAAGGTAACTGGCTTCAGCAGAGCGCAGATACCAAATACTGTCCT
TCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGGGGGTTC
GTGCACACAGCCCAGCTTGGAGCGAACGACCTACACCGAACTGAGATACCTACAGCGTGA
GCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGATGCTCGTCAGG
GGGGCGGAGCCTATGGAAAAACGCCAGCAACGCGGCCTTTTTACGGTTCCTGGCCTTTTG
CTGGCCTTTTGCTCACATGGCTCGACAGATCT

*FIG. 15C* pCIneoERev, EIAV Rev expression plasmid

TCAATATTGGCCATTAGCCATATTATTCATTGGTTATATAGCATAAATCAATATTGGCTA
TTGGCCATTGCATACGTTGTATCTATATCATAATATGTACATTTATATTGGCTCATGTCC
AATATGACCGCCATGTTGGCATTGATTATTGACTAGTTATTAATAGTAATCAATTACGGG
GTCATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTGC
CCACTTGGCAGTACATCAAGTGTATCATATGCCAAGTCCGCCCCCTATTGACGTCAATGA
CGGTAAATGGCCCGCCTGGCATTATGCCCAGTACATGACCTTACGGGACTTTCCTACTTG
GCAGTACATCTACGTATTAGTCATCGCTATTACCATGGTGATGCGGTTTTGGCAGTACAC
CAATGGGCGTGGATAGCGGTTTGACTCACGGGGATTTCCAAGTCTCCACCCCATTGACGT
CAATGGGAGTTTGTTTTGGCACCAAAATCAACGGGACTTTCCAAAATGTCGTAACAACTG
CGATCGCCCGCCCCGTTGACGCAAATGGGCGGTAGGCGTGTACGGTGGGAGGTCTATATA
AGCAGAGCTCGTTTAGTGAACCGTCAGATCACTAGAAGCTTTATTGCGGTAGTTTATCAC
AGTTAAATTGCTAACGCAGTCAGTGCTTCTGACACAACAGTCTCGAACTTAAGCTGCAGT
GACTCTCTTAAGGTAGCCTTGCAGAAGTTGGTCGTGAGGCACTGGGCAGGTAAGTATCAA
GGTTACAAGACAGGTTTAAGGAGACCAATAGAAACTGGGCTTGTCGAGACAGAGAAGACT
CTTGCGTTTCTGATAGGCACCTATTGGTCTTACTGACATCCACTTTGCCTTTCTCTCCAC
AGGTGTCCACTCCCAGTTCAATTACAGCTCTTAAGGCTAGAGTACTTAATACGACTCACT
ATAGGCTAGTAACGGCCGCCAGTGTGCTGGAATTCGGCTTATGGCAGAATCGAAGGAAGC
AAGAGACCAAGAAATGAACCTGAAAGAAGAATCTAAAGAAGAAAAAAGAAGAAATGACTG
GTGGAAAATAGATCCTCAGGGCCCTCTGGAAGGTGACCAGTGGTGCAGGGTCCTCCGGCA
GTCGTTACCTGAAGAAAAAATTCCATCACAAACATGCATCGCGAGAAGACACCTGGGACC
AGGCCCAACACAACATACACCTAGCAGGCGTGACCGGTGGATCAGGGGACAAATACTACA
AGCAGAAGTACTCCAGGAACGACTGGAATGGAGAATCAGAGGAGTACAACAGGCGGCCAA
AGAGCTGGGTGAAGTCAATCGAGGCATTTGGAGAGAGCTATATTTCCGAGAAGACCAAAG
GGGAGATTTCTCAGCCTGGGGCGGCTATCAACGAGCACAAGAACGGCTCTGGGGGGAACA
ATCCTCACCAAGGGTCCTTAGACCTGGAGATTCGAAGCGAAGGAGGAAACATTTATGAAG
CCGAATTCTGCAGATATCCATCACACTGGCGGCCGCTTCCCTTTAGTGAGGGTTAATGCT
TCGAGCAGACATGATAAGATACATTGATGAGTTTGGACAAACCACAACTAGAATGCAGTG
AAAAAAATGCTTTATTTGTGAAATTTGTGATGCTATTGCTTTATTTGTAACCATTATAAG
CTGCAATAAACAAGTTAACAACAACAATTGCATTCATTTTATGTTTCAGGTTCAGGGGGA
GATGTGGGAGGTTTTTTAAAGCAAGTAAAACCTCTACAAATGTGGTAAAATCCGATAAGG
ATCGATCCGGGCTGGCGTAATAGCGAAGAGGCCCGCACCGATCGCCCTTCCCAACAGTTG
CGCAGCCTGAATGGCGAATGGACGCGCCCTGTAGCGGCGCATTAAGCGCGGCGGGTGTGG
TGGTTACGCGCAGCGTGACCGCTACACTTGCCAGCGCCCTAGCGCCCGCTCCTTTCGCTT
TCTTCCCTTCCTTTCTCGCCACGTTCGCCGGCTTTCCCCGTCAAGCTCTAAATCGGGGGC
TCCCTTTAGGGTTCCGATTTAGAGCTTTACGGCACCTCGACCGCAAAAAACTTGATTTGG
GTGATGGTTCACGTAGTGGGCCATCGCCCTGATAGACGGTTTTTCGCCCTTTGACGTTGG
AGTCCACGTTCTTTAATAGTGGACTCTTGTTCCAAACTGGAACAACACTCAACCCTATCT
CGGTCTATTCTTTTGATTTATAAGGGATTTTGCCGATTTCGGCCTATTGGTTAAAAAATG
AGCTGATTTAACAAATATTTAACGCGAATTTTAACAAAATATTAACGTTTACAATTTCGC
CTGATGCGGTATTTTCTCCTTACGCATCTGTGCGGTATTTCACACCGCATACGCGGATCT
GCGCAGCACCATGGCCTGAAATAACCTCTGAAAGAGGAACTTGGTTAGGTACCTTCTGAG
GCGGAAAGAACCAGCTGTGGAATGTGTGTCAGTTAGGGTGTGGAAAGTCCCCAGGCTCCC
CAGCAGGCAGAAGTATGCAAAGCATGCATCTCAATTAGTCAGCAACCAGGTGTGGAAAGT
CCCCAGGCTCCCCAGCAGGCAGAAGTATGCAAAGCATGCATCTCAATTAGTCAGCAACCA
TAGTCCCGCCCCTAACTCCGCCCATCCCGCCCCTAACTCCGCCCAGTTCCGCCCATTCTC
CGCCCCATGGCTGACTAATTTTTTTTATTTATGCAGAGGCCGAGGCCGCCTCGGCCTCTG
AGCTATTCCAGAAGTAGTGAGGAGGCTTTTTTGGAGGCCTAGGCTTTTGCAAAAAGCTTG
ATTCTTCTGACACAACAGTCTCGAACTTAAGGCTAGAGCCACCATGATTGAACAAGATGG
ATTGCACGCAGGTTCTCCGGCCGCTTGGGTGGAGAGGCTATTCGGCTATGACTGGGCACA
ACAGACAATCGGCTGCTCTGATGCCGCCGTGTTCCGGCTGTCAGCGCAGGGGCGCCCGGT
TCTTTTTGTCAAGACCGACCTGTCCGGTGCCCTGAATGAACTGCAGGACGAGGCAGCGCG
GCTATCGTGGCTGGCCACGACGGGCGTTCCTTGCGCAGCTGTGCTCGACGTTGTCACTGA

*FIG. 18A*

AGCGGGAAGGGACTGGCTGCTATTGGGCGAAGTGCCGGGGCAGGATCTCCTGTCATCTCA
CCTTGCTCCTGCCGAGAAAGTATCCATCATGGCTGATGCAATGCGGCGGCTGCATACGCT
TGATCCGGCTACCTGCCCATTCGACCACCAAGCGAAACATCGCATCGAGCGAGCACGTAC
TCGGATGGAAGCCGGTCTTGTCGATCAGGATGATCTGGACGAAGAGCATCAGGGGCTCGC
GCCAGCCGAACTGTTCGCCAGGCTCAAGGCGCGCATGCCCGACGGCGAGGATCTCGTCGT
GACCCATGGCGATGCCTGCTTGCCGAATATCATGGTGGAAAATGGCCGCTTTTCTGGATT
CATCGACTGTGGCCGGCTGGGTGTGGCGGACCGCTATCAGGACATAGCGTTGGCTACCCG
TGATATTGCTGAAGAGCTTGGCGGCGAATGGGCTGACCGCTTCCTCGTGCTTTACGGTAT
CGCCGCTCCCGATTCGCAGCGCATCGCCTTCTATCGCCTTCTTGACGAGTTCTTCTGAGC
GGGACTCTGGGGTTCGAAATGACCGACCAAGCGACGCCCAACCTGCCATCACGATGGCCG
CAATAAAATATCTTTATTTTCATTACATCTGTGTGTTGGTTTTTTGTGTGAATCGATAGC
GATAAGGATCCGCGTATGGTGCACTCTCAGTACAATCTGCTCTGATGCCGCATAGTTAAG
CCAGCCCCGACACCCGCCAACACCCGCTGACGCGCCCTGACGGGCTTGTCTGCTCCCGGC
ATCCGCTTACAGACAAGCTGTGACCGTCTCCGGGAGCTGCATGTGTCAGAGGTTTTCACC
GTCATCACCGAAACGCGCGAGACGAAAGGGCCTCGTGATACGCCTATTTTTATAGGTTAA
TGTCATGATAATAATGGTTTCTTAGACGTCAGGTGGCACTTTTCGGGGAAATGTGCGCGG
AACCCCTATTTGTTTATTTTTCTAAATACATTCAAATATGTATCCGCTCATGAGACAATA
ACCCTGATAAATGCTTCAATAATATTGAAAAAGGAAGAGTATGAGTATTCAACATTTCCG
TGTCGCCCTTATTCCCTTTTTTGCGGCATTTTGCCTTCCTGTTTTTGCTCACCCAGAAAC
GCTGGTGAAAGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACGCCGGGCAAGA
GCAACTCGGTCGCCGCATACACTATTCTCAGAATGACTTGGTTGAGTACTCACCAGTCAC
AGAAAAGCATCTTACGGATGGCATGACAGTAAGAGAATTATGCAGTGCTGCCATAACCAT
GAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCT
GAATGAAGCCATACCAAACGACGAGCGTGACACCACGATGCCTGTAGCAATGGCAACAAC
GTTGCGCAAACTATTAACTGGCGAACTACTTACTCTAGCTTCCCGGCAACAATTAATAGA
CTGGATGGAGGCGGATAAAGTTGCAGGACCACTTCTGCGCTCGGCCCTTCCGGCTGGCTG
GTTTATTGCTGATAAATCTGGAGCCGGTGAGCGTGGGTCTCGCGGTATCATTGCAGCACT
GGGGCCAGATGGTAAGCCCTCCCGTATCGTAGTTATCTACACGACGGGGAGTCAGGCAAC
TATGGATGAACGAAATAGACAGATCGCTGAGATAGGTGCCTCACTGATTAAGCATTGGTA
ACTGTCAGACCAAGTTTACTCATATATACTTTAGATTGATTTAAAACTTCATTTTTAATT
TAAAAGGATCTAGGTGAAGATCCTTTTTGATAATCTCATGACCAAAATCCCTTAACGTGA
GTTTTCGTTCCACTGAGCGTCAGACCCCGTAGAAAAGATCAAAGGATCTTCTTGAGATCC
TTTTTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAGAGC
GCAGATACCAAATACTGTCCTTCTAGTGTAGCCGTAGTTAGGCCACCACTTCAAGAACTC
TGTAGCACCGCCTACATACCTCGCTCTGCTAATCCTGTTACCAGTGGCTGCTGCCAGTGG
CGATAAGTCGTGTCTTACCGGGTTGGACTCAAGACGATAGTTACCGGATAAGGCGCAGCG
GTCGGGCTGAACGGGGGGTTCGTGCACACAGCCCAGCTTGGAGCGAACGACCTACACCGA
ACTGAGATACCTACAGCGTGAGCTATGAGAAAGCGCCACGCTTCCCGAAGGGAGAAAGGC
GGACAGGTATCCGGTAAGCGGCAGGGTCGGAACAGGAGAGCGCACGAGGGAGCTTCCAGG
GGGAAACGCCTGGTATCTTTATAGTCCTGTCGGGTTTCGCCACCTCTGACTTGAGCGTCG
ATTTTTGTGATGCTCGTCAGGGGGGCGGAGCCTATGGAAAAACGCCAGCAACGCGGCCTT
TTTACGGTTCCTGGCCTTTTGCTGGCCTTTTGCTCACATGGCTCGACAGATCT

FIG. 18B pESYNREV, codon-optimised EIAV Rev expression plasmid

TCAATATTGGCCATTAGCCATATTATTCATTGGTTATATAGCATAAATCAATATTGGCTA
TTGGCCATTGCATACGTTGTATCTATATCATAATATGTACATTTATATTGGCTCATGTCC
AATATGACCGCCATGTTGGCATTGATTATTGACTAGTTATTAATAGTAATCAATTACGGG
GTCATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTGC
CCACTTGGCAGTACATCAAGTGTATCATATGCCAAGTCCGCCCCCTATTGACGTCAATGA
CGGTAAATGGCCCGCCTGGCATTATGCCCAGTACATGACCTTACGGGACTTTCCTACTTG
GCAGTACATCTACGTATTAGTCATCGCTATTACCATGGTGATGCGGTTTTGGCAGTACAC
CAATGGGCGTGGATAGCGGTTTGACTCACGGGGATTTCCAAGTCTCCACCCCATTGACGT
CAATGGGAGTTTGTTTTGGCACCAAAATCAACGGGACTTTCCAAAATGTCGTAACAACTG
CGATCGCCCGCCCCGTTGACGCAAATGGGCGGTAGGCGTGTACGGTGGGAGGTCTATATA
AGCAGAGCTCGTTTAGTGAACCGTCAGATCACTAGAAGCTTTATTGCGGTAGTTTATCAC
AGTTAAATTGCTAACGCAGTCAGTGCTTCTGACACAACAGTCTCGAACTTAAGCTGCAGT
GACTCTCTTAAGGTAGCCTTGCAGAAGTTGGTCGTGAGGCACTGGGCAGGTAAGTATCAA
GGTTACAAGACAGGTTTAAGGAGACCAATAGAAACTGGGCTTGTCGAGACAGAGAAGACT
CTTGCGTTTCTGATAGGCACCTATTGGTCTTACTGACATCCACTTTGCCTTTCTCTCCAC
AGGTGTCCACTCCCAGTTCAATTACAGCTCTTAAGGCTAGAGTACTTAATACGACTCACT
ATAGGCTAGCCTCGAGAATTCGCCACCATGGCTGAGAGCAAGGAGGCCAGGGATCAAGAG
ATGAACCTCAAGGAAGAGAGCAAAGAGGAGAAGCGCCGCAACGACTGGTGGAAGATCGAC
CCACAAGGCCCCCTGGAGGGGGACCAGTGGTGCCGCGTGCTGAGACAGTCCCTGCCCGAG
GAGAAGATTCCTAGCCAGACCTGCATCGCCAGAAGACACCTCGGCCCCGGTCCCACCCAG
CACACACCCTCCAGAAGGGATAGGTGGATTAGGGGCCAGATTTTGCAAGCCGAGGTCCTC
CAAGAAAGGCTGGAATGGAGAATTAGGGGCGTGCAACAAGCCGCTAAAGAGCTGGGAGAG
GTGAATCGCGGCATCTGGAGGGAGCTCTACTTCCGCGAGGACCAGAGGGGCGATTTCTCC
GCATGGGGAGGCTACCAGAGGGCACAAGAAAGGCTGTGGGGCGAGCAGAGCAGCCCCCGC
GTCTTGAGGCCCGGAGACTCCAAAAGACGCCGCAAACACCTGTGAAGTCGACCCGGGCGG
CCGCTTCCCTTTAGTGAGGGTTAATGCTTCGAGCAGACATGATAAGATACATTGATGAGT
TTGGACAAACCACAACTAGAATGCAGTGAAAAAAATGCTTTATTTGTGAAATTTGTGATG
CTATTGCTTTATTTGTAACCATTATAAGCTGCAATAAACAAGTTAACAACAACAATTGCA
TTCATTTTATGTTTCAGGTTCAGGGGGAGATGTGGGAGGTTTTTTAAAGCAAGTAAAACC
TCTACAAATGTGGTAAAATCCGATAAGGATCGATCCGGGCTGGCGTAATAGCGAAGAGGC
CCGCACCGATCGCCCTTCCCAACAGTTGCGCAGCCTGAATGGCGAATGGACGCGCCCTGT
AGCGGCGCATTAAGCGCGGCGGGTGTGGTGGTTACGCGCAGCGTGACCGCTACACTTGCC
AGCGCCCTAGCGCCCGCTCCTTTCGCTTTCTTCCCTTCCTTTCTCGCCACGTTCGCCGGC
TTTCCCCGTCAAGCTCTAAATCGGGGGCTCCCTTTAGGGTTCCGATTTAGAGCTTTACGG
CACCTCGACCGCAAAAAACTTGATTTGGGTGATGGTTCACGTAGTGGGCCATCGCCCTGA
TAGACGGTTTTTCGCCCTTTGACGTTGGAGTCCACGTTCTTTAATAGTGGACTCTTGTTC
CAAACTGGAACAACACTCAACCCTATCTCGGTCTATTCTTTTGATTTATAAGGGATTTTG
CCGATTTCGGCCTATTGGTTAAAAAATGAGCTGATTTAACAAATATTTAACGCGAATTTT
AACAAAATATTAACGTTTACAATTTCGCCTGATGCGGTATTTTCTCCTTACGCATCTGTG
CGGTATTTCACACCGCATACGCGGATCTGCGCAGCACCATGGCCTGAAATAACCTCTGAA
AGAGGAACTTGGTTAGGTACCTTCTGAGGCGGAAAGAACCAGCTGTGGAATGTGTGTCAG
TTAGGGTGTGGAAAGTCCCCAGGCTCCCCAGCAGGCAGAAGTATGCAAAGCATGCATCTC
AATTAGTCAGCAACCAGGTGTGGAAAGTCCCCAGGCTCCCCAGCAGGCAGAAGTATGCAA
AGCATGCATCTCAATTAGTCAGCAACCATAGTCCCGCCCCTAACTCCGCCCATCCCGCCC
CTAACTCCGCCCAGTTCCGCCCATTCTCCGCCCCATGGCTGACTAATTTTTTTTATTTAT
GCAGAGGCCGAGGCCGCCTCGGCCTCTGAGCTATTCCAGAAGTAGTGAGGAGGCTTTTTT
GGAGGCCTAGGCTTTTGCAAAAAGCTTGATTCTTCTGACACAACAGTCTCGAACTTAAGG
CTAGAGCCACCATGATTGAACAAGATGGATTGCACGCAGGTTCTCCGGCCGCTTGGGTGG
AGAGGCTATTCGGCTATGACTGGGCACAACAGACAATCGGCTGCTCTGATGCCGCCGTGT
TCCGGCTGTCAGCGCAGGGGCGCCCGGTTCTTTTTGTCAAGACCGACCTGTCCGGTGCCC
TGAATGAACTGCAGGACGAGGCAGCGCGGCTATCGTGGCTGGCCACGACGGGCGTTCCTT
GCGCAGCTGTGCTCGACGTTGTCACTGAAGCGGGAAGGGACTGGCTGCTATTGGGCGAAG
TGCCGGGGCAGGATCTCCTGTCATCTCACCTTGCTCCTGCCGAGAAAGTATCCATCATGG

*FIG. 20A*

CTGATGCAATGCGGCGGCTGCATACGCTTGATCCGGCTACCTGCCCATTCGACCACCAAG
CGAAACATCGCATCGAGCGAGCACGTACTCGGATGGAAGCCGGTCTTGTCGATCAGGATG
ATCTGGACGAAGAGCATCAGGGGCTCGCGCCAGCCGAACTGTTCGCCAGGCTCAAGGCGC
GCATGCCCGACGGCGAGGATCTCGTCGTGACCCATGGCGATGCCTGCTTGCCGAATATCA
TGGTGGAAAATGGCCGCTTTTCTGGATTCATCGACTGTGGCCGGCTGGGTGTGGCGGACC
GCTATCAGGACATAGCGTTGGCTACCCGTGATATTGCTGAAGAGCTTGGCGGCGAATGGG
CTGACCGCTTCCTCGTGCTTTACGGTATCGCCGCTCCCGATTCGCAGCGCATCGCCTTCT
ATCGCCTTCTTGACGAGTTCTTCTGAGCGGGACTCTGGGGTTCGAAATGACCGACCAAGC
GACGCCCAACCTGCCATCACGATGGCCGCAATAAAATATCTTTATTTTCATTACATCTGT
GTGTTGGTTTTTTGTGTGAATCGATAGCGATAAGGATCCGCGTATGGTGCACTCTCAGTA
CAATCTGCTCTGATGCCGCATAGTTAAGCCAGCCCCGACACCCGCCAACACCCGCTGACG
CGCCCTGACGGGCTTGTCTGCTCCCGGCATCCGCTTACAGACAAGCTGTGACCGTCTCCG
GGAGCTGCATGTGTCAGAGGTTTTCACCGTCATCACCGAAACGCGCGAGACGAAAGGGCC
TCGTGATACGCCTATTTTTATAGGTTAATGTCATGATAATAATGGTTTCTTAGACGTCAG
GTGGCACTTTTCGGGGAAATGTGCGCGGAACCCCTATTTGTTTATTTTTCTAAATACATT
CAAATATGTATCCGCTCATGAGACAATAACCCTGATAAATGCTTCAATAATATTGAAAAA
GGAAGAGTATGAGTATTCAACATTTCCGTGTCGCCCTTATTCCCTTTTTTGCGGCATTTT
GCCTTCCTGTTTTTGCTCACCCAGAAACGCTGGTGAAAGTAAAAGATGCTGAAGATCAGT
TGGGTGCACGAGTGGGTTACATCGAACTGGATCTCAACAGCGGTAAGATCCTTGAGAGTT
TTCGCCCCGAAGAACGTTTTCCAATGATGAGCACTTTTAAAGTTCTGCTATGTGGCGCGG
TATTATCCCGTATTGACGCCGGGCAAGAGCAACTCGGTCGCCGCATACACTATTCTCAGA
ATGACTTGGTTGAGTACTCACCAGTCACAGAAAAGCATCTTACGGATGGCATGACAGTAA
GAGAATTATGCAGTGCTGCCATAACCATGAGTGATAACACTGCGGCCAACTTACTTCTGA
CAACGATCGGAGGACCGAAGGAGCTAACCGCTTTTTTGCACAACATGGGGGATCATGTAA
CTCGCCTTGATCGTTGGGAACCGGAGCTGAATGAAGCCATACCAAACGACGAGCGTGACA
CCACGATGCCTGTAGCAATGGCAACAACGTTGCGCAAACTATTAACTGGCGAACTACTTA
CTCTAGCTTCCCGGCAACAATTAATAGACTGGATGGAGGCGGATAAAGTTGCAGGACCAC
TTCTGCGCTCGGCCCTTCCGGCTGGCTGGTTTATTGCTGATAAATCTGGAGCCGGTGAGC
GTGGGTCTCGCGGTATCATTGCAGCACTGGGGCCAGATGGTAAGCCCTCCCGTATCGTAG
TTATCTACACGACGGGGAGTCAGGCAACTATGGATGAACGAAATAGACAGATCGCTGAGA
TAGGTGCCTCACTGATTAAGCATTGGTAACTGTCAGACCAAGTTTACTCATATATACTTT
AGATTGATTTAAAACTTCATTTTTAATTTAAAAGGATCTAGGTGAAGATCCTTTTTGATA
ATCTCATGACCAAAATCCCTTAACGTGAGTTTTCGTTCCACTGAGCGTCAGACCCCGTAG
AAAAGATCAAAGGATCTTCTTGAGATCCTTTTTTTCTGCGCGTAATCTGCTGCTTGCAAA
CAAAAAAACCACCGCTACCAGCGGTGGTTTGTTTGCCGGATCAAGAGCTACCAACTCTTT
TTCCGAAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCTGCTAA
TCCTGTTACCAGTGGCTGCTGCCAGTGGCGATAAGTCGTGTCTTACCGGGTTGGACTCAA
GACGATAGTTACCGGATAAGGCGCAGCGGTCGGGCTGAACGGGGGGTTCGTGCACACAGC
CCAGCTTGGAGCGAACGACCTACACCGAACTGAGATACCTACAGCGTGAGCTATGAGAAA
GCGCCACGCTTCCCGAAGGGAGAAAGGCGGACAGGTATCCGGTAAGCGGCAGGGTCGGAA
CAGGAGAGCGCACGAGGGAGCTTCCAGGGGGAAACGCCTGGTATCTTTATAGTCCTGTCG
GGTTTCGCCACCTCTGACTTGAGCGTCGATTTTTGTGATGCTCGTCAGGGGGGCGGAGCC
TATGGAAAAACGCCAGCAACGCGGCCTTTTTACGGTTCCTGGCCTTTTGCTGGCCTTTTG
CTCACATGGCTCGACAGATCT

FIG. 20B pONY3.1, EIAV gag/pol expression plasmid

TCAATATTGGCCATTAGCCATATTATTCATTGGTTATATAGCATAAATCAATATTGGCTA
TTGGCCATTGCATACGTTGTATCTATATCATAATATGTACATTTATATTGGCTCATGTCC
AATATGACCGCCATGTTGGCATTGATTATTGACTAGTTATTAATAGTAATCAATTACGGG
GTCATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTGC
CCACTTGGCAGTACATCAAGTGTATCATATGCCAAGTCCGCCCCCTATTGACGTCAATGA
CGGTAAATGGCCCGCCTGGCATTATGCCCAGTACATGACCTTACGGGACTTTCCTACTTG
GCAGTACATCTACGTATTAGTCATCGCTATTACCATGGTGATGCGGTTTTGGCAGTACAC
CAATGGGCGTGGATAGCGGTTTGACTCACGGGGATTTCCAAGTCTCCACCCCATTGACGT
CAATGGGAGTTTGTTTTGGCACCAAAATCAACGGGACTTTCCAAAATGTCGTAACAACTG
CGATCGCCCGCCCCGTTGACGCAAATGGGCGGTAGGCGTGTACGGTGGGAGGTCTATATA
AGCAGAGCTCGTTTAGTGAACCGTCAGATCACTAGAAGCTTTATTGCGGTAGTTTATCAC
AGTTAAATTGCTAACGCAGTCAGTGCTTCTGACACAACAGTCTCGAACTTAAGCTGCAGT
GACTCTCTTAAGGTAGCCTTGCAGAAGTTGGTCGTGAGGCACTGGGCAGGTAAGTATCAA
GGTTACAAGACAGGTTTAAGGAGACCAATAGAAACTGGGCTTGTCGAGACAGAGAAGACT
CTTGCGTTTCTGATAGGCACCTATTGGTCTTACTGACATCCACTTTGCCTTTCTCTCCAC
AGGTGTCCACTCCCAGTTCAATTACAGCTCTTAAGGCTAGAGTACTTAATACGACTCACT
ATAGGCTAGCCTCGAGGTCGACGGTATCGCCCGAACAGGGACCTGAGAGGGGCGCAGACC
CTACCTGTTGAACCTGGCTGATCGTAGGATCCCCGGGACAGCAGAGGAGAACTTACAGAA
GTCTTCTGGAGGTGTTCCTGGCCAGAACACAGGAGGACAGGTAAGATGGGAGACCCTTTG
ACATGGAGCAAGGCGCTCAAGAAGTTAGAGAAGGTGACGGTACAAGGGTCTCAGAAATTA
ACTACTGGTAACTGTAATTGGGCGCTAAGTCTAGTAGACTTATTTCATGATACCAACTTT
GTAAAAGAAAAGGACTGGCAGCTGAGGGATGTCATTCCATTGCTGGAAGATGTAACTCAG
ACGCTGTCAGGACAAGAAAGAGAGGCCTTTGAAAGAACATGGTGGGCAATTTCTGCTGTA
AAGATGGGCCTCCAGATTAATAATGTAGTAGATGGAAAGGCATCATTCCAGCTCCTAAGA
GCGAAATATGAAAAGAAGACTGCTAATAAAAAGCAGTCTGAGCCCTCTGAAGAATATCCA
ATCATGATAGATGGGGCTGGAAACAGAAATTTTAGACCTCTAACACCTAGAGGATATACT
ACTTGGGTGAATACCATACAGACAAATGGTCTATTAAATGAAGCTAGTCAAAACTTATTT
GGGATATTATCAGTAGACTGTACTTCTGAAGAAATGAATGCATTTTTGGATGTGGTACCT
GGCCAGGCAGGACAAAAGCAGATATTACTTGATGCAATTGATAAGATAGCAGATGATTGG
GATAATAGACATCCATTACCGAATGCTCCACTGGTGGCACCACCACAAGGGCCTATTCCC
ATGACAGCAAGGTTTATTAGAGGTTTAGGAGTACCTAGAGAAAGACAGATGGAGCCTGCT
TTTGATCAGTTTAGGCAGACATATAGACAATGGATAATAGAAGCCATGTCAGAAGGCATC
AAAGTGATGATTGGAAAACCTAAAGCTCAAAATATTAGGCAAGGAGCTAAGGAACCTTAC
CCAGAATTTGTAGACAGACTATTATCCCAAATAAAAAGTGAGGGACATCCACAAGAGATT
TCAAAATTCTTGACTGATACACTGACTATTCAGAACGCAAATGAGGAATGTAGAAATGCT
ATGAGACATTTAAGACCAGAGGATACATTAGAAGAGAAAATGTATGCTTGCAGAGACATT
GGAACTACAAAACAAAAGATGATGTTATTGGCAAAAGCACTTCAGACTGGTCTTGCGGGC
CCATTTAAAGGTGGAGCCTTGAAAGGAGGGCCACTAAAGGCAGCACAAACATGTTATAAC
TGTGGGAAGCCAGGACATTTATCTAGTCAATGTAGAGCACCTAAAGTCTGTTTTAAATGT
AAACAGCCTGGACATTTCTCAAAGCAATGCAGAAGTGTTCCAAAAAACGGGAAGCAAGGG
GCTCAAGGGAGGCCCCAGAAACAAACTTTCCCGATACAACAGAAGAGTCAGCACAACAAA
TCTGTTGTACAAGAGACTCCTCAGACTCAAAATCTGTACCCAGATCTGAGCGAAATAAAA
AAGGAATACAATGTCAAGGAGAAGGATCAAGTAGAGGATCTCAACCTGGACAGTTTGTGG
GAGTAACATATAATCTAGAGAAAAGGCCTACTACAATAGTATTAATTAATGATACTCCCT
TAAATGTACTGTTAGACACAGGAGCAGATACTTCAGTGTTGACTACTGCACATTATAATA
GGTTAAAATATAGAGGGAGAAAATATCAAGGGACGGGAATAATAGGAGTGGGAGGAAATG
TGGAAACATTTTCTACGCCTGTGACTATAAAGAAAAAGGGTAGACACATTAAGACAAGAA
TGCTAGTGGCAGATATTCCAGTGACTATTTTGGGACGAGATATTCTTCAGGACTTAGGTG
CAAAATTGGTTTTGGCACAGCTCTCCAAGGAAATAAAATTTAGAAAAATAGAGTTAAAAG
AGGGCACAATGGGGCCAAAAATTCCTCAATGGCCACTCACTAAGGAGAAACTAGAAGGGG
CCAAAGAGATAGTCCAAAGACTATTGTCAGAGGGAAAAATATCAGAAGCTAGTGACAATA
ATCCTTATAATTCACCCATATTTGTAATAAAAAAGAGGTCTGGCAAATGGAGGTTATTAC
AAGATCTGAGAGAATTAAACAAAACAGTACAAGTAGGAACGGAAATATCCAGAGGATTGC

*FIG. 21A*

CTCACCCGGGAGGATTAATTAAATGTAAACACATGACTGTATTAGATATTGGAGATGCAT
ATTTCACTATACCCTTAGATCCAGAGTTTAGACCATATACAGCTTTCACTATTCCCTCCA
TTAATCATCAAGAACCAGATAAAAGATATGTGTGGAAATGTTTACCACAAGGATTCGTGT
TGAGCCCATATATATATCAGAAAACATTACAGGAAATTTTACAACCTTTTAGGGAAAGAT
ATCCTGAAGTACAATTGTATCAATATATGGATGATTTGTTCATGGGAAGTAATGGTTCTA
AAAAACAACACAAAGAGTTAATCATAGAATTAAGGGCGATCTTACTGGAAAAGGGTTTTG
AGACACCAGATGATAAATTACAAGAAGTGCCACCTTATAGCTGGCTAGGTTATCAACTTT
GTCCTGAAAATTGGAAAGTACAAAAAATGCAATTAGACATGGTAAAGAATCCAACCCTTA
ATGATGTGCAAAAATTAATGGGGAATATAACATGGATGAGCTCAGGGATCCCAGGGTTGA
CAGTAAAACACATTGCAGCTACTACTAAGGGATGTTTAGAGTTGAATCAAAAAGTAATTT
GGACGGAAGAGGCACAAAAAGAGTTAGAAGAAAATAATGAGAAGATTAAAAATGCTCAAG
GGTTACAATATTATAATCCAGAAGAAGAAATGTTATGTGAGGTTGAAATTACAAAAAATT
ATGAGGCAACTTATGTTATAAAACAATCACAAGGAATCCTATGGGCAGGTAAAAAGATTA
TGAAGGCTAATAAGGGATGGTCAACAGTAAAAAATTTAATGTTATTGTTGCAACATGTGG
CAACAGAAAGTATTACTAGAGTAGGAAAATGTCCAACGTTTAAGGTACCATTTACCAAAG
AGCAAGTAATGTGGGAAATGCAAAAAGGATGGTATTATTCTTGGCTCCCAGAAATAGTAT
ATACACATCAAGTAGTTCATGATGATTGGAGAATGAAATTGGTAGAAGAACCTACATCAG
GAATAACAATATACACTGATGGGGGAAAACAAAATGGAGAAGGAATAGCAGCTTATGTGA
CCAGTAATGGGAGAACTAAACAGAAAAGGTTAGGACCTGTCACTCATCAAGTTGCTGAAA
GAATGGCAATACAAATGGCATTAGAGGATACCAGAGATAAACAAGTAAATATAGTAACTG
ATAGTTATTATTGTTGGAAAAATATTACAGAAGGATTAGGTTTAGAAGGACCACAAAGTC
CTTGGTGGCCTATAATACAAAATATACGAGAAAAAGAGATAGTTTATTTTGCTTGGGTAC
CTGGTCACAAAGGGATATATGGTAATCAATTGGCAGATGAAGCCGCAAAAAATAAAAGAAG
AAATCATGCTAGCATACCAAGGCACACAAATTAAAGAGAAAAGAGATGAAGATGCAGGGT
TTGACTTATGTGTTCCTTATGACATCATGATACCTGTATCTGACACAAAAATCATACCCA
CAGATGTAAAAATTCAAGTTCCTCCTAATAGCTTTGGATGGGTCACTGGGAAATCATCAA
TGGCAAAACAGGGGTTATTAATTAATGGAGGAATAATTGATGAAGGATATACAGGAGAAA
TACAAGTGATATGTACTAATATTGGAAAAAGTAATATTAAATTAATAGAGGGACAAAAAT
TTGCACAATTAATTATACTACAGCATCACTCAAATTCCAGACAGCCTTGGGATGAAAATA
AAATATCTCAGAGAGGGGATAAAGGATTTGGAAGTACAGGAGTATTCTGGGTAGAAAATA
TTCAGGAAGCACAAGATGAACATGAGAATTGGCATACATCACCAAAGATATTGGCAAGAA
ATTATAAGATACCATTGACTGTAGCAAAACAGATAACTCAAGAATGTCCTCATTGCACTA
AGCAAGGATCAGGACCTGCAGGTTGTGTCATGAGATCTCCTAATCATTGGCAGGCAGATT
GCACACATTTGGACAATAAGATAATATTGACTTTTGTAGAGTCAAATTCAGGATACATAC
ATGCTACATTATTGTCAAAAGAAAATGCATTATGTACTTCATTGGCTATTTTAGAATGGG
CAAGATTGTTTTCACCAAAGTCCTTACACACAGATAACGGCACTAATTTTGTGGCAGAAC
CAGTTGTAAATTTGTTGAAGTTCCTAAAGATAGCACATACCACAGGAATACCATATCATC
CAGAAAGTCAGGGTATTGTAGAAAGGGCAAATAGGACCTTGAAAGAGAAGATTCAAAGTC
ATAGAGACAACACTCAAACACTGGAGGCAGCTTTACAACTTGCTCTCATTACTTGTAACA
AAGGGAGGGAAAGTATGGGAGGACAGACACCATGGGAAGTATTTATCACTAATCAAGCAC
AAGTAATACATGAGAAACTTTTACTACAGCAAGCACAATCCTCCAAAAAAATTTTGTTTTT
ACAAAATCCCTGGTGAACATGATTGGAAGGGACCTACTAGGGTGCTGTGGAAGGGTGATG
GTGCAGTAGTAGTTAATGATGAAGGAAAGGGAATAATTGCTGTACCATTAACCAGGACTA
AGTTACTAATAAAACCAAATTGAGTATTGTTGCAGGAAGCAAGACCCAACTACCATTGTC
AGCTGTGTTTCCTGAGGTCTCTAGGAATTGATTACCTCGATGCTTCATTAAGGAAGAAGA
ATAAACAAAGACTGAAGGCAATCCAACAAGGAAGACAACCTCAATATTTGTTATAAGGTT
TGATATATGGGAGTATTTGGTAAAGGGGTAACATGGTCAGCATCGCATTCTATGGGGGAA
TCCCAGGGGGAATCTCAACCCCTATTACCCAACAGTCAGAAAAATCTAAGTGTGAGGAGA
ACACAATGTTTCAACCTTATTGTTATAATAATGACAGTAAGAACAGCATGGCAGAATCGA
AGGAAGCAAGAGACCAAGAAATGAACCTGAAAGAAGAATCTAAAGAAGAAAAAAGAAGAA
ATGACTGGTGGAAAATAGGTATGTTTCTGTTATGCTTAGCAGGAACTACTGGAGGAATAC
TTTGGTGGTATGAAGGACTCCCACAGCAACATTATATAGGGTTGGTGGCGATAGGGGGAA
GATTAAACGGATCTGGCCAATCAAATGCTATAGAATGCTGGGGTTCCTTCCCGGGGTGTA
GACCATTTCAAAATTACTTCAGTTATGAGACCAATAGAAGCATGCATATGGATAATAATA
CTGCTACATTATTAGAAGCTTTAACCAATATAACTGCTCTATAAATAACAAAACAGAATT
AGAAACATGGAAGTTAGTAAAGACTTCTGGCATAACTCCTTTACCTATTTCTTCTGAAGC
TAACACTGGACTAATTAGACATAAGAGAGATTTTGGTATAAGTGCAATAGTGGCAGCTAT

*FIG. 21B*

TGTAGCCGCTACTGCTATTGCTGCTAGCGCTACTATGTCTTATGTTGCTCTAACTGAGGT
TAACAAAATAATGGAAGTACAAAATCATACTTTGAGGTAGAAAATAGTACTCTAAATGG
TATGGATTTAATAGAACGACAAATAAAGATATTATATGCTATGATTCTTCAAACACATGC
AGATGTTCAACTGTTAAAGGAAAGACAACAGGTAGAGGAGACATTTAATTTAATTGGATG
TATAGAAAGAACACATGTATTTTGTCATACTGGTCATCCCTGGAATATGTCATGGGGACA
TTTAAATGAGTCAACACAATGGGATGACTGGGTAAGCAAAATGGAAGATTTAAATCAAGA
GATACTAACTACACTTCATGGAGCCAGGAACAATTTGGCACAATCCATGATAACATTCAA
TACACCAGATAGTATAGCTCAATTTGGAAAAGACCTTTGGAGTCATATTGGAAATTGGAT
TCCTGGATTGGGAGCTTCCATTATAAAATATATAGTGATGTTTTTGCTTATTTATTTGTT
ACTAACCTCTTCGCCTAAGATCCTCAGGGCCCTCTGGAAGGTGACCAGTGGTGCAGGGTC
CTCCGGCAGTCGTTACCTGAAGAAAAAATTCCATCACAAACATGCATCGCGAGAAGACAC
CTGGGACCAGGCCCAACACAACATACACCTAGCAGGCGTGACCGGTGGATCAGGGGACAA
ATACTACAAGCAGAAGTACTCCAGGAACGACTGGAATGGAGAATCAGAGGAGTACAACAG
GCGGCCAAAGAGCTGGGTGAAGTCAATCGAGGCATTTGGAGAGAGCTATATTTCCGAGAA
GACCAAAGGGGAGATTTCTCAGCCTGGGGCGGCTATCAACGAGCACAAGAACGGCTCTGG
GGGGAACAATCCTCACCAAGGGTCCTTAGACCTGGAGATTCGAAGCGAAGGAGGAAACAT
TTATGACTGTTGCATTAAAGCCCAAGAAGGAACTCTCGCTATCCCTTGCTGTGGATTTCC
CTTATGGCTATTTTGGGGACTAGTAATTATAGTAGGACGCATAGCAGGCTATGGATTACG
TGGACTCGCTGTTATAATAAGGATTTGTATTAGAGGCTTAAATTTGATATTTGAAATAAT
CAGAAAAATGCTTGATTATATTGGAAGAGCTTTAAATCCTGGCACATCTCATGTATCAAT
GCCTCAGTATGTTTAGAAAAACAAGGGGGGAACTGTGGGGTTTTTATGAGGGGTTTTATA
AATGATTATAAGAGTAAAAAGAAAGTTGCTGATGCTCTCATAACCTTGTATAACCCAAAG
GACTAGCTCATGTTGCTAGGCAACTAAACCGCAATAACCGCATTTGTGACGCGAGTTCCC
CATTGGTGACGCGTGGTACCTCTAGAGTCGACCCGGGCGGCCGCTTCCCTTTAGTGAGGG
TTAATGCTTCGAGCAGACATGATAAGATACATTGATGAGTTTGGACAAACCACAACTAGA
ATGCAGTGAAAAAAATGCTTTATTTGTGAAATTTGTGATGCTATTGCTTTATTTGTAACC
ATTATAAGCTGCAATAAACAAGTTAACAACAACAATTGCATTCATTTTATGTTTCAGGTT
CAGGGGGAGATGTGGGAGGTTTTTTAAAGCAAGTAAAACCTCTACAAATGTGGTAAAATC
CGATAAGGATCGATCCGGGCTGGCGTAATAGCGAAGAGGCCCGCACCGATCGCCCTTCCC
AACAGTTGCGCAGCCTGAATGGCGAATGGACGCGCCCTGTAGCGGCGCATTAAGCGCGGC
GGGTGTGGTGGTTACGCGCAGCGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTAAA
TCGGGGGCTCCCTTTAGGGTTCCGATTTAGAGCTTTACGGCACCTCGACCGCAAAAAACT
TGATTTGGGTGATGGTTCACGTAGTGGGCCATCGCCCTGATAGACGGTTTTTCGCCCTTT
GACGTTGGAGTCCACGTTCTTTAATAGTGGACTCTTGTTCCAAACTGGAACAACACTCAA
CCCTATCTCGGTCTATTCTTTTGATTTATAAGGGATTTTGCCGATTTCGGCCTATTGGTT
AAAAAATGAGCTGATTTAACAAATATTTAACGCGAATTTTAACAAAATATTAACGTTTAC
AATTTCGCCTGATGCGGTATTTTCTCCTTACGCATCTGTGCGGTATTTCACACCGCATAC
GCGGATCTGCGCAGCACCATGGCCTGAAATAACCTCTGAAAGAGGAACTTGGTTAGGTAC
CTTCTGAGGCGGAAAGAACCAGCTGTGGAATGTGTGTCAGTTAGGGTGTGGAAAGTCCCC
AGGCTCCCCAGCAGGCAGAAGTATGCAAAGCATGCATCTCAATTAGTCAGCAACCAGGTG
TGGAAAGTCCCCAGGCTCCCCAGCAGGCAGAAGTATGCAAAGCATGCATCTCAATTAGTC
AGCAACCATAGTCCCGCCCCTAACTCCGCCCATCCCGCCCCTAACTCCGCCCAGTTCCGC
CCATTCTCCGCCCCATGGCTGACTAATTTTTTTTATTTATGCAGAGGCCGAGGCCGCCTC
GGCCTCTGAGCTATTCCAGAAGTAGTGAGGAGGCTTTTTTGGAGGCCTAGGCTTTTGCAA
AAAGCTTGATTCTTCTGACACAACAGTCTCGAACTTAAGGCTAGAGCCACCATGATTGAA
CAAGATGGATTGCACGCAGGTTCTCCGGCCGCTTGGGTGGAGAGGCTATTCGGCTATGAC
TGGGCACAACAGACAATCGGCTGCTCTGATGCCGCCGTGTTCCGGCTGTCAGCGCAGGGG
CGCCCGGTTCTTTTTGTCAAGACCGACCTGTCCGGTGCCCTGAATGAACTGCAGGACGAG
GCAGCGCGGCTATCGTGGCTGGCCACGACGGGCGTTCCTTGCGCAGCTGTGCTCGACGTT
GTCACTGAAGCGGGAAGGGACTGGCTGCTATTGGGCGAAGTGCCGGGGCAGGATCTCCTG
TCATCTCACCTTGCTCCTGCCGAGAAAGTATCCATCATGGCTGATGCAATGCGGCGGCTG
CATACGCTTGATCCGGCTACCTGCCCATTCGACCACCAAGCGAAACATCGCATCGAGCGA
GCACGTACTCGGATGGAAGCCGGTCTTGTCGATCAGGATGATCTGGACGAAGAGCATCAG
GGGCTCGCGCCAGCCGAACTGTTCGCCAGGCTCAAGGCGCGCATGCCCGACGGCGAGGAT
CTCGTCGTGACCCATGGCGATGCCTGCTTGCCGAATATCATGGTGGAAAATGGCCGCTTT
TCTGGATTCATCGACTGTGGCCGGCTGGGTGTGGCGGACCGCTATCAGGACATAGCGTTG

*FIG. 21C*

GCTACCCGTGATATTGCTGAAGAGCTTGGCGGCGAATGGGCTGACCGCTTCCTCGTGCTT
TACGGTATCGCCGCTCCCGATTCGCAGCGCATCGCCTTCTATCGCCTTCTTGACGAGTTC
TTCTGAGCGGGACTCTGGGGTTCGAAATGACCGACCAAGCGACGCCCAACCTGCCATCAC
GATGGCCGCAATAAAATATCTTTATTTTCATTACATCTGTGTGTTGGTTTTTTGTGTGAA
TCGATAGCGATAAGGATCCGCGTATGGTGCACTCTCAGTACAATCTGCTCTGATGCCGCA
TAGTTAAGCCAGCCCCGACACCCGCCAACACCCGCTGACGCGCCCTGACGGGCTTGTCTG
CTCCCGGCATCCGCTTACAGACAAGCTGTGACCGTCTCCGGGAGCTGCATGTGTCAGAGG
TTTTCACCGTCATCACCGAAACGCGCGAGACGAAAGGGCCTCGTGATACGCCTATTTTTA
TAGGTTAATGTCATGATAATAATGGTTTCTTAGACGTCAGGTGGCACTTTTCGGGGAAAT
GTGCGCGGAACCCCTATTTGTTTATTTTTCTAAATACATTCAAATATGTATCCGCTCATG
AGACAATAACCCTGATAAATGCTTCAATAATATTGAAAAAGGAAGAGTATGAGTATTCAA
CATTTCCGTGTCGCCCTTATTCCCTTTTTTGCGGCATTTTGCCTTCCTGTTTTTGCTCAC
CCAGAAACGCTGGTGAAAGTAAAAGATGCTGAAGATCAGTTGGGTGCACGAGTGGGTTAC
ATCGAACTGGATCTCAACAGCGGTAAGATCCTTGAGAGTTTTCGCCCCGAAGAACGTTTT
CCAATGATGAGCACTTTTAAAGTTCTGCTATGTGGCGCGGTATTATCCCGTATTGACGCC
GGGCAAGAGCAACTCGGTCGCCGCATACACTATTCTCAGAATGACTTGGTTGAGTACTCA
CCAGTCACAGAAAAGCATCTTACGGATGGCATGACAGTAAGAGAATTATGCAGTGCTGCC
ATAACCATGAGTGATAACACTGCGGCCAACTTACTTCTGACAACGATCGGAGGACCGAAG
GAGCTAACCGCTTTTTTGCACAACATGGGGGATCATGTAACTCGCCTTGATCGTTGGGAA
CCGGAGCTGAATGAAGCCATACCAAACGACGAGCGTGACACCACGATGCCTGTAGCAATG
GCAACAACGTTGCGCAAACTATTAACTGGCGAACTACTTACTCTAGCTTCCCGGCAACAA
TTAATAGACTGGATGGAGGCGGATAAAGTTGCAGGACCACTTCTGCGCTCGGCCCTTCCG
GCTGGCTGGTTTATTGCTGATAAATCTGGAGCCGGTGAGCGTGGGTCTCGCGGTATCATT
GCAGCACTGGGGCCAGATGGTAAGCCCTCCCGTATCGTAGTTATCTACACGACGGGGAGT
CAGGCAACTATGGATGAACGAAATAGACAGATCGCTGAGATAGGTGCCTCACTGATTAAG
CATTGGTAACTGTCAGACCAAGTTTACTCATATATACTTTAGATTGATTTAAAACTTCAT
TTTTAATTTAAAAGGATCTAGGTGAAGATCCTTTTTGATAATCTCATGACCAAAATCCCT
TAACGTGAGTTTTCGTTCCACTGAGCGTCAGACCCCGTAGAAAAGATCAAAGGATCTTCT
TGAGATCCTTTTTTTCTGCGCGTAATCTGCTGCTTGCAAACAAAAAAACCACCGCTACCA
GCGGTGGTTTGTTTGCCGGATCAAGAGCTACCAACTCTTTTTCCGAAGGTAACTGGCTTC
AGCAGAGCGCAGATACCAAATACTGTCCTTCTAGTGTAGCCGTAGTTAGGCCACCACTTC
AAGAACTCTGTAGCACCGCCTACATACCTCGCTCTGCTAATCCTGTTACCAGTGGCTGCT
GCCAGTGGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGAACGACC
TACACCGAACTGAGATACCTACAGCGTGAGCTATGAGAAAGCGCCACGCTTCCCGAAGGG
AGAAAGGCGGACAGGTATCCGGTAAGCGGCAGGGTCGGAACAGGAGAGCGCACGAGGGAG
CTTCCAGGGGGAAACGCCTGGTATCTTTATAGTCCTGTCGGGTTTCGCCACCTCTGACTT
GAGCGTCGATTTTTGTGATGCTCGTCAGGGGGGCGGAGCCTATGGAAAAACGCCAGCAAC
GCGGCCTTTTTACGGTTCCTGGCCTTTTGCTGGCCTTTTGCTCACATGGCTCGACAGATC
T

*FIG. 21D*

Comparison of pONY3.1 (nt1246-1606)(TOP) and pONY3.2opti (nt366-726)(BOTTOM)

```
atgggagaccctttgacatggagcaaggcgctcaagaagttagagaaggtgacggtacaa
.....c..t..cc.c..c...tc...a..c..g..a..ac.g..a..a..c..c..t..g

gggtctcagaaattaactactggtaactgtaattgggcgctaagtctagtagacttattt
..tagc..a..gc.t..c..a..c..t..c..c.....at.gtcc..g..g..tc.t..c

catgataccaactttgtaaaagaaaaggactggcagctgagggatgtcattccattgctg
..c..c..t..t..c..t..g..g..a..t.....a..c..a..c..g..c..cc.ct..

gaagatgtaactcagacgctgtcaggacaagaaagagaggcctttgaaagaacatggtgg
..g..c..g..c..a..at....t..g..g..gc.c..a..t..c..gc.c..c......

gcaatttctgctgtaaagatgggcctccagattaataatgtagtagatggaaaggcatca
..c..cagc..a..c..a.....g..g..a..c..c..c..g..t..c..t..a..tagc

ttccagctcctaagagcgaaatatgaaaagaagactgctaataaaaagcagtctgagccc
..t..a..g..cc.c..t..g..c..g..a..a..c..c..c..g..a..a..c..a..t

tctgaagaatatccaatcatgatag
agc..g..g..c.............
```

FIG. 22 pESYNGPRRE, codon-optimised EIAV gag/pol expression plasmid

TCAATATTGGCCATTAGCCATATTATTCATTGGTTATATAGCATAAATCAATATTGGCTA
TTGGCCATTGCATACGTTGTATCTATATCATAATATGTACATTTATATTGGCTCATGTCC
AATATGACCGCCATGTTGGCATTGATTATTGACTAGTTATTAATAGTAATCAATTACGGG
GTCATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTGC
CCACTTGGCAGTACATCAAGTGTATCATATGCCAAGTCCGCCCCCTATTGACGTCAATGA
CGGTAAATGGCCCGCCTGGCATTATGCCCAGTACATGACCTTACGGGACTTTCCTACTTG
GCAGTACATCTACGTATTAGTCATCGCTATTACCATGGTGATGCGGTTTTGGCAGTACAC
CAATGGGCGTGGATAGCGGTTTGACTCACGGGGATTTCCAAGTCTCCACCCCATTGACGT
CAATGGGAGTTTGTTTTGGCACCAAAATCAACGGGACTTTCCAAAATGTCGTAACAACTG
CGATCGCCCGCCCCGTTGACGCAAATGGGCGGTAGGCGTGTACGGTGGGAGGTCTATATA
AGCAGAGCTCGTTTAGTGAACCGTCAGATCACTAGAAGCTTTATTGCGGTAGTTTATCAC
AGTTAAATTGCTAACGCAGTCAGTGCTTCTGACACAACAGTCTCGAACTTAAGCTGCAGT
GACTCTCTTAAGGTAGCCTTGCAGAAGTTGGTCGTGAGGCACTGGGCAGGTAAGTATCAA
GGTTACAAGACAGGTTTAAGGAGACCAATAGAAACTGGGCTTGTCGAGACAGAGAAGACT
CTTGCGTTTCTGATAGGCACCTATTGGTCTTACTGACATCCACTTTGCCTTTCTCTCCAC
AGGTGTCCACTCCCAGTTCAATTACAGCTCTTAAGGCTAGAGTACTTAATACGACTCACT
ATAGGCTAGAGAATTCGCCACCATGGGCGATCCCCTCACCTGGTCCAAAGCCCTGAAGAA
ACTGGAAAAAGTCACCGTTCAGGGTAGCCAAAAGCTTACCACAGGCAATTGCAACTGGGC
ATTGTCCCTGGTGGATCTTTTCCACGACACTAATTTCGTTAAGGAGAAAGATTGGCAACT
CAGAGACGTGATCCCCCTCTTGGAGGACGTGACCCAAACATTGTCTGGGCAGGAGCGCGA
AGCTTTCGAGCGCACCTGGTGGGCCATCAGCGCAGTCAAAATGGGGCTGCAAATCAACAA
CGTGGTTGACGGTAAAGCTAGCTTTCAACTGCTCCGCGCTAAGTACGAGAAGAAAACCGC
CAACAAGAAACAATCCGAACCTAGCGAGGAGTACCCAATTATGATCGACGGCGCCGGCAA
TAGGAACTTCCGCCCACTGACTCCCAGGGGCTATACCACCTGGGTCAACACCATCCAGAC
AAACGGACTTTTGAACGAAGCCTCCCAGAACCTGTTCGGCATCCTGTCTGTGGACTGCAC
CTCCGAAGAAATGAATGCTTTTCTCGACGTGGTGCCAGGACAGGCTGGACAGAAACAGAT
CCTGCTCGATGCCATTGACAAGATCGCCGACGACTGGGATAATCGCCACCCCCTGCCAAA
CGCCCCTCTGGTGGCTCCCCCACAGGGGCCTATCCCTATGACCGCTAGGTTCATTAGGGG
ACTGGGGGTGCCCCGCGAACGCCAGATGGAGCCAGCATTTGACCAATTTAGGCAGACCTA
CAGACAGTGGATCATCGAAGCCATGAGCGAGGGGATTAAAGTCATGATCGGAAAGCCCAA
GGCACAGAACATCAGGCAGGGGGCCAAGGAACCATACCCTGAGTTTGTCGACAGGCTTCT
GTCCCAGATTAAATCCGAAGGCCACCCTCAGGAGATCTCCAAGTTCTTGACAGACACACT
GACTATCCAAAATGCAAATGAAGAGTGCAGAAACGCCATGAGGCACCTCAGACCTGAAGA
TACCCTGGAGGAGAAAATGTACGCATGTCGCGACATTGGCACTACCAAGCAAAAGATGAT
GCTGCTCGCCAAGGCTCTGCAAACCGGCCTGGCTGGTCCATTCAAAGGAGGAGCACTGAA
GGGAGGTCCATTGAAAGCTGCACAAACATGTTATAATTGTGGGAAGCCAGGACATTTATC
TAGTCAATGTAGAGCACCTAAAGTCTGTTTTAAATGTAAACAGCCTGGACATTTCTCAAA
GCAATGCAGAAGTGTTCCAAAAAACGGGAAGCAAGGGGCTCAAGGGAGGCCCCAGAAACA
AACTTTCCCGATACAACAGAAGAGTCAGCACAACAAATCTGTTGTACAAGAGACTCCTCA
GACTCAAAATCTGTACCCAGATCTGAGCGAAATAAAAAAGGAATACAATGTCAAGGAGAA
GGATCAAGTAGAGGATCTCAACCTGGACAGTTTGTGGGAGTAACATACAATCTCGAGAAG
AGGCCCACTACCATCGTCCTGATCAATGACACCCCTCTTAATGTGCTGCTGGACACCGGA
GCCGACACCAGCGTTCTCACTACTGCTCACTATAACAGACTGAAATACAGAGGAAGGAAA
TACCAGGGCACAGGCATCATCGGCGTTGGAGGCAACGTCGAAACCTTTTCCACTCCTGTC
ACCATCAAAAAGAAGGGGAGACACATTAAAACCAGAATGCTGGTCGCCGACATCCCCGTC
ACCATCCTTGGCAGAGACATTCTCCAGGACCTGGGCGCTAAACTCGTGCTGGCACAACTG
TCTAAGGAAATCAAGTTCCGCAAGATCGAGCTGAAAGAGGGCACAATGGGTCCAAAAATC
CCCCAGTGGCCCCTGACCAAAGAGAAGCTTGAGGGCGCTAAGGAAATCGTGCAGCGCCTG
CTTTCTGAGGGCAAGATTAGCGAGGCCAGCGACAATAACCCTTACAACAGCCCCATCTTT
GTGATTAAGAAAAGGAGCGGCAAATGGAGACTCCTGCAGGACCTGAGGGAACTCAACAAG
ACCGTCCAGGTCGGAACTGAGATCTCTCGCGGACTGCCTCACCCCGGCGGCCTGATTAAA
TGCAAGCACATGACAGTCCTTGACATTGGAGACGCTTATTTTACCATCCCCCTCGATCCT
GAATTTCGCCCCTATACTGCTTTTACCATCCCCAGCATCAATCACCAGGAGCCCGATAAA

*FIG. 23B*

CGCTATGTGTGGAAGTGCCTCCCCCAGGGATTTGTGCTTAGCCCCTACATTTACCAGAAG
ACACTTCAAGAGATCCTCCAACCTTTCCGCGAAAGATACCCAGAGGTTCAACTCTACCAA
TATATGGACGACCTGTTCATGGGGTCCAACGGGTCTAAGAAGCAGCACAAGGAACTCATC
ATCGAACTGAGGGCAATCCTCCTGGAGAAAGGCTTCGAGACACCCGACGACAAGCTGCAA
GAAGTTCCTCCATATAGCTGGCTGGGCTACCAGCTTTGCCCTGAAAACTGGAAAGTCCAG
AAGATGCAGTTGGATATGGTCAAGAACCCAACACTGAACGACGTCCAGAAGCTCATGGGC
AATATTACCTGGATGAGCTCCGGAATCCCTGGGCTTACCGTTAAGCACATTGCCGCAACT
ACAAAAGGATGCCTGGAGTTGAACCAGAAGGTCATTTGGACAGAGGAAGCTCAGAAGGAA
CTGGAGGAGAATAATGAAAAGATTAAGAATGCTCAAGGGCTCCAATACTACAATCCCGAA
GAAGAAATGTTGTGCGAGGTCGAAATCACTAAGAACTACGAAGCCACCTATGTCATCAAA
CAGTCCCAAGGCATCTTGTGGGCCGGAAAGAAAATCATGAAGGCCAACAAAGGCTGGTCC
ACCGTTAAAAATCTGATGCTCCTGCTCCAGCACGTCGCCACCGAGTCTATCACCCGCGTC
GGCAAGTGCCCCACCTTCAAAGTTCCCTTCACTAAGGAGCAGGTGATGTGGGAGATGCAA
AAAGGCTGGTACTACTCTTGGCTTCCCGAGATCGTCTACACCCACCAAGTGGTGCACGAC
GACTGGAGAATGAAGCTTGTCGAGGAGCCCACTAGCGGAATTACAATCTATACCGACGGC
GGAAAGCAAAACGGAGAGGGAATCGCTGCATACGTCACATCTAACGGCCGCACCAAGCAA
AAGAGGCTCGGCCCTGTCACTCACCAGGTGGCTGAGAGGATGGCTATCCAGATGGCCCTT
GAGGACACTAGAGACAAGCAGGTGAACATTGTGACTGACAGCTACTACTGCTGGAAAAAC
ATCACAGAGGGCCTTGGCCTGGAGGGACCCCAGTCTCCCTGGTGGCCTATCATCCAGAAT
ATCCGCGAAAAGGAAATTGTCTATTTCGCCTGGGTGCCTGGACACAAAGGAATTTACGGC
AACCAACTCGCCGATGAAGCCGCCAAAATTAAAGAGGAAATCATGCTTGCCTACCAGGGC
ACACAGATTAAGGAGAAGAGAGACGAGGACGCTGGCTTTGACCTGTGTGTGCCATACGAC
ATCATGATTCCCGTTAGCGACACAAAGATCATTCCAACCGATGTCAAGATCCAGGTGCCA
CCCAATTCATTTGGTTGGGTGACCGGAAAGTCCAGCATGGCTAAGCAGGGTCTTCTGATT
AACGGGGGAATCATTGATGAAGGATACACCGGCGAAATCCAGGTGATCTGCACAAATATC
GGCAAAAGCAATATTAAGCTTATCGAAGGGCAGAAGTTCGCTCAACTCATCATCCTCCAG
CACCACAGCAATTCAAGACAACCTTGGGACGAAAACAAGATTAGCCAGAGAGGTGACAAG
GGCTTCGGCAGCACAGGTGTGTTCTGGGTGGAGAACATCCAGGAAGCACAGGACGAGCAC
GAGAATTGGCACACCTCCCCTAAGATTTTGGCCCGCAATTACAAGATCCCACTGACTGTG
GCTAAGCAGATCACACAGGAATGCCCCCACTGCACCAAACAAGGTTCTGGCCCCGCCGGC
TGCGTGATGAGGTCCCCCAATCACTGGCAGGCAGATTGCACCCACCTCGACAACAAAATT
ATCCTGACCTTCGTGGAGAGCAATTCCGGCTACATCCACGCAACACTCCTCTCCAAGGAA
AATGCATTGTGCACCTCCCTCGCAATTCTGGAATGGGCCAGGCTGTTCTCTCCAAAATCC
CTGCACACCGACAACGGCACCAACTTTGTGGCTGAACCTGTGGTGAATCTGCTGAAGTTC
CTGAAAATCGCCCACACCACTGGCATTCCCTATCACCCTGAAAGCCAGGGCATTGTCGAG
AGGGCCAACAGAACTCTGAAAGAAAAGATCCAATCTCACAGAGACAATACACAGACATTG
GAGGCCGCACTTCAGCTCGCCCTTATCACCTGCAACAAAGGAAGAGAAAGCATGGGCGGC
CAGACCCCCTGGGAGGTCTTCATCACTAACCAGGCCCAGGTCATCCATGAAAAGCTGCTC
TTGCAGCAGGCCCAGTCCTCCAAAAAGTTCTGCTTTTATAAGATCCCCGGTGAGCACGAC
TGGAAAGGTCCTACAAGAGTTTTGTGGAAAGGAGACGGCGCAGTTGTGGTGAACGATGAG
GGCAAGGGGATCATCGCTGTGCCCCTGACACGCACCAAGCTTCTCATCAAGCCAAACTGA
ACCCGACGAATCCCAGGGGGAATCTCAACCCCTATTACCCAACAGTCAGAAAAATCTAAG
TGTGAGGAGAACACAATGTTTCAACCTTATTGTTATAATAATGACAGTAAGAACAGCATG
GCAGAATCGAAGGAAGCAAGAGACCAAGAAATGAACCTGAAAGAAGAATCTAAAGAAGAA
AAAAGAAGAAATGACTGGTGGAAAATAGGTATGTTTCTGTTATGCTTAGCCAGGGCCCTC
TGGAAGGTGACCAGTGGTGCAGGGTCCTCCGGCAGTCGTTACCTGAAGAAAAAATTCCAT
CACAAACATGCATCGCGAGAAGACACCTGGGACCAGGCCCAACACAACATACACCTAGCA
GGCGTGACCGGTGGATCAGGGGACAAATACTACAAGCAGAAGTACTCCAGGAACGACTGG
AATGGAGAATCAGAGGAGTACAACAGGCGGCCAAAGAGCTGGGTGAAGTCAATCGAGGCA
TTTGGAGAGAGCTATATTTCCGAGAAGACCAAAGGGGAGATTTCTCAGCCTGGGGCGGCT
ATCAACGAGCACAAGAACGGCTCTGGGGGGAACAATCCTCACCAAGGGTCCTTAGACCTG
GAGATTCGAAGCGAAGGAGGAAACATTTATGACTGTTGCATTAAAGCCCAAGAAGGAACT
CTCGCTATCCCTTGCTGTGGATTTCCCTTATGGCTATTTTGGGGGTCGGGGCGGCCGCTT
CCCTTTAGTGAGGGTTAATGCTTCGAGCAGACATGATAAGATACATTGATGAGTTTGGAC
AAACCACAACTAGAATGCAGTGAAAAAAATGCTTTATTTGTGAAATTTGTGATGCTATTG
CTTTATTTGTAACCATTATAAGCTGCAATAAACAAGTTAACAACAACAATTGCATTCATT
TTATGTTTCAGGTTCAGGGGGAGATGTGGGAGGTTTTTTAAAGCAAGTAAAACCTCTACA

FIG. 23C

AATGTGGTAAAATCCGATAAGGATCGATCCGGGCTGGCGTAATAGCGAAGAGGCCCGCAC
CGATCGCCCTTCCCAACAGTTGCGCAGCCTGAATGGCGAATGGACGCGCCCTGTAGCGGC
GCATTAAGCGCGGCGGGTGTGGTGGTTACGCGCAGCGTGACCGCTACACTTGCCAGCGCC
CTAGCGCCCGCTCCTTTCGCTTTCTTCCCTTCCTTTCTCGCCACGTTCGCCGGCTTTCCC
CGTCAAGCTCTAAATCGGGGGCTCCCTTTAGGGTTCCGATTTAGAGCTTTACGGCACCTC
GACCGCAAAAAACTTGATTTGGGTGATGGTTCACGTAGTGGGCCATCGCCCTGATAGACG
GTTTTTCGCCCTTTGACGTTGGAGTCCACGTTCTTTAATAGTGGACTCTTGTTCCAAACT
GGAACAACACTCAACCCTATCTCGGTCTATTCTTTTGATTTATAAGGGATTTTGCCGATT
TCGGCCTATTGGTTAAAAAATGAGCTGATTTAACAAATATTTAACGCGAATTTTAACAAA
ATATTAACGTTTACAATTTCGCCTGATGCGGTATTTTCTCCTTACGCATCTGTGCGGTAT
TTCACACCGCATACGCGGATCTGCGCAGCACCATGGCCTGAAATAACCTCTGAAAGAGGA
ACTTGGTTAGGTACCTTCTGAGGCGGAAAGAACCAGCTGTGGAATGTGTGTCAGTTAGGG
TGTGGAAAGTCCCCAGGCTCCCCAGCAGGCAGAAGTATGCAAAGCATGCATCTCAATTAG
TCAGCAACCAGGTGTGGAAAGTCCCCAGGCTCCCCAGCAGGCAGAAGTATGCAAAGCATG
CATCTCAATTAGTCAGCAACCATAGTCCCGCCCCTAACTCCGCCCATCCCGCCCCTAACT
CCGCCCAGTTCCGCCCATTCTCCGCCCCATGGCTGACTAATTTTTTTTATTTATGCAGAG
GCCGAGGCCGCCTCGGCCTCTGAGCTATTCCAGAAGTAGTGAGGAGGCTTTTTTGGAGGC
CTAGGCTTTTGCAAAAAGCTTGATTCTTCTGACACAACAGTCTCGAACTTAAGGCTAGAG
CCACCATGATTGAACAAGATGGATTGCACGCAGGTTCTCCGGCCGCTTGGGTGGAGAGGC
TATTCGGCTATGACTGGGCACAACAGACAATCGGCTGCTCTGATGCCGCCGTGTTCCGGC
TGTCAGCGCAGGGGCGCCCGGTTCTTTTTGTCAAGACCGACCTGTCCGGTGCCCTGAATG
AACTGCAGGACGAGGCAGCGCGGCTATCGTGGCTGGCCACGACGGGCGTTCCTTGCGCAG
CTGTGCTCGACGTTGTCACTGAAGCGGGAAGGGACTGGCTGCTATTGGGCGAAGTGCCGG
GGCAGGATCTCCTGTCATCTCACCTTGCTCCTGCCGAGAAAGTATCCATCATGGCTGATG
CAATGCGGCGGCTGCATACGCTTGATCCGGCTACCTGCCCATTCGACCACCAAGCGAAAC
ATCGCATCGAGCGAGCACGTACTCGGATGGAAGCCGGTCTTGTCGATCAGGATGATCTGG
ACGAAGAGCATCAGGGGCTCGCGCCAGCCGAACTGTTCGCCAGGCTCAAGGCGCGCATGC
CCGACGGCGAGGATCTCGTCGTGACCCATGGCGATGCCTGCTTGCCGAATATCATGGTGG
AAAATGGCCGCTTTTCTGGATTCATCGACTGTGGCCGGCTGGGTGTGGCGGACCGCTATC
AGGACATAGCGTTGGCTACCCGTGATATTGCTGAAGAGCTTGGCGGCGAATGGGCTGACC
GCTTCCTCGTGCTTTACGGTATCGCCGCTCCCGATTCGCAGCGCATCGCCTTCTATCGCC
TTCTTGACGAGTTCTTCTGAGCGGGACTCTGGGGTTCGAAATGACCGACCAAGCGACGCC
CAACCTGCCATCACGATGGCCGCAATAAAATATCTTTATTTTCATTACATCTGTGTGTTG
GTTTTTTGTGTGAATCGATAGCGATAAGGATCCGCGTATGGTGCACTCTCAGTACAATCT
GCTCTGATGCCGCATAGTTAAGCCAGCCCCGACACCCGCCAACACCCGCTGACGCGCCCT
GACGGGCTTGTCTGCTCCCGGCATCCGCTTACAGACAAGCTGTGACCGTCTCCGGGAGCT
GCATGTGTCAGAGGTTTTCACCGTCATCACCGAAACGCGCGAGACGAAAGGGCCTCGTGA
TACGCCTATTTTTATAGGTTAATGTCATGATAATAATGGTTTCTTAGACGTCAGGTGGCA
CTTTTCGGGGAAATGTGCGCGGAACCCCTATTTGTTTATTTTTCTAAATACATTCAAATA
TGTATCCGCTCATGAGACAATAACCCTGATAAATGCTTCAATAATATTGAAAAAGGAAGA
GTATGAGTATTCAACATTTCCGTGTCGCCCTTATTCCCTTTTTTGCGGCATTTTGCCTTC
CTGTTTTTGCTCACCCAGAAACGCTGGTGAAAGTAAAAGATGCTGAAGATCAGTTGGGTG
CACGAGTGGGTTACATCGAACTGGATCTCAACAGCGGTAAGATCCTTGAGAGTTTTCGCC
CCGAAGAACGTTTTCCAATGATGAGCACTTTTAAAGTTCTGCTATGTGGCGCGGTATTAT
CCCGTATTGACGCCGGGCAAGAGCAACTCGGTCGCCGCATACACTATTCTCAGAATGACT
TGGTTGAGTACTCACCAGTCACAGAAAAGCATCTTACGGATGGCATGACAGTAAGAGAAT
TATGCAGTGCTGCCATAACCATGAGTGATAACACTGCGGCCAACTTACTTCTGACAACGA
TCGGAGGACCGAAGGAGCTAACCGCTTTTTTGCACAACATGGGGGATCATGTAACTCGCC
TTGATCGTTGGGAACCGGAGCTGAATGAAGCCATACCAAACGACGAGCGTGACACCACGA
TGCCTGTAGCAATGGCAACAACGTTGCGCAAACTATTAACTGGCGAACTACTTACTCTAG
CTTCCCGGCAACAATTAATAGACTGGATGGAGGCGGATAAAGTTGCAGGACCACTTCTGC
GCTCGGCCCTTCCGGCTGGCTGGTTTATTGCTGATAAATCTGGAGCCGGTGAGCGTGGGT
CTCGCGGTATCATTGCAGCACTGGGGCCAGATGGTAAGCCCTCCCGTATCGTAGTTATCT
ACACGACGGGGAGTCAGGCAACTATGGATGAACGAAATAGACAGATCGCTGAGATAGGTG
CCTCACTGATTAAGCATTGGTAACTGTCAGACCAAGTTTACTCATATATACTTTAGATTG
ATTTAAAACTTCATTTTTAATTTAAAAGGATCTAGGTGAAGATCCTTTTTGATAATCTCA
TGACCAAAATCCCTTAACGTGAGTTTTCGTTCCACTGAGCGTCAGACCCCGTAGAAAAGA

FIG. 23D

TCAAAGGATCTTCTTGAGATCCTTTTTTTCTGCGCGTAATCTGCTGCTTGCAAACAAAAA
AACCACCGCTACCAGCGGTGGTTTGTTTGCCGGATCAAGAGCTACCAACTCTTTTTCCGA
AGGTAACTGGCTTCAGCAGAGCGCAGATACCAAATACTGTCCTTCTAGTGTAGCCGTAGT
TAGGCCACCACTTCAAGAACTCTGTAGCACCGCCTACATACCTCGCTCTGCTAATCCTGT
TACCAGTGGCTGCTGCCAGTGGCGATAAGTCGTGTCTTACCGGGTTGGACTCAAGACGAT
AGTTACCGGATAAGGCGCAGCGGTCGGGCTGAACGGGGGGTTCGTGCACACAGCCCAGCT
TGGAGCGAACGACCTACACCGAACTGAGATACCTACAGCGTGAGCTATGAGAAAGCGCCA
CGCTTCCCGAAGGGAGAAAGGCGGACAGGTATCCGGTAAGCGGCAGGGTCGGAACAGGAG
AGCGCACGAGGGAGCTTCCAGGGGGAAACGCCTGGTATCTTTATAGTCCTGTCGGGTTTC
GCCACCTCTGACTTGAGCGTCGATTTTTGTGATGCTCGTCAGGGGGGCGGAGCCTATGGA
AAAACGCCAGCAACGCGGCCTTTTTACGGTTCCTGGCCTTTTGCTGGCCTTTTGCTCACA
TGGCTCGACAGATCT

*FIG. 23E* titres are shown in lacZ forming units (L.F.U.)/ml
vectors used are indicated in boxes above the bars

Primers for cloning TRE into EIAV LTR

P1-U3a1 **(the incorporated *Xho*I site is underlined)**

5'- AAA CTC GAG CAA AGC ATG CCT GCA GGA ATT CG

P2-U3a2 **(the incorporated *Xho*I site is underlined)**

5'- AAA CTC GAG TTT ATA AAA CCC CTC ATA AAA ACC CCA C

P3-U3bRU51 (Bold region corresponds to end of TRE, before homology with U3b region starts; the incorporated *Xma*I site is underlined)

5'- AAA CCC GGG TCG AGT GTT TTT ACA GTA TAT AAG TGC TTG TAT TC

P4-U3bRU52 **(the incorporated *Xma*I site is underlined)**

5'- AAA CCC GGG GAG CGC AGC GAG TCA GTG AGC GAG

*FIG. 30*

Nucleotide sequence of the EIAV-TRE hybrid LTR. The *Xho*I, *Xma*I and *Sap*I sites are marked in bold.

```
                     SbfI
                   ---------
          BstAPI
        ------------
  XhoI        SphI               EcoRVHindIII  ClaI              SapI
 ------      ------             ------------- ------           --------
  1  CTCGAGCAAA GCATGCCTGC AGGAATTCGA TATCAAGCTT ATCGATACCG TCGAATTGGA AGAGCTTTAA ATCCTGGCAC ATCTCATGTA
                                                                   >>...............'ENV...............>

                                                                         PsiI   XhoI
                                                                        ------ -------
 91  TCAATGCCTC AGTATGTTTA GAAAAACAAG GGGGGAACTG TGGGGTTTTT ATGAGGGGTT TTATAAACTC GAGTTTACCA CTCCCTATCA
                                                                                        >>.....TRE'......>
                                                                                        >>.....TRP'......>
                                                  >>...........LTR'............>>
     >........'ENV........>>

181  GTGATAGAGA AAAGTGAAAG TCGAGTTTAC CACTCCCTAT CAGTGATAGA GAAAAGTGAA AGTCGAGTTT ACCACTCCCT ATCagtgata
     >..........................................TRE'...........................................>

271  GAGAAAAGTG AAAGTCGAGT TTACCACTCC CTATCAGTGA TAGAGAAAAG TGAAAGTCGA GTTTACCACT CCCTATCAGT GATAGAGAAA
     >..........................................TRE'...........................................>

361  AGTGAAAGTC GAGTTTACCA CTCCCTATCA GTGATAGAGA AAAGTGAAAG TCGAGTTTAC CACTCCCTAT CAGTGATAGA GAAAAGTGAA
     >..........................................TRE'...........................................>

                    XmaI
                   ------
                    SmaI                                           MunI
                   ------                                         -------
451  AGTCGAGCTC GGTACCCGGG TCGAGTGTTT TTACAGTATA TAAGTGCTTG TATTCTGACA ATTGGGCACT CAGATTCTGC GGTCTGAGTC
                   >>.................................'LTR'...................................>
     >....TRE'.....>>

541  CCTTCTCTGC TGGGCTGAAA AGGCCTTTGT AATAAATATA ATTCTCTACT CAGTCCCTGT CTCTAGTTTG TCTGTTCGAG ATCCTACAGA
     >.........................................'LTR'..........................................>>
          StyI
        -------
631  GCTCATGCCT TGGCGTAATC ATGGTCATAG CTGTTTCCTG TGTGAAATTG TTATCCGCTC ACAATTCCAC ACAACATACG AGCCGGAAGC
```

*FIG. 33A*

```
721  ATAAAGTGTA AAGCCTGGGG TGCCTAATGA GTGAGCTAAC TCACATTAAT TGCGTTGCGC TCACTGCCCG CTTTCCAGTC GGGAAACCTG

           PvuII                                                           SapI
           -------                                                        -------
811  TCGTGCCAGC TGCATTAATG AATCGGCCAA CGCGCGGGGA GAGGCGGTTT GCGTATTGGG CGCTCTTCCG CTTCCTCGCT CACTGACTCG

                  BamHI
                  ------
            XmaI                                      Eco52I                 SalI
           -------                                    ------                ------
            SmaI                PvuII  MluI  NheI      NotI    ClaI HindIII AccI   EcoRV  XbaI
           -------            ---------------------------------------------------------------
901  CTGCGCTCCC CGGGGATCCT CTAGTCAGCT GACGCGTGCT AGCGCGGCCG CATCGATAAG CTTGTCGACG ATATCTCTAG AGCTGAGAAC
```

FIG. 33B

METHODS FOR PRODUCING HIGH TITRE VECTORS AND COMPOSITIONS USED IN SUCH METHODS

FIELD OF THE INVENTION

The present invention relates to packaging and producer cell lines for producing recombinant viral vectors. In particular, the present invention relates to methods for producing pseudotyped viral vectors with a broad host range which can be produced at sufficient titres in packaging and/or producer cells. Most specifically, the invention relates to the generation of pseudotyped retroviral vectors, from stable producer cell lines, having vesicular stomatitis virus-G protein (VSV-G) as the membrane-associated viral envelope protein. The present invention also relates to VSV-G pseudotyped retroviral vectors useful in gene delivery and more specifically, to lentiviral vectors, in particular those derived from equine infectious anaemia virus (EIAV), useful in gene delivery to non-dividing and dividing cells.

BACKGROUND OF THE INVENTION

Retroviruses and vectors derived from them require an envelope protein in order to transduce efficiently a target cell. The envelope protein is expressed in the cell producing the virus or vector and becomes incorporated into the virus or vector particles. Retrovirus particles are composed of a proteinaceous core derived from the gag gene that encases the viral RNA. The core is then encased in a portion of cell membrane that contains an envelope protein derived from the viral env gene.

The envelope protein is produced as a precursor, which is processed into two or three units. These are the surface protein (SU) which is completely external to the envelope, the transmembrane protein (TM) which interacts with the SU and contains a membrane spanning region and a cytoplasmic tail (Coffin 1992 In The Retroviridae, Pleum Press, ed Levy). In some retroviruses a small peptide is removed from the TM.

In order to act as an effective envelope protein, capable of binding to a target cell surface and mediating viral entry, the envelope protein has to interact in a precise manner with the appropriate receptor or receptors on the target cell. This must occur in such a way as to result in intemalisation of the viral particle in an appropriate manner to deliver the genome to the correct compartment of the cell to allow a productive infection to occur.

There have been many attempts to use the envelope protein derived from one virus to package a different virus, this is known as pseudotyping. The efficiency of pseudotyping is highly variable and appears to be strongly influenced by interactions between the cytoplasmic tail of the envelope and the core proteins of the viral particle. The process by which envelope proteins are recruited into budding virions is poorly understood, although it is known that the process is in someway ordered as most cellular proteins are excluded from retroviral particles (Hunter 1994 Semin. Virol. 5:71–83). In some retroviruses budding may occur in the absence of envelope proteins indicating that the env is not necessary for this process but conversely the core can influence the efficiency of envelope incorporation into the particle (Einfeld 1996 Curr. Top. Microbiol. Immunol. 214:133–176; Kräusslich and Welker 1996 Curr. Top. Microbiol. Immunol. 214:25–63).

There is evidence for a precise molecular interaction between a cytoplasmic domain of the envelope protein and the viral core in some retroviruses. By way of example, Januszeski et al (1997 J. Virol. 71: 3613–3619) have shown that minor deletions or substitutions in the cytoplasmic tail of the murine leukemia virus (MLV) envelope protein strongly inhibit incorporation of the envelope protein into viral particles. In the case of HIV-1, Cosson (1996 EMBO J. 15:5783–5788) has shown a direct interaction between the matrix protein of HIV-1 and the cytoplasmic domain of its envelope protein. This interaction between the matrix and envelope protein plays a key role in the incorporation of the envelope protein into budding HIV-1 virions. This is shown by the fact that visna virus can only be efficiently pseudotyped with HIV-1 envelope protein if the amino terminus of the matrix domain of the visna virus gag polyprotein is replaced by the equivalent HIV-1 matrix domain (Dorfman et al, 1994 J. Virol. 68:1689–1696).

However the situation is complex, since truncation of the HIV-1 envelope protein is required for efficient pseudotyping of Molony murine leukemia virus (Mammano et al, 1997 J. Virol. 71:3341–3345), whilst truncation of the human foamy virus envelope protein reduced its ability to pseudotype murine leukemia virus (Lindemann et al, 1997 J. Virol. 71:4815–4820). There is also an environmental component to the interaction between the core of a retrovirus and the cytoplasmic tail of its envelope protein. Prolonged passage of EIAV in some cell lines results in a truncation of the glycoprotein, suggesting that host cell factors can select for a virus on the basis of the C-terminal domain of the envelope protein (Rice et al, 1990 J. Virol. 1990 64: 3770–3778).

These studies and those of many other workers indicate that it is not possible to predict that even closely related retroviruses may be able to pseudotype each other. Further more, if a given envelope protein fails to pseudotype a particular virus, it is not possible to predict the molecular changes that would confer the ability to pseudotype. Pseudotyping has met with some success, but is clearly constrained by the need for compatibility between the virus components and the heterologous envelope protein.

In the construction of retroviral vectors it is desirable to engineer vectors with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector to replace or add to the native envelope protein of the virus.

The MLV envelope protein is capable of pseudotyping a variety of different retroviruses. MLV envelope protein from an amphotropic virus allows transduction of a broad range of cell types including human cells.

The envelope glycoprotein (G) of Vesicular stomatitis virus (VSV), a rhabdovirus, is another envelope protein that has been shown to be capable of pseudotyping certain retroviruses. Its ability to pseudotype MoMLV-based retroviral vectors in the absence of any retroviral envelope proteins was first shown by Emi et al (1991 Journal of Virology 65:1202–1207). WO94/294440 teaches that retroviral vectors may be successfully pseudotyped with VSV-G. These pseudotyped VSV-G vectors may be used to transduce a wide range of mammalian cells. Even more recently, Abe et al (J Virol 1998 72(8) 6356–6361) teach that non-infectious retroviral particles can be made infectious by the addition of VSV-G.

Burns et al (1993 Proc. Natl. Acad. Sci. USA 90: 8033–7) successfully pseudotyped the retrovirus MLV with VSV-G and this resulted in a vector having an altered host range compared to MLV in its native form. VSV-G pseudotyped vectors have been shown to infect not only mammalian cells, but also cell lines derived from fish, reptiles and insects (Burns et al 1993 ibid). They have also been shown to be more efficient than traditional amphotropic envelopes for a variety of cell lines (Yee et al, 1994 Proc. Natl. Acad. Sci. USA 91: 9564–9568, Lin, Emi et al, 1991 Journal of Virology 65:1202–1207). VSV-G protein can be used to pseudotype certain retroviruses because its cytoplasmic tail is capable of interacting with the retroviral cores.

The provision of a non-retroviral pseudotyping envelope such as VSV-G protein gives the advantage that vector particles can be concentrated to a high titre without loss of infectivity (Akkina et al, 1996 J. Virol. 70: 2581–5). Retrovirus envelope proteins are apparently unable to withstand the shearing forces during ultracentrifugation, probably because they consist of two non-covalently linked subunits. The interaction between the subunits may be disrupted by the centrifugation. In comparison the VSV glycoprotein is composed of a single unit. VSV-G protein pseudotyping can therefore offer potential advantages.

However, there are certain disadvantages involved in using producer cell lines to manufacture retrovirus vectors pseudotyped with VSV-G. The first is the difficulty in producing stable cell lines that express VSV-G; the second is the limited life spans of such cell lines.

A number of workers have reported that constitutive high-level expression of VSV-G is toxic to most mammalian cells (eg Emi et al, 1991 Journal of Virology 65:1202–1207, Yee et al, 1994 Proc. Natl. Acad. Sci. USA 91: 9564–9568). A variety of approaches have been used to solve these problems. By way of example, Yee et al (1994 Proc. Natl. Acad. Sci. USA 91: 9564–9568) developed a scheme for producing VSV-G pseudotypes by first producing 293 cell lines that constitutively express gag-pol proteins and contain a retroviral genome. These cell lines were then transfected with a plasmid containing the VSV-G gene downstream of a human cytomegalovirus immediate early promoter followed by the splicing and polyadenylation signals derived from the rabbit β-globin gene. Maximal production of transducing particles was obtained between 48 and 72 hours after transfection.

WO96/35454 teaches that a tetracycline responsive promoter may be used in combination with a nucleotide sequence enocoding vesicular stomatitis virus (VSV-G) to derive a retroviral packaging cell line that inducibly expresses the VSV-G protein, at levels sufficient to support high level virus production, but without the toxic effects of constitutive expression of VSV-G. Ory et al (1996 Proc. Natl. Acad. Sci. USA 93:11400–11406) used the tetR/VP 16 transactivator and tetracycline responsive operator (tet0) minimal promoter system for inducible, tetracycline-regulatable expression of VSV-G in the production of packaging 293 cell lines. Yang et al (1995 Human Gene Therapy 6:1203–1213) used a similar strategy linking seven copies of the tet0 to a minimal HCMV promoter to construct packaging lines derived from NIH-3T3 cells. Chen et al (1996 Proc. Natl. Acad. Sci. USA 93: 10057–10062) modified the tetracycline-inducible system (Gossen & Bujard, 1992 Proc. Natl. Acad. Sci. USA 89: 5547–5551) by fusing the ligand binding domain of the estrogen receptor to the carboxy terminus of a tetracycline-regulated transactivator. Using this system, they constructed cell lines that expressed VSV-G in the absence of tetracycline. VSV-G expression could be induced by β-estradiol regardless of whether the cells were grown with or without tetracycline. However, induction of VSV-G expression was higher when tetracycline was not present. This allowed the construction of stable packaging cell lines that produced transducing viral particles.

Yoshida et al (1997) developed an adenovirus system to produce MoMLV vectors pseudotyped with VSV-G. First a cell line was produced containing a genome plasmid. Secondly this cell line was infected with three different adenoviruses, one encoding the gag-pol gene of MoMLV under the control of the tetracycline transactivator, the second encoding VSV-G under the control of the tetracycline transactivator and the third encoding a nuclear localising transactivator. Transducing particles could be harvested from the resultant cells for a limited time period. Other researchers developing systems to study the export and processing of VSV glycoprotein mutants have used vaccinia virus systems in which the glycoprotein gene was cloned downstream of a bacteriophage T7 promoter. Co-infection of cells with the glycoprotein encoding vaccinia and a vaccinia virus expressing T7 polymerase resulted in a high level of expression of the VSV-G protein (Lefkowitz et al, 1990, Virology 178;373–383).

Arai et al (1998 J. Virol. 72:1115–1121) commented on the fact that the cell lines, in which the expression of VSV-G was controlled by the tetracycline-inducible system, produced low titres of transducing particles in the presence of tetracycline when VSV-G expression should be repressed. This leaky virus production by these packaging cell lines before induction could cause both virus re-entry into the cell culture and accumulation of the vector DNA in the chromosomes during the process of selection and subsequent passages of the packaging cell lines harbouring the virus vector.

Arai et al (1998) reported the development of packaging cell lines in which a completely silent gene for the VSV glycoprotein was present to negate the above problem. This was achieved using a system in which a cassette was produced which encoded the CAG (the chicken β-actin gene promoter connected with the cytomegalovirus immediate-early promoter) followed by the 5' loxP sequence followed by the neo gene with an associated poly A signal followed by the 3' loxP sequence followed by the coding sequence for VSV-G and an associated poly A signal. When transfected into cells only the neo gene product is produced. If an adenovirus encoding the Cre recombinase is then introduced into the cell the neo sequence is removed by recombination and the VSV-G gene is expressed from the CAG promoter.

None of these approaches actually solve the problem associated with genome re-entry into cells once VSV-G expression has been initiated. Although the cell lines produced by Arai et al (1998) will be stable until infected with the Cre recombinase encoding adenoviruses, their results indicated that virus production dropped significantly 5 days after adenovirus infection allowing a limited number of harvests from each batch of producer cells.

Chen et al (1996 Proc. Natl. Acad. Sci. USA 93: 10057–10062) produced two tetracycline/β-estradiol-inducible cell lines which expressed VSV-G. The numbers of transducing particles produced every 48 hours increased over a sixteen days period after induction by either the removal of tetracycline from the medium or by the addition of β-estradiol in the absence of tetracycline in the cell line that produced the lowest level of VSV-G. However in the cell line that produced larger amounts of VSV-G, although an increase in titre was observed in the absence of tetracycline, a rapid fall in the number of transducing particles produced was found when high levels of VSV-G were produced upon β-estradiol induction in the absence of tetracycline. This fall was attributed to the toxic effects of high levels of VSV-G expression. Additional examples of proteins toxic to cells when expressed at high levels are the gag/pol proteins of FIV and HIV.

The present invention seeks to provide an improved method for regulating expression of toxic proteins required for vector production but which are inhibitory to cell growth.

SUMMARY OF THE INVENTION

It is well known that a regulatory system such as a tetracycline system has been used to control expression of VSV-G is the tetracycline system. This system has been used previously in construction of MLV and HIV vector producer lines. In these systems formation of infectious vector particles is initiated by either addition of, or withdrawal of the tetracycline analogue, doxycycline.

The present invention describes a novel system for producing high titre vectors, such as lentiviral vectors wherein the production of the vectors is activated by doxycycline, but only after an initial stimulus with sodium butyrate—full activation is not observed in the presence of doxycycline alone. However following an initial treatment with sodium butyrate, the system can be maintained in an active state by supplying doxycycline alone. This latter feature is a novel, advantageous and unexpected feature of the system described here.

Safety is an important feature of any viral vector system, such as a retroviral system, the main concern being the formation of replication competent retrovirus (RCR) from the packaging system. It is known that the safety profile of the producer system may be improved by minimising the amount of sequence overlap between the components of the system, i.e., the RNA's corresponding to vector genome, the gag/pol open reading frame and envelope. This has the effect of reducing the chance of homologous recombination events between these components. Recombination is thought to take place within the vector particle during the reverse transcription therefore a procedure which minimises the amount of gag/pol or envelope RNA, but particularly the former, in particles is desirable. The strategy of the present invention is to remove sequences which direct inclusion of the gag/pol transcript but which do not influence the levels of protein production.

A construct in which sequences upstream of the major splice donor were deleted was able to produce high levels of gag/pol protein when expressed in stable cell lines created in the selected HEK 293 clone. Transcripts produced from this were efficiently packaged into vector particles. This was a surprising result since although deletion analysis of vector RNA had indicated that the packaging signal was localised to within the R-U5-leader sequence and the 5' 360 nucleotides of the gag open reading frame, it was assumed that sequences vital for packaging were likely to be located upstream of the major splice donor. Furthermore by analogy with observations on the location of the packaging signal in HIV-1 it was also expected that the psi sequence would be located upstream and just downstream of the major splice donor site. In order to reduce the packaging efficiency of gag/pol-encoding RNA the 5' 360 nt of the gag ORF (the region of overlap with the vector RNA) were optimised for expression in human cells. This process results in a base change approximately every third base and would be expected to 1) disrupt any signals important for RNA packaging, 2) virtually eliminate the chance of recombination between the gag/pol and vector RNAs and 3) potentially improve expression of Gag/Pol. Surprisingly Gag/Pol protein production was severely reduced by this manipulation therefore codon optimisation of the entire Gag/Pol ORF was undertaken except for the region in which translational slippage occurs to allow polymerase synthesis and the region of overlap between the C-terminus of gag and the N-terminus of pol. An additional benefit that results from creation of this 'synthetic' gag/pol is that its expression becomes independent of REV/RRE. Therefore if expression of the vector component RNA can be made REV/RRE independent the potential problems of supplying REV at a sufficient level within a packaging cell to allow efficient production of infectious vector particles can be avoided. Previously we have discovered that high levels of REV expression can not be tolerated in TE671 or 293 cells. Thus, collectively our invention relates to a method for making a producer cell capable of making EIAV vector efficiently, safely and in an REV/RRE independent manner.

Previous experiments have shown that the titre obtained from EIAV vectors is increased if it carries an RNA sequence termed the RRE which is acted on by REV. It has been shown in other vector systems that the RRE/REV sequence can be substituted by other elements. For example the cytoplasmic transport element from Mason-Pfizer monkey virus, has been shown to operate effectively in the FIV vector system. However there have been no reports indicating that woodchuck post-transcriptional regulatory element (WPRE) can substitute for the REV/RRE. We have found that in the EIAV vector system this is indeed the case.

Although the experimental work disclosed herein is directed to cell lines for producing infectious, recombinant retroviral vectors, such as lentiviral vectors, the concepts and design are broadly applicable to cell lines for the production of any viral vector where harmful or otherwise undesirable viral proteins must be produced by the cell in order for the viral vector to be produced. The constructs and methods of invention are used to prevent or minimize the production of these proteins until they are needed. At that time, expression is induced for a period of time necessary for the production of the proteins and the assembly of the viral vectors. Examples of such viral vectors include other RNA viral vectors besides retroviral vectors, and DNA viral vectors, such as adenoviral vectors, adeno-associated viral vectors, Herpesvirus vectors (preferably Herpes simplex I virus vectors), and vaccinia virus vectors. Examples of hannful or undesirable proteins include, for adenoviral vectors, products of the E1, E2, E4, and major late genes; for adeno-associated viruses, the rep protein; and for Herpesvirus, the capsid protein. Methods for the construction of such cell lines will be readily apparent to those skilled in the art, given the teachings contained herein. A preferred application of this approach would be the induction of the E2 and E4 adenoviral proteins in the cell lines disclosed in U.S. patent application Ser. No. 08/355,087, "Improved Adenoviral Vectors and Producer Cells, II incorporated herein by reference.

In one broad aspect, the present invention relates to:

A packaging cell comprising:

(a) a first nucleotide sequence (NS) encoding a toxic viral envelope protein operably linked to a promoter; wherein the promoter is operably linked to a promoter; and wherein the promoter is operably linked to at least one copy of a tetracycline responsive element (TRE);

(b) a second NS wherein the second NS comprises a sequence encoding a tetracycline modulator; and (c) a third NS encoding a retrovirus nucleocapsid protein;

such that the expression of the first NS is regulatable by tetracycline or a functional equivalent thereof and optionally an initial stimulus with sodium butyrate or a functional analogue thereof.

A producer cell comprising:

(a) a first nucleotide sequence (NS) encoding a toxic viral envelope protein operably linked to a promoter; wherein the promoter is operably linked to at least one copy of a TRE;

(b) a second NS wherein the second NS comprises a sequence encoding a tetracycline modulator;

(c) a third NS encoding a retrovirus nucleocapsid protein;and (d) a fourth NS comprising a retroviral sequence capable of being encapsidated in the nucleocapsid protein;

such that the retroviral vector particle titre obtainable from the producer cell is regulatable by tetracycline or a functional analogue thereof and optionally an initial stimulus with sodium butyrate or a functional analogue thereof.

A virus producer cell comprising:

(a) a first nucleotide sequence (NS) encoding a toxic viral envelope protein operably linked to a promoter; and wherein the promoter is operably linked to at least one copy of a TRE;

(b) a second NS wherein the second NS comprises a sequence encoding a tetracycline modulator; and (c) a third NS comprising a viral sequence sufficient to produce viral vector particles from the cell;

such that the viral vector particle titre obtainable from the producer cell is regulatable by tetracycline or a functional analogue thereof and optionally an initial stimulus with sodium butyrate or a functional analogue thereof.

A method for producing a retroviral vector wherein the method comprises:

(i) selecting a host cell for retroviral vector production;

(ii) introducing into the host cell:

a first nucleotide sequence (NS) encoding a toxic viral envelope protein operably linked to a promoter; and wherein the promoter is operably linked to at least one copy of a TRE;

a second NS wherein the second NS comprises a sequence encoding a tetracycline modulator;

a third NS encoding a retrovirus nucleocapsid protein;

a fourth NS comprising a retroviral sequence capable of being encapsidated in the nucleocapsid protein; and (iii) incubating the host cell in a culture medium comprising tetracycline or a functional analogue thereof and optionally an initial stimulus withsodium butyrate or a functional analogue thereof.

such that sufficient retroviral vector transducing particles are produced from the host cell.

DETAILED DISCLOSURE

Aspects of the present invention are presented in the accompanying claims and in the following description and drawings. These aspects are presented under separate section headings. However, it is to be understood that the teachings under each section are not necessarily limited to that particular section heading.

Surprising Findings/Advantages

The present invention demonstrates the surprising finding that VSV-G expression in these packaging/producer cells is regulatable by sodium butyrate and doxycycline or functional analogues thereof. Moreover, the present invention demonstrates that full activation of genes under the control of the tetracycline-responsive element (TRE) is only achieved in the presence of an initial stimulus with sodium butyrate. This is different to the performance of the tetracycline system in other situations.

The surprising findings of the present invention are advantageous because, after vector production has been regulated by treatment with sodium butyrate and doxycycline or functional analogues thereof for about 24 hours, sodium butyrate can be removed from the culture medium and vector production can be maintained for at least about five days. More specifically, vector production may be maintained by doxycycline alone. This feature of the producer system is advantageous because sodium butyrate is a toxic compound causing cell cycle arrest and thus is an important compound to remove from vector preparations.

Thus, the present invention is advantageous because it demonstrates that, despite the toxicity of VSV-G, it is possible to construct a stable retroviral producer line that is capable of producing transducing vector particles expressing VSV-G. Thus, the present invention demonstrates that the difficulty associated with producing stable cell lines capable of expressing VSV-G can be overcome.

In one embodiment of the invention, the inclusion of a codon-optimised gag/pol in the vector production system of the present invention is also advantageous because the expression of the gag/pol proteins becomes independent of REV/RRE. Therefore if expression of the vector component RNA can be made REV/RRE independent the potential problems of supplying REV at a sufficient level within a packaging cell to allow efficient production of infectious vector particles can be avoided. This effect is particularly advantageous for cells such as TE671 or HEK 293 cells that cannot tolerate high levels of Rev expression. Moreover, a codon-optimised gag/pol gene is advantageous because codon-optimised gag/pol gene is packaged significantly less efficiently than the wild type gene and represents a significant improvement to the safety profile of the system.

Other advantages are discussed and are made apparent in the following commentary.

Envelope Protein

As used herein, the term "viral envelope protein" refers to the protein embedded in the membrane which encapsulates the nucleocapsid and which protein is responsible for binding to and entry of the infectious virus into the target cell. The viral envelope protein may also be a fusogenic protein. A "fusogenic protein" refers to glycoproteins which cause cells within a culture to fuse in a multinucleate syncytia. Representative examples of fusogenic proteins include but are not limited to VSV-G and Rabies G protein.

Nucleocapsid

As used herein, the term "nucleocapsid" refers to at least the group specific viral core proteins (gag) and the viral polymerase (pl) of a retrovirus genome. These proteins encapsidate the retrovirus-packagable sequences and themselves are further surrounded by a membrane containing an envelope glycoprotein.

Packaging Cell

As used herein, the term "packaging cell" refers to a cell which contains those elements necessary for production of infectious recombinant virus which are lacking in a recombinant viral vector. Typically, such packaging cells contain one or more expression cassettes which are capable of expressing viral structural proteins (such as gag, pol and env) but they do not contain a packaging signal.

In preferred packaging and producer cells, the toxic envelope protein sequences, and nucleocapsid sequences are all stably integrated in the cell. However, one or more of these sequences could also exist in episomal form and gene expression could occur from the episome.

Packaging cell lines may be readily prepared (see also WO 92/05266), and utilised to create producer cell lines for the production of retroviral vector particles. A summary of the available packaging lines is presented in "Retroviruses" (see below). Packaging cell lines suitable for use with the present invention are readily prepared (see also WO 92/05266).

Simple packaging cell lines, comprising a provirus in which the packaging signal has been deleted, have been found to lead to the rapid production of undesirable replication competent viruses through recombination. In order to improve safety, second generation cell lines have been produced wherein the 3'LTR of the provirus is deleted. In such cells, two recombinations would be necessary to produce a wild type virus. A further improvement involves the introduction of the gag-pol genes and the env gene on separate constructs so-called third generation packaging cell lines. These constructs are introduced sequentially to prevent recombination during transfection.

Preferably, the packaging cell lines are second generation packaging cell lines.

Preferably, the packaging cell lines are third generation packaging cell lines.

In these split-construct, third generation cell lines, a further reduction in recombination may be achieved by changing the codons. This technique, based on the redundancy of the genetic code, aims to reduce homology between the separate constructs, for example between the regions of overlap in the gag-pol and env open reading frames.

The packaging cell lines are useful for providing the gene products necessary to encapsidate and provide a membrane protein for a high titre vector particle production. The packaging cell may be a cell cultured in vitro such as a tissue culture cell line. Suitable cell lines include but are not limited to mammalian cells such as murine fibroblast derived cell lines or human cell lines. Preferably the packaging cell line is a human cell line, such as for example: HEK 293, HEK 293T, TE671, HT1080.

Preferably the packaging cell line is selected from the group consisting of Phoenix, 293-SPA and BOSC retroviral vector packaging cell lines.

Preferably the packaging cell is derived from a HEK 293 cell.

Preferably the packaging cell is derived from a HEK 293 101 cell.

Alternatively, the packaging cell may be a cell derived from the individual to be treated such as a monocyte, macrophage, blood cell or fibroblast. The cell may be isolated from an individual and the packaging and vector components administered ex vivo followed by re-administration of the autologous packaging cells.

The packaging cell lines of the present invention provide the gene products necessary to encapsidate and provide a membrane protein for a viral vehicle such as a retrovirus and retrovirus nucleic gene delivery vehicle. As described below, when viral sequences such as retrovirus sequences are introduced into the packaging cell lines, such sequences are encapsidated with the nucleocapsid proteins and these units then bud through the cell membrane to become surrounded in cell membrane and to contain the envelope protein produced in the packaging cell line. These infectious retroviruses are useful as infectious units per se or as gene delivery vectors Producer Cell As used herein, the term "producer cell" or "vector producing cell" refers to a cell which contains all the elements necessary for production of a viral vector such as recombinant viral vectors, recombinant viral vector particles and retroviral delivery systems.

The process of making a producer cell for a viral vector, such as a retroviral or lentiviral vector, involves establishment of cell lines that express the components required for vector particle production (for example gag/pol, vector genome and envelope). In such cell lines, viral sequences such as retroviral sequences are capable of being packaged with the nucleocapsid proteins. Further, the viral sequences such as retroviral sequences that are capable of being packaged may also contain one or more heterologous nucleotide of interest (NOI) that are capable of being expressed in a target cell that is infected by the virions produced in the producer cell.

Preferably, the producer cell is obtainable from a stable producer cell line.

The producer cell lines of the present invention as utilised for the production of infectious pseudotyped retrovirus, and vector particles and especially high titer virions which may also contain one or more NOIs capable of being expressed in a target cell or tissue. The cells are thus useful for packaging a viral vector genome such as a retrovirus genome which may also contain a heterologous NOI capable of being expressed in a target cell or tissue.

There are two common procedures for generating viral producer cells such as retroviral producer cells. In one, the sequences encoding retroviral Gag, Pol and Env proteins are introduced into the cell and stably integrated into the cell genome; a stable cell line is produced which is referred to as the packaging cell line. The packaging cell line produces the proteins required for packaging retroviral RNA but it cannot bring about encapsidation due to the lack of a psi region. However, when a vector genome (having a psi region) is introduced into the packaging cell line, the helper proteins can package the psi-positive recombinant vector RNA to produce the recombinant vector stock. This can be used to transduce the NOI into recipient cells. The recombinant virus whose genome lacks all genes required to make viral proteins can infect only once and cannot propagate. Hence, the NOI is introduced into the host cell genome without the generation of potentially harmful retrovirus. As already mentioned above, a summary of the available packaging lines is presented in "Retroviruses" (1997 Cold Spring Harbour Laboratory Press Eds: J M Coffin, S M Hughes, H E Varmus pp 449).

The second approach is to introduce the three different DNA sequences that are required to produce a retroviral vector particle i.e. the env coding sequences, the gag-pol coding sequence and the defective retroviral genome containing one or more NOIs into the cell at the same time by transient transfection and the procedure is referred to as transient triple transfection (Landau & Littman 1992; Pear et al 1993). The triple transfection procedure has been optimised (Soneoka et al 1995; Finer et al 1994). WO 94/29438 describes the production of producer cells in vitro using this multiple DNA transient transfection method. WO 97/27310 describes a set of DNA sequences for creating retroviral producer cells either in vivo or in vitro for re-implantation.

The components of the viral system which are required to complement the vector genome may be present on one or more "producer plasmids" for transfecting into cells. The present invention also provides a kit for producing a viral vector system, comprising (i) a viral vector genome which is incapable of encoding one or more proteins which are required to produce a vector particle;

(ii) one or more producer plasmid(s) capable of encoding the protein which is not encoded by (i); and optionally (iii) a cell suitable for conversion into a producer cell.

In a preferred embodiment, the viral vector genome is incapable of encoding the proteins gag, pol and env. Preferably the kit comprises one or more producer plasmids encoding env, gag and pol, for example, one producer plasmid encoding env and one encoding gag-pol. Preferably the gag-pol sequence is codon optimised for use in the particular producer cell (see below).

The present invention also provides a producer cell expressing the vector genome and the producer plasmid(s) capable of producing a retroviral vector system useful in the present invention.

By using producer/packaging cell lines, it is possible to propagate and isolate quantities of retroviral vector particles (e.g. to prepare suitable titres of the retroviral vector particles) for subsequent transduction of, for example, a site of interest (such as adult brain tissue). Producer cell lines are usually better for large scale production or vector particles.

Transient transfection has some advantages over the packaging cell method. In this regard, transient transfection avoids the longer time required to generate stable vector-producing cell lines and is used if the vector genome or retroviral packaging components are toxic to cells. If the vector genome encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, PNAS 90:8392–8396). However, the transient method for production of vector has the disadvantage that it is labour intensive, it is not readily adapted to production of vector on a large scale and it is difficult to ensure uniformity between vectors produced by the method at different times.

Producer cells/packaging cells can be of any suitable cell type. Producer cells are generally mammalian cells but can be, for example, insect cells.

As used herein, the term "producer cell" or "vector producing cell" refers to a cell which contains all the elements necessary for production of retroviral vector particles.

Preferably, the producer cell is obtainable from a stable producer cell line.

Preferably, the producer cell is obtainable from a derived stable producer cell line.

Preferably, the producer cell is obtainable from a derived producer cell line.

As used herein, the term "derived producer cell line" is a transduced producer cell line which has been screened and selected for high expression of a marker gene. Such cell lines support high level expression from the retroviral genome. The term "derived producer cell line" is used interchangeably with the term "derived stable producer cell line" and the term "stable producer cell line.

Preferably the derived producer cell line includes but is not limited to a retroviral and/or a lentiviral producer cell.

Preferably the derived producer cell line is an HIV or EIAV producer cell line, more preferably an EIAV producer cell line.

Preferably the envelope protein sequences, and nucleocapsid sequences are all stably integrated in the producer and/or packaging cell. However, one or more of these sequences could also exist in episomal form and gene expression could occur from the episome.

Tetracycline Responsive Element (TRE)

The packaging/producer cell of the present invention comprises a tetracycline responsive element (TRE). In this regard, a first NS encoding a VSV-G env protein is operably linked to promoter and the promoter is operably linked to a TRE.

As used herein, the term "TRE" refers to an element required for activation of transcription in response to a tetracycline modulator. TREs contemplated for use in the present invention (relating to the modulation of expression of a env protein, such as a VSV-G protein), include native, synthetic as well as modified TREs. The TRE may be present in multiple copies and is operatively linked to suitable promoter for expression of the required env protein. As used herein the term "promoter" refers to a specific nucleotide sequence recognised by RNA polymerase, the enzyme that initiates RNA synthesis. This sequence is the site at which transcription can be specifically initiated under proper conditions. When a first NS encoding an env protein, operatively linked to a suitable promoter and a TRE is introduced into a packaging/producer cell, the expression of the env protein may be controlled by either the presence or absence of a tetracycline modulator which is not normally present in the packaging/producer cell.

Tetracycline Modulator

As used herein, the term "tetracycline modulator" refers to a system through which tetracycline compound effects activation of transcription of a first NS encoding an env protein. The actual effect of the tetracycline compound on the activational activity of the TRE will vary depending on the TRE with which the compound interacts. By way of example, in one embodiment of the present invention, the expression of an env protein, such as VSV-G protein, may be controlled, in part, by a tetracycline repressor protein. In this regard, a tetracycline repressor protein is capable of binding to the TRE in the absence of the antibiotic tetracycline or a functional analogue thereof. Thus, in the presence of the antibiotic tetracycline or a functional analogue thereof, the bound tetracycline repressor protein is displaced from the TRE and transcription of the first NS encoding an env protein, such as VSV-G is activated.

In another embodiment of the present invention, the tetracycline modulator may be a fusion product of the amino-terminal DNA binding domain of a tetracycline repressor protein and the carboxy-terminal activation domain of VP-16 from herpes simplex virus (see Gossen and Bujard 1992: PNAS (USA) 89: 1766–1769). In the absence of tetracycline, the modulator binds to the tet-responsive elements (TRE) and efficiently activates transcription. The association between the modulator and the TRE is prevented by tetracycline or a functional analogue thereof. Therefore, in the presence of low concentrations of tetracycline or a functional analogue thereof (such as doxycycline), transcription from TRE is turned off.

Initial Stimulus

The present invention demonstrates that full activation of genes under the control of the tetracycline-responsive element (TRE) is only achieved in the presence of an initial stimulus with sodium butyrate.

As used herein, the term "initial stimulus" with sodium butyrate or a functional analogue thereof means that the activation of genes under the control of a TRE is regulatable by treatment with an effective amount of sodium butyrate or a functional analogue thereof for an initial period of from about 15 hours to about 30 hours. Following this initial treatment with sodium butyrate or a functional analogue thereof the system can be maintained in an active state by supplying a tetracycline analogue alone, such as doxycycline.

Preferably the activation of genes under the control of a TRE is regulatable by treatment with sodium sodium butyrate or a functional analogue thereof for an initial period of from about 18 hours to about 28 hours.

Preferably the activation of genes under the control of a TRE is regulatable by treatment with sodium butyrate or a functional analogue thereof for a period of from about 20 hours to about 25 hours.

Preferably the activation of genes under the control of a TRE is regulatable by treatment with sodium butyrate or a functional analogue thereof for a period of from about 22 hours to about 24 hours.

As used herein, the term "initial stimulus" can also include an additional treatment of the genes under the control of a TRE, with an effective amount of sodium butyrate or a functional analogue, after the initial stimulus in order to boost viral vector production.

Preferably the additional treatment of genes under the control of a TRE with sodium butyrate or a functional analogue thereof is initiated about 5 days after the intial stimulus with sodium butyrate or a functional analogue thereof.

Preferably the additional treatment of genes under the control of a TRE with sodium butyrate or a functional analogue thereof is initiated at a time after the intial stimulus with sodium butyrate or a functional analogue thereof when viral vector production has started to decline.

Functional Analogues

As used herein, the term "functional analogue" refers to any compound that can modulate the activity of a TRE and thus modulate transcription of a NS maintained under the control of the TRE such as a first NS encoding an env protein. By way of example, a functional analogue of tetracycline includes but is not limited to doxycycline. A functional analogue of sodium butyrate includes but is not limited to calcium butyrate.

The constructs of the present invention are incorporated into vectors for introduction into the packaging/producer cells of the present invention.

Vector

As it is well known in the art, a vector is a tool that allows or faciliates the transfer of an entity from one environment to another. In accordance with the present invention, and by way of example, some vectors used in recombinant DNA techniques allow entities, such as a segment of DNA (such as a heterologous DNA segment, such as a heterologous cDNA segment), to be transferred into a host and/or a target cell for the purpose of replicating the vectors comprising the nucleotide sequences (NS) of the present invention and/or expressing the proteins of the invention encoded by the nucleotide sequences (NS) of the present invention. Examples of vectors used in recombinant DNA techniques include but are not limited to plasmids, chromosomes, artificial chromosomes or viruses.

The term "vector" includes expression vectors and/or transformation vectors.

The term "transformation vector" means a construct capable of being transferred from one species to another.

The term "expression vector" means a construct capable of in vivo or in vitrolex vivo expression.

Expression Vector

Preferably, a nucleotide sequence (NS) of present invention which is inserted into a vector is operably linked to a control sequence that is capable of providing for the expression of the coding sequence by the host cell, i.e. the vector is an expression vector. The NS produced by a host recombinant cell may be secreted or may be contained intracellularly depending on the sequence and/or the vector used.

Expression Vector

The term "expression vector" as used in the present invention refers to an assembly which is capable of directing the expression of a nucleotide sequence. The NS expression vector must include a promoter which, when transcribed, is operably linked to the NS, as well as a polyadenylation sequence. Within other embodiments of the invention, the expression vectors described herein may be contained within a plasmid construct.

Expression Cassette

The term "expression cassette" refers to a recombinant DNA molecule containing a desired coding sequence and appropriate nucleic acid sequences necessary for the expression of the operably linked coding sequence in a particular host cell such as a packaging cell. Nucleic acid sequences necessary for expression in eucaryotic cells usually include promoters, enhancers, and termination and polyadenylation signals. The cassette can be removed and inserted into a vector or plasmid as a single unit.

Expression in Vitro

The vectors of the present invention may be transformed or transfected into a suitable host cell (such as a packaging/producer cell) as described below to provide for expression of an NS. This process may comprise culturing a host cell and/or target cell transformed with an expression vector under conditions to provide for expression by the vector of an NS and optionally recovering the expressed NS. The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. The expression of the NOI may be constitutive such that they are continually produced, or inducible, requiring a stimulus to initiate expression. In the case of inducible expression, the production of the NOI may be initiated when required by, for example, addition of an inducer substance to the culture medium, for example tetracycline or a functional analogue thereof.

Non-Viral Delivery

Alternatively, the vectors comprising nucleotide sequences (NS) of the present invention may be introduced into suitable host cells, such as packaging cells, using a variety of non-viral techniques known in the art, such as transfection, transformation, electroporation and biolistic transformation.

As used herein, the term "transfection" refers to a process using a non-viral vector to deliver a gene to a target mammalian cell.

Typical transfection methods include electroporation, DNA biolistics, lipid-mediated transfection, compacted DNA-mediated transfection, liposomes, immunoliposomes, lipofectin, cationiC enzyme-mediated, cationic facial amphiphiles (CFAs) (Nature Biotechnology 1996 14; 556), multivalent cations such as spermine, cationic lipids or polylysine, 1, 2,-bis (oleoyloxy)-3-(trimethylammonio) propane (DOTAP)-cholesterol complexes (Wolff and Trubetskoy 1998 Nature Biotechnology 16: 421) and combinations thereof.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example lipofectam and transfectam™). Typically, nucleic acid constructs are mixed with the transfection agent to produce a composition.

Viral Vectors

The producer cells of the present invention are used to produce viral vectors.

Preferably the vector is a recombinant viral vectors. Suitable recombinant viral vectors include but are not limited to adenovirus vectors, adeno-associated viral (AAV) vectors, herpes-virus vectors, a retroviral vector, lentiviral vectors, baculoviral vectors, pox viral vectors or parvovirus vectors (see Kestler et al 1999 Human Gene Ther 10(10):1619–32).

Retroviral Vectors

Examples of retroviruses include but are not limited to: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV).

Preferred vectors for use in accordance with the present invention are recombinant viral vectors, in particular recombinant retroviral vectors (RRV) such as lentiviral vectors.

The term "recombinant retroviral vector" (RRV) refers to a vector with sufficient retroviral genetic information to allow packaging of an RNA genome, in the presence of packaging components, into a viral particle capable of infecting a target cell. Infection of the target cell includes reverse transcription and integration into the target cell genome. The RRV carries non-viral coding sequences which are to be delivered by the vector to the target cell. An RRV is incapable of independent replication to produce infectious retroviral particles within the final target cell. Usually the RRV lacks a functional gag-pol and/or env gene and/or other genes essential for replication. The vector of the present invention may be configured as a split-intron vector. A split intron vector is described in PCT patent application WO 99/15683.

A detailed list of retroviruses may be found in Coffin et al("Retroviruses" 1997 Cold Spring Harbour Laboratory Press Eds: J M Coffin, S M Hughes, H E Varmus pp 758–763).

Viral Particles

In the present invention, several terms are used interchangeably. Thus, "virion", "virus", "viral particle", "viral vector", and "vector particle" mean virus and virus-like particles that are capable of introducing a nucleic acid into a cell through a viral-like entry mechanism. Such vector particles can, under certain circumstances, mediate the transfer of NOIs into the cells they infect. By way of example, a retrovirus is capable of reverse transcribing its genetic material into DNA and incorporating this genetic material into a target cell's DNA upon transduction. Such cells are designated herein as "target cells".

Lentiviral Vectors

In one embodiment of the present invention, lentiviral vectors are produced.

Lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells (Lewis et al1992 EMBO. J 11: 3053–3058; Lewis and Emerman 1994 J. Virol. 68: 510–516). In contrast, other retroviruses—such as MLV—are unable to infect non-dividing cells such as those that make up a large proportion of, for example, muscle, brain, lung and liver tissue.

Preferred vectors for use in accordance with the present invention are recombinant retroviral vectors, in particular recombinant lentiviral vectors, in particular minimal lentiviral vectors, teachings relating to which are disclosed in WO 99/32646 and in WO98/17815.

Preferably the recombinant lentiviral vector (RLV) of the present invention has a minimal viral genome.

As used herein, the term "minimal viral genome" means that the viral vector has been manipulated so as to remove the non-essential elements and to retain the essential elements in order to provide the required functionality to infect, transduce and deliver a nucleotide sequence of interest to a target host cell.

Minimal Symptoms

It has been demonstrated that a primate lentivirus minimal system can be constructed which requires none of the HIV/SIV additional genes vif, vpr, vpx, vpu, tat, rev and nef for either vector production or for transduction of dividing and non-dividing cells. It has also been demonstrated that an EIAV minimal vector system can be constructed which does not require S2 for either vector production or for transduction of dividing and non-dividing cells. The deletion of additional genes is highly advantageous. Firstly, it permits vectors to be produced without the genes associated with disease in lentiviral (e.g. HIV) infections. In particular, tat is associated with disease. Secondly, the deletion of additional genes permits the vector to package more heterologous DNA. Thirdly, genes whose function is unknown, such as S2, may be omitted, thus reducing the risk of causing undesired effects. Examples of minimal lentiviral vectors are disclosed in WO-A-99/32646 and in WO-A-98/17815.

Thus, preferably, the delivery system used in the invention is devoid of at least tat and S2 (if it is an EIAV vector system), and possibly also vif, vpr, vpx, vpu and nef. More preferably, the systems of the present invention are also devoid of rev. Rev was previously thought to be essential in some retroviral genomes for efficient virus production. For example, in the case of HIV, it was thought that rev and RRE sequence should be included. However, it has been found that the requirement for rev and RRE can be reduced or eliminated by codon-optimisation (see below) or by replacement with other functional equivalent systems such as the Mason-Pfizer monkey virus (MPMV) constitutive transport element (CTE) system. As expression of the codon optimised gag-pol is REV independent, RRE can be removed from the gag-pol expression cassette, thus removing any potential for recombination with any RRE contained on the vector genome.

In a preferred embodiment, the viral genome of the present invention lacks the Rev response element (RRE).

In another preferred embodiment, the viral genome of the present invention comprises a polynucleotide response element.

Preferably the retroviral genome of the present invention comprises a polynucleotide response element.

Preferably the polynucleotide response element is an RRE.

Preferably the polynucleotide response element is responsive to a nucleus to cytoplasm transport factor.

Preferably the polynucleotide response element is a wood chuck hepatitis virus post-transcriptional regulatory element (WHV PRE).

In a preferred embodiment, the system used in the present invention is based on a so-called "minimal" system in which some or all of the additional genes have be removed.

A minimal lentiviral genome for use in the present invention will therefore comprise (5') R-U5—one or more first nucleotide sequences—U3-R (3'). However, the plasmid vector used to produce the lentiviral genome within a host cell/packaging cell will also include transcriptional regulatory control sequences operably linked to the lentiviral genome to direct transcription of the genome in a host cell/packaging cell. These regulatory sequences may be the natural sequences associated with the transcribed retroviral sequence, i.e. the 5' U3 region, or they may be a heterologous promoter such as another viral promoter, for example the CMV promoter. Some lentiviral genomes require additional sequences for efficient virus production. For example, in the case of HIV, rev and RRE sequence are preferably included. However the requirement for rev and RRE may be reduced or eliminated by codon optimisation.

Codon Optimisation

As used herein, the terms "codon optimised" and "codon optimisation" refer to an improvement in codon usage. By way of example, alterations to the coding sequences for viral components may improve the levels of expression of those sequences in the mammalian cells or other cells which are to act as the producer cells for retroviral vector particle production. This is referred to as "codon optimisation". Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation has previously been described in WO99/41397. Different cells differ it their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corrsponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation has a number of other advantages. By virtue of alterations in their sequences, the nucleotide sequences encoding the packaging components of the viral particles, for example lentiviral particles, required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised.

Codon optimisation also overcomes the Rev/RRE requirement for nuclear-cytoplasmic export of lentiviral gag/pol mRNA, rendering expression from the codon-optimised sequences Rev-independent. Codon optimisation also reduces the potential for homologous recombination between different constructs within the vector system (for example between the regions of overlap in the vector, gag-pol and env open reading frames). The overall effect of codon optimisation is therefore a notable increase in viral titre and improved safety.

The gag-pol sequences of the present invention are codon optimised in their entirety, with the exception of the sequence encompassing the frameshift site.

The gag-pol gene comprises two overlapping reading frames encoding the gag-pol proteins. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the -gag-pol gene. For HIV, the region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is not codon optimised. Retaining this fragment enables more efficient expression of the gag-pol proteins.

For EIAV the beginning of the overlap has been taken to be nt 1262 (where nucleotide 1 is the A of the gag ATG). The end of the overlap is at 1461 bp. In order to ensure that the frameshift site and the gag-pol overlap are preserved, the wild type sequence has been retained from nt 1156 to 1465.

Derivations from optimal codon usage may be made, for example, in order to accommodate convenient restriction sites, and conservative amino acid changes may be introduced into the gag-pol proteins.

In a highly preferred embodiment, codon optimisation may be based on highly expressed mammalian genes. The third and sometimes the second and third base may be changed.

Due to the degenerate nature of the Genetic Code, it will be appreciated that numerous gag-pol sequences may be achieved by a skilled worker. Also there are many retroviral variants described which can be used as a starting point for generating a codon optimised gag-pol sequence. Lentiviral genomes can be quite variable. For example there are many quasi-species of HIV-1 which are still functional. This is also the case for EIAV. These variants may be used to enhance particular parts of the transduction process. Examples of HIV-1 variants may be found at http://hiv-web.lanl.gov. Details of EIAV clones may be found at the NCBI database: http://www.ncbi.nlm.nih.gov.

The strategy for codon optimised gag-pol sequences can be used in relation to any retrovirus. This would apply to all lentiviruses, including EIAV, FIV, BIV, CAEV, VMR, SIV, HIV-1 and HIV-2. In addition this method could be used to increase expression of genes from HTLV-1, HTLV-2, HFV, HSRV and human endogenous retroviruses (HERV), MLV and other retroviruses.

In one embodiment, the he vector of the present invention is produced using a codon-optimised gag-pol in the vector production system.

A codon-optimised gag/pol gene is advantageous because codon-optimised gag/pol gene is packaged significantly less efficiently than the wild type gene and represents a significant improvement to the safety profile of the system.

An additional benefit that results from creation of a 'synthetic' codon-optimised gag/pol is that its expression becomes independent of REV/RRE. Therefore if expression of the vector component RNA can be made REV/RRE independent the potential problems of supplying REV at a sufficient level within a packaging cell to allow efficient production of infectious vector particles can be avoided. Thus, the use of a codon-optimised gag/pol gene is advantageous in cells, such as TE671 or 293 cells, where high levels of REV expression can not be tolerated, As described above, the packaging components for a retroviral vector include expression products of gag, pol and env genes. In addition, efficient packaging may depend on a short sequence of 4 stem loops followed by a partial sequence from gag and env (the "packaging signal"). Thus, inclusion of a deleted gag sequence in the retroviral vector genome (in addition to the full gag sequence on the packaging construct) may optimise vector titre. To date efficient packaging has been reported to require from 255 to 360 nucleotides of gag in vectors that still retain env sequences, or about 40 nucleotides of gag in a particular combination of splice donor mutation, gag and env deletions. The present invention demonstrates the surprising finding that a deletion of all but the N-termnial 360 or so nucleotides in gag leads to an increase in vector titre. Thus, preferably, the retroviral vector genome includes a gag sequence which comprises one or more deletions, more preferably the gag sequence comprises about 360 nucleotides derivable from the N-terminus.

Self-Inactivating (SIN) Vector

In one embodiment of the present invention, the viral vector, such as a lentiviral vector, is a self-inactivating vector.

By way of example, self-inactivating retroviral vectors have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus (Yu et al 1986 Proc Natl Acad Sci 83: 3194–3198; Dougherty and Temin 1987 Proc Natl Acad Sci 84: 1197–1201; Hawley et al 1987 Proc Natl Acad Sci 84: 2406–2410; Yee et al 1987 Proc Natl Acad Sci 91: 9564–9568). However, any promoter(s) internal to the LTRs in such vectors will still be transcriptionally active. This strategy has been employed to eliminate effects of the enhancers and promoters in the viral LTRs on transcription from internally placed genes. Such effects include increased transcription (Jolly et al 1983 Nucleic Acids Res 11: 1855–1872) or suppression of transcription (Emerman and Temin 1984 Cell 39: 449–467). This strategy can also be used to eliminate downstream transcription from the 3' LTR into genomic DNA (Herman and Coffin 1987 Science 236: 845–848). This is of particular concern in human gene therapy where it is of critical importance to prevent the adventitious activation of an endogenous oncogene.

Although a SIN vector may improve biosafety, the self-inactivating feature of some SIN vectors precludes vector transduction of packaging cell lines as a method of generating stable SIN vector-producing lines. Although stable SIN vector-producing cell lines have been generated by co-transfecting vector DNA with a selection marker gene into packaging cells and screening for stable cell clones yielding the highest vector titres, this approach has the shortcoming that most of the positively screening clones are genetically unstable and often subject to transcription shut off.

Recently, another approach has been the generation of stable SIN lentivirus vector producer cell lines by transduction using a conditional SIN (cSIN) vector. This approach allows efficient transcription and packaging of full length vector RNA in vector-transduced packaging cells only, yet retains its self-inactivating properties when infecting normal target cells. In this regard, Xu et al (Mol Therapy 2001 3 (1): 97–104) have developed a new vector design using a tetracycline-inducible system in which the 3'LTR U3 transcription regulatory elements (including the TATA box) with the Tetracycline responsive element (TRE) which contains seven copies of the 42 bp tet operator sequence. Consequently, after transduction, transcription of full-length vector RNA becomes dependent on the presence of the synthetic tetracycline-regulated transactivator (tTA). The Xu et al study demonstrates that a stable SIN lentivirus vector producer line can be produced using a non transient production protocol. Thus, high vector titres can be produced from stable packaging cell lines which retain the vectors' self-inactivating properties in target cells that do not express tTA.

Thus, in one embodiment of the present invention, preferably the SIN vector is a conditional SIN (cSIN) vector.

Pseudotyping

In the design of viral vector systmes it is desirable to engineer particles with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector particle to replace or add to the native envelope protein of the virus.

As used herein, the term "pseudotyping" refers to a a technique or strategy whereby an env gene is replaced with a heterologous env gene. Pseudotyping is not a new phenomenon and examples may be found in WO-A-98/05759, WO-A-98/05754, WO-A-97/17457, WO-A-96/09400, WO-A-91/00047 and Mebatsion et al 1997 Cell 90, 841–847. Thus, the term "pseudotype" refers to progeny virions bearing the genome of one virus encapsidated by the envelope protein of another.

Pseudotyping can improve retroviral vector stability and transduction efficiency. A pseudotype of murine leukemia virus packaged with lymphocytic choriomeningitis virus (LCMV) has been described (Miletic et al (1999) J. Virol. 73:6114–6116) and shown to be stable during ultracentrifugation and capable of infecting several cell lines from different species.

Preferably the env protein is an LCMV env protein.

In one embodiment of the present invention the vector system may be pseudotyped with at least a part of a rabies G protein or a mutant, variant, homologue or fragment thereof, or at least a part of a VSV G protein or a mutant, variant, homologue or fragment thereof.

The heterologous env region may be encoded by a gene which is present on a producer plasmid. The producer plasmid may be present as part of a kit for the production of retroviral vector particles.

Rabies G Protein

In one embodiment of the present invention the vector system may be pseudotyped with at least a part of a rabies G protein or a mutant, variant, homologue or fragment thereof.

Teachings on the rabies G protein, as well as mutants thereof, may be found in in WO 99/61639 and well as Rose et al., 1982 J. Virol. 43: 361–364, Hanham et al., 1993 J. Virol.,67, 530–542, Tuffereau et al.,1998 J. Virol., 72, 1085–1091, Kucera et al., 1985 J. Virol 55, 158–162, Dietzschold et al., 1983 PNAS 80, 70–74, Seif et al., 1985 J.Virol., 53, 926–934, Coulon et al.,1998 J. Virol., 72, 273–278, Tuffereau et al.,1998 J. Virol., 72, 1085–10910, Burger et al., 1991 J.Gen. Virol. 72. 359–367, Gaudin et al 1995 J Virol 69, 5528–5534, Benmansour et al 1991 J Virol 65, 4198–4203, Luo et al 1998 Microbiol Immunol 42, 187–193, Coll 1997 Arch Virol 142, 2089–2097, Luo et al 1997 Virus Res 51, 35–41, Luo et al 1998 Microbiol Immunol 42, 187–193, Coll 1995 Arch Virol 140, 827–851, Tuchiya et al 1992 Virus Res 25, 1–13, Morimoto et al 1992 Virology 189, 203–216, Gaudin et al 1992 Virology 187, 627–632, Whitt et al 1991 Virology 185, 681–688, Dietzschold et al 1978 J Gen Virol 40, 131–139, Dietzschold et al 1978 Dev Biol Stand 40, 45–55, Dietzschold et al 1977 J Virol 23, 286–293, and Otvos et al 1994 Biochim Biophys Acta 1224, 68–76. A rabies G protein is also described in EP-A-0445625.

The use of rabies G protein provides vectors which, in vivo, preferentially transduce targeted cells which rabies virus preferentially infects. This includes in particular neuronal target cells in vivo. For a neuron-targeted vector, rabies G from a pathogenic strain of rabies such as ERA may be particularly effective. On the other hand rabies G protein confers a wider target cell range in vitro including nearly all mammalian and avian cell types tested (Seganti et al., 1990 Arch Virol. 34,155–163; Fields et al., 1996 Fields Virology, Third Edition, vol.2, Lippincott-Raven Publishers, Philadelphia, New York).

The tropism of the pseudotyped vector particles may be modified by the use of a mutant rabies G which is modified in the extracellular domain. Rabies G protein has the advantage of being mutatable to restrict target cell range. The uptake of rabies virus by target cells in vivo is thought to be mediated by the acetylcholine receptor (AchR) but there may be other receptors to which in binds in vivo (Hanham et al., 1993 J. Virol.,67, 530–542; Tuffereau et al.,1998 J. Virol., 72, 1085–1091). It is thought that multiple receptors are used in the nervous system for viral entry, including NCAM (Thoulouze et al (1998) J. Virol 72(9):7181–90) and p75 Neurotrophin receptor (Tuffereau C et al (1998) Embo J 17(24) 7250–9).

The effects of mutations in antigenic site III of the rabies G protein on virus tropism have been investigated, this region is not thought to be involved in the binding of the virus to the acetylcholine receptor (Kucera et al., 1985 J. Virol 55, 158–162; Dietzschold et al., 1983 Proc Natl Acad Sci 80, 70–74; Seif et al., 1985 J.Virol., 53, 926–934; Coulon et al.,1998 J. Virol., 72, 273–278; Tuffereau et al.,1998 J. Virol., 72, 1085–10910). For example a mutation of the arginine at amino acid 333 in the mature protein to glutamine can be used to restrict viral entry to olfactory and peripheral neurons in vivo while reducing propagation to the central nervous system. These viruses were able to penetrate motor neurons and sensory neurons as efficiently as the wild type virus, yet transneuronal transfer did not occur (Coulon et al., 1989, J. Virol. 63, 3550–3554). Viruses in which amino acid 330 has been mutated are further attenuated, being unable to infect either motor neurons or sensory neurons after intra-muscular injection (Coulon et al.,1998 J. Virol., 72, 273–278).

Alternatively or additionally, rabies G proteins from laboratory passaged strains of rabies may be used. These can be screened for alterations in tropism. Such strains include the following:

| Genbank accession number | Rabies Strain |
|---|---|
| J02293 | ERA |
| U52947 | COSRV |
| U27214 | NY 516 |
| U27215 | NY771 |
| U27216 | FLA125 |
| U52946 | SHBRV |
| M32751 | HEP-Flury |

By way of example, the ERA strain is a pathogenic strain of rabies and the rabies G protein from this strain can be used for transduction of neuronal cells. The sequence of rabies G from the ERA strains is in the GenBank database (accession number J02293). This protein has a signal peptide of 19 amino acids and the mature protein begins at the lysine residue 20 amino acids from the translation initiation methionine. The HEP-Flury strain contains the mutation from arginine to glutamine at amino acid position 333 in the mature protein which correlates with reduced pathogenicity and which can be used to restrict the tropism of the viral envelope.

WO 99/61639 discloses the nucleic and amino acid sequences for a rabies virus strain ERA (Genbank locus RAVGPLS, accession M38452).

VSV-G Protein

The envelope glycoprotein (G) of Vesicular stomatitis virus (VSV), a rhabdovirus, is another envelope protein that has been shown to be capable of pseudotyping certain retroviruses.

Its ability to pseudotype MoMLV-based retroviral vectors in the absence of any retroviral envelope proteins was first shown by Emi et al (1991 Journal of Virology 65:1202–1207). WO94/294440 teaches that retroviral vectors may be successfully pseudotyped with VSV-G. These pseudotyped VSV-G vectors may be used to transduce a wide range of mammalian cells. Even more recently, Abe et al (J Virol 1998 72(8) 6356–6361) teach that non-infectious retroviral particles can be made infectious by the addition of VSV-G.

Burns et al (1993 Proc. Natl. Acad. Sci. USA 90: 8033–7) successfully pseudotyped the retrovirus MLV with VSV-G and this resulted in a vector having an altered host range compared to MLV in its native form. VSV-G pseudotyped vectors have been shown to infect not only mammalian cells, but also cell lines derived from fish, reptiles and insects (Burns et al 1993 ibid). They have also been shown to be more efficient than traditional amphotropic envelopes for a variety of cell lines (Yee et al, 1994 Proc. Natl. Acad. Sci. USA 91: 9564–9568, Lin, Emi et al, 1991 Journal of Virology 65:1202–1207). VSV-G protein can be used to pseudotype certain retroviruses because its cytoplasmic tail is capable of interacting with the retroviral cores. The provision of a non-retroviral pseudotyping envelope such as VSV-G protein gives the advantage that vector particles can be concentrated to a high titre without loss of infectivity (Akkina et al, 1996 J. Virol. 70: 2581–5). Retrovirus envelope proteins are apparently unable to withstand the shearing forces during ultracentrifugation, probably because they consist of two non-covalently linked subunits. The interaction between the subunits may be disrupted by the centrifugation. In comparison the VSV glycoprotein is composed of a single unit. VSV-G protein pseudotyping can therefore offer potential advantages.

WO 00/52188 describes the generation of pseudotyped retroviral vectors, from stable producer cell lines, having vesicular stomatitis virus-G protein (VSV-G) as the membrane-associated viral envelope protein, and provides a gene sequence for the VSV-G protein.

Mutants, Variants, Homologues and Fragments

In one embodiment, the retroviral vector system used in the present invention may be pseudotyped with a mutant, variant, homologue or fragment of the wild-type Rabies G or VSV-G protein.

The term "wild type" is used to mean an polypeptide having a primary amino acid sequence which is identical with the native protein (i.e., the viral protein).

The term "mutant" is used to mean a polypeptide having a primary amino acid sequence which differs from the wild type sequence by one or more amino acid additions, substitutions or deletions. A mutant may arise naturally, or may be created artificially (for example by site-directed mutagenesis).Preferably the mutant has at least 90% sequence identity with the wild type sequence. Preferably the mutant has 20 mutations or less over the whole wild-type sequence. More preferably the mutant has 10 mutations or less, most preferably 5 mutations or less over the whole wild-type sequence.

The term "variant" is used to mean a naturally occurring polypeptide which differs from a wild-type sequence. A variant may be found within the same viral strain (i.e. if there is more than one isoform of the protein) or may be found within a different strains. Preferably the variant has at least 90% sequence identity with the wild type sequence. Preferably the variant has 20 mutations or less over the whole wild-type sequence. More preferably the variant has 10 mutations or less, most preferably 5 mutations or less over the whole wild-type sequence.

Here, the term "homologue" means an entity having a certain homology with the wild type amino acid sequence and the wild type nucleotide sequence. Here, the term "homology" can be equated with "identity".

In the present context, an homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, an homologous sequence is taken to include a nucleotide sequence which may be at least 75, 85 or 90% identical, preferably at least 95 or 98% identical to the subject sequence. Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, orie residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403–410) and the GENEWORKS suite of comparison tools. Both BLAST and FASTA are available for offline and online searching (see Ausubel et al., 1999 ibid, pages 7–58 to 7–60). However, for some applications, it is preferred to use the GCG Bestfit program. A new tool, called BLAST 2 Sequences is also available for comparing protein and nucleotide sequence (see FEMS Microbiol Lett 1999 174(2): 247–50; FEMS Microbiol Lett 1999 177(1): 187–8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as omithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367–9371 and Horwell D C, Trends Biotechnol. (1995) 13(4), 132–134.

The term "fragment" indicates that the polypeptide comprises a fraction of the wild-type amino acid sequence. It may comprise one or more large contiguous sections of sequence or a plurality of small sections. The polypeptide may also comprise other elements of sequence, for example, it may be a fusion protein with another protein. Preferably the polypeptide comprises at least 50%, more preferably at least 65%, most preferably at least 80% of the wild-type sequence.

With respect to function, the mutant, variant, homologue or fragment should be capable of transducing the target cell when used to pseudotype an appropriate vector.

The viral delivery system used in the present invention may comprise nucleotide sequences that can hybridise to the nucleotide sequence presented herein (including complementary sequences of those presented herein). In a preferred aspect, the present invention covers nucleotide sequences that can hybridise to the nucleotide sequence of the present invention under stringent conditions (e.g. 65° C. and 0.1 SSC) to the nucleotide sequence presented herein (including complementary sequences of those presented herein).

A potential advantage of using the rabies glycoprotein in comparison to the VSV glycoprotein is the detailed knowledge of its toxicity to man and other animals due to the extensive use of rabies vaccines. In particular phase I clinical trials have been reported on the use of rabies glycoprotein expressed from a canarypox recombinant virus as a human vaccine (Fries et al., 1996 Vaccine 14, 428–434), these studies concluded that the vaccine was safe for use in humans.

Adenovirus Vectors

In one embodiment of the present invention, adenoviral vectors are produced.

The adenovirus is a double-stranded, linear DNA virus that does not go through an RNA intermediate. There are over 50 different human serotypes of adenovirus divided into 6 subgroups based on the genetic sequence homology. The natural target of adenovirus is the respiratory and gastrointestinal epithelia, generally giving rise to only mild symptoms. Serotypes 2 and 5 (with 95% sequence homology) are most commonly used in adenoviral vector systems and are normally associated with upper respiratory tract infections in the young.

Adenoviruses are nonenveloped, regular icosohedrons. A typical adenovirus comprises a 140 nm encapsidated DNA virus. The icosahedral symmetry of the virus is composed of 152 capsomeres: 240 hexons and 12 pentons. The core of the particle contains the 36 kb linear duplex DNA which is covalently associated at the 5' ends with the Terminal Protein (TP) which acts as a primer for DNA replication. The DNA has inverted terminal repeats (ITR) and the length of these varies with the serotype.

Entry of adenovirus into cells involves a series of distinct events. Attachment of the virus to the cell occurs via an interaction between the viral fibre (37 nm) and the fibre receptors on the cell. This receptor has recently been identified for Ad2/5 serotypes and designated as CAR (Coxsackie and Adeno Receptor, Tomko et al (1997 Proc Natl Acad Sci 94: 3352–2258). Internalisation of the virus into the endosome via the cellular αvβ3 and αvβ5 integrins is mediated by and viral RGD sequence in the penton-base capsid protein (Wickham et al., 1993 Cell 73: 309–319). Following internalisation, the endosome is disrupted by a process known as endosomolysis, an event which is believed to be preferentially promoted by the cellular αvβ5 integrin (Wickham et al., 1994 J Cell Biol 127: 257–264). In addition, there is recent evidence that the Ad5 fibre knob binds with high affinity to the MHC class 1 α2 domain at the surface of certain cell types including human epithelial and B lymphoblast cells (Hong et al., 1997 EMBO 16: 2294–2306).

Subsequently the virus is translocated to the nucleus where activation of the early regions occurs and is shortly followed by DNA replication and activation of the late regions. Transcription, replication and packaging of the adenoviral DNA requires both host and viral functional protein machinery.

Viral gene expression can be divided into early (E) and late (L) phases. The late phase is defined by the onset of viral DNA replication. Adenovirus structural proteins are generally synthesised during the late phase. Following adenovirus infection, host cellular mRNA and protein synthesis is inhibited in cells infected with most serotypes. The adenovirus lytic cycle with adenovirus 2 and adenovirus 5 is very efficient and results in approximately 10,000 virions per infected cell along with the synthesis of excess viral protein and DNA that is not incorporated into the virion. Early adenovirus transcription is a complicated sequence of interrelated biochemical events but it entails essentially the synthesis of viral RNAs prior to the onset of DNA replication.

Figure 28:
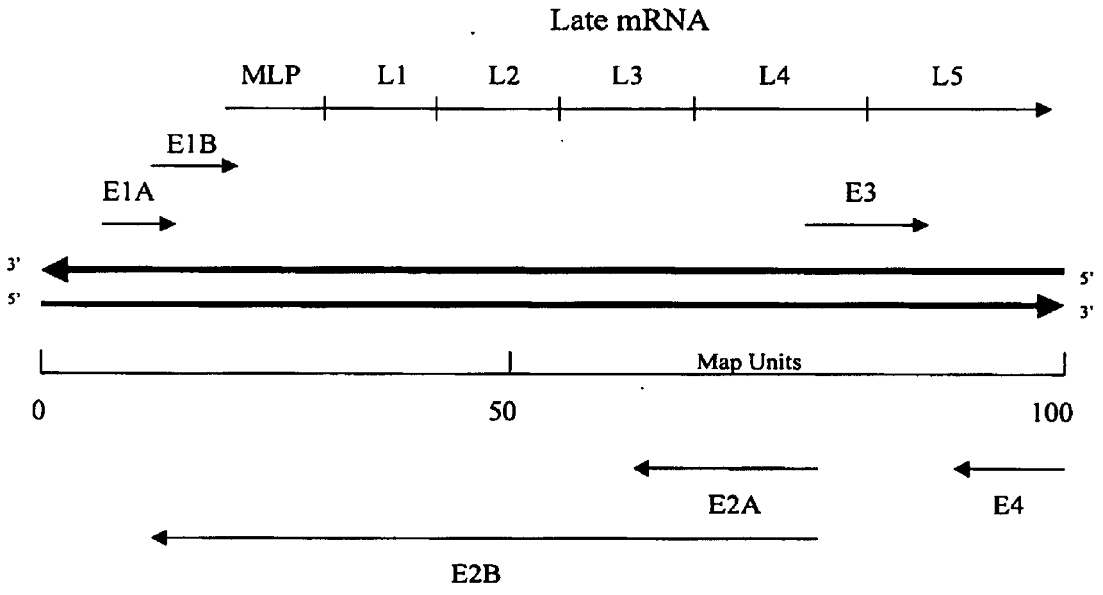

The Schematic diagram presented in FIG. 28 is of the adenovirus genome showing the relative direction and position of early and late gene transcription:

The organisation of the adenovirus genome is similiar in all of the adenovirus groups and specific functions are generally positioned at identical locations for each serotype studied. Early cytoplasmic messenger RNAs are complementary to four defined, noncontiguous regions on the viral DNA. These regions are designated E1–E4. The early transcripts have been classified into an array of intermediate early (E1a), delayed early (E1b, E2a, E2b, E3 and E4), and intermediate regions.

The early genes are expressed about 6–8 hours after infection and are driven from 7 promoters in gene blocks E1–4.

The E1a region is involved in transcriptional transactivation of viral and cellular genes as well as transcriptional repression of other sequences. The E1a gene exerts an important control function on all of the other early adenovirus messenger RNAs. In normal tisssues, in order to transcribe regions E1b, E2a, E2b, E3 or E4 efficiently, active E1a product is required. However, the E1a function may be bypassed. Cells may be manipulated to provide E1a-like functions or may naturally contain such functions. The virus may also be manipulated to bypass the E1a function. The viral packaging signal overlaps with the E1a enhancer (194–358 nt).

The E1b region influences viral and cellular metabolism and host protein shut-off. It also includes the gene encoding the pIX protein (3525–4088 nt) which is required for packaging of the full length viral DNA and is important for the thermostability of the virus. The E1b region is required for the normal progression of viral events late in infection. The E1b product acts in the host nucleus. Mutants generated within the E1b sequences exhibit diminished late viral mRNA accumulation as well as impairment in the inhibition of host cellular transport normally observed late in adenovirus infection. E1b is required for altering functions of the host cell such that processing and transport are shifted in favour of viral late gene products. These products then result in viral packaging and release of virions. E1b produces a 19 kD protein that prevents apoptosis. E1b also produces a 55 kD protein that binds to p53. For a review on adenoviruses and their replication, see WO 96/17053.

The E2 region is essential as it encodes the 72 kDa DNA binding protein, DNA polymerase and the 80 kDa precurser of the 55 kDa Terminal Protein (TP) needed for protein priming to initiate DNA synthesis.

A 19 kDa protein (gp19K) is encoded within the E3 region and has been implicated in modulating the host immune response to the virus. Expression of this protein is upregulated in response to TNF alpha during the first phase of the infection and this then binds and prevents migration of the MHC class I antigens to the epithelial surface, thereby dampening the recognition of the adenoviral infected cells by the cytotoxic T lymphocytes. The E3 region is dispensible in in vitro studies and can be removed by deletion of a 1.9 kb XbaI fragment.

The E4 region is concerned with decreasing the host protein synthesis and increasing the DNA replication of the virus.

There are 5 families of late genes and all are initiated from the major late promoter. The expression of the late genes includes a very complex post-transcriptional control mechanism involving RNA splicing. The fibre protein is encoded within the L5 region. The adenoviral genome is flanked by the inverted terminal repeat which in Ad5 is 103 bp and is essential for DNA replication. 30–40 hours post infection viral production is complete.

Adenoviruses may be converted for use as vectors for gene transfer by deleting the E1 gene, which is important for the induction of the E2, E3 and E4 promoters. The E1-replication defective virus may be propagated in a cell line that provides the E1 polypeptides in trans, such as the human embryonic kidney cell line 293. A therapeutic gene or genes can be inserted by recombination in place of the E1 gene. Expression of the gene is driven from either the E1 promoter or a heterologous promoter.

Even more attenuated adenoviral vectors have been developed by deleting some or all of the E4 open reading frames (ORFs): However, certain second generation vectors appear not to give longer-term gene expression, even though the DNA seems to be maintained. Thus, it appears that the function of one or more of the E4 ORFs may be to enhance gene expression from at least certain viral promoters carried by the virus.

An alternative approach to making a more defective virus has been to "gut" the virus completely maintaining only the terminal repeats required for viral replication. The "gutted" or "gutless" viruses can be grown to high titres with a first generation helper virus in the 293 cell line but it has been difficult to separate the "gutted" vector from the helper virus.

The adenovirus provides advantages as a vector over other gene delivery vector systems for the following reasons:

It is a double stranded DNA nonenveloped virus that is capable of in vivo and in vitro transduction of a broad range of cell types of human and non-human origin. These cells include respiratory airway epithelial cells, hepatocytes, muscle cells, cardiac myocytes, synoviocytes, primary mammary epithelial cells and post-mitotically terminally differentiated cells such as neurons.

Adenoviral vectors are also capable of transducing non dividing cells. This is very important for diseases, such as cystic fibrosis, in which the affected cells in the lung epithelium, have a slow turnover rate. In fact, several trials are underway utilising adenovirus-mediated transfer of cystic fibrosis transporter (CFTR) into the lungs of afflicted adult cystic fibrosis patients.

Adenoviruses have been used as vectors for gene therapy and for expression of heterologous genes. The large (36 kilobase) genome can accommodate up to 8 kb of foreign insert DNA and is able to replicate efficiently in complementing cell lines to produce very high titres of up to $10^{12}$. An adenovirus vector system is thus one of the best systems to study the expression of genes in primary non-replicative cells.

The expression of viral or foreign genes from the adenovirus genome does not require a replicating cell. Adenoviral vectors enter cells by receptor mediated endocytosis. Once inside the cell, adenovirus vectors rarely integrate into the host chromosome. Instead, it functions episomally (independently from the host genome) as a linear genome in the host nucleus. Hence the use of recombinant adenovirus alleviates the problems associated with random integration into the host genome.

In one embodiment of the present invention, the features of adenoviruses may be combined with the genetic stability of retroviruses/lentiviruses which can be used to transduce target cells to become transient retroviral producer cells capable of stably infect neighbouring cells. Such retroviral producer cells which are engineered to express an NOI of the present invention can be implanted in organisms such as animals or humans for use in the treatment of disease such as cancer.

Pox Viruses

In one embodiment of the present invention, poxviral vectors are produced.

Pox viral vectors may be used in accordance with the present invention, as large fragments of DNA are easily cloned into its genome and recombinant attenuated vaccinia variants have been described (Meyer, et al., 1991, J. Gen. Virol. 72: 1031–1038, Smith and Moss 1983 Gene, 25:21–28).

Examples of pox viral vectors include but are not limited to leporipoxvirus: Upton, et al J. Virology 60:920 (1986) (shope fibroma virus); capripoxvirus: Gershon, et al J. Gen. Virol. 70:525 (1989) (Kenya sheep-1); orthopoxvirus: Weir, et al J. Virol 46:530 (1983) (vaccinia); Esposito, et al Virology 135:561 (1984) (monkeypox and variola virus); Hruby, et al PNAS, 80:3411 (1983) (vaccinia); Kilpatrick, et al Virology 143:399 (1985) (Yaba monkey tumour virus); avipoxvirus: Binns, et al J. Gen. Virol 69:1275 (1988) (fowlpox); Boyle, et al Virology 156:355 (1987) (fowlpox); Schnitzlein, et al J. Virological Method, 20:341 (1988) (fowlpox, quailpox); entomopox (Lytvyn, et al J. Gen. Virol 73:3235–3240 (1992)]. Poxvirus vectors are used extensively as expression vehicles for genes of interest in eukaryotic cells. Their ease of cloning and propagation in a variety of host cells has led, in particular, to the widespread use of poxvirus vectors for expression of foreign protein and as delivery vehicles for vaccine antigens (Moss, B. 1991, Science 252: 1662–7).

Preferred vectors for use in accordance with the present invention are recombinant pox viral vectors such as fowl pox virus (FPV), entomopox virus, vaccinia virus such as NYVAC, canarypox virus, MVA or other non-replicating viral vector systems such as those described for example in WO 95/30018. Pox virus vectors have also been described where at least one immune evasion gene has been deleted (see WO 00/29428).

In one preferred embodiment, the pox virus vector is an entomopox virus vector.

Vaccinia Viral Vectors

Preferably the pox viral vector is a vaccinia viral vector.

Preferably, the vector is a vaccinia virus vector such as MVA or NYVAC. Most preferred is the vaccinia strain modified virus ankara (MVA) or a strain derived therefrom. Alternatives to vaccinia vectors include avipox vectors such as fowlpox or canarypox known as ALVAC and strains derived therefrom which can infect and express recombinant proteins in human cells but are unable to replicate.

Preferred vectors for use in accordance with the present invention are recombinant pox viral vectors such as fowl pox virus (FPV), entomopox virus, vaccinia virus such as NYVAC, canarypox virus, MVA or other non-replicating viral vector systems such as those described for example in WO 95/30018.

Hybrid Viral Vectors

In a further broad aspect, the present invention provides a hybrid viral vector system for in vivo delivery of a nucleotide sequence encoding an NOI of the present invention, which system comprises one or more primary viral vectors which encode a secondary viral vector, the primary vector or vectors capable of infecting a first target cell and of expressing therein the secondary viral vector, which secondary vector is capable of transducing a secondary target cell.

Preferably the primary vector is obtainable from or is based on an adenoviral vector and/or the secondary viral vector is obtainable from or is based on a retroviral vector preferably a lentiviral vector.

Retroviral Vector Structure

In one embodiment of the present invention, retroviral vectors are produced.

By way of background information, each retroviral genome comprises genes called gag, pol and env which code for virion proteins and enzymes. The viral core proteins (gag) and the viral polymerase (po) proteins encapsidate the retrovirus-packagable sequences and themselves are further surrounded by a membrane containing an envelope glycoprotein (also known as env).

In the provirus, these genes are flanked at both ends by regions called long terminal repeats (LTRs). The LTRs are responsible for proviral integration, and transcription. They also serve as enhancer-promoter sequences. In other words, the LTRs can control the expression of the viral gene. Encapsidation of the retroviral RNAs occurs by virtue of a psi sequence located at the 5' end of the viral genome.

As used herein, the term "long terminal repeat (LTR) is used in reference to domains of base pairs located at the end of retroviral DNAs.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

Figure 29:
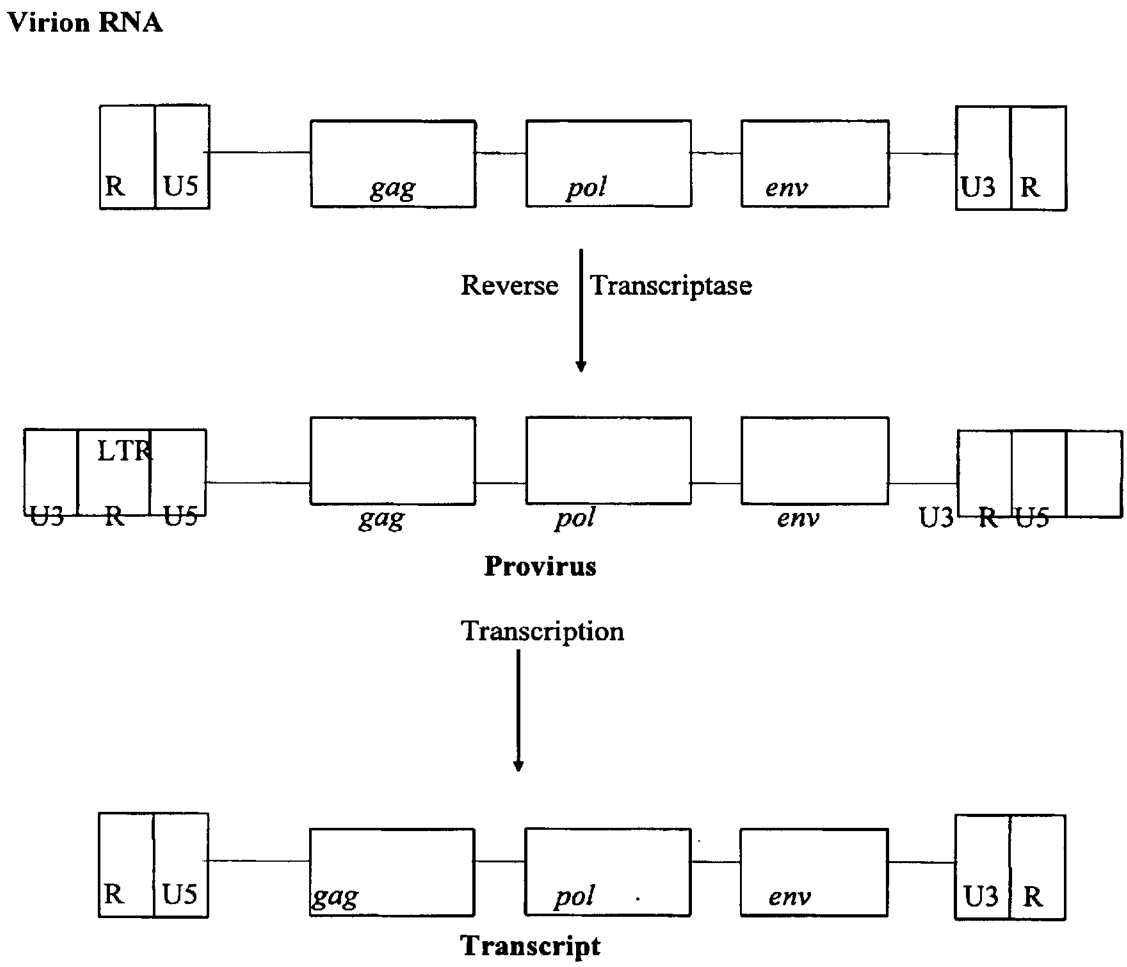

For ease of understanding, a simple, generic structures (not to scale) of the RNA and the DNA forms of the MLV retroviral genome is presented in FIG. 29 in which the elementary features of the LTRs and the relative positioning of gag/pol and env are indicated. Please note that (i) gag/pol and env are normally not spaced apart; and (ii) the overlap normally present between the pco and env genes and the poly A tail normally present at the 3' end of the RNA transcript are not illustrated in FIG. 29.

The basic molecular organisation of an infectious retroviral RNA genome is (5') R-U5—gag/pol, env—U3-R (3'). In a defective retroviral vector genome gag, pol and env may be absent or not functional. The R regions at both ends of the RNA are repeated sequences. U5 and U3 represent unique sequences at the 5' and 3' ends of the RNA genome respectively.

Upon cellular transduction, reverse transcription of the virion RNA into double stranded DNA takes place in the cytoplasm and involves two jumps of the reverse transcriptase from the 5' terminus to the 3' terminus of the template molecule. The result of these jumps is a duplication of sequences located at the 5' and 3' ends of the virion RNA. These sequences then occur fused in tandem on both ends of the viral DNA, forming the long terminal repeats (LTRs) which comprise R U5 and U3 regions. On completion of the reverse transcription, the viral DNA is translocated into the nucleus where the linear copy of the retroviral genome, called a preintegration complex (PIC), is randomly inserted into chromosomal DNA with the aid of the virion integrase to form a stable provirus. The number of possible sites of integration into the host cellular genome is very large and very widely distributed.

Preferably the retroviral genome is introduced into packaging cell lines using retroviral transduction.

Preferably retroviral vector particles (such as MLV vector particles) are prepared in a transient expression system with a different envelope pseudotype to the packaging cell, and used to transduce a retroviral packaging cell.

Preferably the retroviral transduction step identifies retroviral insertions in integration sites that support high level expression of the resulting regulated retroviral genome.

Regulated Retroviral Vectors

In one aspect of the present invention, the retroviral vector is a regulated retroviral vector.

As used herein, the term "regulated retroviral vectors" means a retroviral vector comprising a "regulatable 3'LTR region. As used herein, the terms "regulatable LTR" and "regulatable 3'LTR" include vectors which contain responsive elements which are present in retroviral 3' LTR sequences, either by design or by their nature. Within the regulatable 3'LTR region, the 3'U3 sequence contains most of the transcriptional control elements of the provirus, which include the promoter and multiple enhancer sequences responsive to cellular and in some cases, viral transcriptional activator proteins.

Viral Delivery Systems

When the vector particles are used to transfer NOIs into cells which they transduce, such vector particles also designated "viral delivery systems" or "retroviral delivery systems". Viral vectors, including retroviral vectors, have been used to transfer NOIs efficiently by exploiting the viral transduction process. NOIs cloned into the retroviral genome can be delivered efficiently to cells susceptible to transduction by a retrovirus. Through other genetic manipulations, the replicative capacity of the retroviral genome can be destroyed. The vectors introduce new genetic material into a cell but are unable to replicate.

Preferably the genome of the vector system used in the present invention comprises a cPPT sequence.

The presence of a sequence termed the central polypurine tract (cPPT) may improve the efficiency of gene delivery to non-dividing cells (see WO 00/31200). This cis-acting element is located, for example, in the EIAV polymerase coding region element.

High Titre

It is highly desirable to use high-titre virus preparations in both experimental and practical applications. Techniques for increasing viral titre include using a psi plus packaging signal, as discussed above, and concentration of viral stocks.

As used herein, the term "high titre" means an effective amount of a viral vector or particle which is capable of transducing a target site such as a cell.

As used herein, the term "effective amount" means an amount of a regulated viral or vector particle which is sufficient to induce expression of the NOIs at a target site. In some instances, the term "sufficient amount" is used interchangeably with the term "effective amount".

A high-titre viral preparation for a producer/packaging cell is usually of the order of $10^5$ to $10^7$ t.u. per ml. (The titer is expressed in transducing units per ml (t.u./ml) as titred on the canine osteosarcoma D17 cell line). For transduction in tissues such as the brain, it is necessary to use very small volumes, so the viral preparation is concentrated by ultracentrifugation. The resulting preparation should have at least $10^8$ t.u./ml, preferably from $10^8$ to $10^9$ t.u./ml, more preferably at least $10^9$ t.u./ml.

Preferably the retroviral vector is produced at high titre.

Preferably the retroviral vector produced at high titre is a lentiviral vector.

Preferably a recombinase assisted mechanism is used which facilitates the production of high titre regulated lentiviral vectors from the producer cells of the present invention.

As used herein, the term "recombinase assisted system" includes but is not limited to a system using the Cre recombinase/loxP recognition sites of bacteriophage P1 or the site-specific FLP recombinase of *S. cerevisiae* which catalyses recombination events between 34 bp FLP recognition targets (FRTs).

The site-specific FLP recombinase of *S. cerevisiae* which catalyses recombination events between 34 bp FLP recognition targets (FRTs) has been configured into DNA constructs in order to generate high level producer cell lines using recombinase-assisted recombination events (Karreman et al (1996) NAR 24:1616–1624). A similar system has been developed using the Cre recombinase/loxP recognition sites of bacteriophage P1 (see PCT/GB00/03837; Vanin et al (1997) J. Virol 71:7820–7826). This was configured into a lentiviral genome such that high titre lentiviral producer cell lines were generated.

Preferably a high titre retroviral vector is produced using a modified and/or extended packaging signal.

Packaging Signal

As used herein, the term "packaging signal" which is refered to interchangeably as "packaging sequence" or "psi" is used in reference to the non-coding sequence located within the retroviral genome which is required for encapsidation of retroviral RNA strands during viral particle formation. In HIV-1, this sequence has been mapped to loci extending from upstream of the major splice donor site (SD) to at least the gag start codon. Several retroviral vectors use the minimal packaging signal (also referred to as the psi sequence) needed for encapsidation of the viral genome. By way of example, this minimal packaging signal encompasses bases 212 to 563 of the Mo-MLV genome (Mann et al 1983: Cell 33:153

As used herein, the term "extended packaging signal" or "extended packaging sequence" refers to the use of sequences around the psi sequence with further extension into the gag gene. The inclusion of these additional packaging sequences may increase the efficiency of insertion of vector RNA into viral particles.

Preferably a high titre lentiviral vector is produced using a modified packaging signal.

Preferably the lentiviral construct is a based on an EIAV vector genome where all the accessory genes are removed.

Accessory Genes

As used herein, the term "accessory genes" refer to a variety of virally encoded accessory proteins capable of modulating various aspects of retroviral replication and infectivity. These proteins are discussed in Coffin et al (ibid) (Chapters 6 and 7). Examples of accessory proteins in lentiviral vectors include but are not limited to tat, rev, nef, vpr, vpu, vif, vpx. An example of a lentiviral vector useful in the present invention is one which has all of the accessory genes removed.

Transcriptional Control

The control of proviral transcription remains largely with the noncoding sequences of the viral LTR. The site of transcription initiation is at the boundary between U3 and R in the 5'LTR (as shown in FIG. 29) and the site of poly (A) addition (termination) is at the boundary between R and U5 in the 3'LTR (as shown in FIG. 29). The U3 sequence contains most of the transcriptional control elements of the provirus, which include the promoter and multiple enhancer sequences responsive to cellular and in some cases, viral transcriptional activator proteins.

An LTR present, for example, in a construct of the present invention and as a 3'LTR in the provirus of, for example, a target cell of the invention may be a native LTR or a heterologous regulatable LTR. It may also be a transcriptionally quiescent LTR for use in SIN vector technology.

The term "regulated LTR" also includes an inactive LTR such that the resulting provirus in the target cell can not produce a packagable viral genome (self-inactivating (SIN) vector technology).

Preferably the regulated retroviral vector of the present invention is a self-inactivating (SIN) vector.

Targeted Vector

The term "targeted vector" refers to a vector whose ability to infect/transfect/transduce a cell or to be expressed in a host and/or target cell is restricted to certain cell types within the host organism, usually cells having a common or similar phenotype. Preferably the targeted vector comprises a nucleotide sequence of interest (NOI) for delivery to a specific cell type.

Nucleotide Sequence of Interest (NOI)

With the present invention, the term NOI (i.e. nucleotide sequence of interest) includes any suitable nucleotide sequence, which need not necessarily be a complete naturally occuring DNA sequence. Thus, the DNA sequence can be, for example, a synthetic DNA sequence, a recombinant DNA sequence (i.e. prepared by use of recombinant DNA techniques), a cDNA sequence or a partial genomic DNA sequence, including combinations thereof. The DNA sequence need not be a coding region. If it is a coding region, it need not be an entire coding region. In addition, the DNA sequence can be in a sense orientation or in an anti-sense orientation. Preferably, it is in a sense orientation. Preferably, the DNA is or comprises cDNA.

The NOI or NOIs may be under the expression control of an expression regulatory element, usually a promoter or a promoter and enhancer. The enhancer and/or promoter may be preferentially active in a hypoxic or ischaemic or low glucose environment, such that the NOI is preferentially expressed in the particular tissues of interest, such as in the environment of a tumour, arthritic joint or other sites of ischaemia. Thus any significant biological effect or deleterious effect of the NOI on the individual being treated may be reduced or eliminated. The enhancer element or other elements conferring regulated expression may be present in multiple copies. Likewise, or in addition, the enhancer and/or promoter may be preferentially active in one or more specific cell types—such as any one or more of macrophages, endothelial cells or combinations thereof. Further examples include include respiratory airway epithelial cells, hepatocytes, muscle cells, cardiac myocytes, synoviocytes, primary mammary epithelial cess and post-mitotically terminally differentiated non-replicating cells such as macrophages neurons.

NOIs

In accordance with the present invention, suitable NOI sequences include those that are of therapeutic and/or diagnostic application such as, but are not limited to: sequences encoding cytokines, chemokines, hormones, antibodies, engineered immunoglobulin-like molecules, a single chain antibody, fusion proteins, enzymes, immune co-stimulatory molecules, immunomodulatory molecules, anti-sense RNA, a transdominant negative mutant of a target protein, a toxin, a conditional toxin, an antigen, a tumour suppressor protein and growth factors, membrane proteins, vasoactive proteins and peptides, anti-viral proteins and ribozymes, and derivatives therof (such as with an associated reporter group). When included, such coding sequences may be typically operatively linked to a suitable promoter, which may be a promoter driving expression of a ribozyme(s), or a different promoter or promoters, such as in one or more specific cell types.

Suitable NOIs for use in the invention in the treatment or prophylaxis of cancer include NOIs encoding proteins which: destroy the target cell (for example a ribosomal toxin), act as: tumour suppressors (such as wild-type p53); activators of anti-tumour immune mechanisms (such as cytokines, co-stimulatory molecules and immunoglobulins); inhibitors of angiogenesis; or which provide enhanced drug sensitivity (such as pro-drug activation enzymes); indirectly stimulate destruction of target cell by natural effector cells (for example, strong antigen to stimulate the immune system or convert a precursor substance to a toxic substance which destroys the target cell (for example a prodrug activating enzyme). Encoded proteins could also destroy bystander tumour cells (for example with secreted antitumour antibody-ribosomal toxin fused protein), indirectly stimulated destruction of bystander tumour cells (for example cytokines to stimulate the immune system or procoagulant proteins causing local vascular occlusion) or convert a precursor substance to a toxic substance which destroys bystander tumour cells (eg an enzyme which activates a prodrug to a diffusible drug).

Also, the delivery of NOI(s) encoding antisense transcripts or ribozymes which interfere with expression of cellular genes for tumour persistence (for example against aberrant myc transcripts in Burkitts lymphoma or against bcr-abl transcripts in chronic myeloid leukemia. The use of combinations of such NOIs is also envisaged.

Suitable NOIs for use in the treatment or prevention of ischaemic heart disease include NOIs encoding plasminogen activators. Suitable NOIs for the treatment or prevention of rheumatoid arthritis or cerebral malaria include genes encoding anti-inflammatory proteins, antibodies directed against tumour necrosis factor (TNF) alpha, and anti-adhesion molecules (such as antibody molecules or receptors specific for adhesion molecules).

Examples of hypoxia regulatable therapeutic NOIs can be found in PCT/GB95/00322 (WO-A-9521927).

The expression products encoded by the NOIs may be proteins which are secreted from the cell. Alternatively the NOI expression products are not secreted and are active within the cell. In either event, it is preferred for the NOI expression product to demonstrate a bystander effector or a distant bystander effect; that is the production of the expression product in one cell leading to the killing of additional, related cells, either neighbouring or distant (e.g. metastatic), which possess a common phenotype.

The NOI or NOIs of the present invention may also comprise one or more cytokine-encoding NOIs. Suitable cytokines and growth factors include but are not limited to: ApoE, Apo-SAA, BDNF, Cardiotrophin-1, EGF, ENA-78, Eotaxin, Eotaxin-2, Exodus-2, FGF-acidic, FGF-basic, fibroblast growth factor-10 (Marshall 1998 Nature Biotechnology 16: 129) FLT3 ligand (Kimura et al (1997), Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein (Marshall 1998 ibid), M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNIL-1, TPO, VEGF, GCP-2, GRO/MGSA, GRO-β, GRO-γ, HCC1, 1–309.

Replication Vectors

The nucleotide sequences encoding a NOI may be incorporated into a recombinant replicable vector. The vector may be used to replicate the nucleotide sequence in a compatible host cell. Thus in one embodiment of the present invention, the invention provides a method of delivering an NOI by introducing an NOI into a replicable vector, introducing the vector into a compatible host cell, and growing the host cell under conditions which bring about replication of the vector. The vector may be recovered from the host cell.

Fusion Protein

The NOI of the invention may also be produced as fusion proteins, for example to aid in extraction and purification. Examples of fusion protein partners include glutathione-S-transferase (GST), 6×His (SEQ ID NO: 25), GAL4-(DNA binding and/or transcriptional activation domains) and β-galactosidase. Other examples of fusion protein partners include but are not limited to a fused recombinant MKP-1 enzyme protein comprising an antigenic co-protein such as GST, J3-galactosidase or the lipoprotein D from *Haemophilus influenzae* which are relatively large co-proteins, which solubilize and facilitate production and purification thereof. Alternatively, the fused protein may comprise a carrier protein such as bovine serum albumin (BSA) or keyhole limpet haemocyanin (KLH). In certain embodiments of the present invention, the marker sequence is hexa-histidine peptide, as provided in the pQE vector (Qiagen Inc) and described in Gentz et al (1989 PNAS 86: 821–824). Such fusion proteins are readily expressable in yeast culture (as described in Mitchell et al 1993 Yeast 5: 715–723) and are easily purified by affinity chromatography.

Other recombinant constructions may join the NOI to a nucleotide sequence encoding a polypeptide domain which will facilitate purification of soluble proteins (Kroll D J et al(1993) DNA Cell Biol 12:441–53). Such purification facilitating domains include, but are not limited to, metal chelating peptides such as histidine-tryptophan modules that allow purification on immobilized metals (Porath J (1992) Protein Expr Purif 3- 0.26328 1), protein A domains that allow purification on immobilized immunoglobulin, and the domain utilized in the FLAGS extension/affinity purification system (Immunex Corp, Seattle, Wash.).

It may also be convenient to include a proteolytic cleavage site between the fusion protein partner and the protein sequence of interest to allow removal of fusion protein sequences. By way of example, a fusion protein may also be engineered to contain a cleavage site located between the nucleotide sequence encoding the NOI and the heterologous protein sequence, so that the NOI may be cleaved and purified away from the heterologous moiety. The inclusion of a cleavable linker sequence such as Factor XA or enterokinase (Invitrogen, San Diego, Calif.) between the purification domain and the NOI may also be useful to facilitate purification. Preferably the fusion protein will not hinder the activity of the NOI comprising the amino acid sequence of the present invention.

Target Cells

Target cells transduced by the viral vector of the present invention may be used to express the NOI of the present invention under in vitro, in vivo and ex vivo conditions The term "target cell" includes any cell derivable from a suitable organism which a vector is capable of transfecting or transducing. Examples of target cells can include but are not limited to cells capable of expressing the NOI of the present invention under in vitro, in vivo and ex vivo conditions. Examples of such cells include but are not limited to macrophages, endothelial cells or combinations thereof. Further examples include but are not limited to hematopoietic stem cells, lymphocytes, vascular endothelial cells, respiratory epithelial cells, keratinocytes, skeletal and cardiac muscle cells, neurons, cancer cells respiratory airway epithelial cells, hepatocytes, muscle cells, cardiac myocytes, synoviocytes, primary mammary epithelial cells and post-mitotically terminally differentiated non-replicating cells such as macrophages and/or neurons.

In a preferred embodiment, the target cell is a mammalian cell.

In a highly preferred embodiment, the target cell is a human cell.

The term "organism" includes any suitable organism. In a preferred embodiment, the organism is a mammal. In a highly preferred embodiment, the organism is a human.

The present invention also provides a method comprising transforming a host cell (such as a packaging/producer cell) with a NS(s) of the present invention and/or target cell with a viral vector comprising a NOI of the present invention The term "transformed cell" means a host cell and/or a target cell having a modified genetic structure. With the present invention, a cell has a modified genetic structure when a vector comprising an NOI according to the present invention has been introduced into the cell.

Host cells and/or a target cells may be cultured under suitable conditions which allow expression of the NS and/or NOI of the present invention.

The present invention also provides a method comprising culturing a transformed host cell—which cell has been transformed with one or more NS (s) according to the present invention and/or under conditions suitable for the expression of a POI encoded by an NOI.

Regulation of Expression in Vitro/Vivo/Ex Vivo

The present invention also encompasses gene delivery using a viral vector whereby the expression of the NOI is regulated in vitro/in vivo/ex vivo. For example, expression regulation may be accomplished by administering compounds that bind to the NOI, or control regions associated with the NOI or its corresponding RNA transcript to modify the rate of transcription or translation.

Control Sequences

Control sequences operably linked to sequences encoding the NOI include promoters/enhancers and other expression regulation signals. These control sequences may be selected to be compatible with the host cell and/or target cell in which an expression vector comprising an NS and/or a viral vector comprising an NOI is designed to be used. The control sequences may be modified, for example by the addition of further transcriptional regulatory elements to make the level of transcription directed by the control sequences more responsive to transcriptional modulators.

Operably Linked

The term "operably linked" means that the components described are in a relationship permitting them to function in their intended manner. A regulatory sequence "operably linked" to a coding sequence is ligated in such a way that expression of the coding sequence is achieved under condition compatible with the control sequences.

Preferably the nucleotide sequence of the present invention is operably linked to a transcription unit.

The term "transcription unit(s)" as described herein are regions of nucleic acid containing coding sequences and the signals for achieving expression of those coding sequences independently of any other coding sequences. Thus, each transcription unit generally comprises at least a promoter, an optional enhancer and a polyadenylation signal.

Promoters

The term promoter is well-known in the art and is used in the normal sense of the art, e.g. an RNA polymerase binding site. The term encompasses nucleic acid regions ranging in size and complexity from minimal promoters to promoters including upstream elements and enhancers.

The promoter is typically selected from promoters which are functional in mammalian, cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of α-actin, β-actin, tubulin) or, alternatively, a tissue-specific manner (such as promoters of the genes for pyruvate kinase).

Preferably the promoter is a constitutive promoter such as CMV.

Preferably the promoters of the present invention are tissue specific.

Hypoxic Promoters/Enhancers

The enhancer and/or promoter may be preferentially active in a hypoxic or ischaemic or low glucose environment, such that an NOI is preferentially expressed in the particular tissues of interest, such as in the environment of a tumour, arthritic joint or other sites of ischaemia. Thus, any significant biological effect or deleterious effect of the expressed NOI on the individual being treated may be reduced or eliminated. The enhancer element or other elements conferring regulated expression may be present in multiple copies. Likewise, or in addition, the enhancer and/or promoter may be preferentially active in one or more specific cell types—such as any one or more of macrophages, endothelial cells or combinations thereof. Further examples may include but are not limited to respiratory airway epithelial cells, hepatocytes, muscle cells, cardiac myocytes, synoviocytes, primary mammary epithelial cells and post-mitotically terminally differentiated non-replicating cells such as macrophages and/or neurons.

Tissue-Specific Promoters

The promoters of the present invention may be tissue-specific promoters. Examples of suitable tissue restricted promoters/enhancers are those which are highly active in tumour cells such as a promoter/enhancer from a MUC1 gene, a CEA gene or a 5T4 antigen gene. Examples of temporally restricted promoters/enhancers are those which are responsive to ischaemia and/or hypoxia, such as hypoxia response elements or the promoter/enhancer of a grp78 or a grp94 gene. The alpha fetoprotein (AFP) promoter is also a tumour-specific promoter. One preferred promoter-enhancer combination is a human cytomegalovirus (hCMV) major immediate early (MIE) promoter/enhancer combination.

Preferably the promoters of the present invention are tissue specific. That is, they are capable of driving transcription of an NOI (s) in one tissue while remaining largely "silent" in other tissue types.

The term "tissue specific" means a promoter which is not restricted in activity to a single tissue type but which nevertheless shows selectivity in that they may be active in one group of tissues and less active or silent in another group. A desirable characteristic of the promoters of the present invention is that they possess a relatively low activity in the absence of activated hypoxia-regulated enhancer elements, even in the target tissue. One means of achieving this is to use "silencer" elements which suppress the activity of a selected promoter in the absence of hypoxia.

The level of expression of an NOI under the control of a particular promoter may be modulated by manipulating the promoter region. For example, different domains within a promoter region may possess different gene regulatory activities. The roles of these different regions are typically assessed using vector constructs having different variants of the promoter with specific regions deleted (that is, deletion analysis). This approach may be used to identify, for example, the smallest region capable of conferring tissue specificity or the smallest region conferring hypoxia sensitivity.

A number of tissue specific promoters, described above, may be particularly advantageous in practising the present invention. In most instances, these promoters may be isolated as convenient restriction digestion fragments suitable for cloning in a selected vector. Alternatively, promoter fragments may be isolated using the polymerase chain reaction. Cloning of the amplified fragments may be facilitated by incorporating restriction sites at the 5' end of the primers.

Preferably the ischaemic responsive promoter is a tissue restricted ischaemic responsive promoter.

Preferably the tissue restricted ischaemic responsive promoter is a macrophage specific promoter restricted by repression.

Preferably the tissue restricted ischaemic responsive promoter is an endothelium specific promoter.

Preferably the tissue restricted ischaemic responsive promoter of the present invention is an ILRE responsive promoter.

Preferably the vector comprising ILRE responsive promoter is a lentiviral vector.

Preferably the vector comprising ILRE responsive promoter is an autoregulated hypoxia responsive lentiviral vector.

Preferably the vector of the present invention is regulated by glucose concentration.

For example, the glucose-regulated proteins (grp's) such as grp78 and grp94 are highly conserved proteins known to be induced by glucose deprivation (Attenello and Lee 1984 Science 226 187–190). The grp 78 gene is expressed at low levels in most normal healthy tissues under the influence of basal level promoter elements but has at least two critical "stress inducible regulatory elements" upstream of the TATA element (Attenello 1984 ibid; Gazit et al 1995 Cancer Res 55: 1660–1663). Attachment to a truncated 632 base pair sequence of the 5'end of the grp78 promoter confers high inducibility to glucose deprivation on reporter genes in vitro (Gazit et al 1995 ibid). Furthermore, this promoter sequence in retroviral vectors was capable of driving a high level expression of a reporter gene in tumour cells in murine fibrosarcomas, particularly in central relatively ischaemic/fibrotic sites (Gazit et al 1995 ibid).

Inducible Promoters

The promoters of the present invention may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

Enhancer

In addition, any of these promoters may be modified by the addition of further regulatory sequences, for example enhancer sequences. Chimeric promoters may also be used comprising sequence elements from two or more different promoters described above.

The term "enhancer" includes a DNA sequence which binds to other protein components of the transcription initiation complex and thus facilitates the initiation of transcription directed by its associated promoter.

The in vitrol in vivo/ex vivo expression of an NOI may be used in combination with a protein of interest (POI) or a nucleotide sequence of interest (NOI) encoding same.

ILRE

The term "ischaemia like response element"—otherwise written as ILRE—includes an element that is responsive to or is active under conditions of ischaemia or conditions that are like ischaemia or are caused by ischaemia. By way of example, conditions that are like ischaemia or are caused by ischaemia include hypoxia and/or low glucose concentration(s).

Ischaemia can be an insufficient supply,of blood to a specific organ or tissue. A consequence of decreased blood supply is an inadequate supply of oxygen to the organ or tissue (hypoxia). Prolonged hypoxia may result in injury to the affected organ or tissue.

A preferred ILRE is an hypoxia response element (HRE).

HRE

In one preferred aspect of the present invention, there is hypoxia or ischaemia regulatable expression of the retroviral vector components. In this regard, hypoxia is a powerful regulator of gene expression in a wide range of different cell types and acts by the induction of the activity of hypoxia-inducible transcription factors such as hypoxia inducible factor-1 (HIF-1; Wang & Semenza 1993 Proc Natl Acad Sci 90:430), which bind to cognate DNA recognition sites, the hypoxia-responsive elements (HREs) on various gene promoters. Dachs et al (1997 Nature Med 5: 515) have used a multimeric form of the HRE from the mouse phosphoglycerate kinase-1 (PGK-1) gene (Firth et al 1994 Proc Natl Acad Sci 91:6496–6500) to control expression of both marker and therapeutic genes by human fibrosarcoma cells in response to hypoxia in vitro and within solid tumours in vivo (Dachs et al ibid).

Hypoxia response enhancer elements (HREEs) have also been found in association with a number of genes including the erythropoietin (EPO) gene (Madan et al 1993 Proc Natl Acad Sci 90: 3928; Semenza and Wang 1992 Mol Cell Biol 1992 12: 5447–5454). Other HREEs have been isolated from regulatory regions of both the muscle glycolytic enzyme pyrivate kinase (PKM) gene (Takenaka et al 1989 J Biol Chem 264: 2363–2367), the human muscle-specific β-enolase gene (ENO3; Peshavaria and Day 1991 Biochem J 275: 427–433) and the endothelin-1(ET-1) gene (Inoue et al 1989 J Biol Chem 264: 14954–14959).

Preferably the HRE of the present invention is selected from, for example, the erythropoietin HRE element (HREE1), muscle pyruvate kinase (PKM), HRE element, phosphoglycerate kinase (PGK) HRE, β-enolase (enolase 3; ENO3) HRE element, endothelin-1 (ET-1)HRE element and metallothionein II (MTII) HRE element.

Responsive Element

Preferably the ILRE is used in combination with a transcriptional regulatory element, such as a promoter, which transcriptional regulatory element is preferably active in one or more selected cell type(s), preferably being only active in one cell type.

This combination aspect of the present invention is called a responsive element.

Preferably the responsive element comprises at least the ILRE as herein defined.

Non-limiting examples of such a responsive element are presented as OBHRE1 and XiaMac. Another non-limiting example includes the ILRE in use in conjunction with an MLV promoter and/or a tissue restricted ischaemic responsive promoter. These responsive elements are disclosed in WO99/15684.

Other examples of suitable tissue restricted promoters/enhancers are those which are highly active in tumour cells such as a promoter/enhancer from a MUC1 gene, a CEA gene or a 5T4 antigen gene. The alpha fetoprotein (AFP) promoter is also a tumour-specific promoter. One preferred promoter-enhancer combination is a human cytomegalovirus (hCMV) major immediate early (MIE) promoter/enhancer combination.

In one embodiment of the present invention, preferably the responsive elemtn is an ecdysone response element (see WO 97/38117 and WO 99/58155).

Combination with POIs/NOIs

The POI or NOI encoding same may be used in combination with a POI, such as a pro-drug activating enzyme either directly or by vector delivery to, for example, a target cell or target such as an ischaemic target tissue. Instead of or as well as being selectively expressed in target tissues, the POI or NOI encoding same may be used in combination with another POI such as a pro-drug activation enzyme or enzymes or with a nucleotide sequences of interest (NOI) or NOIs which encode a pro-drug activation enzyme or enzymes. These pro-drug activation enzyme or enzymes may have no significant effect or no deleterious effect until the individual is treated with one or more pro-drugs upon which the appropriate pro-drug enzyme or enzymes act. In the presence of the active POI or NOI encoding same, treatment of an individual with the appropriate pro-drug may lead to enhanced reduction in the disease condition such as a reduction in tumour growth or survival.

Pro-Drug POIs

A POI, such as a pro-drug activating enzyme, may be delivered to a disease site, such as a tumour site for the treatment of a cancer. In each case, a suitable pro-drug is used in the treatment of the patient in combination with the appropriate pro-drug activating enzyme. An appropriate pro-drug may be administered in conjunction with the enzyme or vector comprising the nucleotide sequence encoding same. Examples of pro-drugs include: etoposide phosphate (with alkaline phosphatase, Senter et al1988 Proc Natl Acad Sci 85: 4842–4846); 5-fluorocytosine (with cytosine deaminase, Mullen et al1994 Cancer Res 54: 1503–1506); Doxorubicin-N-p-hydroxyphenoxyacetamide (with Penicillin-V-Amidase, Kerr et al1990 Cancer Immunol Immunother 31: 202–206); Para-N-bis(2-chloroethyl) aminobenzoyl glutamate (with carboxypeptidase G2); Cephalosporin nitrogen mustard carbamates (with βb-lactamase); SR4233 (with P450 Reductase); Ganciclovir (with HSV thymidine kinase, Borrelli et al 1988 Proc Natl Acad Sci 85: 7572–7576); mustard pro-drugs with nitroreductase (Friedlos et al1997 J Med Chem 40: 1270–1275) and Cyclophosphamide (with P450 Chen et al1996 Cancer Res 56: 1331–1340).

Examples of suitable pro-drug activation enzymes for use in the invention include a thymidine phosphorylase which activates the 5-fluoro-uracil pro-drugs capcetabine and furtulon; thymidine kinase from Herpes Simplex Virus which activates ganciclovir; a cytochrome P450 which activates a pro-drug such as cyclophosphamide to a DNA damaging agent; and cytosine deaminase which activates 5-fluorocytosine. Preferably, a pro-drug activating enzyme of human origin is used.

POIs and NOIs

Other suitable proteins of interest (POIs) or NOIs encoding same for use in the present invention include those that are of therapeutic and/or diagnostic application such as, but are not limited to: sequences encoding cytokines, chemokines, hormones, antibodies, engineered immunoglobulin-like molecules, a single chain antibody, fusion proteins, enzymes, immune co-stimulatory molecules, immunomodulatory molecules, anti-sense RNA, a transdominant negative mutant of a target protein, a toxin, a conditional toxin, an antigen, a tumour suppressor protein and growth factors, membrane proteins, vasoactive proteins and peptides, anti-viral proteins and ribozymes, and derivatives therof (such as with an associated reporter group). When included, the POIs or NOIs encoding same may be typically operatively linked to a suitable promoter, which may be a promoter driving expression of a ribozyme(s), or a different promoter or promoters, such as in one or more specific cell types.

Cytokines

In one aspect of the present invention the NOI(s) encodes a POI(s) wherein the POI is a cytokine.

As used herein, the term "cytokines" refers to any varied group of proteins that are released from mammalian cells and act on other cells through specific receptors. The term "cytokine" is often used interchangeably with the term "mediator". Cytokines may elicit from the target cell a variety of responses depending on the cytokine and the target cell. By way of example, cytokines may be important in signalling between cells as inflammatory reactions develop. In the initial stages, cytokines such as IL-1 and IL-6 may be released from cells of the tissue where the inflammatory reaction is occurring. Once lymphocytes and mononuclear cells have started to enter the inflammatory site, they may become activated by antigen and release cytokines of their own such as IL-1, TNF, IL-4 and IFNγ which further enhance cellular migration by their actions on the local endothelium. Other cytokines, such as IL-8, are chemotactic or can activate incoming cells. The term "cytokine" includes but is not limited to factors such as cardiotrophin, EGF, FGF-acidic, FGF-basic, flt3 Ligand, G-CSF, GM-CSF, IFN-γ, IGF-I, IGF-II, IL-1α, IL-1β, IL-2, IL-3, IL-4, IL-5, IL-6, IL-7, IL-8, IL-9, IL-10, IL-11, IL-12, IL-13, IL-15, IL-16, IL-17, IL-18 (IGIF), KGF, LIF, M-CSF, Oncostatin M, PDGF-A, PDGF-AB, PDGF-BB, SCF, SCGF, TGF-α, TGF-$β_1$, TNF-α, TNF-β, TPO and VEGF.

Tumour Necrosis Factor (TNF)

Preferably the POI is TNF.

As used herein, the term "tumour necrosis factor (TNF) refers to either of two structurally and functionally related proteins. These are TNF-α (also known as cachectin) and TNF-β (also known as lymphotoxin) TNF-α is producted mainly by monocytes and macrophages, whereas TNF-β is produced by lymphoid cells. The two proteins are about 30% homologous at the amino-acid level, and bind to the same cell surface receptors; both exist as homotrimers. Both TNF-α (cachectin) and TNF-β (lymphotoxin) were originally thought of as selective antitumour agents, but are now known to have a multiplicity of actions. In binding to their receptors, present on virtually all cells examined, they activate a large array of cellular genes and also multiple signal-transduction pathways, kinases, and transcription factors. Their genes are single-copy genes, closely linked within the MHC cluster.

Tumour Necrosis Factor α (TNF-α)

Preferably the POI is TNF-α.

As used herein, the term tumour necrosis factor α (TNF-α) (also known as cachectin) refers to a cytokine that is produced by macrophages, monocytes, endothelial cells, neutrophils, smooth muscle cells, activated lymphocytes, and astrocytes. It is a transmembrane glycoprotein and cytotoxin with a variety of functions, including the ability to mediate the expression of genes for growth factors, cytokines, transcription factors, and receptors. It can cause cytolysis of certain tumour cell lines, it has been implicated in the induction of cachexia (which is a condition caused by chronic disease, such as cancer), it is a potent pyrogen, causing fever by direct action or by stimulation of interleukin 1 secretion, and it can stimulate cell proliferation and induce cell differentiation under certain conditions. The molecule is a homotrimer. Inflammatory stimulators such as TNF-α also cause a rapid (<1 hour) inhibition of chemotactic migration of monocytes with similar kinetics to hypoxia. TNF-α increases HIF-1 binding to DNA and TNF-α is hypoxia-responsive in many cell types, including macrophages.

Chemokines

In one aspect of the present invention the POI is a chemokine

As used herein, the term "chemokine" (also known as intercrine) refers to any of a superfamily of soluble proteins implicated in a wide range of acute and inflammatory processes and other immunoregulatory functions. The chemokines may related by primary structure, especially conservation of a motif of four cysteines, the first two of which are either adjacent of separated by one other residue. As used herein, the term "chemokines" includes a group of at least 18 heparin-binding molecules, including IL-8, which are released at inflammatory sites. These chemokines act via a group of three receptors (so far identified) that are expressed on different leucocyte populations (see Immunology 1996 4th Ed Roitt Brostoff and Male, Mosby publishers, page Chapter 14, page 14.7). Some of the chemokines act selectively on particular populations of leucocytes. Some of the chemokines can activate cells, some are primarily chemotactic, some have both functions. Several inflammatory mediators may be chemotactic. By way of example, several molecules are chemotactic for neutrophils and macrophages. These molecules include C5a, f.Met-Leu-Phe, LTB4 which act on neutrophils, eosinophils and macrophages (see FIG. 14.12 Immunology 1996 $4^{th}$ Ed Roitt Brostoff and Male, Mosby publishers, page Chapter 14, page 14.7). Other chemokines, such as IL-8, macrophage inflammatory protein alpha (MIP-α), inflammatory protein beta (MIP-β) and RANTES which have selective actions on different leucocyte populations. In this respect, the term "chemokines" includes but is not limited to factors such as ENA-78, Eotaxin, Eotaxin-2, Exodus-2, Fractalkine (CX3C), GCP-2, GRO/MGSA, GRO-β, GRO-γ, HCC1, 1–309, IL-8 (72 a.a.), IL-8 (77 a.a.), IP-10, Lymphotactin, MDC (67 a.a.), MDC (69a.a.), MCP-1 (MCAF), Human MCP-2, MCP-3, MCP-4, MDC (67 a.a.), MDC (69 a.a.), MIG, MIP-1α, MIP-1β, MIP-3α, MIP-3β, Human MIP-4, NAP-2, PF-4, RANTES, SDF1α, SDF1α, TARC, C-10, Eotaxin, Exodus-2, JE (MCP-1), KC, MCP-3, MCP-5, MIP-1α, MIP-1γ, RANTES, GROβ/MIP-2 and MCP-1(MCAF).

Bystander Effect

The POI and/or NOI encoding same may be proteins which are secreted from a cell. Alternatively the POI expression products are not secreted and are active within the cell. In either event, it is preferred for the POI expression product to demonstrate a bystander effector or a distant bystander effect; that is the production of the expression product in one cell leading to the killing of additional, related cells, either neighbouring or distant (e.g. metastatic), which possess a common phenotype.

Suitable POIs or NOIs encoding same for use in the present invention in the treatment or prophylaxis of cancer include proteins which: destroy the target cell (for example a ribosomal toxin), act as: tumour suppressors (such as wild-type p53); activators of anti-tumour immune mechanisms (such as cytokines, co-stimulatory molecules and immunoglobulins); inhibitors of angiogenesis; or which provide enhanced drug sensitivity (such as pro-drug activation enzymes); indirectly stimulate destruction of target cell by natural effector cells (for example, strong antigen to stimulate the immune system or convert a precursor substance to a toxic substance which destroys the target cell (for example a prodrug activating enzyme). Encoded proteins could also destroy bystander tumour cells (for example with secreted antitumour antibody-ribosomal toxin fusion protein), indirectly stimulate destruction of bystander tumour cells (for example cytokines to stimulate the immune system or procoagulant proteins causing local vascular occlusion) or convert a precursor substance to a toxic substance which destroys bystander tumour cells (eg an enzyme which activates a prodrug to a diffusible drug).

Also, the delivery of NOI(s) encoding antisense transcripts or ribozymes which interfere with expression of cellular genes for tumour persistence (for example against aberrant myc transcripts in Burkitts lymphoma or against bcr-abl transcripts in chronic myeloid leukemia. The use of combinations of such POIs and/or NOIs encoding same is also envisaged.

Examples of hypoxia regulatable therapeutic NOIs can be found in PCT/GB95/00322 (WO-A-95/21927).

Pharmaceutical Compositions

In one aspect, the present invention provides a pharmaceutical composition, which comprises a viral vector according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the pharmaceutical composition is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose or chalk, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Administration

The invention further provides a method of preventing and/or treating a disorder, such as a cancer disorder in an individual, the method comprising, for example, administering to an individual an viral vector and/or pharmaceutical composition comprising same to a target site.

As used herein, the term "administered" includes but is not limited to delivery by a mucosal route, for example, as a nasal spray or aerosol for inhalation or as an ingestable solution such as by an oral route, or by a parenteral route where delivery is by an injectable form, such as, for example, by a rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) transdermal, intraperitoneal, intracranial, intracerebroventricular, intracerebral, intravaginal, intrauterine, or parenteral (e.g., intravenous, intraspinal, intracavemosal, subcutaneous, transdermal or intramuscular) route.

The viral vector and/or pharmaceutical composition comprising same of the present invention may be administered alone but will generally be administered in admixture with a suitable pharmaceutical excipient, diluent or carrier selected with regard to the intended route of administration and standard pharmaceutical practice.

For example, the viral vector and/or pharmaceutical composition or modified monocyte/macrophage comprising same can be administered orally, buccally or sublingually in the form of tablets, capsules, ovules, elixirs, solutions or suspensions, which may contain flavouring or colouring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The viral vector and/or pharmaceutical composition comprising same can also be administered parenterally, for example, intravenously, intra-arterially, intraperitoneally, intrathecally, intraventricularly, intraurethrally, intrasternally, intracranially, intramuscularly or subcutaneously, or it may be administered by infusion techniques. For such parenteral administration it is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Thus tablets or capsules of the viral vector and/or pharmaceutical composition or comprising same may contain active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The skilled person will appreciate that, in the treatment of certain conditions the agent may be taken as a single dose as needed or desired.

The viral vector and/or pharmaceutical composition or modified monocyte/macrophage comprising same of the present invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the agent and a suitable powder base such as lactose or starch.

Alternatively, the viral vector and/or pharmaceutical composition comprising same of the present invention can be administered in the form of a suppository or pessary, or it may be applied topically in the form of a gel, hydrogel, lotion, solution, cream, ointment or dusting powder. The viral vector and/or pharmaceutical composition comprising same of the present invention may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Individual

As used herein, the term "individual" refers to vertebrates, particularly members of the mammalian species, more in particular, humans.

Treatment

It is to be appreciated that all references herein to treatment include curative, polliative and prophylactic treatment.

Combination Therapy

The viral vector and/or pharmaceutical composition comprising same may be administered alone or in combination for the treatment of a disorder, such as a disorder associated with hypoxia and/or inflammation.

By way of further example, the viral vector and/or pharmaceutical composition may be administered with another agent, such as an NOI at the same moment in time and at the same site. Alternatively, viral vector and/or pharmaceutical composition comprising same may be delivered at a different time and to a different site. In one embodiment, the viral vector and/or pharmaceutical composition comprising same may even be delivered in the same delivery vehicle for the prevention and/or treatment of a disorder associated with hypoxia and/or inflammation.

Preferably the viral vector and/or pharmaceutical composition comprising same is/are administered simultaneously, separately or sequentially.

Dosage

The dosage of the viral vector and/or pharmaceutical composition comprising same of the present invention will depend on the disease state or condition being treated and other clinical factors such as weight and condition of the individual and the route of administration of the compound. Depending upon the half-life of the viral vector in the particular individual, the viral vector and/or pharmaceutical composition comprising same can be administered between several times per day to once a week. It is to be understood that the present invention has application for both human and veterinary use. The methods of the present invention contemplate single as well as multiple administrations, given either simultaneously or over an extended period of time.

Typically, a physician will determine the actual dosage which will be most suitable for an individual subject and it will vary with the age, weight and response of the particular patient and severity of the condition. The dosages below are exemplary of the average case. There can, of course, be individual instances where higher or lower dosage ranges are merited.

In addition or in the alternative the compositions (or component parts thereof) of the present invention may be administered by direct injection. In addition or in the alternative the compositions (or component parts thereof) of the present invention may be administered topically. In addition or in the alternative the compositions (or component parts thereof) of the present invention may be administered by inhalation. In addition or in the alternative the compositions (or component parts thereof) of the present invention may also be administered by one or more of: a mucosal route, for example, as a nasal spray or aerosol for inhalation or as an ingestable solution such as by an oral route, or by a parenteral route where delivery is by an injectable form, such as, for example, by a rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) transdermal, intraperitoneal, intracranial, intracerebroventricular, intracerebral, intravaginal, intrauterine, or parenteral (e.g., intravenous, intraspinal, intracavemosal, subcutaneous, transdermal or intramuscular) route.

By way of further example, the pharmaceutical composition of the present invention may be administered in accordance with a regimen of 1 to 10 times per day, such as once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Disorders

The present invention is believed to have a wide therapeutic applicability—depending on inter alia the selection of the one or more NOIs.

For example, the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of bums, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

EXAMPLES

Figure 1B:
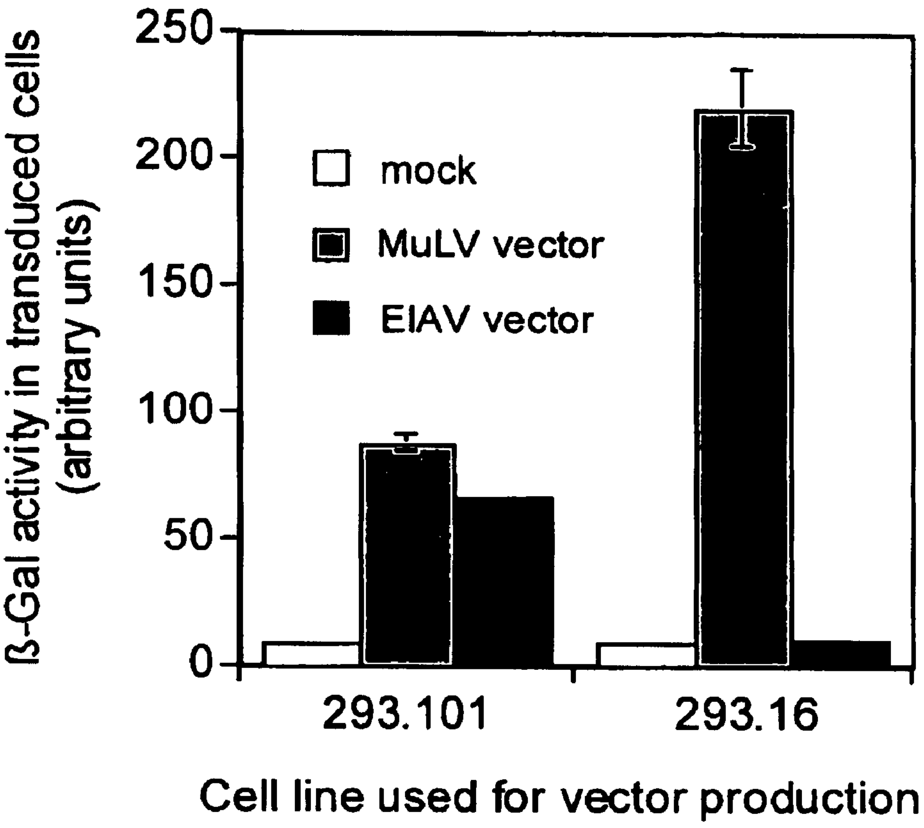
Figure 2:
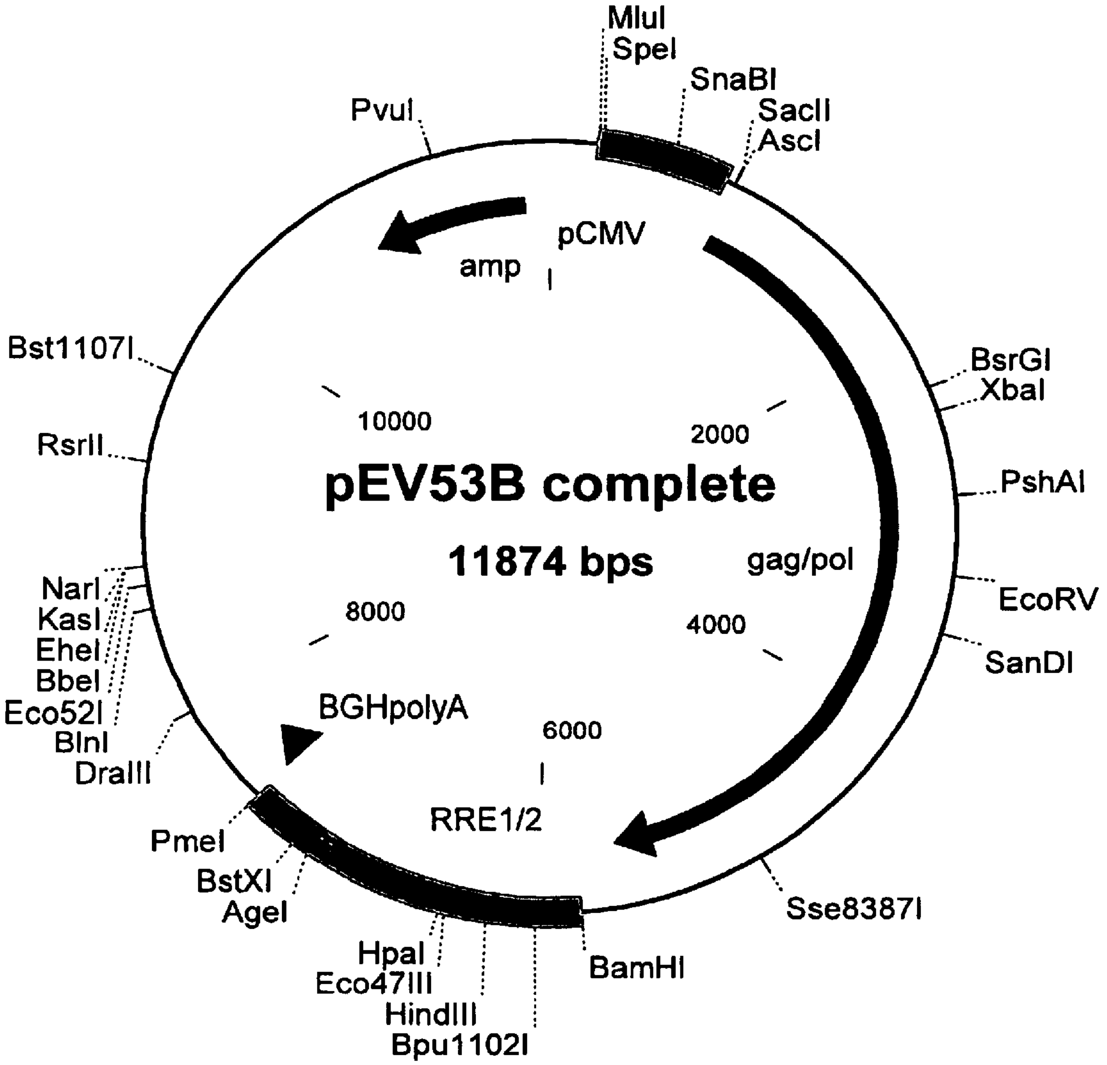
Figure 4:
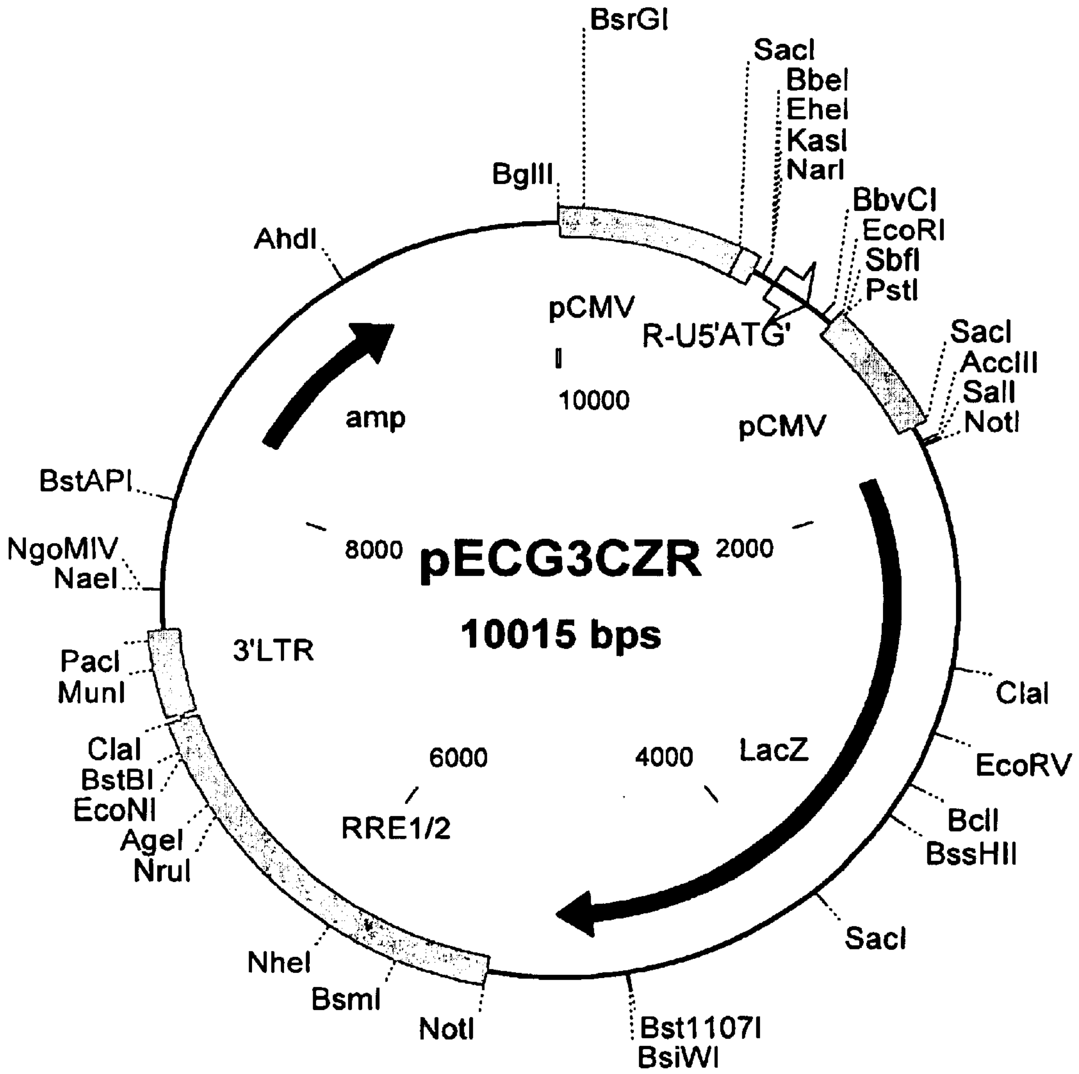
Figure 6:
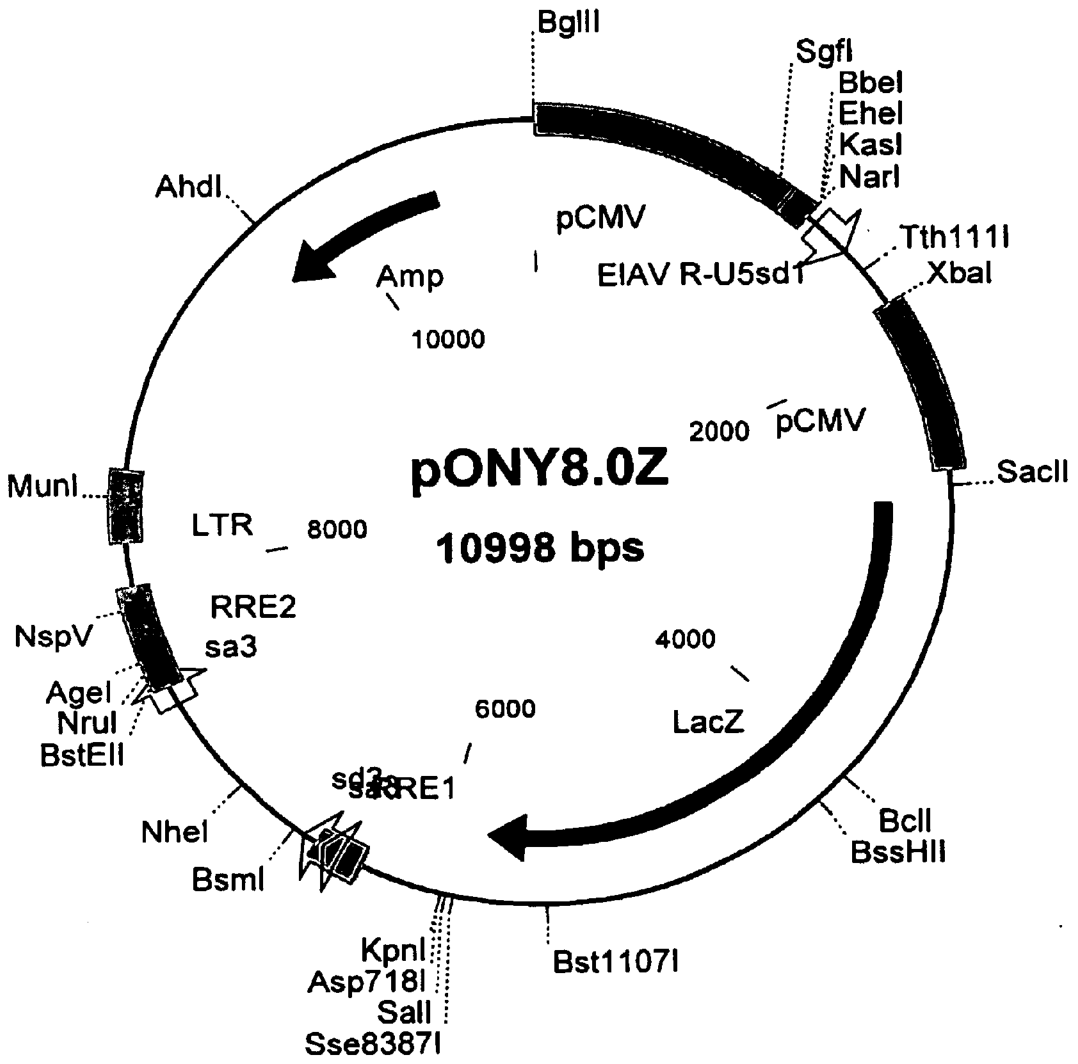
Figure 8:
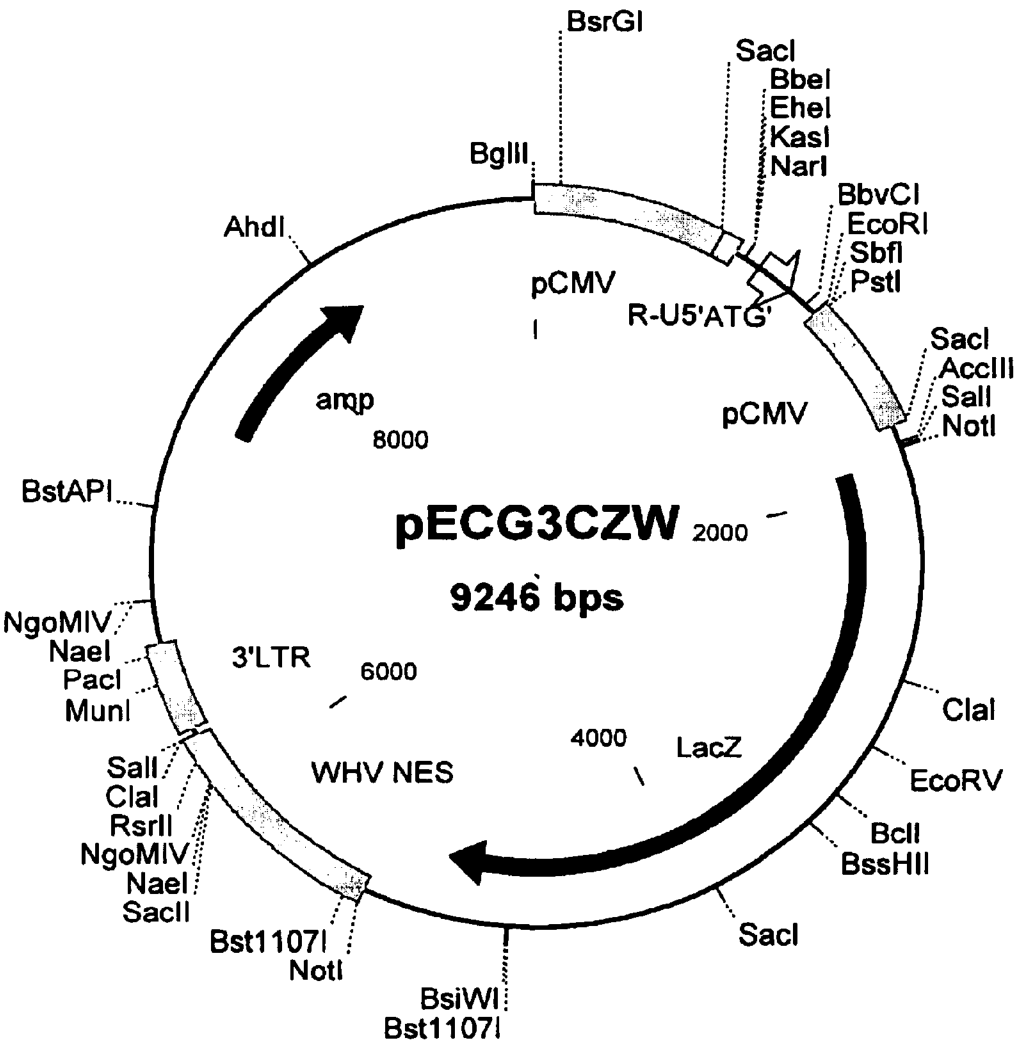
Figure 10:
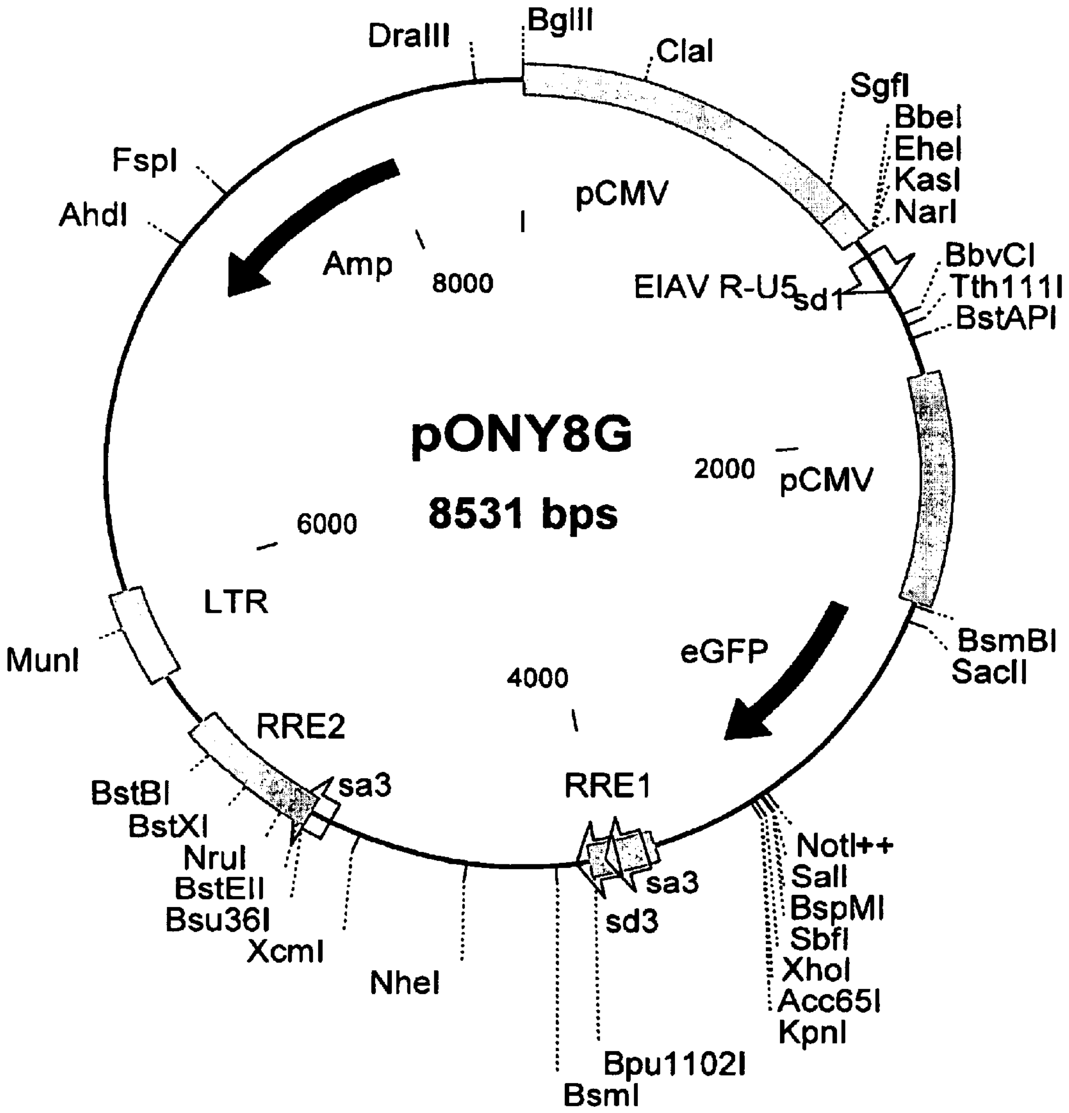
Figure 12A:
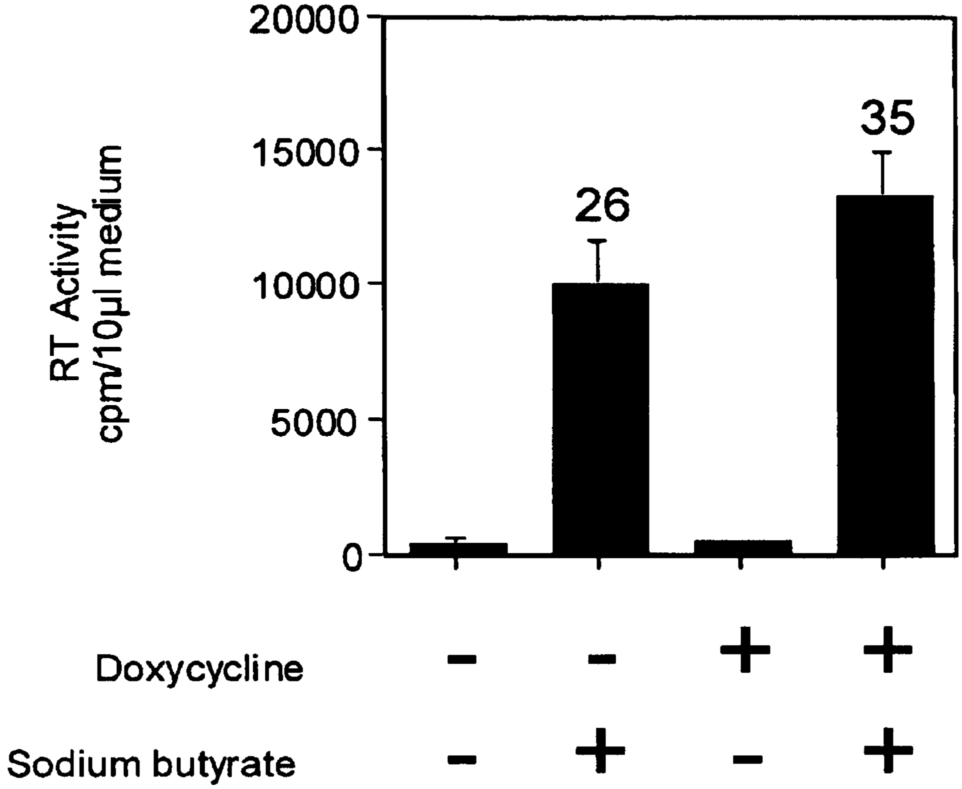
Figure 12B:
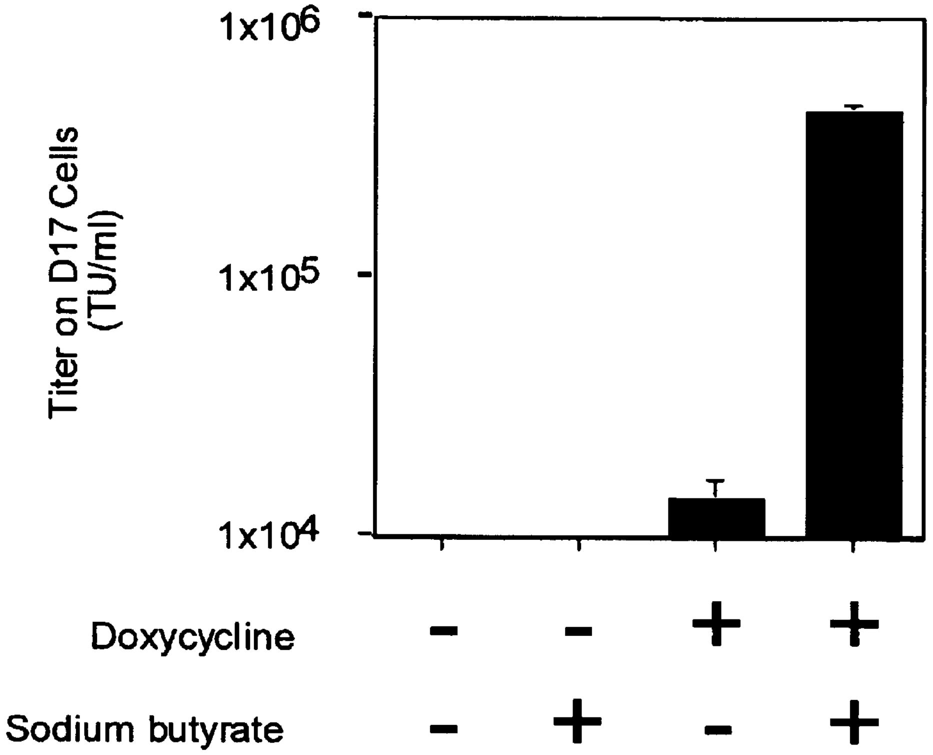
Figure 13:
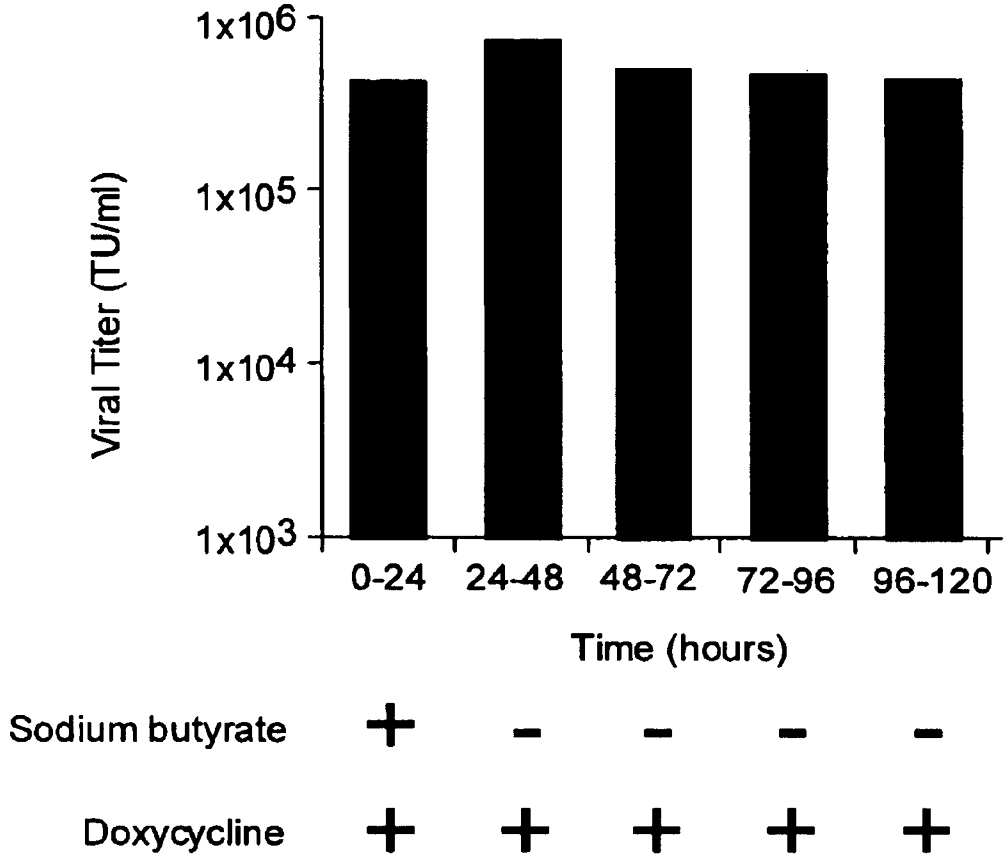
Figure 14:
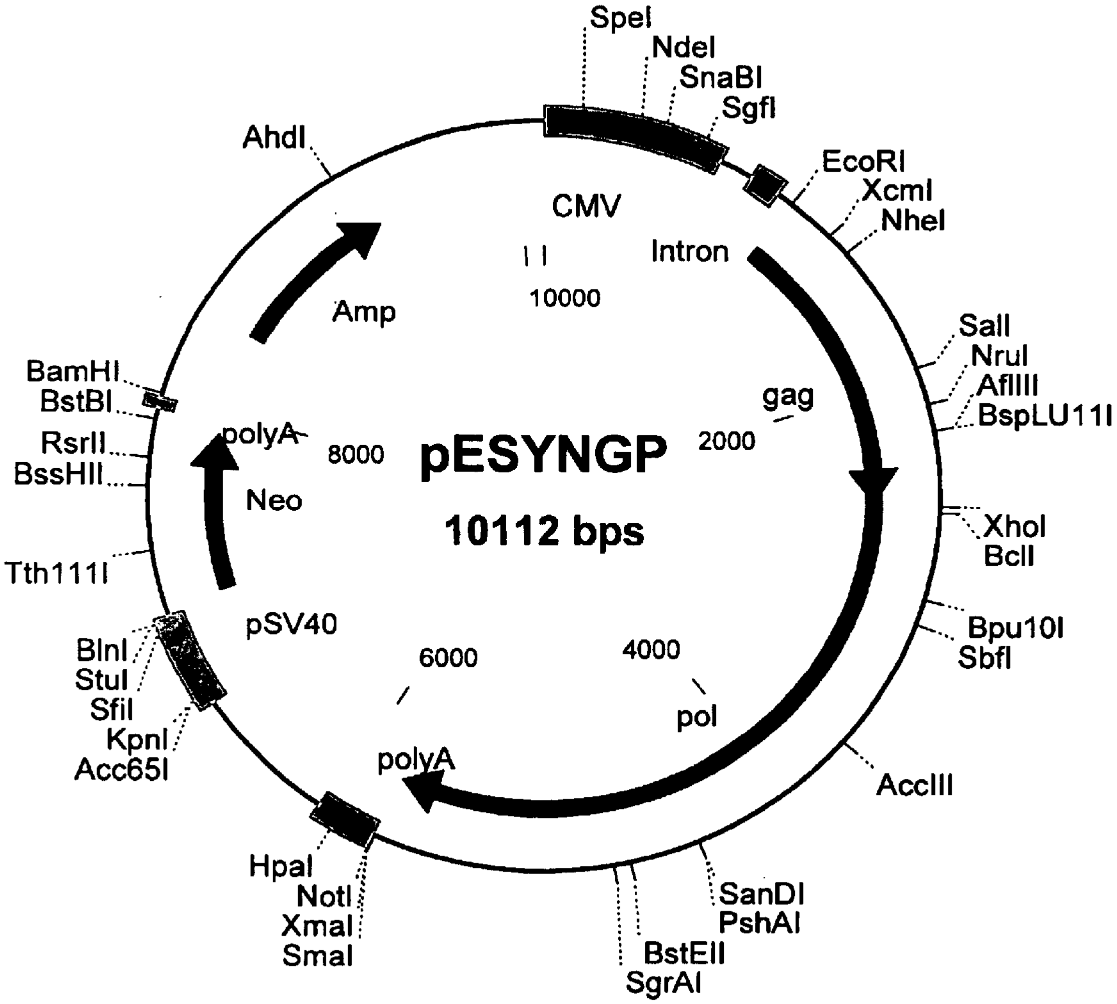
Figure 16:
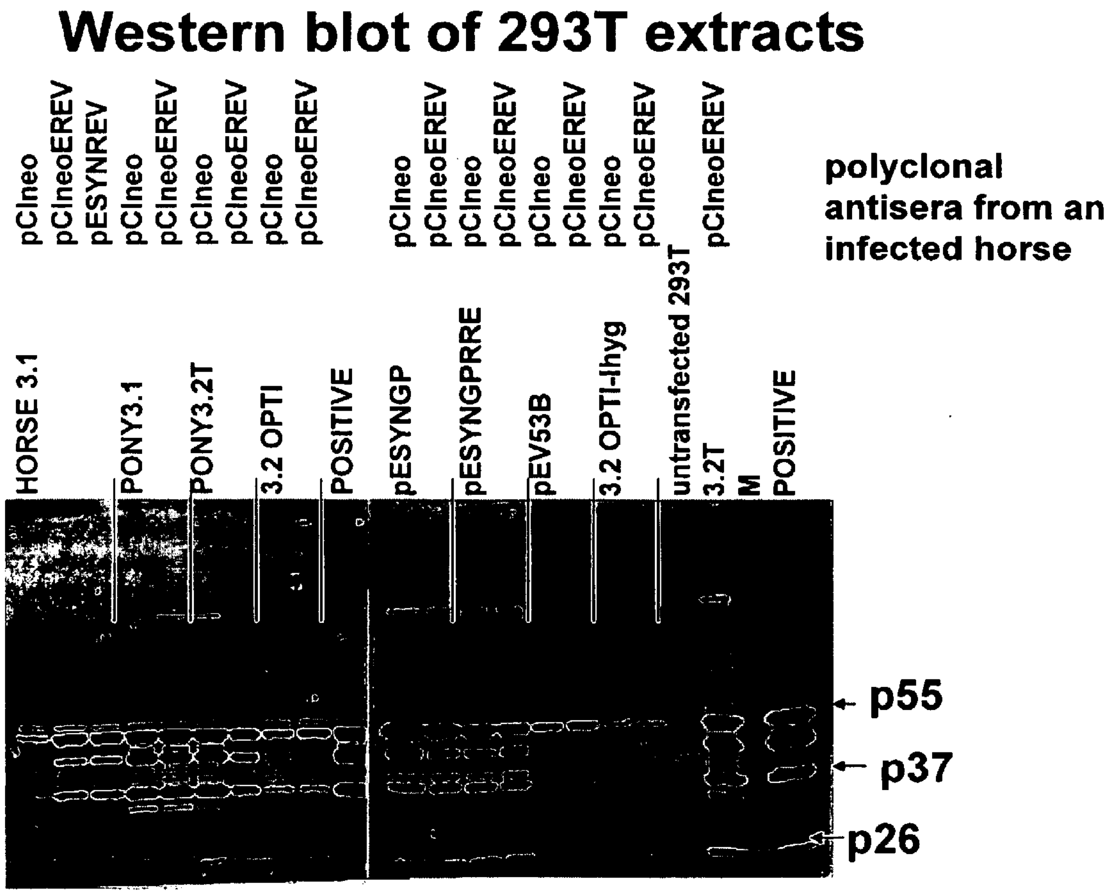
Figure 17:
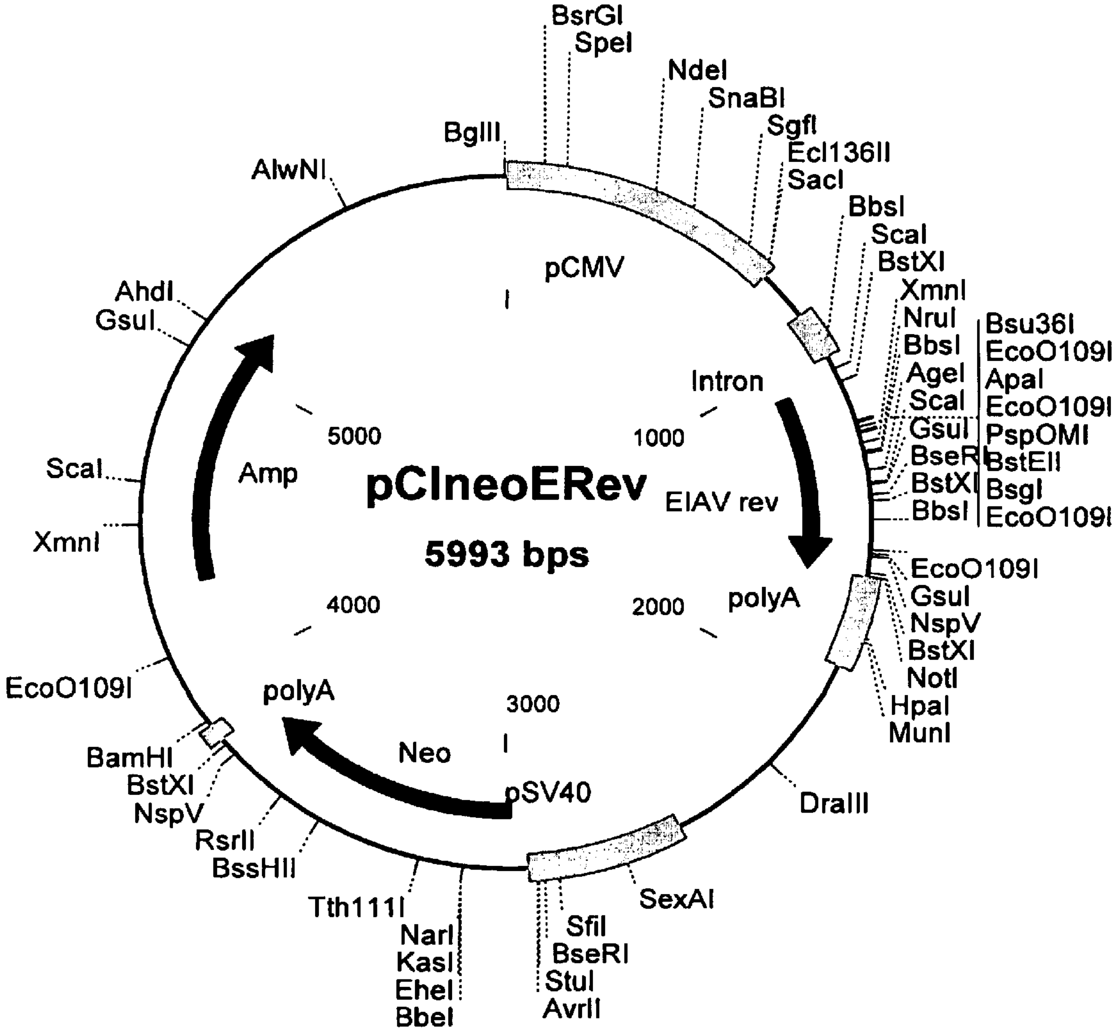
Figure 19:
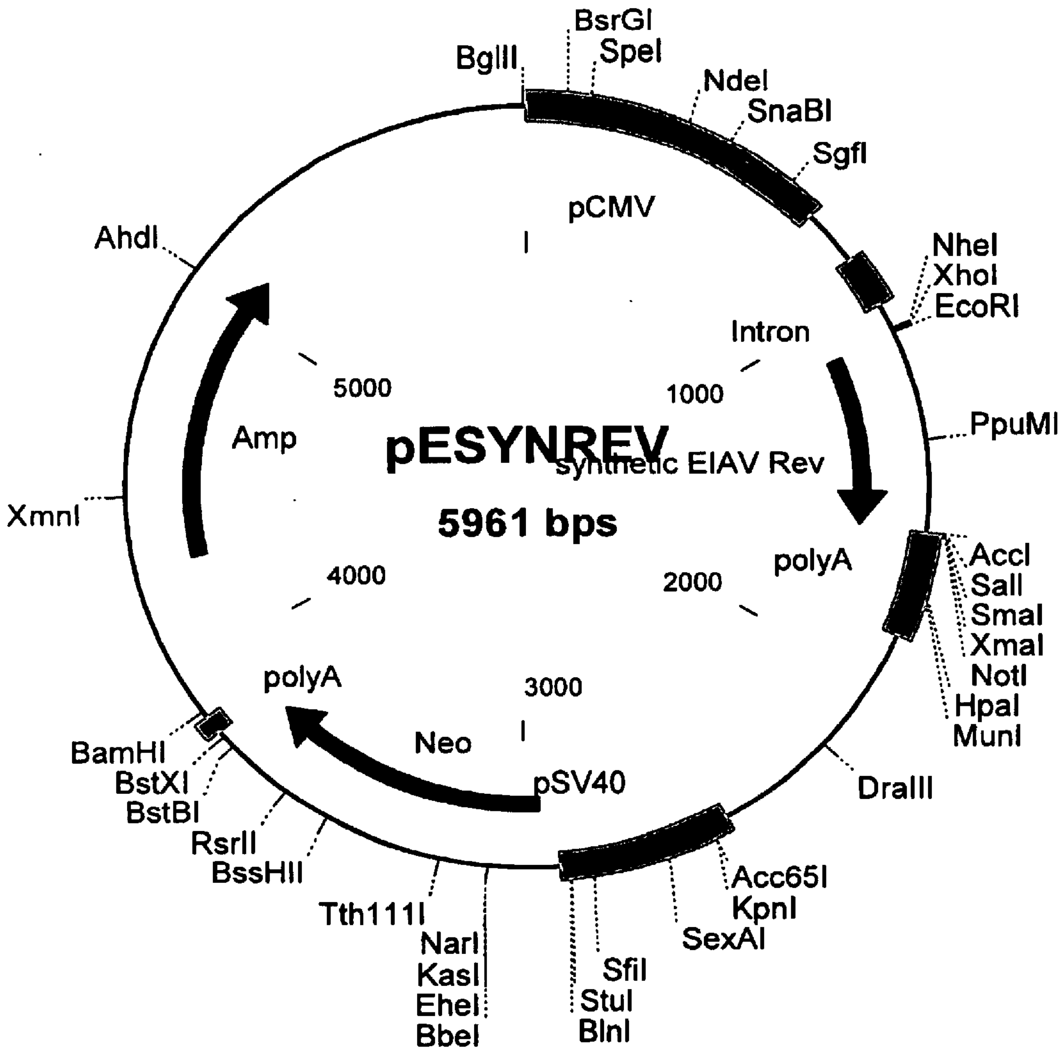
Figure 23A:
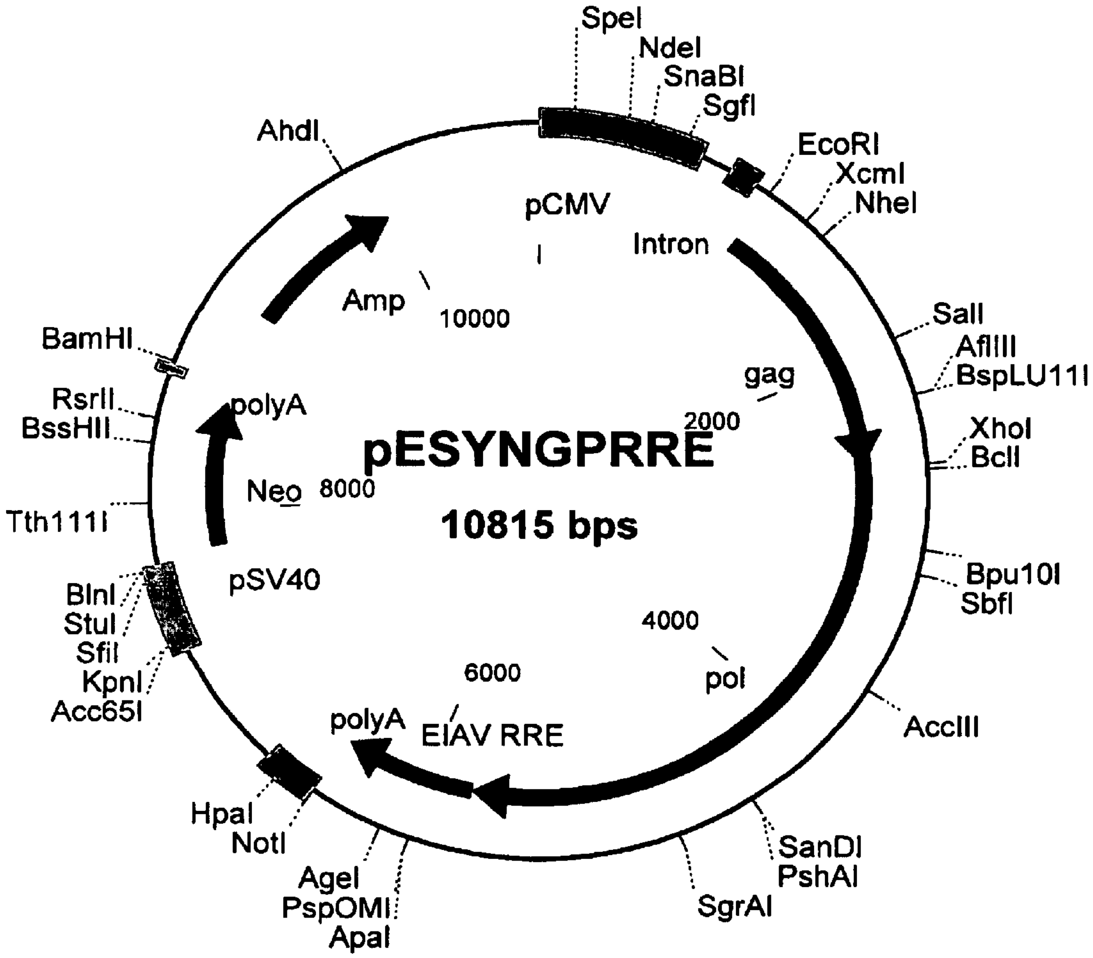

The invention will now be further described only by way of example in which reference is made to the following Figures:

FIG. 1A which shows a graphical representation;

FIG. 1B which shows a graphical representation;

FIG. 2 which shows a schematic representation;

FIG. 3 which provides a sequence listing;

FIG. 4 which shows a schematic representation;

FIG. 5 which provides a sequence listing;

FIG. 6 which shows a schematic representation;

FIG. 7 which provides a sequence listing;

FIG. 8 which shows a schematic representation;

FIG. 9 which provides a sequence listing;

FIG. 10 which shows a schematic representation;

FIG. 11 which provides a sequence listing;

FIG. 12A which shows a graphical representation;

FIG. 12B which shows a graphical representation;

FIG. 13 which shows a graphical representation;

FIG. 14 which shows a schematic representation;

FIG. 15 which provides a sequence listing;

FIG. 16 which shows a photographic representation;

FIG. 17 which shows a schematic representation;

FIG. 18 which provides a sequence listing;

FIG. 19 which shows a schematic representation;

FIG. 20 which provides a sequence listing;

FIG. 21 which provides a sequence listing;

FIG. 22 which shows a comparison of sequence listings;

FIG. 23A which shows a schematic representation;

FIG. 23B which provides a sequence listing

Figure 24:
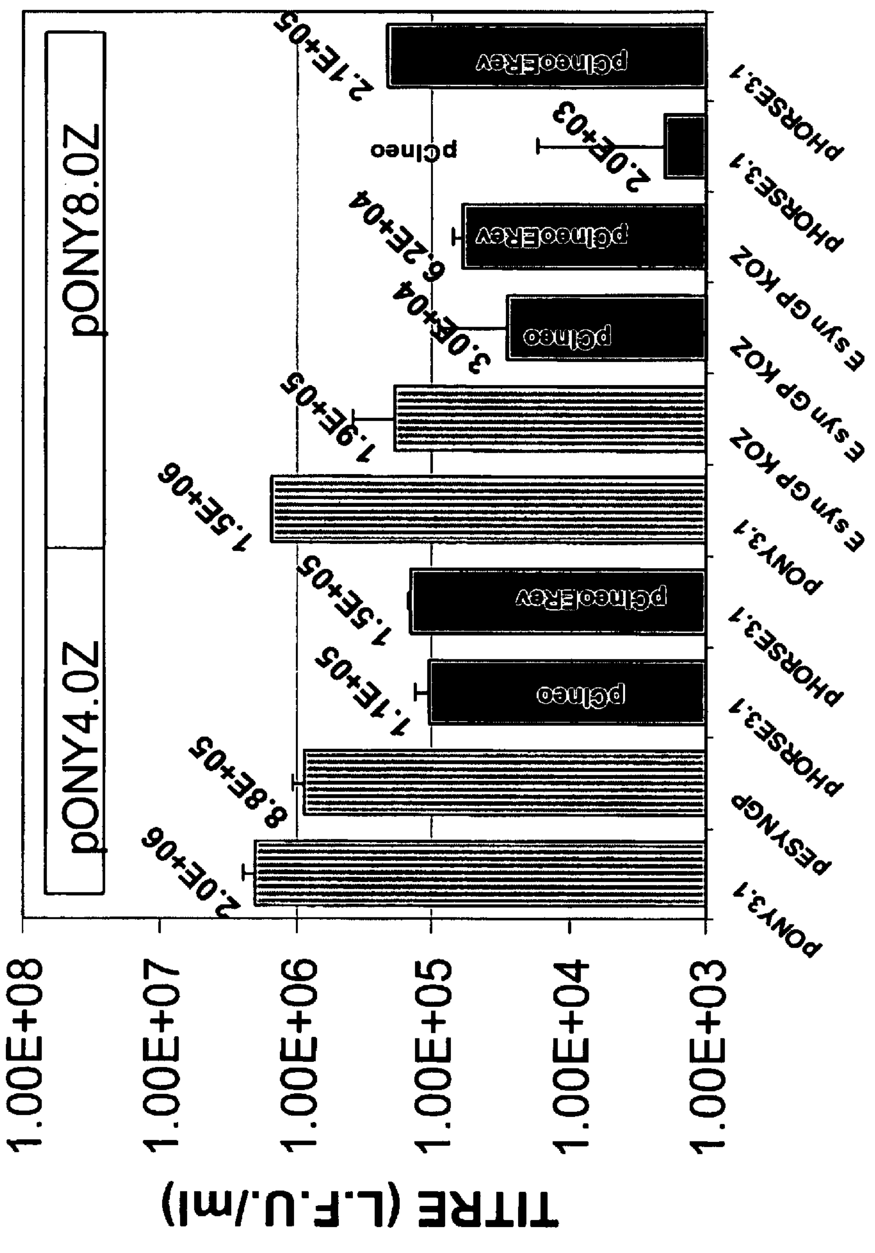
Figure 25A:
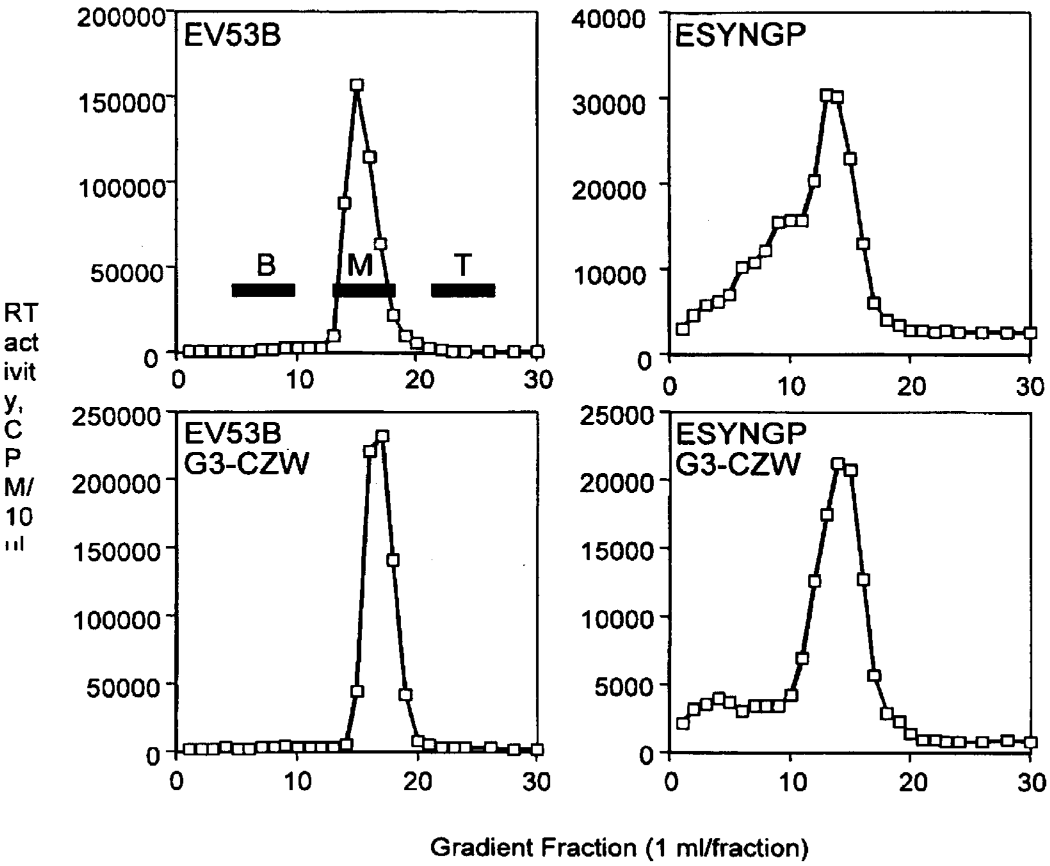
Figure 25B:
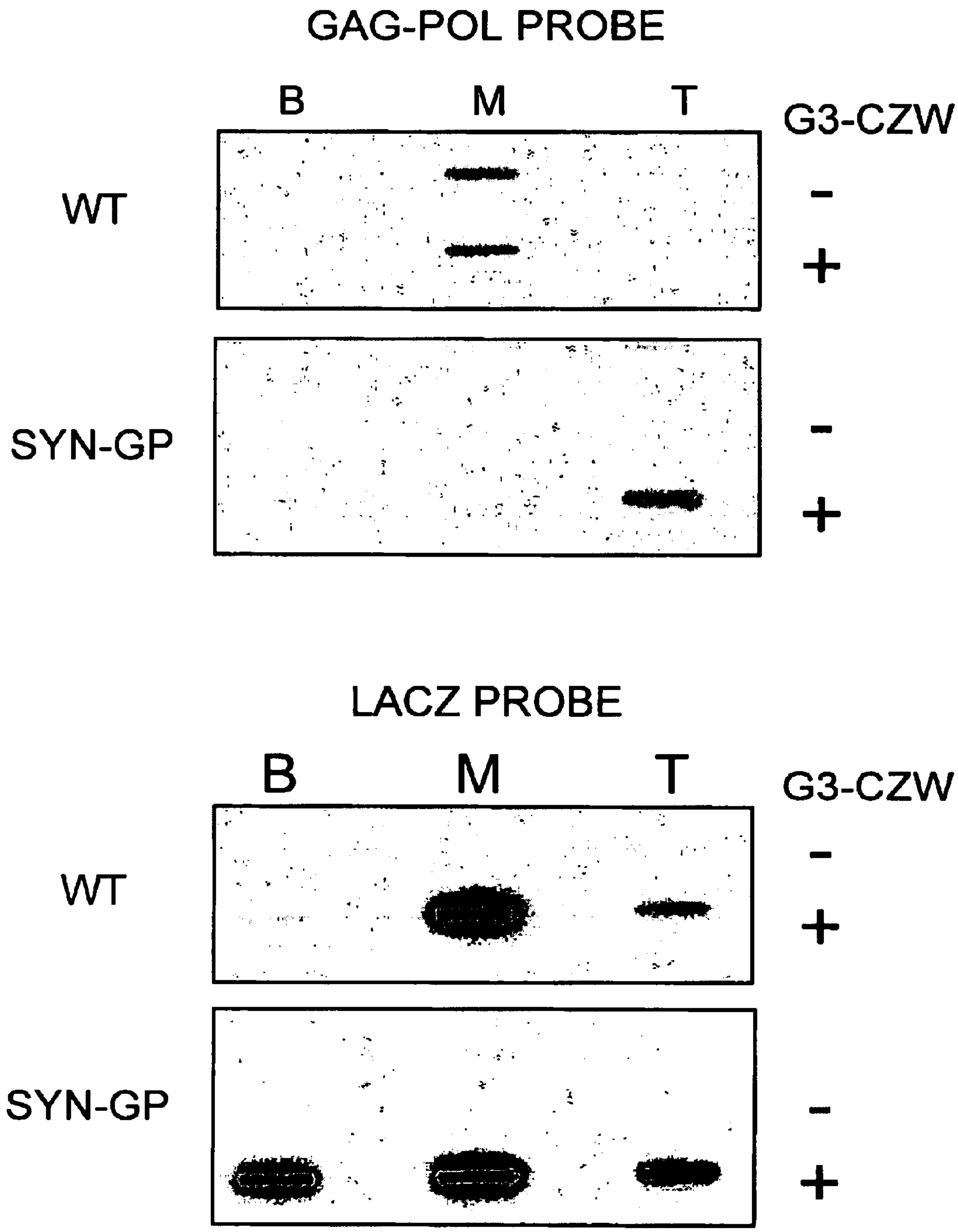
Figure 26:
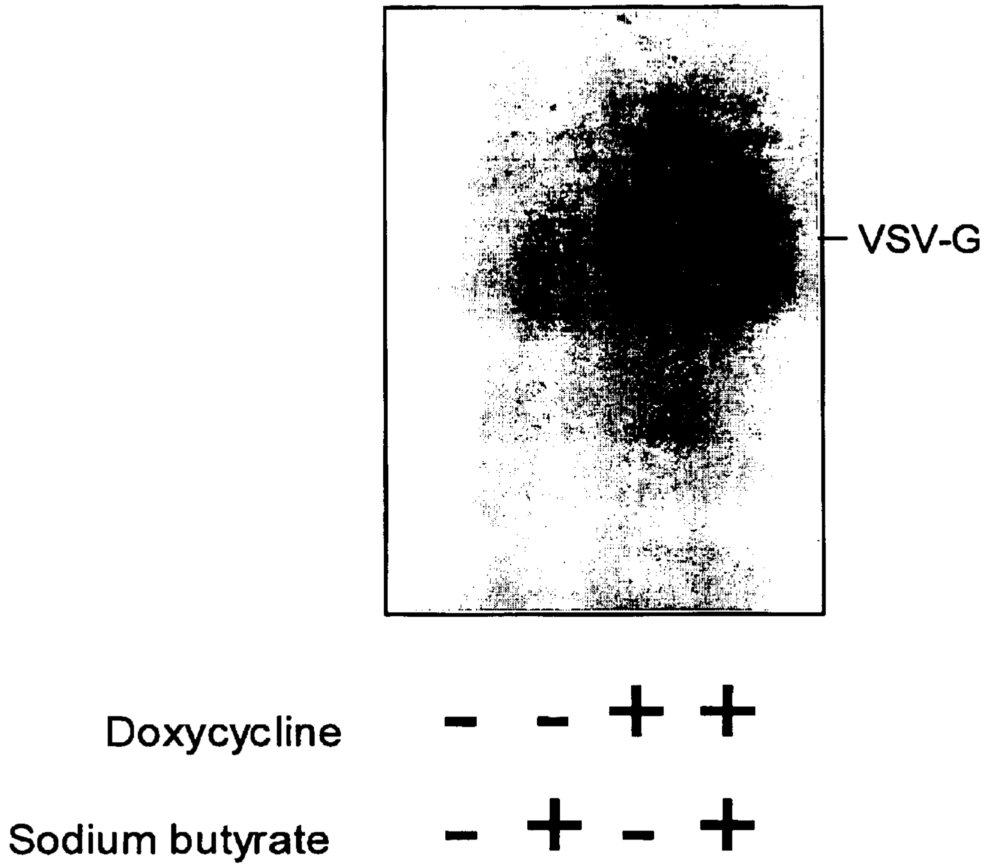
Figure 27:
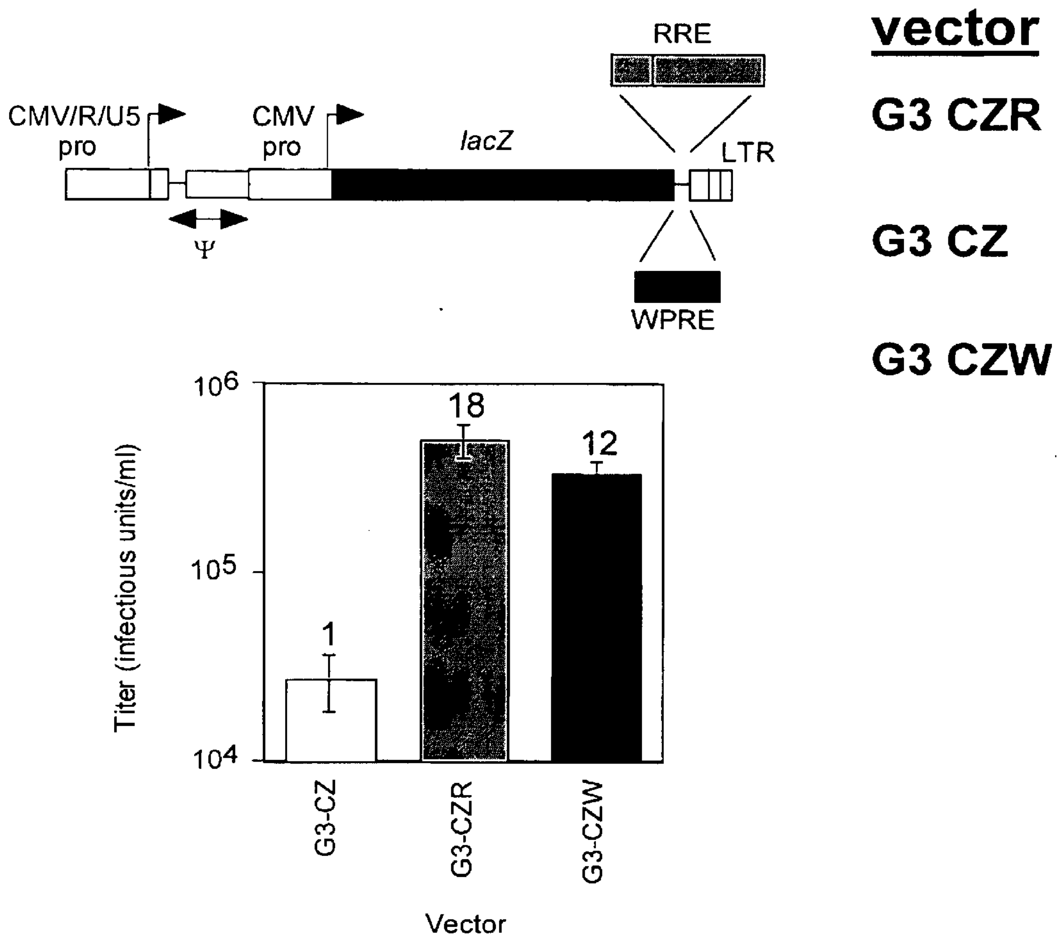
Figure 31:
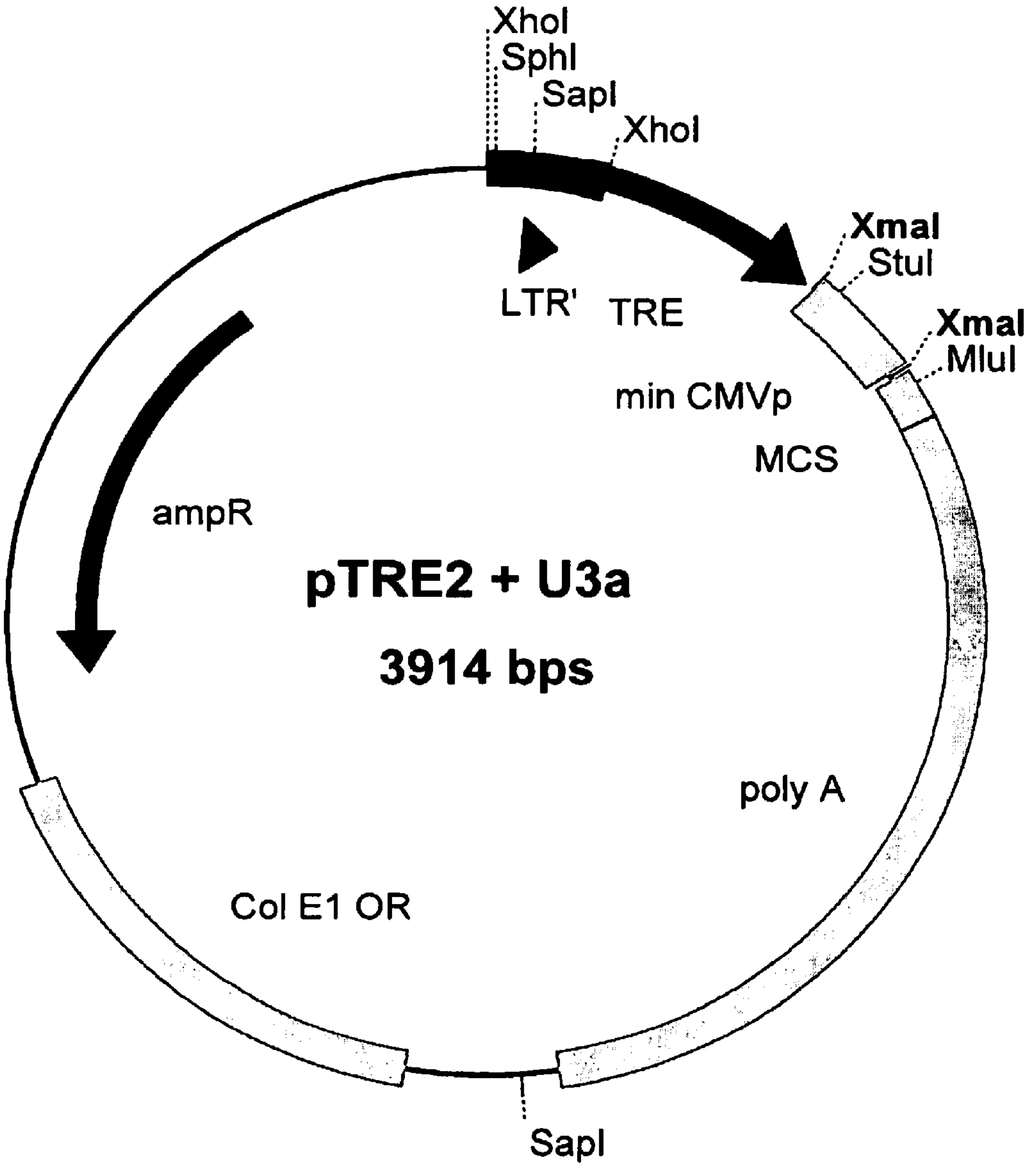
Figure 32:
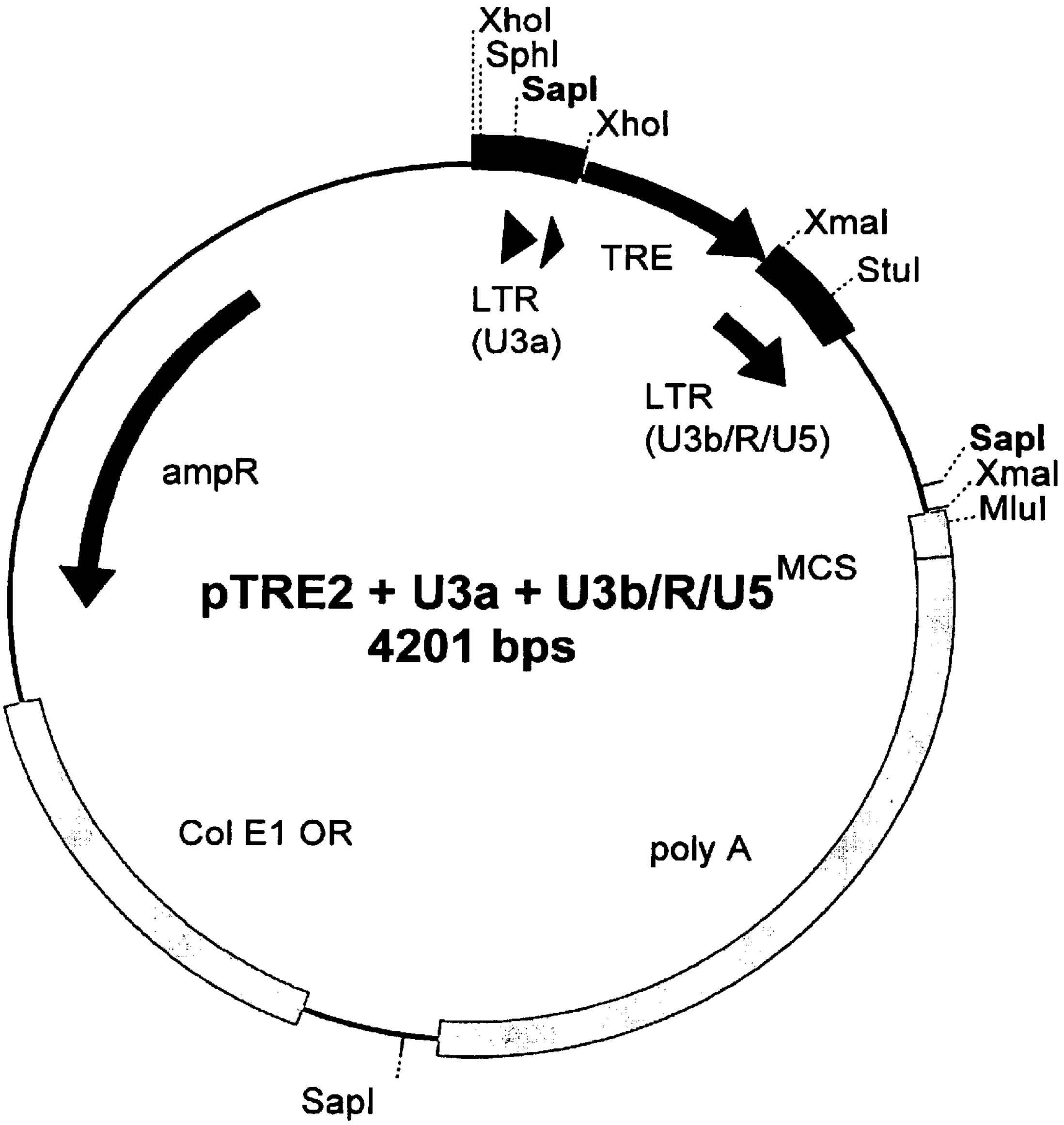

FIG. 24 which shows a graphical representation;

FIG. 25A which shows a graphical representation;

FIG. 25B which shows a photographic representation;

FIG. 26 which shows a photographic representation;

FIG. 27 which shows a schematic representation and a graphical representation;

FIG. 28 which shows a schematic representation;

FIG. 29 which shows a schematic representation;

FIG. 30 provides a primer sequence listing;

FIG. 31 provides a plasmid map;

FIG. 32 provides a plasmid map; and

FIG. 33 provides a sequence listing.

EXAMPLES

Example 1

Identification of Clonal Cell Lines for Efficient EIAV Vector Production.

EIAV packaging cells were derived following a series of steps in which clonal cell lines were derived and tested for various properties desirable in a vector production system. As a starting point, a library of 105 clonal HEK 293-based cell lines was tested for high transfection efficiency and efficient vector production. To do this, a three-plasmid system was used to generate EIAV vectors in each clonal cell line. This consisted of the following:

1) A non-infectious EIAV protein expression cassette plasmid, pEV53 (WO 98/51810), used to provide, in trans, the structural and regulatory proteins required for vector production;
2) The plasmid encoding the EIAV vector, in which a CMV promoter drove production of the vector RNA. The vector RNA contained cis-acting elements required for packaging, reverse transcription and integration of the vector as well as either cassettes for expression of either a lacZ reporter gene, which encodes β-galactosidase (pEC-lacZ; WO 98/51810), or a puromycin resistance marker (pEC-puro; WO 98/51810); and
3) A third expression plasmid, pCI-VSV-G, encoding the vesicular stomatitis virus G protein (VSV-G) used to supply envelope for pseudotyping the viral particles (Johnson L G, Mewshaw J P, Ni H, Friedmann T, Boucher R C, Olsen J C. J. Virol., (1998), 72, 8861–8872. and WO 98/51810).

Transducing vectors encoding β-galactosidase were used for initial screening of the HEK 293-derived cell lines for both estimation of transfection efficiency and for rapid assessment of vector production. Transfection was carried out by the calcium phosphate method. In these studies the transfected cell clones were stained for β-galactosidase expression upon harvesting vector. Vector was then used for transduction of D-17 canine osteosarcoma cells, which were stained for β-galactosidase expression 48 hours after transduction. All of the cell lines showed reasonably good transfection efficiency (>70%), however, some clones, for example, clones 6, 16, and 101 demonstrated superior transfection ability (>98%). By contrast to transfection ability, a marked variability in EIAV vector production was observed for the various cell lines. Almost 60% of the cell lines (62/105) did not produce a significant vector titer (<10 infectious vector particles/ml). This lack of vector production was specific to EIAV vectors, since all of the cell lines produced MuLV vectors with titers greater than $10^5$ infectious vector particles/ml, using an analogous 3-plasmid vector system. The MuLV vector system plasmids were pCI-GPZ and pHIT-SIN2000-CZ, which are the Gag/Pol and vector genome expression plasmids, respectively. pHIT-SIN2000-CZ was derived from pHIT-SIN (Wilcox D A, Olsen J C, Ishizawa L, Griffith M, White G C, 2nd. Proc Natl Acad Sci U S A 1999;96(17):9654–9]. This vector is an empty cloning vector, and was modified to have a unique NotI site in the multiple cloning site region. Then the EcoRI-NotI sequence, containing the CMV promoter-lacZ cassette from pECG3-CZR was cloned into the unique EcoRI-NotI sites of HIT-SIN2000-CZ in a two step procedure, in which the CMV promoter was transferred first and then the lacZ gene.

Cell lines that were positive for EIAV vector production were tested in a second round of screening that included testing for the affects of sodium butyrate on vector production. We previously showed that sodium butyrate can have marked effects on retroviral vector production, both in transient producer systems and from clonal producer cell lines [Olsen J C and Sechelski J (1995) Use of sodium butyrate to enhance production of retroviral vectors expressing CFTR cDNA. Human Gene Therapy 6: 1195–1202; and Soneoka Y, Cannon P M, Ramsdale E E, Griffiths J C, Romano G, Kingsman S M, Kingsman A J (1995) A transient three-plasmid system for the production of high titer retroviral vectors. Nucleic Acids Research 23: 628–633]. In contrast, other researchers (such as Kiges et al Molecular Therapy 2000, 2(2), 170–176) have noted that the addition of sodium butyrate, was neither required or beneficial for the full induction of the LVG clones of a HEK 293 cell line.

Kafri et al (1999) (J Virol 73(1); 576–584) also provides teachings relating to the production of a tetracycline-inducible VSV-G pseudotyped lentivirus packaging cell line using sodium butyrate. However, Kafri et al teaches that: all HIV genes are transcribed in the cell line from a single expression cassette which is regulated by tetracycline whereas the present invention provides only an env gene which is regulated by a tetracycline inducible system and optionally a tetracycline responsive element in the retroviral genome. Moreover, the present invention provides the advantageous feature of full activation of genes under the control of the tetracycline-responsive element (TRE) in the presence of initial stimulus with sodium butyrate. This is different to the performance of the tetracycline system in other situations. By way of example, the continuous production of proteins in the Kafri et al (1999) vector production system requires a continual and sustained stimulus with sodium butyrate and doxycycline whereas the vector production system of the present invention only requires an initial stimulus with sodium butyrate or a functional analogue thereof.

Results I

FIG. 1A shows the variation in the titres of vector produced by various clones and also the variable effect of sodium butyrate treatment on vector production by different cell clones. For example, sodium butyrate had no effect on production of the puromycin-containing vector in cell clone 34. In contrast, vector production was increased in clone 101 cells approximately 20-fold, to titers greater than $2\times10^5$ colony forming units (CFU)/ml.

FIG. 1B shows the induction profile for EIAV and MuLV vector production from two clonal cell lines. Both clone 16 and clone 101 cells produce MuLV vectors with titers greater than $5\times10^6$ infectious units per ml after sodium butyrate treatment. EIAV production is nearly as efficient as MuLV production in clone 101 cells. In clone 16 cells, EIAV vector production was barely detectable.

Discussion I

Collectively, these results illustrate the variability in EIAV vector production, even among clonal sublines derived from a single, parental cell line (HEK 293), and emphasize the importance of a careful selection procedure for choosing the optimal cell line for making vector producers.

Example 2

Construction of stable packaging cell lines

Human cell lines modified to express EIAV gag/pol

The clonal 101 cell line described above was chosen as the starting material for making stable producer lines, and termed 293.101. This cell line was transfected using a standard calcium phosphate procedure with the EIAV gag-pol expression cassette pEV53B.

pEV53B is similar to pEV53A (WO 98/51810) except that all EIAV leader sequences up to 3 nt upstream of the major splice donor have been removed. To construct pEV53B the gag gene and part of pol was amplified from pEV53 by PCR using the primers (SEQ ID NO: 18)
5'-TTTGGCGCGCC*AGGTAAG*ATG*GGAGACCCTTTGAC-3*' (forward)

and (SEQ ID NO: 19)
5'-CTACTTGATCCTTCTCCTTGAC-3'. (reverse)

An AscI restriction site (underlined) was included in the forward primer for cloning purposes. The ATG start codon for gag in the forward primer is indicated in bold and EIAV sequences are shown in italic for the forward primer. The resulting 1.4 kb PCR product was digested with AscI and BsrGI and cloned into AscI-BsrGI digested pEV53A. This resulted in pEV53B (FIGS. 2 and 3). Sequence analysis was used to verify that the gag-pol sequences amplified by PCR were correct.

The cells were selected for G418 (Geneticin) resistance. Individual colonies were selected, expanded, and tested for expression of EIAV Gag/Pol by release of particle-associated reverse transcriptase activity, and the ability to complement viral vector production after transfection with pECG3-CZR (FIGS. 4 and 5) and pCI-VSV-G, which are expression plasmids for an EIAV vector and VSV-G. pECG3-CZR was derived from pEC-LacZ by 1) reduction of gag sequences so that only the first 200 nt of gag, rather than the first 577nt, was included and 2) inclusion of the two sequences shown to have RRE activity (Martarano L, Stephens R, Rice N, Derse D J Virol 1994 May;68(5):3102–11). The RRE sequences were included in the vector as a fusion of the two regions shown to have RRE activity, placed downstream of the reporter gene. The EIAV sequences were nt 5303–5746 and 6477–7684 with respect to pER2.1 (Acc. No. M87581).

Clonal packaging cells showing the greatest activity were frozen or maintained for analysis of persistence of packaging activity. Altogether 245 colonies were initially screened. Cell derived from eight of the colonies were chosen to assess persistence of packaging activity and reanalyzed. One particular clone, B-241, showed stable packaging activity for at least three months.

Generation of VSV-G Pseudotyping EIAV Packaging Cells.

The B-241 cell line was stably modified to express VSV-G under regulation by the tetracycline repressor. This was done by co-transfection of a plasmid expressing VSV-G under transcriptional control of a doxycycline regulatable CMV promoter (pTOG) and a plasmid expressing the tetracycline repressor (pcDNA6/TR; Invitrogen). Doxycycline is an analogue of tetracycline. pTOG is a derivative of pcDNA4/TO (Invitrogen) in which a HindIII-NotI fragment from pCI-VSV-G containing the VSV-G gene was cloned into the HindIII-NotI site. For construction of B-241 derivatives capable of inducibly expressing VSV-G, pTOG was co-transfected with pcDNA6/TR at a ratio of 1:7. Prior to transfection both plasmids were linearised with BstZ17 I. These plasmids also expressed zeocin and blasticidin drug selection markers, respectively. Cells were placed under dual selection with blasticidin and zeocin. Drug resistant colonies were expanded and 60 colonies were tested for the ability to complement viral vector production following transfection of the EIAV vector plasmid, pECG3-CZR. Six clonal cell lines were chosen for further comparison, and one of these cell lines, BiG-45, was chosen for all further studies.

Modification of EIAV Packaging Cells to Make an EIAV Vector, Producer Cell

To generate stable cell lines containing EIAV gene transfer vectors, BiG-45 cells were co-transfected with an EIAV vector plasmid encoding a β-galactosidase or GFP reporter gene and a plasmid encoding a puromycin selection marker. Clonal cell lines were expanded and tested for vector production following a 24 hour treatment with 10 mM sodium butyrate and 1.5 µg/ml doxycycline. The vector genome plasmids used were pONY8.0 Z, pECG3-CZW and pONY8 G.

The titres obtained were assessed on D17 or HEK 293T cells and are shown in Table 1.

Table 1. The Titers of Vectors Produced from Stable Packaging Cell Lines Producing EIAV Vectors.

TABLE 1

Transduction efficiency of VSV-G pseudotyped EIAV vectors produced by clonal producer cells derived from BiG-45 cells

| Vector (reporter gene) | Titer‡, TU/ml (Cell line) |
|---|---|
| pONY8.0Z (lacZ), clone 20 | $8 \times 10^5$ (D17) |
| | $3 \times 10^6$ (293T) |

TABLE 1-continued

Transduction efficiency of VSV-G pseudotyped EIAV vectors produced by clonal producer cells derived from BiG-45 cells

| Vector (reporter gene) | Titer‡, TU/ml (Cell line) |
|---|---|
| G3-CZW (lacZ), clone 9 | $5 \times 10^5$ (D17) |
| pONY8G (GFP), clone 72 | $3 \times 10^5$ (D17) |

‡Canine D17 osteosarcoma cells or human HEK 293T cells were analyzed for expression of reporter genes 48 hr after transduction. Titers of vectors containing lacZ (pONY8.0Z and G3-CZW) were determined by counting fixed/X-Gal-stained cells in suspension. Titers of pONY8G were determined by FACS analysis of GFP-expressing cells. TU, transducing units.

pONY8.0 Z (FIGS. 6 and 7) was derived from pONY4.0 Z (WO99/32646) by introducing mutations which:
1) prevented expression of Tat by an 83 nt deletion in the exon 2 of tat
2) prevented S2 ORF expression by a 5lnt deletion in S2
3) prevented Rev expression by deletion of a single base within exon 1 of rev and
4) prevented expression of the N-terminal portion of gag by insertion of T in ATG start codons, thereby changing the sequence to ATTG from ATG.

With respect to the wild type EIAV sequence Acc. No. U01 866 these correspond to deletion of nt 5234–5316 inclusive, nt 5346–5396 inclusive and nt 5538. The insertion of T residues was after nt 526 and 543.

pECG3-CZW (FIGS. 8 and 9) was derived from pECG3-CZR by replacement of the DNA fragment corresponding to the EIAV RRE, excised by digestion with NotI and ClaI, with a fragment containing the woodchuck hepatitis virus post-transcriptional regulatory element (WHV PRE) (corresponding to nt 901–1800 of Acc. No. J04514). The fragment containing the WHV PRE was made by PCR using primers containing NotI and ClaI to assist placement into the EIAV vector genome. pECG3-CZ was derived from pEC-LacZ by reduction of the amount of gag sequence as described previously for pECG3-CZR. pONY8G (FIGS. 10 and 11) was derived from pONY8.0 Z by exchange of the LacZ reporter gene for the enhanced green fluorescent protein (GFP) gene. This was done by transferring the SacII-KpnI fragment corresponding to the GFP gene and flanking sequences from pONY2.13GFP (WO/9932646) into pONY8.0 Z cut with the same enzymes.

Example 3

Induction of EIAV Gag/Pol Expression by Sodium Butyrate and Doxycycline

FIG. 12 shows the expression of EIAV gag/pol from a wild type open reading frame in BiG-45 cells and the induction obtained following treatment with sodium butyrate and doxycycline. In these experiments a clonal derivative of BiG-45 cells (clone 8Z.20; $5 \times 10^6$ cells/60-mm dish) expressing pONY8.0 Z was treated with 10 mM sodium butyrate and/or 1.5 µg/ml doxycycline for 24 hr at 37° C.

Results 3

Panel A

Panel A shows the reverse transcriptase activity appearing in the cell-free supernatant as a measure of reverse transcriptase activity. It shows that sodium butyrate treatment has a significant effect on gag/pol expression, as measured by reverse transcriptase activity appearing in the medium. Also indicated are the fold-induction in reverse-transcriptase activity relative to that observed when no treatments were given. Virion associated reverse transcriptase activity was increased about 30-fold. Doxycycline treatment alone had little effect on reverse transcriptase activity, as expected.

Panel B

Panel B shows the synergistic effect of sodium butyrate and doxycycline on production of the pONY8.0Z vector from the 8Z.20 cell line. In this experiment cell-free supernatant containing the vector used to obtain the data shown in Panel A was titered on D17 cells. This revealed that without induction, or with sodium butyrate treatment alone, <1 transducing vector particle was produced per ml of medium. Doxycycline treatment resulted in a titer of $1.4 \times 10^4$ transducing units (TU)/ml. However, with both sodium butyrate and doxycycline treatment, a titer of $4.3 \times 10^5$ TU/ml was achieved. This is 31-fold higher than doxycycline treatment alone and greater than $10^5$ higher than with sodium butyrate treatment alone. The synergistic effect between doxycycline and sodium butyrate was a suprising result.

These results demonstrate that in the uninduced state virtually no vector particles were formed. Therefore the problems associated with self transduction of the producer cell line, leading to an uncontrolled increase in the number of vector genomes present, are effectively eliminated. This is an important feature of the system since it allows production of genetically stable producer cell lines, which is desirable from a manufacturing and regulatory point of view.

Example 4

Maintenance of Virus Production does not Require Sodium Butyrate

FIG. 13 shows that, once vector production has been induced by treatment with sodium butyrate and doxycycline for 24 hours, sodium butyrate can be removed from the culture medium and vector production can be maintained for at least five days. More specifically, vector production is maintained by doxycycline atone. This feature of the producer system is advantageous because sodium butyrate is a toxic compound causing cell cycle arrest and thus is an important compound to remove from vector preparations.

In this experiment production of pONY8.0 Z by the 8Z.20 cells was induced by treatment for 24 hours with 10 mM sodium butyrate and 1.5 μg/ml doxycycline. The medium was changed daily and replaced with regular cell growth medium containing only 1.5 μg/ml doxycycline. The results in FIG. 13 indicate that a reasonably steady level of virus production (range $4.3 \times 10^5$ TU/ml to $7.4 \times 10^5$ TU ml) occurred over a five-day period.

Example 5

Expression of EIAV from Codon-optimized ORF

The sequence of the gag-pol gene of EIAV was altered so that the codon-usage was that of a highly expressed mammalian gene. This process is referred to as codon optimisation. The codon optimised gag-pol was subcloned into the expression vector pCI-neo (Promega) and called pESYNGP (FIGS. 14 and 15). The codon-optimisation process is elaborated in GB Application 0009760.0.

The expression of Gag/Pol from the codon-optimised gene was assessed with respect to that from various wild type EIAV gag/pol expression constructs by transient transfection of HEK 293T cells (FIG. 16). Transfections were carried out using the calcium phosphate technique, using equal moles of each Gag/Pol expression plasmid together with a plasmid which expressed EIAV Rev either from the wild type sequence or from a codon-optimised version of the gene (pCIneoEREV (FIGS. 17 and 18) or pESYNREV (FIGS. 19 and 20), respectively). In transfections in which a Rev expression plasmid was omitted, a similar mass of pCIneo (Promega) was used instead (lanes labelled pCIneo). Cytoplasmic extracts were prepared 48 hours post transfection and 15 μg amounts of protein were fractionated by SDS-PAGE and then transferred to Hybond ECL. The Western blot was probed with a polyclonal antisera from an EIAV-infected horse and then with a secondary antibody, anti-horse, horse-radish peroxidase conjugate. Development of the blot was carried out using the ECL kit (Amersham). Positive controls for the blotting and development procedure, and cytoplasmic extract from untransfected HEK 293T cells are as indicated. The positions of various EIAV proteins are indicated.

Expression from wild type .gag/pol was achieved from various plasmids. pONY3.2T is a derivative of pONY3.1 (W099/32646)(FIG. 21) in which mutations which ablate expression of Tat and 52 have been made. In addition, the EIAV sequence is truncated downstream of the second exon of rev. Specifically, expression of Tat is ablated by an 83 nt deletion in exon 2 of tat which corresponds with respect to the wild type EIAV sequence, Acc. No. U01866, to deletion of nt 5234–5316 inclusive. S2 ORF expression is ablated by a 51 nt deletion, corresponding to nt 5346–5396 of Acc. No. U01866. The EIAV sequence is deleted downstream of a position corresponding to nt 7815 of Acc. No. U01866. These alterations do not alter rev, hence this gene is expressed as for pONY3.1. 3.2 OPTI is a derivative of pONY3.1, and has the same deletions for ablation of Tat and S2 expression as described above. In addition, the first 372 nt of gag have been 'codon-optimised' for expression in human cells. The sequence of the wild type and codon-optimised sequences in this region are compared in FIG. 22. Base differences between the sequences are indicated. The region which was codon-optimised represents the region of overlap between the vector genome and wild-type Gag/Pol expression constructs.

Reduction of homology within this region would be expected to improve the safety profile of the vector system due to the reduced chances of recombination between the vector genome and the gag/pol transcripts.

3.2 OPTI-Ihyg is a derivative of 3.2 OPTI in which the SnaBI-NotI fragment of 3.2 OPTI is transferred to pIRE 1 hygro (Clontech) prepared for ligation by digestion with the same sites. The resulting construct thus contains the intron from pCIneo, not from pIRES1hygro. pEV53B is a derivative of pEV53A (WO 98/51810) in which the EIAV-derived sequence upstream of the Gag initiation codon is reduced to include the major splice donor and surrounding sequences. CAG.GTAAGATG (SEQ ID NO: 20), where the gag initiation codon is shown in bold face.

Results 5

The results show the Rev-dependence of Gag/Pol expression from pHORSE3.1, which has an EIAV-derived leader sequence starting just downstream of the primer binding site, the wild type gag/pol sequence and then an RRE composed of the two EIAV sequences reported to have RRE activity (see WO99/32646). Expression was enhanced by the same amount when Rev expression was driven by wild type (pCIneoERev) or codon-optimised (pESYNREV) genes. This result confirms the functionality of the codon-optimised Rev expression plasmid.

In contrast expression of Gag/PoI from pESYNGP was not influenced by the presence of Rev, however it was only slightly lower than from pONY3.1 or pON3.2T. Expression from pESYNGPRRE (see GB Application 0009760.0) (FIGS. 22 and 23), in which the EIAV RRE (see WO 99/32646) is placed downstream of gag/pol, appeared slightly lower than from pESYNGP. The levels of expression from 3.2 OPTI and 3.2OPTI-Ihyg were significantly lower than from pESYNGP or pONY3.1, even in the presence of Rev. This result suggested that there may be determinants of Gag/Pol expression within the first 372 nt of the gag and showed that 3.2 OPTI was unlikely to be useful as a basis for EIAV vector production. Furthermore it demonstrates that codon-optimisation of only certain regions of the whole gag/pol gene may not lead to high levels of Rev-independent expression.

The ability of pESYNGP to generate viral vectors, when co-transfected with plasmids for the vector genome and envelope was assessed by transient transfection of HEK 293T, as described previously. Briefly, 293T cells were seeded on 6 cm dishes ($1.2\times10^6$/dish) and 24 hours later they-were transfected by the calcium phosphate procedure. The medium was replaced 12 hours post-transfection and supernatants were harvested 48 hours post-transfection, filtered (0.45 $\mu$m filters) and titered by transduction of D17, canine osteosarcoma cells, in the presence of 8 $\mu$g/ml Polybrene (Sigma). Cells were seeded at $0.9\times10^5$/well in 12 well plates 24 hours prior to use in titration assays. Dilutions of supernatant were made in complete media (DMEM/10% FBS) and 0.5 ml aliquots plated out onto the D17 cells. 4 hours after addition of the vector the media was supplemented with a further 1 ml of media. Transduction was assessed by X-gal staining of cells 48 hours after addition of viral dilutions.

The vector genomes used for these experiments were pONY4.0 Z (WO 99/32646) and pONY8.0 Z. pONY4.0 Z (WO 99/32646) was derived from pONY2.11Z (WO 99/32646) by replacement of the U3 region in the 5'LTR with the cytomegalovirus immediate early promoter (pCMV). This was carried out in such a way that the first base of the transcript derived from this CMV promoter corresponds to the first base of the R region. This manipulation results in the production of high levels of vector genome in transduced cells, particularly HEK 293T cells, and has been described previously (Soneoka, Y., P. M. Cannon, E. E. Ramsdale, J. C. Griffiths, G. Romano, S. M. Kingsman, and A. J. Kingsman. 1995. Nucleic Acids Res. 23:628–33). pONY4.0 Z expresses all EIAV proteins except for envelope, expression of which is ablated by a deletion of 736 nt between the HindIII sites present in env. pONY8.0 Z was derived from pONY4.0 Z as described above, and is a minimal EIAV vector genome. The results of this analysis are shown graphically in FIG. 24.

Example 6

Lack of Packaging of Codon-optimized Gag/pol ORF Improves the Safety Profile of the Vector System The construction and properties of an EIAV gag/pol expression plasmid in which the gene is codon-optimised for expression in human cells are described in Example 5 and GB Patent Application 0009760.0. In summary, the main feature of this expression cassette are 1) that expression of the gag/pol gene is rendered independent of REV/RRE and 2) that the extent of homology between the vector and gag region (in the region corresponding to the packaging signal) is reduced. The latter is predicted to improve the safety of the vector system by reducing the chances of recombination between the vector and gag/pol RNAs. Furthermore, due to the number of alterations in the sequence which result from the codon-optimisation process it is likely that the gag/pol RNA will no longer be packaged into virions. This concept was examined as described below.

The packaging of mRNA's derived from a wild type gag/pol pEV53B expression cassette, and from the codon-optimised EIAV gag/pol expression cassette, pESYNGP was compared (FIG. 25). In this experiment, medium was collected from B-241 cells, or from 293.101 cells stably transfected with the synthetic EIAV gag/pol expression cassette (pESYNGP). Both cell lines produce vector particles which do not contain vector RNA and do not have envelopes. In some experiments, an EIAV vector genome plasmid (pECG3-CZW) was transfected into the cells to serve as an internal positive control for hybridisation and for the presence of particles capable of packaging RNA.

Viral particles derived from each of the cell lines were then partially purified from the medium by equilibrium density gradient centrifugation. To do this 10 ml of medium from producer cells, harvested at 24 hours after induction with sodium butyrate, was layered onto a 20–60% (w/w) sucrose gradient in TNE buffer (pH 7.4) and centrifuged for 24 hours at 25,000 rpm and 4° C. in a SW28 rotor. Fractions were collected from the bottom and 10 $\mu$l of each fraction assayed for reverse transcriptase activity to locate viral particles. The results of this analysis are shown in Panel A (FIG. 26) where the profile of reverse transcriptase activity is shown as a function of gradient fraction. In these figures, the top of the gradient is on the right. It should be noted that the levels of RT activity from the 293.101-derived cell line expressing the codon-optimised gag/pol were significantly lower than from B-241 cells, which expresses the wild type gag/pol gene. To determine the RNA content of the purified virions, aliquots from the top, middle or bottom fractions were pooled (as indicated by the bars labeled T, M and B) and the RNA from each fraction was subjected to slot-blot hybridization analysis. Using a probe specific for a common region of wild type and synthetic gag/pol, encapsidation of RNA was easily detectable in the peak fractions (M) of virions synthesized from the wild type construct, but was not detected from virions synthesized from the synthetic gag-pol construct (Panel B). The positive control for encapsidation was the EIAV G3-CZW vector genome which was readily detected in peak fractions from cells expressing EIAV Gag/Pol from either the wild type or codon-optimised geness.

This result indicates that the RNA from the codon-optimised gag/pol gene is packaged significantly less efficiently than the wild type. Furthermore the lack of significant homology between the gag/pol and vector components eliminates the possibility of homolgous recombination. The codon-optimisation process therefore improves the safety profile of the system in two distinct ways.

Example 7

Western Blot Analysis of VSV-G Induction

FIG. 26 shows that efficient inducible expression of VSV-G protein in BiG-45 cells is dependent upon treatment by both sodium butyrate and doxycycline. In these experiments a clonal derivative of BiG-45 cells (clone 8Z.20; $5\times10^6$ cells/60-mm dish) producing the pONY8.0 Z vector was treated with 10 mM sodium butyrate and/or 1.5 $\mu$g/ml doxycycline for 24 hr at 37° C. Proteins were extracted from the cells and 20 $\mu$g protein from each sample was subjected to SDS-PAGE and protein blotting analysis using a monoclonal antibody to VSV-G. It is shown that both sodium butyrate and doxycycline treatment have a synergistic effect on VSV-G expression in these cells. This result further demonstrates that in the system described here full activation of genes under the control of the tetracycline-responsive element is only achieved in the presence of sodium butyrate, however once the system is activated by the dual signal there is no further requirement for sodium butyrate. This is different to the performance of the tetracycline system in other situations and desirable from a manufacturing point of view.

Example 8

Enhancement of EIAV Vector Titer Using the Post-transcriptional Regulatory Element from Woodchuck Hepatitis Virus The vectors used to demonstrate the feasibility of an EIAV-based vector system (Olsen J C Gene transfer vectors derived from equine infectious anemia virus. Gene Ther. 1998 Nov ;5(11):1481–7 and WO 98/51810) did not have sequences corresponding to the RRE's present in the env coding region of the wild type virus. Experiments with vector genomes in which the RRE regions were included demonstrated that titres could be enhanced in the presence of Rev. The increased titre is obviously desirable from the perspective of production, however, from the point of view of safety and simplicity it would desirable to remove the RRE/Rev requirement from the system.

The present invention demonstrate that the activity of the RRE/Rev system can be replaced by that of the post-transcriptional regulatory element from woodchuck hepatitis virus (WPRE). FIG. 27 shows the results of a comparison of titers obtained with EIAV vector genome plasmids containing the EIAV Rev responsive elements, RRE (RRE1+RRE2) (pECG3-CZR) or the WPRE (pECG3-CZW), or no post-transcriptional regulatory element (pECG3-CZ). The RRE and WPRE increased vector titers 18-fold and 12-fold, respectively, to yield titers greater than $10^5$ TU/ml. Thus the use of the WPRE provides a way of obtaining high-titers without having to use Rev in the vector production system. The use of WPRE as a substitute for Rev/RRE in the production of retroviral vectors has not been disclosed or suggested. The ability of of WPRE to improve vector titre is a surprising and unexpected finding because other researchers such as Zufferey J. Virol (1999), 73(4), 2886–2892 in a document entitled 'Woodchuck hepatitis virus post-transcriptional regulatory element enhances expression of transgenes delivered by retroviral vectors' have found that a dilution analysis of the vector stocks on 293T cells showed that the WPRE did not influence the vector titers obtained (data not shown).

Example 9

Construction of a Producer Cell Line for EIAV Vectors

A producer cell line is created from a packaging cell line by introduction of a system for expression of the vector component of the system. This is achieved either by transfection or transduction. By transfection of a plasmid for the vector genome component, only low numbers of vector genomes are introduced and this may represent a limitation on the titre of vector produced. The producer line 8Z.20 described in Example 2 was created by this route and contains 3 copies of the vector genome, as judged by Southern blot analysis.

It is more convenient to introduce vector by transduction and furthermore high numbers of genome copies can be achieved by using high mulitplicities of infection. In terms of vector production the critical point is that each of integrated copies of the vector can be transcriptionally active, and therefore contribute to the production of vector genome. For MLV-based vectors very high titres of vector have been obtained using this approach. (Sheridan, P L., et al. Molecular Therapy (2000), 2 (3), 262–275). This approach relies on high levels of transcription from the 5'LTR of the integrated vector therefore will not work for vectors with self-inactivating (SIN) configurations. The SIN configuration is desirable from a safety perspective for both retroviral and lentiviral vectors. For lentiviral vectors the situation is further complicated by the low transcriptional activity of the LTR's in the absence of Tat, and the unacceptability of having this protein expressed by the vector system. A method to overcome these limitations is therefore required.

One route to overcome the limitations is to arrange for a strong promoter, such as the CMV immediate early promoter, to be present in the 5'LTR following transduction. This promoter gives high level of production in the absence of Tat. However a drawback to this approach is that the titre of such vectors may be reduced relative to vectors which have the normal viral LTR. In addition, it may not be desirable from a safety perspective to have a highly active promoter present within the 3'LTR as it may activate transcription from genes located downstream of the integration site in patient's cells. Another way to overcome the problem is to use a conditional SIN vector such as described previously for an HIV-1-based vector system (Zu, K., et al., Molecular Therapy, (2001), 3(1), 97–104).

The construction of an EIAV-based conditional SIN vector is described below as is the construction of a packaging cell line based on 293.101 in which expression of the EIAV gag/pol is driven by the codon-optimised EIAV gag/pol ORF and the expression of VSV-G is driven by a tetracycline responsive promoter. It should be noted that the latter system of regulation is different from that for pTOG described in Example 2.

Construction Details

1. Introduction of the Gag/Pol Component.

The first step in the creation of the packaging cell line for EIAV-based vectors was the introduction of an expression cassette for expression of EIAV Gag/Pol from the codon optimised gene. The plasmid used was derived from pESYNGP (Example 5 and Patent Application GB0009760.0) and was termed pIRES1hyg ESYNGP. In this plasmid EIAV Gag/pol expression is driven by a CMV promoter, and is linked to an ORF for expression of hygromycin phosphotransferase by an EMCV IRES. pIRES1hyg ESYNGP was made as follows. The synthetic EIAV gag/pol gene and flanking sequences was transferred from pESYNGP into pIRES1hygro expression vector (Clontech). First, pESYNGP was digested with EcoRI, and the ends filled in by treatment with T4DNA polymerase and then digested with NotI. pIRES1hygro was prepared for ligation with this fragment by digestion with NsiI, the ends trimmed flush by treatment with T4 DNA polymerase, then digested with NotI. Prior to transfection into 293.101 cells pIRES1hyg ESYNGP was digested with AhdI. Cell lines which stably contained pIRES1hyg ESYNGP, were obtained by transfection, selection of transfectants by hygromycin B treatment and limiting dilution. The levels of Gag/Pol expression from different cell lines so obtained were compared by product enhanced reverse transcriptase (PERT) assay of reverse transcriptase in the supernatants. The cell line with the highest level of gag/pol expression, termed 293.101-ESYNGP, was then used to create a cell line in which expression of VSV-G was under control of the Tet-inducible system.

2. Introduction of the VSV-G Envelope Component

The VSV-G ORF was introduced into 293.101-ESYNGP cells by transfection of the plasmid, pTKneo-TREHCMV-G, in which expression of the neomycin resistance gene (neo) is driven by the thymidine kinase (TK) promoter. The expression of the VSV-G was from the TREHCMV-G cassette in which the tetracycline responsive element (TRE) promoter motif is placed upstream of the VSV-G sequence obtained from plasmid HCMV-G. The TKneo cassette was located upstream of the TREVSV-G and was orientated in terms of transcription in the same direction. However, a cassette in which it is orientated in the opposite direction could also be used. pTKneo-TREHCMV-G was constructed as follows. The herpes simplex virus TK promoter and intron was obtained by PCR amplification using primers

```
                                        (SEQ ID NO: 21)
TK POS   (TACGGAAGATCTAAATGAGTCTTCGGACCT)

and

                                        (SEQ ID NO: 22)
TKNEG    (CTCAACGCTAGCGTACTCTAGCCTTAAGAGCTG)
```

and as template the plasmid, pRL-TK (Promega). The 3' end of the sequence which was amplified was just upstream of the T7 promoter of pRL-TK. Following digestion with Bg/II and NheI the fragment was ligated into pSL1 1180 (Pharmacia) prepared for ligation by digestion with the same enzymes. The resultant plasmid was termed pSL1 1804-K. The neomycin phosphotransferase gene (neo) was obtained by PCR amplification using as template the pCIneo plasmid (Promega) and the primers

```
                                        (SEQ ID NO: 23)
NEO POS
(5'-GAATTGGTACCGCCACCATGATTGAACAAGATGGATTGCACGC)

and

                                       (SEQ ID NO: 24).
NEONEG
(5'GAATTGGCTAGCTCAGAAGAACTCGTCAAGAAGGCGATAGAAGGCG)
```

plasmid contains as a cassette, the TK-promoter/intron upstream of the neo gene. This cassette was excised by digestion with KpnI and Bg/II and ligated into pCI (Promega) prepared for ligation by digestion with the same enzymes. The resultant plasmid was termed pCI-TKneo. This manipulation places the TKneo cassette upstream of a polyadenylation signal.

A plasmid containing the VSV-G ORF downstream of the TRE was created as follows. The BamHI fragment containing the VSV-G sequence from plasmid HCMV-G was ligated into pTRE2 (Clontech) prepared for ligation by digestion with BamHI. The resultant plasmid was termed pTREHCMV-G and has, from 5' to 3', the tetracycline responsive element upstream of a minimal CMV promoter, the VSV-G ORF and polyadenylation signal. Of note is the fact that the VSV-G ORF differs from the published VSV-G (Indiana) (Genbank Acc. No. K01639) sequence by a single aminoacid coding alteration which means that our clone encodes histidine not glutamine at position 96.

pTKneo-TREHCMV-G was made by taking the TKneo-plyadenylation cassette from pCI-TKneo and introducing it into pTREHCMV-G. This was achieved by digestion of pCI-TKneo with PvuI and Bg/II, followed by blunting of the ends by T4 DNA polymerase treatment. This fragment was introduced into pTREHCMV-G prepared for ligation by digestion with AatII, followed by blunting of the ends by treatment with T4 DNA polymerase. A plasmid in which the two cassette were orientated so that transcription was in the same direction was selected and termed pTKneo-TREHCMV-G. Prior to use in transfections the plasmid was modified to remove the ClaI site is located between the polyadenylation signal of neo and the TRE and is useful for linearisation of the plasmid prior to use in transfections carried out for the creation of stable cell lines. This modification was achieved by partial digestion of pTKneo-TREHCMV-G with ClaI, followed by T4 DNA polymerase treatment to blunt the ends of the fragment, and then religation. A plasmid in which the ClaI site immediately downstream of the VSV-G expression cassette was deleted was selected for further work and termed pTKneo-TREHCMV-GClaI.

Prior to introduction of the pTKneo-TREHCMV-GClaI plasmid into 293.101-ESYNGP cells it was necessary to introduce a plasmid which encodes the tetracycline regulator-VP16 fusion protein. The plasmid used for this purpose was a derivative of pTet-off (Clontech) and pIRE-Spuro (Clontech) in which the EcoRI to BamHI fragment containing the fusion protein ORF was ligated into pIRE-Spuro prepared for digestion with the same enzymes. The resulting plasmid, pIRESpuro-Tet-off, has the following order of elements: CMV promoter-fusion protein ORF-intron-IRES-puromycin resistance gene-polyadenylation signal. pIRESpuro-Tet-off was introduced into 293.101-ESYNGP and stably transfected cells were selected by growth in media containing puromycin and then cloned by limiting dilution. 20 cell lines were examined for a suitable level of fusion protein expression following transfection with the test plasmid, pTRE2-luc, supplied by Clontech for this purpose. A cell line which showed a 20-fold induction of luciferase expression following withdrawal of doxycycline was selected as advised in product information by Clontech and was then used for transfection with the pTKneo-TREHCMV-GClaI plasmid prepared by linearisation with ClaI. Following transfection, cells which stably expressed the plasmid were selected by treatment with G418 and then cloned by limiting dilution. The VSV-G expression profile of these cells was then examined under conditions where doxycycline was present (the 'off' situation) or absent (the 'on' situation). A cell line in which the expression of VSV-G was very low in the presence of doxycycline but induced to the same levels as observed for BiG-45 cells (Example 7) was selected for use as an EIAV packaging cell line and termed, pac293.101EV1.

3. Introduction of the Vector Component into Pac293.101EV1

An EIAV vector in which the 3'LTR was modified to contain 7 direct repeats of the tetracycline responsive element (TRE) was created as follows. The starting point for construction of the modified LTR was vector pTRE2 (Clontech). The flanking of the TRE in pTRE2 with EIAV LTR sequences was carried out in several stages: In the first a sequence including the 3'PPT and sequences required for integration derived from the 5' end of the EIAV U3 region were placed to the 5'side of the TRE. In the second, sequences including the EIAV TATA box, R and U5 and further downstream sequences were placed to the 3'-side of the TRE.

Stage 1. Cloning of the U3a Region of the EIAV LTR Upstream of the TRE in pTRE2

The PCR was used to amplify the U3a region of the EIAV LTR from pONY8.1Z. Pfx polymerase (Gibco BRL) was used together with the primers P1-U3a1 and P2-U3a2 (FIG. 30) to incorporate an XhoI restriction endonuclease site at both ends of the resultant 157 bp DNA fragment. This PCR product was digested with XhoI and ligated into similarly digested pTRE2. The resultant clones were analysed using the restriction endonucleases MluI and SphI; those that contained the U3a region in the correct orientation were digested into 2 DNA fragments of 630 bp and 3284 bp. Those clones that contained the U3a region in the incorrect orientation were digested into 2 DNA fragments of 493 bp and 3421 bp. One of the correct clones was selected for the next stage of cloning and was designated pTRE2+U3a. A map of this vector is shown in FIG. 31.

Stage 2. Cloning of the U3b/R/U5 Region of the EIAV LTR Downstream of the TRE in pTRE2+U3a The PCR was used to amplify the U3b/R/U5 region of the EIAV LTR from pONY8.1Z. Pfx polymerase (Gibco BRL) was used together with the primers P3-U3bRU51 and P4-U3bRU52 (FIG. 28) to incorporate an XmaI restriction endonuclease site at both ends of the resultant 444 bp fragment. The primer U3bRU51 was designed to include the sequence derived from the TRE that would be removed when the TRE was digested with XmaI. This PCR product was digested with XmaI and ligated into similarly digested pTRE2+U3a. The resultant clones were digested with the restriction endonucleases StuI and SphI; those that contained the U3b/R/U5 region in the correct orientation were digested into 2 DNA fragments of 548 bp and 3653 bp. Those that contained the U3b/R/U5 region in the incorrect orientation were digested into 2 DNA fragments of 800 bp and 3401 bp. One of the correct clones was selected for the next stage of cloning and was designated pTRE2+U3a+U3bRU5. A map of this vector is shown in FIG. 32.

Stage 3. Cloning of the TRE-EIAV Hybrid LTR from pTRE2+U3a+U3bRU5 into EIAV Vectors Genome Plasmids The transfer of the TRE-EIAV hybrid LTR into EIAV vector genome plasmids is carried out by making use of the SapI sites flanking the hybrid LTR in pTRE2+U3a+U3bRU5 and virtually all EIAV vector genome plasmids. These sites allow directional cloning of the TRE-EIAV hybrid LTR into the EIAV vector genome plasmid. For example, for construction of a pONY8.0 Z derivative , pTRE2+U3a+U3bRU5 is digested with SapI to release an 825 bp fragment, which is then ligated to the 10351 bp fragment released from pONY8.0 Z by digestion with SapI. The sequence of the SapI fragment and some flanking sequences present in pTRE2+U3a+U3bRU5 is shown in FIG. 33.

Vectors containing LTR's modified by introduction of the TRE can be used to create producer cells lines using procedures similar to those described previously (Sheridan, P L., et al. Molecular Therapy (2000), 2 (3), 262–275). In brief VSV-G pseudotyped vector particles are produced by transient transfection of HEK 293 cells and use to infect, at high multiplicities of infection, pac293.101EV1 packaging cells. Subclones of the transduced population are then screened for production of high titres of vector after induction of vector formation by growth in doxycycline-free media. Thus for clarity, in this embodiment of the present invention, env protein expression, such as VSV-G expression, and vector genome expression are prevented in the presence of a tetracycline modulator, such as doxycycline, ("the "off" situation) and activated in the absence of doxycycline (the "on" situation).

Provision of EIAV Rev Expression

From experiments in which EIAV vector is made by transient transfection of HEK 293T cells using pESYNGP to supply Gag/Pol, it is known that the titres obtained from vectors which do not express Rev, such as pONY8.0Z and derivatives, are increased when Rev is added to the system. One way to avoid this requirement is to utilise a vector genome which contains a WPRE as described in Example 8. Alternatively Rev can be supplied from a separate expression cassette. Such a cassette may be linked to the vector genome cassette as described previously (PCT/GB 00/03837) or may be an cassette independent of other components of the vector system, for example pESYNREV. One potential difficulty is that continuous expression of Rev at high levels is toxic in cells. Thus there is a requirement for controlled expression of Rev. Expression may be controlled in an 'off-on' manner by use of the tetracycline inducible system, however it may be desirable to use a system of regulation which allows a precise level of Rev expression to be achieved. An example of a system that allows the latter is the ecdysone-inducible system through which precise control of the level of expression of a transgene can be obtained. Examples of TRE-mediated and ecdysone-system-mediated regulation of expression of Rev are described below.

Expression of Rev from pTRE-ESYN-TK-blast.

This plasmid was made using multiple cloning steps as follows. The blasticidin gene was excised from pCEB (Cosset F L, Takeuchi Y, Battini J L, Weiss R A, Collins M K. J Virol. 1995 Decemeber;69(12):7430–6) by digestion with ScaI and NheI and the 654 bp fragment ligated into pSL1180-TK prepared for ligation by digestion with HpaI and SpeI. The resulting plasmid has a thymdine kinase promoter (TK) upstream of the blasticidin gene and is termed pSL1180-TKblast. This is digested with BamHI and EcoRV and the 1573 bp fragment ligated to the 2907 bp fragment derived from pCIneo by digestion with BglII and SmaI. This manipulation introduces a polyadenylation signal downstream of the TK-blast cassette and is a plasmid termed pTKblast-pA. The expression cassette is released from pTKblast-pA by digestion with BamHI, the ends filled in by treatment with T4 DNA polymerase, and then digestion with BclI. The released fragment is then ligated into pTRE REV prepared for ligation by digestion with AatII, followed by filling-in of the ends by treatment with T4 DNA polymerase. The resulting plasmid was termed pTKblast-TRE-ESYNREV. pTRE REV was made by ligation of the 3731 bp fragment released by NheI and SalI digestion of pTRE2 (Clontech) with the 522 bp fragment from pESYN-REV produced by digestion with the same enzymes. Cells which were stably transfected with pTKblast-TRE-ESYNREV were selected by treatment with blasticidin.

Thus, in this embodiment of the present invention Rev protein expression is prevented in the presence of a tetracycline modulator, such as doxycycline, ("the "off" situation) and activated in the absence of doxycycline (the "on" situation).

Regulated Expression of EIAV Rev Using the Ecdysone Inducible System.

It may be necessary to optimise the level of Rev expression in the producer cell line for each vector genome. This could be achieved using a regulatable system, for example the Ecdysone regulatable system (Invitrogen, and WO 97/38117 and WO 99/58155) with which expression can be varied in a dose-dependent manner by treatment of the cell line with the ecdysone analogues, ponasterone A or Muristerone A.

Example 10

Use of Insulator Elements to Improve the Performance of LTR's in Producer Cells

The level of transcription from the LTR of an integrated retrovirus is determined by the chromosomal environment. Therefore the performance of a particular integrated conditional SIN vector will also be influenced similarly. The levels of LTR driven transcription can be improved and made more uniform across a collection of integrated copies of a vector by flanking the vector genome with insulator elements, such as the chicken β-globin insulator (Emery D W, Yannaki E, Tubb J, Stamatoyannopoulos G. Proc Natl Acad Sci U S A 2000 Aug 1;97(16):9150–5; Rivella S, Callegari J A, May C, Tan C W, Sadelain M. J Virol. 2000 May;74(10):4679–87). These observations suggest that inclusion of an insulator sequence in the conditional SIN vectors described above would result in an improved level of transcription and hence production of higher titres of virus. An additional benefit is that the transcriptional activity from LTR's flanked in this manner will be maintained for an increased period relative to that from LTR's not protected from the effects of the local chromosomal environment, thereby extending the productive lifetime of the producer cell line.

The cHS4 element from the chicken beta-globin locus (Genbank: Accession Number U78775) was obtained from plamsid pJC 13.1(Chung J H, Whiteley M, Felsenfeld Cell. 1993 Aug 13;74(3):505–14) as an XbaI fragment and prepared for ligation by filling-in the ends by treatment with T4 DNA polymerase. This fragment was ligated into pTRE2+U3a+U3bRU5 prepared for ligation by partial digestion with XhoI, followed by treament with T4 DNA polymerase. The products of ligation and transformation were screened for the presence of the cHS4 element located in either orientation and located between the 5'EIAV U3 sequence and the TRE multimer. For clarity the order of components in the LTR is thus 5'end of the EIAV U3—cHS4—TRE multimer—EIAV TATA box-EIAV R-U5: The cHS4/TRE hybrid LTR's, with the cHS4 in the plus or minus orientations, were then transferred to vector genomes by carrying out 3-way ligations with vector genome fragment prepared by SapI ligation and the two SapI fragments representing the 5' and 3' ends of the hybrid LTR.

Example 11

It can be advantageous from the point of view of production of vectors at large scale to utilize a cell that can be propagated in suspension culture. Technologies for handling of cells in suspension and for separation of substances secreted into the growth media of such cells are well established. A number of cell lines are available for the generation of of producer cell lines. These include cells derived from leukemias (e.g. HL-60) and cells derived from lymphomas (e.g. CEM, WIL2, Namalwa, JM-1, IM-9). A longer list of human and non-human cells lines is available from the ATCC (American Type Culture Collection, http:\\www.atcc.org). Preferably the cell line would be human. For example CEM cells can form the basis of an EIAV-vector producer cell using the approach outlined in Example 9.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described mode's for carrying out the invention which are obvious to those skilled in molecular biology or related fields are intended to be within the scope of the following claims.

What is claimed is:

1. A packaging cell comprising:

(i) a first nucleotide sequence (NS) encoding a toxic viral envelope protein operably linked to a promoter; and wherein the promoter is operably linked to at least one copy of a tetracycline responsive element (TRE);

(ii) a second NS wherein the second NS comprises a sequence encoding a tetracycline modulator; and (iii) a third NS encoding a retrovirus nucleocapsid protein;

such that the expression of the first NS is regulatable by tetracycline and an initial stimulus with sodium butyrate or a functional analogues thereof.

2. A packaging cell according to claim 1 wherein the first NS encodes a vesicular stomatitis virus (VSV)-G protein or a mutant, variant, homologue or fragment thereof.

3. A packaging cell according to claim 1 or claim 2 wherein the third NS is a codon optimised gag/pol protein.

4. A packaging cell according to claim 1 or claim 2 wherein the tetracycline analogue is doxycycline.

5. A producer cell comprising:

(i) a first nucleotide sequence (NS) encoding a toxic viral envelope protein operably linked to a promoter; wherein the promoter is operably linked to at least one copy of a TRE;

(ii) a second NS wherein the second NS comprises a sequence encoding a tetracycline modulator;

(iii) a third NS encoding a retrovirus nucleocapsid protein; and (iv) a fourth NS comprising a retroviral sequence to be packaged in a retroviral particle;

such that the retroviral vector particle titre obtainable from the producer cell is regulatable by tetracycline and an initial stimulus with sodium butyrate or functional analogues thereof.

6. A producer cell according to claim 5 wherein the first NS encodes a VSV-G protein or a mutant, variant, homologue or fragment thereof.

7. A producer cell according to claim 5 or claim 6 wherein the third NS is a codon optimized gag/pol protein.

8. A producer cell according to claim 5 or claim 6 wherein the tetracycline analogue is doxycycline.

9. A producer cell according to claim 5 or claim 6 wherein the fourth NS comprises at least one nucleotide sequence of interest (NOI).

10. A producer cell according to claim 5 or claim 6 wherein the 3' LTR U3 region of the fourth NS comprises at least one copy of a TRE.

11. A virus producer cell comprising:

(i) a first nucleotide sequence (NS) encoding a toxic viral envelope protein operably linked to a promoter; and wherein the promoter is operably linked to at least one copy of a TRE;

(ii) a second NS wherein the second NS comprises a sequence encoding a tetracycline modulator; and (iii) a third NS comprising a viral sequence sufficient to produce viral vector particles from the cell;

such that the viral vector particle titre obtainable from the producer cell is regulatable by tetracycline and an initial stimulus with sodium butyrate or functional analogues thereof.

12. A producer cell according to claim 11 wherein the viral sequence comprises at least one NOI.

13. A producer cell according to claim 11 or claim 12 wherein the tetracycline analogue is doxycycline.

14. A method for producing a retroviral vector wherein the method comprises:

(i) selecting a host cell for retroviral vector production;

(ii) introducing into the host cell:

a first nucleotide sequence (NS) encoding a toxic viral envelope protein operably linked to a promoter; and wherein the promoter is operably linked to at least one copy of a TRE;

a second NS wherein the second NS comprises a sequence encoding a tetracycline modulator;

a third NS encoding a retrovirus nucleocapsid protein;

a fourth NS comprising a retroviral sequence to be packaged in a retroviral particle; and (iii) incubating the host cell in a culture medium comprising tetracycline and an initial stimulus with sodium butyrate or functional analogues thereof such that sufficient retroviral vector transducing particles are producible from the host cell.

15. A method according to claim 14 wherein the toxic viral envelope protein is VSV-G or a mutant, variant, homologue or fragment thereof.

16. A method according to claim 14 or claim 15 wherein the tetracycline analogue is doxycycline.

17. A method according to claim 14 or claim 15 wherein the nucleocapsid protein is a codon optimised gag/pol protein.

18. A method according to claim 14 or claim 15 wherein the fourth NS comprises at least one nucleotide sequence of interest (NOI).

19. A method according to claim 14 or claim 15 wherein the 3' LTR U3 region of the fourth NS comprises at least one copy of a TRE.

20. A method according to any one of claim 14 or 15, wherein the fourth NS comprises a polynucleotide response element.

21. A method according to claim 20 wherein the polynucleotide response element is the Rev response element (RRE).

22. A method according to claim 20 wherein the polynucleotide response element is a woodchuck hepatitis virus post-transcriptional regulatory element (WHY PRE).

23. A method according to claim 14 or 15 wherein the fourth NS is a minimal vector genome.

24. A method according to claim 23 wherein the minimal vector genome is a lentiviral vector genome.

25. A method according to claim 24 wherein the lentiviral vector genome is an EIAV vector.

26. A method according to claim 14 or 15 wherein the cell is a TE671 cell or a HEK 293 cell.

27. A retroviral vector producible by the method according to claim 14 or 15 wherein the retroviral vector is producible in sufficient amounts to effectively transduce a target site.

28. A retroviral vector according to claim 27 wherein the target site is a cell.

29. A cell transduced with a retroviral vector according to claim 28.

30. A retroviral vector according to claim 27 or 28 for use in medicine.

31. A method for making a pharmaceutical composition comprising a retroviral vector wherein the method comprises admixing the retroviral vector according to claim 27 or 28 with a pharmaceutically acceptable carrier.

32. A method for producing a retroviral gene delivery system comprising incubating the producer cell of claim 5 in a culture medium comprising tetracycline and sodium butyrate or functional analogues thereof in a sufficient amount and for a sufficient time such that an effective amount of a retroviral vector is produced.

33. A method for producing a viral gene delivery system comprising incubating the cell of claim 12 in a culture medium comprising tetracycline or a sodium butyrate or functional analogues thereof in a sufficient amount and for a sufficient time such that an effective amount of a viral vector is produced.

34. A retroviral delivery system according to claim 32 or a viral delivery system according to claim 33 wherein the retroviral delivery system or the viral delivery system is produced in sufficient amounts to effectively transduce a target site.

35. A retroviral delivery system or a viral delivery system according to claim 34 wherein the target site is a cell.

36. A cell transduced with a retroviral delivery system or a viral delivery system according to claim 35.

37. A retroviral delivery system according to claim 32 or a viral delivery system according to claim 33 for use in medicine.

38. A method for delivering an NOI to a target site, said method comprising introducing into the target site the viral delivery system according to claim 33.

39. A stable temperature regulated producer cell line according to claim 11 wherein the producer cell line produces sufficient amounts of a viral vector.

* * * * *

SEQUENCE LISTING

```
<160> NUMBER OF SEQ ID NOS: 25

<210> SEQ ID NO 1
<211> LENGTH: 11874
<212> TYPE: DNA
<213> ORGANISM: Artificial Sequence
<220> FEATURE:
<223> OTHER INFORMATION: Description of Artificial Sequence: Synthetic
      nucleic acid pEV53B

<400> SEQUENCE: 1

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900
```

-continued

```
cgcgggcgcg ccaggtaaga tgggagaccc tttgacatgg agcaaggcgc tcaagaagtt    960
agagaaggtg acggtacaag ggtctcagaa attaactact ggtaactgta attgggcgct   1020
aagtctagta gacttatttc atgataccaa ctttgtaaaa gaaaaggact ggcagctgag   1080
ggatgtcatt ccattgctgg aagatgtaac tcagacgctg tcaggacaag aaagagaggc   1140
ctttgaaaga acatggtggg caatttctgc tgtaaagatg ggcctccaga ttaataatgt   1200
agtagatgga aaggcatcat tccagctcct aagagcgaaa tatgaaaaga agactgctaa   1260
taaaaagcag tctgagccct ctgaagaata tccaatcatg atagatgggg ctggaaacag   1320
aaattttaga cctctaacac ctagaggata tactacttgg gtgaatacca tacagacaaa   1380
tggtctatta aatgaagcta gtcaaaactt atttgggata ttatcagtag actgtacttc   1440
tgaagaaatg aatgcatttt tggatgtggt acctggccag gcaggacaaa agcagatatt   1500
acttgatgca attgataaaa tagcagatga ttgggataat agacatccat taccgaatgc   1560
tccactggtg gcaccaccac aagggcctat tcccatgaca gcaaggttta ttagaggttt   1620
aggagtacct agagaaagac agatggagcc tgcttttgat cagtttaggc agacatatag   1680
acaatggata atagaagcca tgtcagaagg catcaaagtg atgattggaa aacctaaagc   1740
tcaaaatatt aggcaaggag ctaaggaacc ttacccagaa tttgtagaca gactattatc   1800
ccaaataaaa agtgagggac atccacaaga gatttcaaaa ttcttgactg atacactgac   1860
tattcagaac gcaaatgagg aatgtagaaa tgctatgaga catttaagac cagaggatac   1920
attagaagag aaaatgtatg cttgcagaga cattggaact acaaaacaaa agatgatgtt   1980
attggcaaaa gcacttcaga ctggtcttgc gggcccattt aaaggtggag ccttaaaagg   2040
agggccacta aaggcagcac aaacatgtta taactgtggg aagccaggac atttatctag   2100
tcaatgtaga gcacctaaag tctgttttaa atgtaaacag cctggacatt tctcaaagca   2160
atgcagaagt gttccaaaaa acgggaagca aggggctcaa gggaggcccc agaaacaaac   2220
tttcccgata caacagaaga gtcagcacaa caaatctgtt gtacaagaga ctcctcagac   2280
tcaaaatctg tacccagatc tgagcgaaat aaaaaaggaa tacaatgtca aggagaagga   2340
tcaagtagag gatctcaacc tggacagttt gtgggagtaa catataatct agagaaaagg   2400
cctactacaa tagtattaat taatgatact cccttaaatg tactgttaga cacaggagca   2460
gatacttcag tgttgactac tgcacattat aataggttaa aatatagagg gagaaaatat   2520
caagggacgg gaataatagg agtgggagga aatgtggaaa cattttctac gcctgtgact   2580
ataaaggaaa agggtagaca cattaagaca agaatgctag tggcagatat tccagtgact   2640
attttgggac gagatattct tcaggactta ggtgcaaaat tggttttggc acagctctcc   2700
aaggaaataa aatttagaaa aatagagtta aaagagggca caatggggcc aaaaattcct   2760
caatggccac tcactaagga gaaactagaa ggggctaaag agatagtcca aagactattg   2820
tcagagggaa aaatatcaga agctagtgac aataatcctt ataattcacc catatttgta   2880
ataaaaaaga ggtctggcaa atggaggtta ttacaagatc tgagagaatt aaacaaaaca   2940
gtacaagtag gaacggaaat atccagagga ttgcctcacc cgggaggatt aattaaatgt   3000
aaacacatga ctgtattaga tattggagat gcatatttca ctataccctt agatccagag   3060
tttagaccat atacagcttt cactattccc tccattaatc atcaagaacc agataaaaga   3120
tatgtgtgga attgtttacc acaaggattc gtgttgagcc catatatata tcagaaaaca   3180
ttacaggaaa ttttacaacc ttttagggaa agatatcctg aagtacaatt gtatcaatat   3240
```

-continued

```
atggatgatt tgttcgtggg aagtaatggt tctaaaaaac aacacaaaga gttaatcata   3300
gaattaaggg caatcttact ggaaaagggt tttgagacac cagatgataa attacaagaa   3360
gtgccacctt atagctggct aggttatcaa ctttgtcctg aaaattggaa agtacaaaaa   3420
atgcaattag acatggtaaa gaatccaacc cttaatgatg tgcaaaaatt aatggggaat   3480
ataacatgga tgagctcagg ggtcccaggg ttgacagtaa aacacatagc agctactact   3540
aagggatgtt tagagttgaa tcaaaaagta atttggacgg aagaggcaca aaaagagtta   3600
gaagaaaata atgagaagat taaaaatgct caagggttac aatattataa tccagaagaa   3660
gaaatgttat gtgaggttga aattacaaaa aattatgagg caacttatgt tataaaacaa   3720
tcacaaggaa tcctatgggc aggtaaaaag attatgaagg ctaataaggg atggtcaaca   3780
gtaaaaaatt taatgttact gttgcaacat gtggcaacag aaagtattac tagagtagga   3840
aaatgtccaa cgtttaaggt accatttacc aaagagcaag taatgtggga aatgcaaaaa   3900
ggatggtatt attcttggct cccagaaata gtatatacac atcaagtagt tcatgatgat   3960
tggagaatga aattggtaga agaacctaca tcaggaataa caatatacac tgatggggga   4020
aaacaaaatg gagaaggaat agcagcttat gtgaccagta atgggagaac taaacagaaa   4080
aggttaggac ctgtcactca tcaagttgct gaaagaatgg caatacaaat ggcattagag   4140
gataccagag ataaacaagt aaatatagta actgatagtt attattgttg gaaaaatatt   4200
acagaaggat taggtttaga aggaccacaa agtccttggt ggcctataat acaaaatata   4260
cgagaaaaag agatagttta ttttgcttgg gtacctggtc acaaagggat atgtggtaat   4320
caattggcag atgaagccgc aaaaataaaa gaagaaatca tgctagcata ccaaggcaca   4380
caaattaaag agaaaagaga tgaagatgca gggtttgact tatgtgttcc ttatgacatc   4440
atgatacctg tatctgacac aaaaatcata cccacagatg taaaaattca agttcctcct   4500
aatagctttg gatgggtcac tgggaaatca tcaatggcaa aacaggggtt attaattaat   4560
ggaggaataa ttgatgaagg atatacagga gaaatacaag tgatatgtac taatattgga   4620
aaaagtaata ttaaattaat agagggacaa aaatttgcac aattaattat actacagcat   4680
cactcaaatt ccagacagcc ttgggatgaa aataaaatat ctcagagagg ggataaagga   4740
tttggaagta caggagtatt ctgggtagaa aatattcagg aagcacaaga tgaacatgag   4800
aattggcata catcaccaaa gatattggca agaaattata agataccatt gactgtagca   4860
aaacagataa ctcaagaatg tcctcattgc actaagcaag gatcaggacc tgcaggttgt   4920
gtcatgagat ctcctaatca ttggcaggca gattgcacac atttggacaa taagataata   4980
ttgacttttg tagagtcaaa ttcaggatac atacatgcta cattattgtc aaaagaaaat   5040
gcattatgta cttcattggc tattttagaa tgggcaagat tgttttcacc aaagtcctta   5100
cacacagata acggcactaa ttttgtggca gaaccagttg taaatttgtt gaagttccta   5160
aagatagcac ataccacagg aataccatat catccagaaa gtcagggtat tgtagaaagg   5220
gcaaatagga ccttgaaaga gaagattcaa agtcatagag acaacactca aacactggag   5280
gcagctttac aacttgctct cattacttgt aacaaaggga gggaaagtat gggaggacag   5340
acaccatggg aagtatttat cactaatcaa gcacaagtaa tacatgagaa acttttacta   5400
cagcaagcac aatcctccaa aaaattttgt ttttacaaaa tccctggtga acatgattgg   5460
aagggaccta ctagggtgct gtggaagggt gatggtgcag tagtagttaa tgatgaagga   5520
aagggaataa ttgctgtacc attaaccagg actaagttac taataaagcc aaattgagta   5580
ttgttgcagg aagcaagacc caactaccat tgtcagctgt gtttcctgag gtctctagga   5640
```

-continued

```
attgattacc tcgatgcttc attaaggaag aagaataaac aaagactgaa ggcaatccaa   5700
caaggaagac aacctcaata tttgttataa ggtttgatat atgggattat ttggtaaagg   5760
ggtaacatgg tcagcatcgc attctatggg gggatcccag ggggaatctc aacccctatt   5820
acccaacagt cagaaaaatc taagtgtgag gagaacacaa tgtttcaacc ttattgttat   5880
aataatgaca gtaagaacag catggcagaa tcgaaggaag caagagacca agaaatgaac   5940
ctgaaagaag aatctaaaga agaaaaaaga agaaatgact ggtggaaaaa aggtatgttt   6000
ctgttatgct tagcaggaac tactggagga atactttggt ggtatgaagg actcccacag   6060
caacattata tagggttggt ggcgataggg ggaagattaa acggatctgg ccaatcaaat   6120
gctatagaat gctggggttc cttcccgggg tgtagaccat ttcaaaatta cttcagttat   6180
gagaccaata gaagcatgca tatggataat aatactgcta cattattaga agctttaacc   6240
aatataactg ctctataaat aacaaaacag aattagaaac atggaagtta gtaaagactt   6300
ctggcgtaac tcctttacct atttcttctg aagctaacac tggactaatt agacataaga   6360
gagattttgg tataagtgca atagtggcag ctattgtagc cgctactgct attgctgcta   6420
gcgctactat gtcttatgtt gctctaactg aggttaacaa aataatggaa gtacaaaatc   6480
atacttttga ggtagaaaat agtactctaa atggtatgga tttaatagaa cgacaaataa   6540
agatattata tgctatgatt cttcaaacac atgcagatgt tcaactgtta aaggaaagac   6600
aacaggtaga ggagacattt aatttaattg gatgtataga aagaacacat gtattttgtc   6660
atactggtca tccctggaat atgtcatggg gacatttaaa tgagtcaaca caatgggatg   6720
actgggtaag caaaatggaa gatttaaatc aagagatact aactacactt catggagcta   6780
ggaacaattt ggcacaatcc atgataacat tcaatacacc agatagtata gctcaatttg   6840
gaaaagacct ttggagtcat attggaaatt ggattcctgg attgggagct tccattataa   6900
aatatatagt gatgtttttg cttatttatt tgttactaac ctcttcgcct aagatcctca   6960
gggccctctg gaaagtgacc agtggtgcag ggtcctccgg cagtcgttac ctgaagaaaa   7020
aattccatca caaacatgca tcgcgagaag acacctggga ccaggcccaa cacaacatac   7080
acctagcagg cgtgaccggt ggatcagggg acaaatacta caaacagaag tactccagga   7140
acgactggaa tggagaatca gaggagtaca acaggcggcc aaagagctgg gtgaagtcaa   7200
tcgaggcatt tggagagagc tatatttccg agaagaccaa aggggagatt tctcagcctg   7260
gggcggctat caacgagcac aagaacggct ctgggggggaa caatcctcac caagggtcct   7320
tagacctgga gattcgaagc gaaggaggaa acatttatga ctgttgcatt aaagcccaag   7380
aaggaactct cgctatccct tgctgtggat ttcccttatg gctattttgg ggactagagg   7440
gcccgtttaa acccgctgat cagcctcgac tgtgccttct agttgccagc catctgttgt   7500
ttgcccctcc cccgtgcctt ccttgaccct ggaaggtgcc actcccactg tcctttccta   7560
ataaaatgag gaaattgcat cgcattgtct gagtaggtgt cattctattc tggggggtgg   7620
ggtggggcag gacagcaagg gggaggattg ggaagacaat agcaggcatg ctggggatgc   7680
ggtgggctct atggcttctg aggcggaaag aaccagctgg ggctctaggg ggtatcccca   7740
cgcgccctgt agcggcgcat taagcgcggc gggtgtggtg gttacgcgca gcgtgaccgc   7800
tacacttgcc agcgccctag cgcccgctcc tttcgctttc ttcccttcct ttctcgccac   7860
gttcgccggc tttccccgtc aagctctaaa tcggggcatc cctttagggt tccgatttag   7920
tgctttacgg cacctcgacc ccaaaaaact tgattagggt gatggttcac gtagtgggcc   7980
```

-continued atcgccctga tagacggttt ttcgcccttt gacgttggag tccacgttct ttaatagtgg 8040
actcttgttc caaactggaa caacactcaa ccctatctcg gtctattctt ttgatttata 8100
agggattttg gggatttcgg cctattggtt aaaaaatgag ctgatttaac aaaaatttaa 8160
cgcgaattaa ttctgtggaa tgtgtgtcag ttagggtgtg gaaagtcccc aggctcccca 8220
ggcaggcaga agtatgcaaa gcatgcatct caattagtca gcaaccaggt gtggaaagtc 8280
cccaggctcc ccagcaggca gaagtatgca aagcatgcat ctcaattagt cagcaaccat 8340
agtcccgccc ctaactccgc ccatcccgcc cctaactccg cccagttccg cccattctcc 8400
gccccatggc tgactaattt tttttattta tgcagaggcc gaggccgcct ctgcctctga 8460
gctattccag aagtagtgag gaggcttttt tggaggccta ggcttttgca aaaagctccc 8520
gggagcttgt atatccattt tcggatctga tcaagagaca ggatgaggat cgtttcgcat 8580
gattgaacaa gatggattgc acgcaggttc tccggccgct tgggtggaga ggctattcgg 8640
ctatgactgg gcacaacaga caatcggctg ctctgatgcc gccgtgttcc ggctgtcagc 8700
gcaggggcgc ccggttcttt ttgtcaagac cgacctgtcc ggtgccctga atgaactgca 8760
ggacgaggca gcgcggctat cgtggctggc cacgacgggc gttccttgcg cagctgtgct 8820
cgacgttgtc actgaagcgg gaagggactg gctgctattg ggcgaagtgc cggggcagga 8880
tctcctgtca tctcaccttg ctcctgccga gaaagtatcc atcatggctg atgcaatgcg 8940
gcggctgcat acgcttgatc cggctacctg cccattcgac caccaagcga aacatcgcat 9000
cgagcgagca cgtactcgga tggaagccgg tcttgtcgat caggatgatc tggacgaaga 9060
gcatcagggg ctcgcgccag ccgaactgtt cgccaggctc aaggcgcgca tgcccgacgg 9120
cgaggatctc gtcgtgaccc atggcgatgc ctgcttgccg aatatcatgg tggaaaatgg 9180
ccgcttttct ggattcatcg actgtggccg gctgggtgtg gcggaccgct atcaggacat 9240
agcgttggct acccgtgata ttgctgaaga gcttggcggc gaatgggctg accgcttcct 9300
cgtgctttac ggtatcgccg ctcccgattc gcagcgcatc gccttctatc gccttcttga 9360
cgagttcttc tgagcgggac tctggggttc gaaatgaccg accaagcgac gcccaacctg 9420
ccatcacgag atttcgattc caccgccgcc ttctatgaaa ggttgggctt cggaatcgtt 9480
ttccgggacg ccggctggat gatcctccag cgcggggatc tcatgctgga gttcttcgcc 9540
caccccaact tgtttattgc agcttataat ggttacaaat aaagcaatag catcacaaat 9600
ttcacaaata aagcattttt ttcactgcat tctagttgtg gtttgtccaa actcatcaat 9660
gtatcttatc atgtctgtat accgtcgacc tctagctaga gcttggcgta atcatggtca 9720
tagctgtttc ctgtgtgaaa ttgttatccg ctcacaattc cacacaacat acgagccgga 9780
agcataaagt gtaaagcctg gggtgcctaa tgagtgagct aactcacatt aattgcgttg 9840
cgctcactgc ccgctttcca gtcgggaaac ctgtcgtgcc agctgcatta atgaatcggc 9900
caacgcgcgg ggagaggcgg tttgcgtatt gggcgctctt ccgcttcctc gctcactgac 9960
tcgctgcgct cggtcgttcg gctgcggcga gcggtatcag ctcactcaaa ggcggtaata 10020
cggttatcca cagaatcagg ggataacgca ggaaagaaca tgtgagcaaa aggccagcaa 10080
aaggccagga accgtaaaaa ggccgcgttg ctggcgtttt tccataggct ccgcccccct 10140
gacgagcatc acaaaaatcg acgctcaagt cagaggtggc gaaacccgac aggactataa 10200
agataccagg cgtttccccc tggaagctcc ctcgtgcgct ctcctgttcc gaccctgccg 10260
cttaccggat acctgtccgc ctttctccct tcgggaagcg tggcgctttc tcaatgctca 10320
cgctgtaggt atctcagttc ggtgtaggtc gttcgctcca agctgggctg tgtgcacgaa 10380

-continued

```
ccccccgttc agcccgaccg ctgcgcctta tccggtaact atcgtcttga gtccaacccg  10440

gtaagacacg acttatcgcc actggcagca gccactggta acaggattag cagagcgagg  10500

tatgtaggcg gtgctacaga gttcttgaag tggtggccta actacggcta cactagaagg  10560

acagtatttg gtatctgcgc tctgctgaag ccagttacct tcggaaaaag agttggtagc  10620

tcttgatccg gcaaacaaac caccgctggt agcggtggtt tttttgtttg caagcagcag  10680

attacgcgca gaaaaaaagg atctcaagaa gatcctttga tcttttctac ggggtctgac  10740

gctcagtgga acgaaaactc acgttaaggg attttggtca tgagattatc aaaaaggatc  10800

ttcacctaga tccttttaaa ttaaaaatga agttttaaat caatctaaag tatatatgag  10860

taaacttggt ctgacagtta ccaatgctta atcagtgagg cacctatctc agcgatctgt  10920

ctatttcgtt catccatagt tgcctgactc cccgtcgtgt agataactac gatacgggag  10980

ggcttaccat ctggccccag tgctgcaatg ataccgcgag acccacgctc accggctcca  11040

gatttatcag caataaacca gccagccgga agggccgagc gcagaagtgg tcctgcaact  11100

ttatccgcct ccatccagtc tattaattgt tgccgggaag ctagagtaag tagttcgcca  11160

gttaatagtt tgcgcaacgt tgttgccatt gctacaggca tcgtggtgtc acgctcgtcg  11220

tttggtatgg cttcattcag ctccggttcc caacgatcaa ggcgagttac atgatccccc  11280

atgttgtgca aaaaagcggt tagctccttc ggtcctccga tcgttgtcag aagtaagttg  11340

gccgcagtgt tatcactcat ggttatggca gcactgcata attctcttac tgtcatgcca  11400

tccgtaagat gcttttctgt gactggtgag tactcaacca agtcattctg agaatagtgt  11460

atgcggcgac cgagttgctc ttgcccggcg tcaatacggg ataataccgc gccacatagc  11520

agaactttaa aagtgctcat cattggaaaa cgttcttcgg ggcgaaaact ctcaaggatc  11580

ttaccgctgt tgagatccag ttcgatgtaa cccactcgtg cacccaactg atcttcagca  11640

tcttttactt tcaccagcgt ttctgggtga gcaaaaacag gaaggcaaaa tgccgcaaaa  11700

aagggaataa gggcgacacg gaaatgttga atactcatac tcttcctttt tcaatattat  11760

tgaagcattt atcagggtta ttgtctcatg agcggataca tatttgaatg tatttagaaa  11820

aataaacaaa taggggttcc gcgcacattt ccccgaaaag tgccacctga cgtc        11874
```

<210> SEQ ID NO 2
<211> LENGTH: 10015
<212> TYPE: DNA
<213> ORGANISM: Artificial Sequence
<220> FEATURE:
<223> OTHER INFORMATION: Description of Artificial Sequence: Synthetic nucleic acid pECG3-CZR, vector genome plasmid

<400> SEQUENCE: 2

```
tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480

gcagtacatc tacgtattag tcatcgctat taccatggtg atgcggtttt ggcagtacac    540
```

-continued

```
caatgggcgt ggatagcggt ttgactcacg gggatttcca agtctccacc ccattgacgt    600
caatgggagt ttgttttggc accaaaatca acgggacttt ccaaaatgtc gtaataaccc    660
cgccccgttg acgcaaatgg gcggtaggcg tgtacggtgg gaggtctata taagcagagc    720
tcgtttagtg aaccgggcac tcagattctg cggtctgagt cccttctctg ctgggctgaa    780
aaggcctttg taataaatat aattctctac tcagtccctg tctctagttt gtctgttcga    840
gatcctacag ttggcgcccg aacagggacc tgagaggggc gcagacccta cctgttgaac    900
ctggctgatc gtaggatccc cgggacagca gaggagaact tacagaagtc ttctggaggt    960
gttcctggcc agaacacagg aggacaggta agtagggaga ccctttgaca tggagcaagg   1020
cgctcaagaa gttagagaag gtgacggtac aagggtctca gaaattaact actggtaact   1080
gtaattgggc gctaagtcta gtagacttat ttcatgatac caactttgta aaagaaaagg   1140
actggcagct gagggatgtc attccattgc tggaagatgt aactcagacg ctggaattcg   1200
agcttgcatg cctgcaggtc gttacataac ttacggtaaa tggcccgcct ggctgaccgc   1260
ccaacgaccc ccgcccattg acgtcaataa tgacgtatgt tcccatagta acgccaatag   1320
ggactttcca ttgacgtcaa tgggtggagt atttacggta aactgcccac ttggcagtac   1380
atcaagtgta tcatatgcca agtacgcccc ctattgacgt caatgacggt aaatggcccg   1440
cctggcatta tgcccagtac atgaccttat gggactttcc tacttggcag tacatctacg   1500
tattagtcat cgctattacc atggtgatgc ggttttggca gtacatcaat gggcgtggat   1560
agcggtttga ctcacgggga tttccaagtc tccaccccat tgacgtcaat gggagtttgt   1620
tttggcacca aaatcaacgg gactttccaa aatgtcgtaa caactccgcc ccattgacgc   1680
aaatgggcgg taggcgtgta cggtgggagg tctatataag cagagctcgt ttagtgaacc   1740
gtcagatcgc ctggagacgc catccacgct gttttgacct ccatagaaga caccgggacc   1800
gatccagcct ccggactcta gagtcgaccc gggcggccgc aattcccggg gatcgaaaga   1860
gcctgctaaa gcaaaaaaga agtcaccatg tcgtttactt tgaccaacaa gaacgtgatt   1920
ttcgttgccg gtctgggagg cattggtctg gacaccagca aggagctgct caagcgcgat   1980
cccgtcgttt tacaacgtcg tgactgggaa aaccctggcg ttacccaact taatcgcctt   2040
gcagcacatc cccctttcgc cagctggcgt aatagcgaag aggcccgcac cgatcgccct   2100
tcccaacagt tgcgcagcct gaatggcgaa tggcgctttg cctggtttcc ggcaccagaa   2160
gcggtgccgg aaagctggct ggagtgcgat cttcctgagg ccgatactgt cgtcgtcccc   2220
tcaaactggc agatgcacgg ttacgatgcg cccatctaca ccaacgtaac ctatcccatt   2280
acggtcaatc cgccgtttgt tcccacggag aatccgacgg gttgttactc gctcacattt   2340
aatgttgatg aaagctggct acaggaaggc cagacgcgaa ttattttga tggcgttaac    2400
tcggcgtttc atctgtggtg caacgggcgc tgggtcggtt acggccagga cagtcgtttg   2460
ccgtctgaat ttgacctgag cgcattttta cgcgccggag aaaaccgcct cgcggtgatg   2520
gtgctgcgtt ggagtgacgg cagttatctg gaagatcagg atatgtggcg gatgagcggc   2580
attttccgtg acgtctcgtt gctgcataaa ccgactacac aaatcagcga tttccatgtt   2640
gccactcgct ttaatgatga tttcagccgc gctgtactgg aggctgaagt tcagatgtgc   2700
ggcgagttgc gtgactacct acgggtaaca gtttctttat ggcagggtga aacgcaggtc   2760
gccagcggca ccgcgccttt cggcggtgaa attatcgatg agcgtggtgg ttatgccgat   2820
cgcgtcacac tacgtctgaa cgtcgaaaac ccgaaactgt ggagcgccga aatcccgaat   2880
```

-continued

```
ctctatcgtg cggtggttga actgcacacc gccgacggca cgctgattga agcagaagcc   2940
tgcgatgtcg gtttccgcga ggtgcggatt gaaaatggtc tgctgctgct gaacggcaag   3000
ccgttgctga ttcgaggcgt taaccgtcac gagcatcatc ctctgcatgg tcaggtcatg   3060
gatgagcaga cgatggtgca ggatatcctg ctgatgaagc agaacaactt taacgccgtg   3120
cgctgttcgc attatccgaa ccatccgctg tggtacacgc tgtgcgaccg ctacggcctg   3180
tatgtggtgg atgaagccaa tattgaaacc cacggcatgg tgccaatgaa tcgtctgacc   3240
gatgatccgc gctggctacc ggcgatgagc gaacgcgtaa cgcgaatggt gcagcgcgat   3300
cgtaatcacc cgagtgtgat catctggtcg ctggggaatg aatcaggcca cggcgctaat   3360
cacgacgcgc tgtatcgctg gatcaaatct gtcgatcctt cccgcccggt gcagtatgaa   3420
ggcggcggag ccgacaccac ggccaccgat attatttgcc cgatgtacgc gcgcgtggat   3480
gaagaccagc ccttcccggc tgtgccgaaa tggtccatca aaaaatggct ttcgctacct   3540
ggagagacgc gcccgctgat cctttgcgaa tacgcccacg cgatgggtaa cagtcttggc   3600
ggtttcgcta aatactggca ggcgtttcgt cagtatcccc gtttacaggg cggcttcgtc   3660
tgggactggg tggatcagtc gctgattaaa tatgatgaaa acggcaaccc gtggtcggct   3720
tacggcggtg attttggcga tacgccgaac gatcgccagt tctgtatgaa cggtctggtc   3780
tttgccgacc gcacgccgca tccagcgctg acggaagcaa aacaccagca gcagtttttc   3840
cagttccgtt tatccgggca aaccatcgaa gtgaccagcg aatacctgtt ccgtcatagc   3900
gataacgagc tcctgcactg gatggtggcg ctggatggta agccgctggc aagcggtgaa   3960
gtgcctctgg atgtcgctcc acaaggtaaa cagttgattg aactgcctga actaccgcag   4020
ccggagagcg ccgggcaact ctggctcaca gtacgcgtag tgcaaccgaa cgcgaccgca   4080
tggtcagaag ccgggcacat cagcgcctgg cagcagtggc gtctggcgga aaacctcagt   4140
gtgacgctcc ccgccgcgtc ccacgccatc ccgcatctga ccaccagcga aatggatttt   4200
tgcatcgagc tgggtaataa gcgttggcaa tttaaccgcc agtcaggctt tctttcacag   4260
atgtggattg gcgataaaaa acaactgctg acgccgctgc gcgatcagtt cacccgtgca   4320
ccgctggata acgacattgg cgtaagtgaa gcgacccgca ttgaccctaa cgcctgggtc   4380
gaacgctgga aggcggcggg ccattaccag gccgaagcag cgttgttgca gtgcacggca   4440
gatacacttg ctgatgcggt gctgattacg accgctcacg cgtggcagca tcaggggaaa   4500
accttattta tcagccggaa aacctaccgg attgatggta gtggtcaaat ggcgattacc   4560
gttgatgttg aagtggcgag cgatacaccg catccggcgc ggattggcct gaactgccag   4620
ctggcgcagg tagcagagcg ggtaaactgg ctcggattag ggccgcaaga aaactatccc   4680
gaccgcctta ctgccgcctg ttttgaccgc tgggatctgc cattgtcaga catgtatacc   4740
ccgtacgtct tcccgagcga aaacggtctg cgctgcggga cgcgcgaatt gaattatggc   4800
ccacaccagt ggcgcggcga cttccagttc aacatcagcc gctacagtca acagcaactg   4860
atggaaacca gccatcgcca tctgctgcac gcggaagaag gcacatggct gaatatcgac   4920
ggtttccata tggggattgg tggcgacgac tcctggagcc cgtcagtatc ggcggaatta   4980
cagctgagcg ccggtcgcta ccattaccag ttggtctggt gtcaaaaata ataataaccg   5040
ggcaggccat gtctgcccgt atttcgcgta aggaaatcca ttatgtacta tttaaaaaac   5100
acaaactttt ggatgttcgg tttattcttt ttcttttact tttttatcat gggagcctac   5160
ttcccgtttt tcccgatttg gctacatgac atcaaccata tcagcaaaag tgatacgggt   5220
attattttttg ccgctatttc tctgttctcg ctattattcc aaccgctgtt tggtctgctt   5280
```

-continued

```
tctgacaaac tcggcctcga ctctaggcgg ccgctctaga actagtggat cccaggggga   5340
atctcaaccc ctattaccca acagtcagaa aaatctaagt gtgaggagaa cacaatgttt   5400
caaccttatt gttataataa tgacagtaag aacagcatgg cagaatcgaa ggaagcaaga   5460
gaccaagaaa tgaacctgaa agaagaatct aaagaagaaa aaagaagaaa tgactggtgg   5520
aaaaaaggta tgtttctgtt atgcttagca ggaactactg gaggaatact ttggtggtat   5580
gaaggactcc cacagcaaca ttatataggg ttggtggcga taggggggaag attaaacgga   5640
tctggccaat caaatgctat agaatgctgg ggttccttcc cggggtgtag accatttcaa   5700
aattacttca gttatgagac caatagaagc atgcatatgg ataataatac tgctacatta   5760
ttagaagctt taaccaatat aactgctcta taaataacaa aacagaatta gaaacatgga   5820
agttagtaaa gacttctggc gtaactcctt tacctatttc ttctgaagct aacactggac   5880
taattagaca taagagagat tttggtataa gtgcaatagt ggcagctatt gtagccgcta   5940
ctgctattgc tgctagcgct actatgtctt atgttgctct aactgaggtt aacaaaataa   6000
tggaagtaca aaatcatact tttgaggtag aaaatagtac tctaaatggt atggatttaa   6060
tagaacgaca aataaagata ttatatgcta tgattcttca aacacatgca gatgttcaac   6120
tgttaaagga aagacaacag gtagaggaga catttaattt aattggatgt atagaaagaa   6180
cacatgtatt ttgtcatact ggtcatccct ggaatatgtc atggggacat ttaaatgagt   6240
caacacaatg ggatgactgg gtaagcaaaa tggaagattt aaatcaagag atactaacta   6300
cacttcatgg agctaggaac aatttggcac aatccatgat aacattcaat acaccagata   6360
gtatagctca atttggaaaa gacctttgga gtcatattgg aaattggatt cctggattgg   6420
gagcttccat tataaaatat atagtgatgt ttttgcttat ttatttgtta ctaacctctt   6480
cgcctaagat cctcagggcc ctctggaaag tgaccagtgg tgcagggtcc tccggcagtc   6540
gttacctgaa gaaaaaattc catcacaaac atgcatcgcg agaagacacc tgggaccagg   6600
cccaacacaa catacaccta gcaggcgtga ccggtggatc aggggacaaa tactacaaac   6660
agaagtactc caggaacgac tggaatggag aatcagagga gtacaacagg cggccaaaga   6720
gctgggtgaa gtcaatcgag gcatttggag agagctatat ttccgagaag accaaagggg   6780
agatttctca gcctggggcg gctatcaacg agcacaagaa cggctctggg gggaacaatc   6840
ctcaccaagg gtccttagac ctggagattc gaagcgaagg aggaaacatt tatgactgtt   6900
gcattaaagc ccaagaagga actctcgcta tcccttgctg tggatttccc ttatggctat   6960
tttggggact agagggcccg tttatcaagc ttatcgatag aaaaacaagg ggggaactgt   7020
ggggttttta tgaggggttt tataaatgat tataagagta aaaagaaagt tgctgatgct   7080
ctcataacct tgtataaccc aaaggactag ctcatgttgc taggcaacta aaccgcaata   7140
accacatttg tgacgcgagt tccgcattgg tgacgcgtta agttcctgtt tttacagtat   7200
ataagtgctt gtattctgac aattgggcac tcagattctg cggtctgagt cccttctctg   7260
ctgggctgaa aaggcctttg taataaatat aattctctac tcagtccctg tctctagttt   7320
gtctgttcga gatcctacat taattaagga gatccgggct ggcgtaatag cgaagaggcc   7380
cgcaccgatc gcccttccca acagttgcgc agcctgaatg gcgaatggac gcgccctgta   7440
gcggcgcatt aagcgcggcg ggtgtggtgg ttacgcgcag cgtgaccgct acacttgcca   7500
gcgccctagc gcccgctcct ttcgctttct tcccttcctt tctcgccacg ttcgccggct   7560
ttccccgtca agctctaaat cgggggctcc ctttagggtt ccgatttaga gctttacggc   7620
```

-continued

```
acctcgaccg caaaaaactt gatttgggtg atggttcacg tagtgggcca tcgccctgat   7680
agacggtttt tcgccctttg acgttggagt ccacgttctt taatagtgga ctcttgttcc   7740
aaactggaac aacactcaac cctatctcgg tctattcttt tgatttataa gggattttgc   7800
cgatttcggc ctattggtta aaaaatgagc tgatttaaca aatatttaac gcgaatttta   7860
acaaaatatt aacgtttaca atttcgcctg atgcggtatt ttctccttac gcatctgtgc   7920
ggtatttcac accgcatatg gtgcactctc agtacaatct gctctgatgc cgcatagtta   7980
agccagcccc gacacccgcc aacacccgct gacgcgccct gacgggcttg tctgctcccg   8040
gcatccgctt acagacaagc tgtgaccgtc tccgggagct gcatgtgtca gaggttttca   8100
ccgtcatcac cgaaacgcgc gagacgaaag ggcctcgtga tacgcctatt tttataggtt   8160
aatgtcatga taataatggt ttcttagacg tcaggtggca cttttcgggg aaatgtgcgc   8220
ggaaccccta tttgtttatt tttctaaata cattcaaata tgtatccgct catgagacaa   8280
taaccctgat aaatgcttca ataatattga aaaaggaaga gtatgagtat tcaacatttc   8340
cgtgtcgccc ttattccctt ttttgcggca ttttgccttc ctgtttttgc tcacccagaa   8400
acgctggtga aagtaaaaga tgctgaagat cagttgggtg cacgagtggg ttacatcgaa   8460
ctggatctca acagcggtaa gatccttgag agttttcgcc ccgaagaacg ttttccaatg   8520
atgagcactt ttaaagttct gctatgtggc gcggtattat cccgtattga cgccgggcaa   8580
gagcaactcg gtcgccgcat acactattct cagaatgact tggttgagta ctcaccagtc   8640
acagaaaagc atcttacgga tggcatgaca gtaagagaat tatgcagtgc tgccataacc   8700
atgagtgata acactgcggc caacttactt ctgacaacga tcggaggacc gaaggagcta   8760
accgcttttt tgcacaacat gggggatcat gtaactcgcc ttgatcgttg ggaaccggag   8820
ctgaatgaag ccataccaaa cgacgagcgt gacaccacga tgcctgtagc aatggcaaca   8880
acgttgcgca aactattaac tggcgaacta cttactctag cttcccggca acaattaata   8940
gactggatgg aggcggataa agttgcagga ccacttctgc gctcggccct tccggctggc   9000
tggtttattg ctgataaatc tggagccggt gagcgtgggt ctcgcggtat cattgcagca   9060
ctggggccag atggtaagcc ctcccgtatc gtagttatct acacgacggg gagtcaggca   9120
actatggatg aacgaaatag acagatcgct gagataggtg cctcactgat taagcattgg   9180
taactgtcag accaagttta ctcatatata ctttagattg atttaaaact tcatttttaa   9240
tttaaaagga tctaggtgaa gatccttttt gataatctca tgaccaaaat cccttaacgt   9300
gagttttcgt tccactgagc gtcagacccc gtagaaaaga tcaaaggatc ttcttgagat   9360
cctttttttc tgcgcgtaat ctgctgcttg caaacaaaaa aaccaccgct accagcggtg   9420
gtttgtttgc cggatcaaga gctaccaact ctttttccga aggtaactgg cttcagcaga   9480
gcgcagatac caaatactgt ccttctagtg tagccgtagt taggccacca cttcaagaac   9540
tctgtagcac cgcctacata cctcgctctg ctaatcctgt taccagtggc tgctgccagt   9600
ggcgataagt cgtgtcttac cgggttggac tcaagacgat agttaccgga taaggcgcag   9660
cggtcgggct gaacgggggg ttcgtgcaca cagcccagct tggagcgaac gacctacacc   9720
gaactgagat acctacagcg tgagctatga gaaagcgcca cgcttcccga agggagaaag   9780
gcggacaggt atccggtaag cggcagggtc ggaacaggag agcgcacgag ggagcttcca   9840
gggggaaacg cctggtatct ttatagtcct gtcgggtttc gccacctctg acttgagcgt   9900
cgatttttgt gatgctcgtc aggggggcgg agcctatgga aaaacgccag caacgcggcc   9960
tttttacggt tcctggcctt ttgctggcct tttgctcaca tggctcgaca gatct       10015
```

-continued

<210> SEQ ID NO 3
<211> LENGTH: 10998
<212> TYPE: DNA
<213> ORGANISM: Artificial Sequence
<220> FEATURE:
<223> OTHER INFORMATION: Description of Artificial Sequence: Synthetic
nucleic acid pONY8.0Z vector genome plasmid

<400> SEQUENCE: 3
agatcttgaa taataaaatg tgtgtttgtc cgaaatacgc gttttgagat ttctgtcgcc 60
gactaaattc atgtcgcgcg atagtggtgt ttatcgccga tagagatggc gatattggaa 120
aaattgatat ttgaaaatat ggcatattga aaatgtcgcc gatgtgagtt tctgtgtaac 180
tgatatcgcc atttttccaa aagtgatttt tgggcatacg cgatatctgg cgatagcgct 240
tatatcgttt acgggggatg gcgatagacg actttggtga cttgggcgat tctgtgtgtc 300
gcaaatatcg cagtttcgat ataggtgaca gacgatatga ggctatatcg ccgatagagg 360
cgacatcaag ctggcacatg gccaatgcat atcgatctat acattgaatc aatattggcc 420
attagccata ttattcattg gttatatagc ataaatcaat attggctatt ggccattgca 480
tacgttgtat ccatatcgta atatgtacat ttatattggc tcatgtccaa cattaccgcc 540
atgttgacat tgattattga ctagttatta atagtaatca attacggggt cattagttca 600
tagcccatat atggagttcc gcgttacata acttacggta aatggcccgc ctggctgacc 660
gcccaacgac ccccgcccat tgacgtcaat aatgacgtat gttcccatag taacgccaat 720
agggactttc cattgacgtc aatgggtgga gtatttacgg taaactgccc acttggcagt 780
acatcaagtg tatcatatgc caagtccgcc ccctattgac gtcaatgacg gtaaatggcc 840
cgcctggcat tatgcccagt acatgacctt acgggacttt cctacttggc agtacatcta 900
cgtattagtc atcgctatta ccatggtgat gcggttttgg cagtacacca atgggcgtgg 960
atagcggttt gactcacggg gatttccaag tctccacccc attgacgtca atgggagttt 1020
gttttggcac caaaatcaac gggactttcc aaaatgtcgt aacaactgcg atcgcccgcc 1080
ccgttgacgc aaatgggcgg taggcgtgta cggtgggagg tctatataag cagagctcgt 1140
ttagtgaacc gggcactcag attctgcggt ctgagtccct tctctgctgg gctgaaaagg 1200
cctttgtaat aaatataatt ctctactcag tccctgtctc tagtttgtct gttcgagatc 1260
ctacagttgg cgcccgaaca gggacctgag aggggcgcag accctacctg ttgaacctgg 1320
ctgatcgtag gatccccggg acagcagagg agaacttaca gaagtcttct ggaggtgttc 1380
ctggccagaa cacaggagga caggtaagat tgggagaccc tttgacattg gagcaaggcg 1440
ctcaagaagt tagagaaggt gacggtacaa gggtctcaga aattaactac tggtaactgt 1500
aattgggcgc taagtctagt agacttattt catgatacca actttgtaaa agaaaaggac 1560
tggcagctga gggatgtcat tccattgctg gaagatgtaa ctcagacgct gtcaggacaa 1620
gaaagagagg cctttgaaag aacatggtgg gcaatttctg ctgtaaagat gggcctccag 1680
attaataatg tagtagatgg aaaggcatca ttccagctcc taagagcgaa atatgaaaag 1740
aagactgcta ataaaaagca gtctgagccc tctgaagaat atctctagaa ctagtggatc 1800
ccccgggctg caggagtggg gaggcacgat ggccgctttg gtcgaggcgg atccggccat 1860
tagccatatt attcattggt tatatagcat aaatcaatat tggctattgg ccattgcata 1920
cgttgtatcc atatcataat atgtacattt atattggctc atgtccaaca ttaccgccat 1980
gttgacattg attattgact agttattaat agtaatcaat tacggggtca ttagttcata 2040

-continued gcccatatat ggagttccgc gttacataac ttacggtaaa tggcccgcct ggctgaccgc 2100
ccaacgaccc ccgcccattg acgtcaataa tgacgtatgt tcccatagta acgccaatag 2160
ggactttcca ttgacgtcaa tgggtggagt atttacggta aactgcccac ttggcagtac 2220
atcaagtgta tcatatgcca agtacgcccc ctattgacgt caatgacggt aaatggcccg 2280
cctggcatta tgcccagtac atgaccttat gggactttcc tacttggcag tacatctacg 2340
tattagtcat cgctattacc atggtgatgc ggttttggca gtacatcaat gggcgtggat 2400
agcggtttga ctcacgggga tttccaagtc tccaccccat tgacgtcaat gggagtttgt 2460
tttggcacca aaatcaacgg gactttccaa aatgtcgtaa caactccgcc ccattgacgc 2520
aaatgggcgg taggcatgta cggtgggagg tctatataag cagagctcgt ttagtgaacc 2580
gtcagatcgc ctggagacgc catccacgct gttttgacct ccatagaaga caccgggacc 2640
gatccagcct ccgcggcccc aagcttcagc tgctcgagga tctgcggatc cggggaattc 2700
cccagtctca ggatccacca tgggggatcc cgtcgtttta caacgtcgtg actgggaaaa 2760
ccctggcgtt acccaactta atcgccttgc agcacatccc cctttcgcca gctggcgtaa 2820
tagcgaagag gcccgcaccg atcgcccttc ccaacagttg cgcagcctga atggcgaatg 2880
gcgctttgcc tggtttccgg caccagaagc ggtgccggaa agctggctgg agtgcgatct 2940
tcctgaggcc gatactgtcg tcgtcccctc aaactggcag atgcacggtt acgatgcgcc 3000
catctacacc aacgtaacct atcccattac ggtcaatccg ccgtttgttc ccacggagaa 3060
tccgacgggt tgttactcgc tcacatttaa tgttgatgaa agctggctac aggaaggcca 3120
gacgcgaatt atttttgatg gcgttaactc ggcgtttcat ctgtggtgca acgggcgctg 3180
ggtcggttac ggccaggaca gtcgtttgcc gtctgaattt gacctgagcg catttttacg 3240
cgccggagaa aaccgcctcg cggtgatggt gctgcgttgg agtgacggca gttatctgga 3300
agatcaggat atgtggcgga tgagcggcat tttccgtgac gtctcgttgc tgcataaacc 3360
gactacacaa atcagcgatt tccatgttgc cactcgcttt aatgatgatt tcagccgcgc 3420
tgtactggag gctgaagttc agatgtgcgg cgagttgcgt gactacctac gggtaacagt 3480
ttctttatgg cagggtgaaa cgcaggtcgc cagcggcacc gcgcctttcg gcggtgaaat 3540
tatcgatgag cgtggtggtt atgccgatcg cgtcacacta cgtctgaacg tcgaaaaccc 3600
gaaactgtgg agcgccgaaa tcccgaatct ctatcgtgcg gtggttgaac tgcacaccgc 3660
cgacggcacg ctgattgaag cagaagcctg cgatgtcggt ttccgcgagg tgcggattga 3720
aaatggtctg ctgctgctga acggcaagcc gttgctgatt cgaggcgtta accgtcacga 3780
gcatcatcct ctgcatggtc aggtcatgga tgagcagacg atggtgcagg atatcctgct 3840
gatgaagcag aacaacttta acgccgtgcg ctgttcgcat tatccgaacc atccgctgtg 3900
gtacacgctg tgcgaccgct acggcctgta tgtggtggat gaagccaata ttgaaaccca 3960
cggcatggtg ccaatgaatc gtctgaccga tgatccgcgc tggctaccgg cgatgagcga 4020
acgcgtaacg cgaatggtgc agcgcgatcg taatcacccg agtgtgatca tctggtcgct 4080
ggggaatgaa tcaggccacg gcgctaatca cgacgcgctg tatcgctgga tcaaatctgt 4140
cgatccttcc cgcccggtgc agtatgaagg cggcggagcc gacaccacgg ccaccgatat 4200
tatttgcccg atgtacgcgc gcgtggatga agaccagccc ttcccggctg tgccgaaatg 4260
gtccatcaaa aaatggcttt cgctacctgg agagacgcgc ccgctgatcc tttgcgaata 4320
cgcccacgcg atgggtaaca gtcttggcgg tttcgctaaa tactggcagg cgtttcgtca 4380

-continued gtatccccgt ttacagggcg gcttcgtctg ggactgggtg gatcagtcgc tgattaaata 4440
tgatgaaaac ggcaacccgt ggtcggctta cggcggtgat tttggcgata cgccgaacga 4500
tcgccagttc tgtatgaacg gtctggtctt tgccgaccgc acgccgcatc cagcgctgac 4560
ggaagcaaaa caccagcagc agtttttcca gttccgttta tccgggcaaa ccatcgaagt 4620
gaccagcgaa tacctgttcc gtcatagcga taacgagctc ctgcactgga tggtggcgct 4680
ggatggtaag ccgctggcaa gcggtgaagt gcctctggat gtcgctccac aaggtaaaca 4740
gttgattgaa ctgcctgaac taccgcagcc ggagagcgcc gggcaactct ggctcacagt 4800
acgcgtagtg caaccgaacg cgaccgcatg gtcagaagcc gggcacatca gcgcctggca 4860
gcagtggcgt ctggcggaaa acctcagtgt gacgctcccc gccgcgtccc acgccatccc 4920
gcatctgacc accagcgaaa tggatttttg catcgagctg ggtaataagc gttggcaatt 4980
taaccgccag tcaggctttc tttcacagat gtggattggc gataaaaaac aactgctgac 5040
gccgctgcgc gatcagttca cccgtgcacc gctggataac gacattggcg taagtgaagc 5100
gacccgcatt gaccctaacg cctgggtcga acgctggaag gcggcgggcc attaccaggc 5160
cgaagcagcg ttgttgcagt gcacggcaga tacacttgct gatgcggtgc tgattacgac 5220
cgctcacgcg tggcagcatc aggggaaaac cttatttatc agccggaaaa cctaccggat 5280
tgatggtagt ggtcaaatgg cgattaccgt tgatgttgaa gtggcgagcg atacaccgca 5340
tccggcgcgg attggcctga actgccagct ggcgcaggta gcagagcggg taaactggct 5400
cggattaggg ccgcaagaaa actatcccga ccgccttact gccgcctgtt ttgaccgctg 5460
ggatctgcca ttgtcagaca tgtatacccc gtacgtcttc ccgagcgaaa acggtctgcg 5520
ctgcgggacg cgcgaattga attatggccc acaccagtgg cgcggcgact tccagttcaa 5580
catcagccgc tacagtcaac agcaactgat ggaaaccagc catcgccatc tgctgcacgc 5640
ggaagaaggc acatggctga atatcgacgg tttccatatg gggattggtg gcgacgactc 5700
ctggagcccg tcagtatcgg cggaattcca gctgagcgcc ggtcgctacc attaccagtt 5760
ggtctggtgt caaaaataat aataaccggg caggggggat ccgcagatcc ggctgtggaa 5820
tgtgtgtcag ttagggtgtg gaaagtcccc aggctcccca gcaggcagaa gtatgcaaag 5880
catgcctgca ggaattcgat atcaagctta tcgataccgt cgacctcgag ggggggcccg 5940
gtacccagct tttgttccct ttagtgaggg ttaattgcgc gggaagtatt tatcactaat 6000
caagcacaag taatacatga gaaactttta ctacagcaag cacaatcctc caaaaaattt 6060
tgtttttaca aaatccctgg tgaacatgat tggaagggac ctactagggt gctgtggaag 6120
ggtgatggtg cagtagtagt taatgatgaa ggaaagggaa taattgctgt accattaacc 6180
aggactaagt tactaataaa accaaattga gtattgttgc aggaagcaag acccaactac 6240
cattgtcagc tgtgtttcct gacctcaata tttgttataa ggtttgatat gaatcccagg 6300
gggaatctca acccctatta cccaacagtc agaaaaatct aagtgtgagg agaacacaat 6360
gtttcaacct tattgttata ataatgacag taagaacagc atggcagaat cgaaggaagc 6420
aagagaccaa gaatgaacct gaaagaagaa tctaaagaag aaaaaagaag aaatgactgg 6480
tggaaaatag gtatgtttct gttatgctta gcaggaacta ctggaggaat actttggtgg 6540
tatgaaggac tcccacagca acattatata gggttggtgg cgatagggggg aagattaaac 6600
ggatctggcc aatcaaatgc tatagaatgc tggggttcct tcccggggtg tagaccattt 6660
caaaattact tcagttatga gaccaataga agcatgcata tggataataa tactgctaca 6720
ttattagaag ctttaaccaa tataactgct ctataaataa caaaacagaa ttagaaacat 6780

-continued

```
ggaagttagt aaagacttct ggcataactc ctttacctat ttcttctgaa gctaacactg   6840
gactaattag acataagaga gattttggta taagtgcaat agtggcagct attgtagccg   6900
ctactgctat tgctgctagc gctactatgt cttatgttgc tctaactgag gttaacaaaa   6960
taatggaagt acaaaatcat acttttgagg tagaaaatag tactctaaat ggtatggatt   7020
taatagaacg acaaataaag atattatatg ctatgattct tcaaacacat gcagatgttc   7080
aactgttaaa ggaaagacaa caggtagagg agacatttaa tttaattgga tgtatagaaa   7140
gaacacatgt attttgtcat actggtcatc cctggaatat gtcatgggga catttaaatg   7200
agtcaacaca atgggatgac tgggtaagca aaatggaaga tttaaatcaa gagatactaa   7260
ctacacttca tggagccagg aacaatttgg cacaatccat gataacattc aatacaccag   7320
atagtatagc tcaatttgga aaagaccttt ggagtcatat tggaaattgg attcctggat   7380
tgggagcttc cattataaaa tatatagtga tgtttttgct tatttatttg ttactaacct   7440
cttcgcctaa gatcctcagg gccctctgga aggtgaccag tggtgcaggg tcctccggca   7500
gtcgttacct gaagaaaaaa ttccatcaca aacatgcatc gcgagaagac acctgggacc   7560
aggcccaaca caacatacac ctagcaggcg tgaccggtgg atcaggggac aaatactaca   7620
agcagaagta ctccaggaac gactggaatg gagaatcaga ggagtacaac aggcggccaa   7680
agagctgggt gaagtcaatc gaggcatttg gagagagcta tatttccgag aagaccaaag   7740
gggagatttc tcagcctggg gcggctatca acgagcacaa gaacggctct gggggggaaca   7800
atcctcacca agggtcctta gacctggaga ttcgaagcga aggaggaaac atttatgact   7860
gttgcattaa agcccaagaa ggaactctcg ctatcccttg ctgtggattt cccttatggc   7920
tattttgggg actagtaatt atagtaggac gcatagcagg ctatggatta cgtggactcg   7980
ctgttataat aaggatttgt attagaggct taaatttgat atttgaaata atcagaaaaa   8040
tgcttgatta tattggaaga gctttaaatc ctggcacatc tcatgtatca atgcctcagt   8100
atgtttagaa aaacaagggg ggaactgtgg ggtttttatg aggggtttta taaatgatta   8160
taagagtaaa aagaaagttg ctgatgctct cataaccttg tataacccaa aggactagct   8220
catgttgcta ggcaactaaa ccgcaataac cgcatttgtg acgcgagttc cccattggtg   8280
acgcgttaac ttcctgtttt tacagtatat aagtgcttgt attctgacaa ttgggcactc   8340
agattctgcg gtctgagtcc cttctctgct gggctgaaaa ggcctttgta ataaatataa   8400
ttctctactc agtccctgtc tctagtttgt ctgttcgaga tcctacagag ctcatgcctt   8460
ggcgtaatca tggtcatagc tgtttcctgt gtgaaattgt tatccgctca caattccaca   8520
caacatacga gccggaagca taaagtgtaa agcctggggt gcctaatgag tgagctaact   8580
cacattaatt gcgttgcgct cactgcccgc tttccagtcg ggaaacctgt cgtgccagct   8640
gcattaatga atcggccaac gcgcggggag aggcggtttg cgtattgggc gctcttccgc   8700
ttcctcgctc actgactcgc tgcgctcggt cgttcggctg cggcgagcgg tatcagctca   8760
ctcaaaggcg gtaatacggt tatccacaga atcaggggat aacgcaggaa agaacatgtg   8820
agcaaaaggc cagcaaaagg ccaggaaccg taaaaaggcc gcgttgctgg cgtttttcca   8880
taggctccgc ccccctgacg agcatcacaa aaatcgacgc tcaagtcaga ggtggcgaaa   8940
cccgacagga ctataaagat accaggcgtt tccccctgga agctccctcg tgcgctctcc   9000
tgttccgacc ctgccgctta ccggatacct gtccgccttt ctcccttcgg gaagcgtggc   9060
gctttctcat agctcacgct gtaggtatct cagttcggtg taggtcgttc gctccaagct   9120
```

-continued gggctgtgtg cacgaacccc ccgttcagcc cgaccgctgc gccttatccg gtaactatcg 9180
tcttgagtcc aacccggtaa gacacgactt atcgccactg gcagcagcca ctggtaacag 9240
gattagcaga gcgaggtatg taggcggtgc tacagagttc ttgaagtggt ggcctaacta 9300
cggctacact agaaggacag tatttggtat ctgcgctctg ctgaagccag ttaccttcgg 9360
aaaaagagtt ggtagctctt gatccggcaa acaaaccacc gctggtagcg gtggtttttt 9420
tgtttgcaag cagcagatta cgcgcagaaa aaaaggatct caagaagatc ctttgatctt 9480
ttctacgggg tctgacgctc agtggaacga aaactcacgt taagggattt tggtcatgag 9540
attatcaaaa aggatcttca cctagatcct tttaaattaa aaatgaagtt ttaaatcaat 9600
ctaaagtata tatgagtaaa cttggtctga cagttaccaa tgcttaatca gtgaggcacc 9660
tatctcagcg atctgtctat ttcgttcatc catagttgcc tgactccccg tcgtgtagat 9720
aactacgata cgggagggct taccatctgg ccccagtgct gcaatgatac cgcgagaccc 9780
acgctcaccg gctccagatt tatcagcaat aaaccagcca gccggaaggg ccgagcgcag 9840
aagtggtcct gcaactttat ccgcctccat ccagtctatt aattgttgcc gggaagctag 9900
agtaagtagt tcgccagtta atagtttgcg caacgttgtt gccattgcta caggcatcgt 9960
ggtgtcacgc tcgtcgtttg gtatggcttc attcagctcc ggttcccaac gatcaaggcg 10020
agttacatga tcccccatgt tgtgcaaaaa agcggttagc tccttcggtc ctccgatcgt 10080
tgtcagaagt aagttggccg cagtgttatc actcatggtt atggcagcac tgcataattc 10140
tcttactgtc atgccatccg taagatgctt ttctgtgact ggtgagtact caaccaagtc 10200
attctgagaa tagtgtatgc ggcgaccgag ttgctcttgc ccggcgtcaa tacgggataa 10260
taccgcgcca catagcagaa ctttaaaagt gctcatcatt ggaaaacgtt cttcggggcg 10320
aaaactctca aggatcttac cgctgttgag atccagttcg atgtaaccca ctcgtgcacc 10380
caactgatct tcagcatctt ttactttcac cagcgtttct gggtgagcaa aaacaggaag 10440
gcaaaatgcc gcaaaaaagg gaataagggc gacacggaaa tgttgaatac tcatactctt 10500
cctttttcaa tattattgaa gcatttatca gggttattgt ctcatgagcg gatacatatt 10560
tgaatgtatt tagaaaaata aacaaatagg ggttccgcgc acatttcccc gaaaagtgcc 10620
acctaaattg taagcgttaa tattttgtta aaattcgcgt taaatttttg ttaaatcagc 10680
tcatttttta accaataggc cgaaatcggc aaaatccctt ataaatcaaa agaatagacc 10740
gagatagggt tgagtgttgt tccagtttgg aacaagagtc cactattaaa gaacgtggac 10800
tccaacgtca aagggcgaaa aaccgtctat cagggcgatg gcccactacg tgaaccatca 10860
ccctaatcaa gttttttggg gtcgaggtgc cgtaaagcac taaatcggaa ccctaaaggg 10920
agcccccgat ttagagcttg acggggaaag ccaacctggc ttatcgaaat taatacgact 10980
cactataggg agaccggc 10998

<210> SEQ ID NO 4
<211> LENGTH: 9246
<212> TYPE: DNA
<213> ORGANISM: Artificial Sequence
<220> FEATURE:
<223> OTHER INFORMATION: Description of Artificial Sequence: Synthetic
nucleic acid pECG3-CZW, vector genome plasmid

<400> SEQUENCE: 4
tcaatattgg ccattagcca tattattcat tggttatata gcataaatca atattggcta 60
ttggccattg catacgttgt atctatatca taatatgtac atttatattg gctcatgtcc 120

-continued

```
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg ccccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaataaccc    660
cgccccgttg acgcaaatgg gcggtaggcg tgtacggtgg gaggtctata taagcagagc    720
tcgtttagtg aaccgggcac tcagattctg cggtctgagt cccttctctg ctgggctgaa    780
aaggcctttg taataaatat aattctctac tcagtccctg tctctagttt gtctgttcga    840
gatcctacag ttggcgcccg aacagggacc tgagaggggc gcagacccta cctgttgaac    900
ctggctgatc gtaggatccc cgggacagca gaggagaact tacagaagtc ttctggaggt    960
gttcctggcc agaacacagg aggacaggta agtagggaga ccctttgaca tggagcaagg   1020
cgctcaagaa gttagagaag gtgacggtac aagggtctca gaaattaact actggtaact   1080
gtaattgggc gctaagtcta gtagacttat ttcatgatac caactttgta aaagaaaagg   1140
actggcagct gagggatgtc attccattgc tggaagatgt aactcagacg ctggaattcg   1200
agcttgcatg cctgcaggtc gttacataac ttacggtaaa tggcccgcct ggctgaccgc   1260
ccaacgaccc ccgcccattg acgtcaataa tgacgtatgt tcccatagta acgccaatag   1320
ggactttcca ttgacgtcaa tgggtggagt atttacggta aactgcccac ttggcagtac   1380
atcaagtgta tcatatgcca agtacgcccc ctattgacgt caatgacggt aaatggcccg   1440
cctggcatta tgcccagtac atgaccttat gggactttcc tacttggcag tacatctacg   1500
tattagtcat cgctattacc atggtgatgc ggttttggca gtacatcaat gggcgtggat   1560
agcggtttga ctcacgggga tttccaagtc tccaccccat tgacgtcaat gggagtttgt   1620
tttggcacca aaatcaacgg gactttccaa aatgtcgtaa caactccgcc ccattgacgc   1680
aaatgggcgg taggcgtgta cggtgggagg tctatataag cagagctcgt ttagtgaacc   1740
gtcagatcgc ctggagacgc catccacgct gttttgacct ccatagaaga caccgggacc   1800
gatccagcct ccggactcta gagtcgaccc gggcggccgc aattcccggg gatcgaaaga   1860
gcctgctaaa gcaaaaaaga agtcaccatg tcgtttactt tgaccaacaa gaacgtgatt   1920
ttcgttgccg gtctgggagg cattggtctg gacaccagca aggagctgct caagcgcgat   1980
cccgtcgttt tacaacgtcg tgactgggaa aaccctggcg ttacccaact taatcgcctt   2040
gcagcacatc ccccttttcgc cagctggcgt aatagcgaag aggcccgcac cgatcgccct   2100
tcccaacagt tgcgcagcct gaatggcgaa tggcgctttg cctggtttcc ggcaccagaa   2160
gcggtgccgg aaagctggct ggagtgcgat cttcctgagg ccgatactgt cgtcgtcccc   2220
tcaaactggc agatgcacgg ttacgatgcg cccatctaca ccaacgtaac ctatcccatt   2280
acggtcaatc cgccgtttgt tcccacggag aatccgacgg gttgttactc gctcacattt   2340
aatgttgatg aaagctggct acaggaaggc cagacgcgaa ttattttttga tggcgttaac   2400
tcggcgtttc atctgtggtg caacgggcgc tgggtcggtt acggccagga cagtcgtttg   2460
ccgtctgaat ttgacctgag cgcatttttta cgcgccggag aaaaccgcct cgcggtgatg   2520
```

-continued

```
gtgctgcgtt ggagtgacgg cagttatctg gaagatcagg atatgtggcg gatgagcggc   2580
attttccgtg acgtctcgtt gctgcataaa ccgactacac aaatcagcga tttccatgtt   2640
gccactcgct ttaatgatga tttcagccgc gctgtactgg aggctgaagt tcagatgtgc   2700
ggcgagttgc gtgactacct acgggtaaca gtttctttat ggcagggtga aacgcaggtc   2760
gccagcggca ccgcgccttt cggcggtgaa attatcgatg agcgtggtgg ttatgccgat   2820
cgcgtcacac tacgtctgaa cgtcgaaaac ccgaaactgt ggagcgccga aatcccgaat   2880
ctctatcgtg cggtggttga actgcacacc gccgacggca cgctgattga agcagaagcc   2940
tgcgatgtcg gtttccgcga ggtgcggatt gaaaatggtc tgctgctgct gaacggcaag   3000
ccgttgctga ttcgaggcgt taaccgtcac gagcatcatc ctctgcatgg tcaggtcatg   3060
gatgagcaga cgatggtgca ggatatcctg ctgatgaagc agaacaactt taacgccgtg   3120
cgctgttcgc attatccgaa ccatccgctg tggtacacgc tgtgcgaccg ctacggcctg   3180
tatgtggtgg atgaagccaa tattgaaacc cacggcatgg tgccaatgaa tcgtctgacc   3240
gatgatccgc gctggctacc ggcgatgagc gaacgcgtaa cgcgaatggt gcagcgcgat   3300
cgtaatcacc cgagtgtgat catctggtcg ctggggaatg aatcaggcca cggcgctaat   3360
cacgacgcgc tgtatcgctg gatcaaatct gtcgatcctt cccgcccggt gcagtatgaa   3420
ggcggcggag ccgacaccac ggccaccgat attatttgcc cgatgtacgc gcgcgtggat   3480
gaagaccagc ccttcccggc tgtgccgaaa tggtccatca aaaaatggct ttcgctacct   3540
ggagagacgc gcccgctgat cctttgcgaa tacgcccacg cgatgggtaa cagtcttggc   3600
ggtttcgcta aatactggca ggcgtttcgt cagtatcccc gtttacaggg cggcttcgtc   3660
tgggactggg tggatcagtc gctgattaaa tatgatgaaa acggcaaccc gtggtcggct   3720
tacggcggtg attttggcga tacgccgaac gatcgccagt tctgtatgaa cggtctggtc   3780
tttgccgacc gcacgccgca tccagcgctg acggaagcaa aacaccagca gcagtttttc   3840
cagttccgtt tatccgggca aaccatcgaa gtgaccagcg aatacctgtt ccgtcatagc   3900
gataacgagc tcctgcactg gatggtggcg ctggatggta agccgctggc aagcggtgaa   3960
gtgcctctgg atgtcgctcc acaaggtaaa cagttgattg aactgcctga actaccgcag   4020
ccggagagcg ccgggcaact ctggctcaca gtacgcgtag tgcaaccgaa cgcgaccgca   4080
tggtcagaag ccgggcacat cagcgcctgg cagcagtggc gtctggcgga aaacctcagt   4140
gtgacgctcc ccgccgcgtc ccacgccatc ccgcatctga ccaccagcga aatggatttt   4200
tgcatcgagc tgggtaataa gcgttggcaa tttaaccgcc agtcaggctt tctttcacag   4260
atgtggattg gcgataaaaa acaactgctg acgccgctgc gcgatcagtt cacccgtgca   4320
ccgctggata acgacattgg cgtaagtgaa gcgacccgca ttgaccctaa cgcctgggtc   4380
gaacgctgga aggcggcggg ccattaccag gccgaagcag cgttgttgca gtgcacggca   4440
gatacacttg ctgatgcggt gctgattacg accgctcacg cgtggcagca tcaggggaaa   4500
accttattta tcagccggaa aacctaccgg attgatggta gtggtcaaat ggcgattacc   4560
gttgatgttg aagtggcgag cgatacaccg catccggcgc ggattggcct gaactgccag   4620
ctggcgcagg tagcagagcg ggtaaactgg ctcggattag ggccgcaaga aaactatccc   4680
gaccgcctta ctgccgcctg ttttgaccgc tgggatctgc cattgtcaga catgtatacc   4740
ccgtacgtct tcccgagcga aaacggtctg cgctgcggga cgcgcgaatt gaattatggc   4800
ccacaccagt ggcgcggcga cttccagttc aacatcagcc gctacagtca acagcaactg   4860
```

-continued atggaaacca gccatcgcca tctgctgcac gcggaagaag gcacatggct gaatatcgac 4920
ggtttccata tggggattgg tggcgacgac tcctggagcc cgtcagtatc ggcggaatta 4980
cagctgagcg ccggtcgcta ccattaccag ttggtctggt gtcaaaaata ataataaccg 5040
ggcaggccat gtctgcccgt atttcgcgta aggaaatcca ttatgtacta tttaaaaaac 5100
acaaactttt ggatgttcgg tttattcttt ttcttttact tttttatcat gggagcctac 5160
ttcccgtttt tcccgatttg gctacatgac atcaaccata tcagcaaaag tgatacgggt 5220
attatttttg ccgctatttc tctgttctcg ctattattcc aaccgctgtt tggtctgctt 5280
tctgacaaac tcggcctcga ctctaggcgg ccgccgagca tcttaccgcc atttattccc 5340
atatttgttc tgtttttctt gatttgggta tacatttgaa tgtcaataaa acaaaatggt 5400
ggggcaatca tctacatttc atgggatatg tgattactag ttcaggtgta ttgccacaag 5460
acaaacatgt taagaaaatt tcccgttatt tgcactctgt tcctgttaat caacctctgg 5520
attacaaaat ttgtgaaaga ttgactggta ttcttaacta tgttgctcct tttacgctat 5580
gtggatacgc tgctttaatg cctttgtatc atgctattgc ttcccgtatg gctttcattt 5640
tctcctcctt gtataaatcc tggttgctgt ctctttatga ggagttgtgg cccgttgtca 5700
ggcaacgtgg cgtggtgtgc actgtgtttg ctgacgcaac ccccactggt tggggcattg 5760
ccaccacctg tcagctcctt tccgggactt tcgctttccc cctccctatt gccacggcgg 5820
aactcatcgc cgcctgcctt gcccgctgct ggacaggggc tcggctgttg ggcactgaca 5880
attccgtggt gttgtcgggg aagctgacgt cctttccatg gctgctcgcc tgtgttgcca 5940
cctggattct gcgcgggacg tccttctgct acgtcccttc ggccctcaat ccagcggacc 6000
ttccttcccg cggcctgctg ccggctctgc ggcctcttcc gcgtcttcgc cttcgccctc 6060
agacgagtcg gatctccctt tgggccgcct ccccgcctgt ttcgcctcgg cgtccggtcc 6120
gtgttgcttg gtcttcacct gtgcagactt gcgaaccatg gattccaccg tgaactttgt 6180
ctcctggcat gcaaatcgtc aacttggcat gccaaatcga tgtcgacata gaaaaacaag 6240
gggggaactg tggggttttt atgaggggtt ttataaatga ttataagagt aaaaagaaag 6300
ttgctgatgc tctcataacc ttgtataacc caaaggacta gctcatgttg ctaggcaact 6360
aaaccgcaat aaccacattt gtgacgcgag ttccgcattg gtgacgcgtt aagttcctgt 6420
ttttacagta tataagtgct tgtattctga caattgggca ctcagattct gcggtctgag 6480
tcccttctct gctgggctga aaaggccttt gtaataaata taattctcta ctcagtccct 6540
gtctctagtt tgtctgttcg agatcctaca ttaattaagg agatccgggc tggcgtaata 6600
gcgaagaggc ccgcaccgat cgcccttccc aacagttgcg cagcctgaat ggcgaatgga 6660
cgcgccctgt agcggcgcat taagcgcggc gggtgtggtg gttacgcgca gcgtgaccgc 6720
tacacttgcc agcgccctag cgcccgctcc tttcgctttc ttcccttcct ttctcgccac 6780
gttcgccggc tttccccgtc aagctctaaa tcgggggctc cctttagggt tccgatttag 6840
agctttacgg cacctcgacc gcaaaaaact tgatttgggt gatggttcac gtagtgggcc 6900
atcgccctga tagacggttt ttcgcccttt gacgttggag tccacgttct ttaatagtgg 6960
actcttgttc caaactggaa caacactcaa ccctatctcg gtctattctt ttgatttata 7020
agggattttg ccgatttcgg cctattggtt aaaaaatgag ctgatttaac aaatatttaa 7080
cgcgaatttt aacaaaatat taacgtttac aatttcgcct gatgcggtat tttctcctta 7140
cgcatctgtg cggtatttca caccgcatat ggtgcactct cagtacaatc tgctctgatg 7200
ccgcatagtt aagccagccc cgacacccgc caacacccgc tgacgcgccc tgacgggctt 7260

-continued

```
gtctgctccc ggcatccgct tacagacaag ctgtgaccgt ctccgggagc tgcatgtgtc   7320

agaggttttc accgtcatca ccgaaacgcg cgagacgaaa gggcctcgtg atacgcctat   7380

ttttataggt taatgtcatg ataataatgg tttcttagac gtcaggtggc acttttcggg   7440

gaaatgtgcg cggaacccct atttgtttat ttttctaaat acattcaaat atgtatccgc   7500

tcatgagaca ataaccctga taaatgcttc aataatattg aaaaaggaag agtatgagta   7560

ttcaacattt ccgtgtcgcc cttattccct tttttgcggc attttgcctt cctgtttttg   7620

ctcacccaga aacgctggtg aaagtaaaag atgctgaaga tcagttgggt gcacgagtgg   7680

gttacatcga actggatctc aacagcggta agatccttga gagttttcgc cccgaagaac   7740

gttttccaat gatgagcact tttaaagttc tgctatgtgg cgcggtatta tcccgtattg   7800

acgccgggca agagcaactc ggtcgccgca tacactattc tcagaatgac ttggttgagt   7860

actcaccagt cacagaaaag catcttacgg atggcatgac agtaagagaa ttatgcagtg   7920

ctgccataac catgagtgat aacactgcgg ccaacttact tctgacaacg atcggaggac   7980

cgaaggagct aaccgctttt ttgcacaaca tgggggatca tgtaactcgc cttgatcgtt   8040

gggaaccgga gctgaatgaa gccataccaa acgacgagcg tgacaccacg atgcctgtag   8100

caatggcaac aacgttgcgc aaactattaa ctggcgaact acttactcta gcttcccggc   8160

aacaattaat agactggatg gaggcggata aagttgcagg accacttctg cgctcggccc   8220

ttccggctgg ctggtttatt gctgataaat ctggagccgg tgagcgtggg tctcgcggta   8280

tcattgcagc actggggcca gatggtaagc cctcccgtat cgtagttatc tacacgacgg   8340

ggagtcaggc aactatggat gaacgaaata gacagatcgc tgagataggt gcctcactga   8400

ttaagcattg gtaactgtca gaccaagttt actcatatat actttagatt gatttaaaac   8460

ttcattttta atttaaaagg atctaggtga agatcctttt tgataatctc atgaccaaaa   8520

tcccttaacg tgagttttcg ttccactgag cgtcagaccc cgtagaaaag atcaaaggat   8580

cttcttgaga tccttttttt ctgcgcgtaa tctgctgctt gcaaacaaaa aaaccaccgc   8640

taccagcggt ggtttgtttg ccggatcaag agctaccaac tctttttccg aaggtaactg   8700

gcttcagcag agcgcagata ccaaatactg tccttctagt gtagccgtag ttaggccacc   8760

acttcaagaa ctctgtagca ccgcctacat acctcgctct gctaatcctg ttaccagtgg   8820

ctgctgccag tggcgataag tcgtgtctta ccgggttgga ctcaagacga tagttaccgg   8880

ataaggcgca gcggtcgggc tgaacggggg gttcgtgcac acagcccagc ttggagcgaa   8940

cgacctacac cgaactgaga tacctacagc gtgagctatg agaaagcgcc acgcttcccg   9000

aagggagaaa ggcggacagg tatccggtaa gcggcagggt cggaacagga gagcgcacga   9060

gggagcttcc agggggaaac gcctggtatc tttatagtcc tgtcgggttt cgccacctct   9120

gacttgagcg tcgatttttg tgatgctcgt caggggggcg gagcctatgg aaaaacgcca   9180

gcaacgcggc ctttttacgg ttcctggcct tttgctggcc ttttgctcac atggctcgac   9240

agatct                                                               9246
```

<210> SEQ ID NO 5
<211> LENGTH: 8531
<212> TYPE: DNA
<213> ORGANISM: Artificial Sequence
<220> FEATURE:
<223> OTHER INFORMATION: Description of Artificial Sequence: Synthetic
nucleic acid pONY8G, vector genome plasmid

<400> SEQUENCE: 5

-continued

```
agatcttgaa taataaaatg tgtgtttgtc cgaaatacgc gttttgagat ttctgtcgcc    60
gactaaattc atgtcgcgcg atagtggtgt ttatcgccga tagagatggc gatattggaa   120
aaattgatat ttgaaaatat ggcatattga aaatgtcgcc gatgtgagtt tctgtgtaac   180
tgatatcgcc atttttccaa aagtgatttt tgggcatacg cgatatctgg cgatagcgct   240
tatatcgttt acgggggatg gcgatagacg actttggtga cttgggcgat tctgtgtgtc   300
gcaaatatcg cagtttcgat ataggtgaca gacgatatga ggctatatcg ccgatagagg   360
cgacatcaag ctggcacatg gccaatgcat atcgatctat acattgaatc aatattggcc   420
attagccata ttattcattg gttatatagc ataaatcaat attggctatt ggccattgca   480
tacgttgtat ccatatcgta atatgtacat ttatattggc tcatgtccaa cattaccgcc   540
atgttgacat tgattattga ctagttatta atagtaatca attacggggt cattagttca   600
tagcccatat atggagttcc gcgttacata acttacggta aatggcccgc ctggctgacc   660
gcccaacgac ccccgcccat tgacgtcaat aatgacgtat gttcccatag taacgccaat   720
agggactttc cattgacgtc aatgggtgga gtatttacgg taaactgccc acttggcagt   780
acatcaagtg tatcatatgc caagtccgcc ccctattgac gtcaatgacg gtaaatggcc   840
cgcctggcat tatgcccagt acatgacctt acgggacttt cctacttggc agtacatcta   900
cgtattagtc atcgctatta ccatggtgat gcggttttgg cagtacacca atgggcgtgg   960
atagcggttt gactcacggg gatttccaag tctccacccc attgacgtca atgggagttt  1020
gttttggcac caaaatcaac gggactttcc aaaatgtcgt aacaactgcg atcgcccgcc  1080
ccgttgacgc aaatgggcgg taggcgtgta cggtgggagg tctatataag cagagctcgt  1140
ttagtgaacc gggcactcag attctgcggt ctgagtccct tctctgctgg gctgaaaagg  1200
cctttgtaat aaatataatt ctctactcag tccctgtctc tagtttgtct gttcgagatc  1260
ctacagttgg cgcccgaaca gggacctgag aggggcgcag accctacctg ttgaacctgg  1320
ctgatcgtag gatccccggg acagcagagg agaacttaca gaagtcttct ggaggtgttc  1380
ctggccagaa cacaggagga caggtaagat tgggagaccc tttgacattg gagcaaggcg  1440
ctcaagaagt tagagaaggt gacggtacaa gggtctcaga aattaactac tggtaactgt  1500
aattgggcgc taagtctagt agacttattt catgatacca actttgtaaa agaaaaggac  1560
tggcagctga gggatgtcat tccattgctg gaagatgtaa ctcagacgct gtcaggacaa  1620
gaaagagagg cctttgaaag aacatggtgg gcaatttctg ctgtaaagat gggcctccag  1680
attaataatg tagtagatgg aaaggcatca ttccagctcc taagagcgaa atatgaaaag  1740
aagactgcta ataaaaagca gtctgagccc tctgaagaat atctctagaa ctagtggatc  1800
ccccgggctg caggagtggg gaggcacgat ggccgctttg gtcgaggcgg atccggccat  1860
tagccatatt attcattggt tatatagcat aaatcaatat tggctattgg ccattgcata  1920
cgttgtatcc atatcataat atgtacattt atattggctc atgtccaaca ttaccgccat  1980
gttgacattg attattgact agttattaat agtaatcaat tacggggtca ttagttcata  2040
gcccatatat ggagttccgc gttacataac ttacggtaaa tggcccgcct ggctgaccgc  2100
ccaacgaccc ccgcccattg acgtcaataa tgacgtatgt tcccatagta acgccaatag  2160
ggactttcca ttgacgtcaa tgggtggagt atttacggta aactgcccac ttggcagtac  2220
atcaagtgta tcatatgcca agtacgcccc ctattgacgt caatgacggt aaatggcccg  2280
cctggcatta tgcccagtac atgaccttat gggactttcc tacttggcag tacatctacg  2340
```

-continued

```
tattagtcat cgctattacc atggtgatgc ggttttggca gtacatcaat gggcgtggat   2400
agcggtttga ctcacgggga tttccaagtc tccaccccat tgacgtcaat gggagtttgt   2460
tttggcacca aaatcaacgg gactttccaa aatgtcgtaa caactccgcc ccattgacgc   2520
aaatgggcgg taggcatgta cggtgggagg tctatataag cagagctcgt ttagtgaacc   2580
gtcagatcgc ctggagacgc catccacgct gttttgacct ccatagaaga caccgggacc   2640
gatccagcct ccgcggcccc aagcttgttg ggatccaccg gtcgccacca tggtgagcaa   2700
gggcgaggag ctgttcaccg gggtggtgcc catcctggtc gagctggacg gcgacgtaaa   2760
cggccacaag ttcagcgtgt ccggcgaggg cgagggcgat gccacctacg gcaagctgac   2820
cctgaagttc atctgcacca ccggcaagct gcccgtgccc tggcccaccc tcgtgaccac   2880
cctgacctac ggcgtgcagt gcttcagccg ctaccccgac cacatgaagc agcacgactt   2940
cttcaagtcc gccatgcccg aaggctacgt ccaggagcgc accatcttct tcaaggacga   3000
cggcaactac aagacccgcg ccgaggtgaa gttcgagggc gacaccctgg tgaaccgcat   3060
cgagctgaag ggcatcgact tcaaggagga cggcaacatc ctggggcaca agctggagta   3120
caactacaac agccacaacg tctatatcat ggccgacaag cagaagaacg gcatcaaggt   3180
gaacttcaag atccgccaca acatcgagga cggcagcgtg cagctcgccg accactacca   3240
gcagaacacc cccatcggcg acggccccgt gctgctgccc gacaaccact acctgagcac   3300
ccagtccgcc ctgagcaaag accccaacga gaagcgcgat cacatggtcc tgctggagtt   3360
cgtgaccgcc gccgggatca ctctcggcat ggacgagctg tacaagtaaa gcggccgcga   3420
ctctagagtc gacctgcagg catgcaagct tcagctgctc gagggggggc ccggtaccca   3480
gcttttgttc cctttagtga gggttaattg cgcgggaagt atttatcact aatcaagcac   3540
aagtaataca tgagaaactt ttactacagc aagcacaatc ctccaaaaaa ttttgttttt   3600
acaaaatccc tggtgaacat gattggaagg gacctactag ggtgctgtgg aagggtgatg   3660
gtgcagtagt agttaatgat gaaggaaagg gaataattgc tgtaccatta accaggacta   3720
agttactaat aaaaccaaat tgagtattgt tgcaggaagc aagacccaac taccattgtc   3780
agctgtgttt cctgacctca atatttgtta taaggtttga tatgaatccc agggggaatc   3840
tcaaccccta ttacccaaca gtcagaaaaa tctaagtgtg aggagaacac aatgtttcaa   3900
ccttattgtt ataataatga cagtaagaac agcatggcag aatcgaagga agcaagagac   3960
caagaatgaa cctgaaagaa gaatctaaag aagaaaaaag aagaaatgac tggtggaaaa   4020
taggtatgtt tctgttatgc ttagcaggaa ctactggagg aatactttgg tggtatgaag   4080
gactcccaca gcaacattat atagggttgg tggcgatagg gggaagatta aacggatctg   4140
gccaatcaaa tgctatagaa tgctggggtt ccttcccggg gtgtagacca tttcaaaatt   4200
acttcagtta tgagaccaat agaagcatgc atatggataa taatactgct acattattag   4260
aagctttaac caatataact gctctataaa taacaaaaca gaattagaaa catggaagtt   4320
agtaaagact tctggcataa ctcctttacc tatttcttct gaagctaaca ctggactaat   4380
tagacataag agagattttg gtataagtgc aatagtggca gctattgtag ccgctactgc   4440
tattgctgct agcgctacta tgtcttatgt tgctctaact gaggttaaca aaataatgga   4500
agtacaaaat catacttttg aggtagaaaa tagtactcta aatggtatgg atttaataga   4560
acgacaaata aagatattat atgctatgat tcttcaaaca catgcagatg ttcaactgtt   4620
aaaggaaaga caacaggtag aggagacatt taatttaatt ggatgtatag aaagaacaca   4680
tgtattttgt catactggtc atccctggaa tatgtcatgg ggacatttaa atgagtcaac   4740
```

-continued

```
acaatgggat gactgggtaa gcaaaatgga agatttaaat caagagatac taactacact   4800
tcatggagcc aggaacaatt tggcacaatc catgataaca ttcaatacac cagatagtat   4860
agctcaattt ggaaaagacc tttggagtca tattggaaat tggattcctg gattgggagc   4920
ttccattata aaatatatag tgatgttttt gcttatttat ttgttactaa cctcttcgcc   4980
taagatcctc agggccctct ggaaggtgac cagtggtgca gggtcctccg gcagtcgtta   5040
cctgaagaaa aaattccatc acaaacatgc atcgcgagaa gacacctggg accaggccca   5100
acacaacata cacctagcag gcgtgaccgg tggatcaggg gacaaatact acaagcagaa   5160
gtactccagg aacgactgga atggagaatc agaggagtac aacaggcggc caaagagctg   5220
ggtgaagtca atcgaggcat ttggagagag ctatatttcc gagaagacca aaggggagat   5280
ttctcagcct ggggcggcta tcaacgagca caagaacggc tctgggggga acaatcctca   5340
ccaagggtcc ttagacctgg agattcgaag cgaaggagga aacatttatg actgttgcat   5400
taaagcccaa gaaggaactc tcgctatccc ttgctgtgga tttcccttat ggctattttg   5460
gggactagta attatagtag gacgcatagc aggctatgga ttacgtggac tcgctgttat   5520
aataaggatt tgtattagag gcttaaattt gatatttgaa ataatcagaa aaatgcttga   5580
ttatattgga agagctttaa atcctggcac atctcatgta tcaatgcctc agtatgttta   5640
gaaaaacaag gggggaactg tggggttttt atgaggggtt ttataaatga ttataagagt   5700
aaaaagaaag ttgctgatgc tctcataacc ttgtataacc caaaggacta gctcatgttg   5760
ctaggcaact aaaccgcaat aaccgcattt gtgacgcgag ttccccattg gtgacgcgtt   5820
aacttcctgt ttttacagta tataagtgct tgtattctga caattgggca ctcagattct   5880
gcggtctgag tcccttctct gctgggctga aaaggccttt gtaataaata taattctcta   5940
ctcagtccct gtctctagtt tgtctgttcg agatcctaca gagctcatgc cttggcgtaa   6000
tcatggtcat agctgtttcc tgtgtgaaat tgttatccgc tcacaattcc acacaacata   6060
cgagccggaa gcataaagtg taaagcctgg ggtgcctaat gagtgagcta actcacatta   6120
attgcgttgc gctcactgcc cgctttccag tcgggaaacc tgtcgtgcca gctgcattaa   6180
tgaatcggcc aacgcgcggg gagaggcggt ttgcgtattg ggcgctcttc cgcttcctcg   6240
ctcactgact cgctgcgctc ggtcgttcgg ctgcggcgag cggtatcagc tcactcaaag   6300
gcggtaatac ggttatccac agaatcaggg gataacgcag gaaagaacat gtgagcaaaa   6360
ggccagcaaa aggccaggaa ccgtaaaaag gccgcgttgc tggcgttttt ccataggctc   6420
cgcccccctg acgagcatca caaaaatcga cgctcaagtc agaggtggcg aaacccgaca   6480
ggactataaa gataccaggc gtttccccct ggaagctccc tcgtgcgctc tcctgttccg   6540
accctgccgc ttaccggata cctgtccgcc tttctccctt cgggaagcgt ggcgctttct   6600
catagctcac gctgtaggta tctcagttcg gtgtaggtcg ttcgctccaa gctgggctgt   6660
gtgcacgaac cccccgttca gcccgaccgc tgcgccttat ccggtaacta tcgtcttgag   6720
tccaacccgg taagacacga cttatcgcca ctggcagcag ccactggtaa caggattagc   6780
agagcgaggt atgtaggcgg tgctacagag ttcttgaagt ggtggcctaa ctacggctac   6840
actagaagga cagtatttgg tatctgcgct ctgctgaagc cagttacctt cggaaaaaga   6900
gttggtagct cttgatccgg caaacaaacc accgctggta gcggtggttt ttttgtttgc   6960
aagcagcaga ttacgcgcag aaaaaaagga tctcaagaag atcctttgat cttttctacg   7020
gggtctgacg ctcagtggaa cgaaaactca cgttaaggga ttttggtcat gagattatca   7080
```

-continued

```
aaaaggatct tcacctagat ccttttaaat taaaaatgaa gttttaaatc aatctaaagt   7140

atatatgagt aaacttggtc tgacagttac caatgcttaa tcagtgaggc acctatctca   7200

gcgatctgtc tatttcgttc atccatagtt gcctgactcc ccgtcgtgta gataactacg   7260

atacgggagg gcttaccatc tggccccagt gctgcaatga taccgcgaga cccacgctca   7320

ccggctccag atttatcagc aataaaccag ccagccggaa gggccgagcg cagaagtggt   7380

cctgcaactt tatccgcctc catccagtct attaattgtt gccgggaagc tagagtaagt   7440

agttcgccag ttaatagttt gcgcaacgtt gttgccattg ctacaggcat cgtggtgtca   7500

cgctcgtcgt ttggtatggc ttcattcagc tccggttccc aacgatcaag gcgagttaca   7560

tgatccccca tgttgtgcaa aaaagcggtt agctccttcg gtcctccgat cgttgtcaga   7620

agtaagttgg ccgcagtgtt atcactcatg gttatggcag cactgcataa ttctcttact   7680

gtcatgccat ccgtaagatg cttttctgtg actggtgagt actcaaccaa gtcattctga   7740

gaatagtgta tgcggcgacc gagttgctct tgcccggcgt caatacggga taataccgcg   7800

ccacatagca gaactttaaa agtgctcatc attggaaaac gttcttcggg gcgaaaactc   7860

tcaaggatct taccgctgtt gagatccagt tcgatgtaac ccactcgtgc acccaactga   7920

tcttcagcat cttttacttt caccagcgtt tctgggtgag caaaaacagg aaggcaaaat   7980

gccgcaaaaa agggaataag ggcgacacgg aaatgttgaa tactcatact cttccttttt   8040

caatattatt gaagcattta tcagggttat tgtctcatga gcggatacat atttgaatgt   8100

atttagaaaa ataaacaaat aggggttccg cgcacatttc cccgaaaagt gccacctaaa   8160

ttgtaagcgt taatattttg ttaaaattcg cgttaaattt ttgttaaatc agctcatttt   8220

ttaaccaata ggccgaaatc ggcaaaatcc cttataaatc aaaagaatag accgagatag   8280

ggttgagtgt tgttccagtt tggaacaaga gtccactatt aaagaacgtg gactccaacg   8340

tcaaagggcg aaaaaccgtc tatcagggcg atggcccact acgtgaacca tcaccctaat   8400

caagtttttt ggggtcgagg tgccgtaaag cactaaatcg gaaccctaaa gggagccccc   8460

gatttagagc ttgacgggga aagccaacct ggcttatcga aattaatacg actcactata   8520

gggagaccgg c                                                        8531
```

<210> SEQ ID NO 6
<211> LENGTH: 10112
<212> TYPE: DNA
<213> ORGANISM: Artificial Sequence
<220> FEATURE:
<223> OTHER INFORMATION: Description of Artificial Sequence: Synthetic
nucleic acid pESYNGP, codon-optimized EIAV
gag/pol expression plasmid

<400> SEQUENCE: 6

```
tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480

gcagtacatc tacgtattag tcatcgctat taccatggtg atgcggtttt ggcagtacac    540
```

-continued

```
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctaga gaattcgcca ccatgggcga tcccctcacc tggtccaaag ccctgaagaa   1140
actggaaaaa gtcaccgttc agggtagcca aaagcttacc acaggcaatt gcaactgggc   1200
attgtccctg gtggatcttt tccacgacac taatttcgtt aaggagaaag attggcaact   1260
cagagacgtg atcccccctct tggaggacgt gacccaaaca ttgtctgggc aggagcgcga   1320
agctttcgag cgcacctggt gggccatcag cgcagtcaaa atggggctgc aaatcaacaa   1380
cgtggttgac ggtaaagcta gctttcaact gctccgcgct aagtacgaga agaaaaccgc   1440
caacaagaaa caatccgaac ctagcgagga gtacccaatt atgatcgacg gcgccggcaa   1500
taggaacttc cgcccactga ctcccagggg ctataccacc tgggtcaaca ccatccagac   1560
aaacggactt ttgaacgaag cctcccagaa cctgttcggc atcctgtctg tggactgcac   1620
ctccgaagaa atgaatgctt ttctcgacgt ggtgccagga caggctggac agaaacagat   1680
cctgctcgat gccattgaca agatcgccga cgactgggat aatcgccacc ccctgccaaa   1740
cgcccctctg gtggctcccc cacaggggcc tatccctatg accgctaggt tcattagggg   1800
actgggggtg ccccgcgaac gccagatgga gccagcattt gaccaattta ggcagaccta   1860
cagacagtgg atcatcgaag ccatgagcga ggggattaaa gtcatgatcg gaaagcccaa   1920
ggcacagaac atcaggcagg gggccaagga accatacct gagtttgtcg acaggcttct   1980
gtcccagatt aaatccgaag gccaccctca ggagatctcc aagttcttga cagacacact   2040
gactatccaa aatgcaaatg aagagtgcag aaacgccatg aggcacctca gacctgaaga   2100
taccctggag gagaaaatgt acgcatgtcg cgacattggc actaccaagc aaaagatgat   2160
gctgctcgcc aaggctctgc aaaccggcct ggctggtcca ttcaaaggag gagcactgaa   2220
gggaggtcca ttgaaagctg cacaaacatg ttataattgt gggaagccag gacatttatc   2280
tagtcaatgt agagcaccta aagtctgttt taaatgtaaa cagcctggac atttctcaaa   2340
gcaatgcaga agtgttccaa aaaacgggaa gcaaggggct caagggaggc cccagaaaca   2400
aactttcccg atacaacaga agagtcagca caacaaatct gttgtacaag agactcctca   2460
gactcaaaat ctgtacccag atctgagcga aataaaaaag gaatacaatg tcaaggagaa   2520
ggatcaagta gaggatctca acctggacag tttgtgggag taacatacaa tctcgagaag   2580
aggcccacta ccatcgtcct gatcaatgac acccctctta atgtgctgct ggacaccgga   2640
gccgacacca gcgttctcac tactgctcac tataacagac tgaaatacag aggaaggaaa   2700
taccagggca caggcatcat cggcgttgga ggcaacgtcg aaacctttc cactcctgtc   2760
accatcaaaa agaaggggag acacattaaa accagaatgc tggtcgccga catccccgtc   2820
accatccttg gcagagacat tctccaggac ctgggcgcta aactcgtgct ggcacaactg   2880
```

-continued

```
tctaaggaaa tcaagttccg caagatcgag ctgaaagagg gcacaatggg tccaaaaatc   2940
ccccagtggc ccctgaccaa agagaagctt gagggcgcta aggaaatcgt gcagcgcctg   3000
ctttctgagg gcaagattag cgaggccagc gacaataacc cttacaacag ccccatcttt   3060
gtgattaaga aaaggagcgg caaatggaga ctcctgcagg acctgaggga actcaacaag   3120
accgtccagg tcggaactga gatctctcgc ggactgcctc accccggcgg cctgattaaa   3180
tgcaagcaca tgacagtcct tgacattgga gacgcttatt ttaccatccc cctcgatcct   3240
gaatttcgcc cctatactgc ttttaccatc cccagcatca atcaccagga gcccgataaa   3300
cgctatgtgt ggaagtgcct cccccaggga tttgtgctta gcccctacat ttaccagaag   3360
acacttcaag agatcctcca acctttccgc gaaagatacc cagaggttca actctaccaa   3420
tatatggacg acctgttcat ggggtccaac gggtctaaga agcagcacaa ggaactcatc   3480
atcgaactga gggcaatcct cctggagaaa ggcttcgaga cacccgacga caagctgcaa   3540
gaagttcctc catatagctg gctgggctac cagctttgcc ctgaaaactg gaaagtccag   3600
aagatgcagt tggatatggt caagaaccca acactgaacg acgtccagaa gctcatgggc   3660
aatattacct ggatgagctc cggaatccct gggcttaccg ttaagcacat tgccgcaact   3720
acaaaaggat gcctggagtt gaaccagaag gtcatttgga cagaggaagc tcagaaggaa   3780
ctggaggaga ataatgaaaa gattaagaat gctcaagggc tccaatacta caatcccgaa   3840
gaagaaatgt tgtgcgaggt cgaaatcact aagaactacg aagccaccta tgtcatcaaa   3900
cagtcccaag gcatcttgtg ggccggaaag aaaatcatga aggccaacaa aggctggtcc   3960
accgttaaaa atctgatgct cctgctccag cacgtcgcca ccgagtctat cacccgcgtc   4020
ggcaagtgcc ccaccttcaa agttcccttc actaaggagc aggtgatgtg ggagatgcaa   4080
aaaggctggt actactcttg gcttcccgag atcgtctaca cccaccaagt ggtgcacgac   4140
gactggagaa tgaagcttgt cgaggagccc actagcggaa ttacaatcta taccgacggc   4200
ggaaagcaaa acggagaggg aatcgctgca tacgtcacat ctaacggccg caccaagcaa   4260
aagaggctcg gccctgtcac tcaccaggtg gctgagagga tggctatcca gatggccctt   4320
gaggacacta gagacaagca ggtgaacatt gtgactgaca gctactactg ctggaaaaac   4380
atcacagagg gccttggcct ggagggaccc cagtctccct ggtggcctat catccagaat   4440
atccgcgaaa aggaaattgt ctatttcgcc tgggtgcctg gacacaaagg aatttacggc   4500
aaccaactcg ccgatgaagc cgccaaaatt aaagaggaaa tcatgcttgc ctaccagggc   4560
acacagatta aggagaagag agacgaggac gctggctttg acctgtgtgt gccatacgac   4620
atcatgattc ccgttagcga cacaaagatc attccaaccg atgtcaagat ccaggtgcca   4680
cccaattcat ttggttgggt gaccggaaag tccagcatgg ctaagcaggg tcttctgatt   4740
aacgggggaa tcattgatga aggatacacc ggcgaaatcc aggtgatctg cacaaatatc   4800
ggcaaaagca atattaagct tatcgaaggg cagaagttcg ctcaactcat catcctccag   4860
caccacagca attcaagaca accttgggac gaaaacaaga ttagccagag aggtgacaag   4920
ggcttcggca gcacaggtgt gttctgggtg gagaacatcc aggaagcaca ggacgagcac   4980
gagaattggc acacctcccc taagattttg gcccgcaatt acaagatccc actgactgtg   5040
gctaagcaga tcacacagga atgcccccac tgcaccaaac aaggttctgg ccccgccggc   5100
tgcgtgatga ggtcccccaa tcactggcag gcagattgca cccacctcga caacaaaatt   5160
atcctgacct tcgtggagag caattccggc tacatccacg caacactcct ctccaaggaa   5220
aatgcattgt gcacctccct cgcaattctg gaatgggcca ggctgttctc tccaaaatcc   5280
```

-continued

```
ctgcacaccg acaacggcac caactttgtg gctgaacctg tggtgaatct gctgaagttc   5340
ctgaaaatcg cccacaccac tggcattccc tatcaccctg aaagccaggg cattgtcgag   5400
agggccaaca gaactctgaa agaaaagatc caatctcaca gagacaatac acagacattg   5460
gaggccgcac ttcagctcgc ccttatcacc tgcaacaaag gaagagaaag catgggcggc   5520
cagacccccct gggaggtctt catcactaac caggcccagg tcatccatga aaagctgctc   5580
ttgcagcagg cccagtcctc caaaaagttc tgcttttata agatccccgg tgagcacgac   5640
tggaaaggtc ctacaagagt tttgtggaaa ggagacggcg cagttgtggt gaacgatgag   5700
ggcaagggga tcatcgctgt gcccctgaca cgcaccaagc ttctcatcaa gccaaactga   5760
acccggggcg gccgcttccc tttagtgagg gttaatgctt cgagcagaca tgataagata   5820
cattgatgag tttggacaaa ccacaactag aatgcagtga aaaaaatgct ttatttgtga   5880
aatttgtgat gctattgctt tatttgtaac cattataagc tgcaataaac aagttaacaa   5940
caacaattgc attcatttta tgtttcaggt tcaggggggag atgtgggagg ttttttaaag   6000
caagtaaaac ctctacaaat gtggtaaaat ccgataagga tcgatccggg ctggcgtaat   6060
agcgaagagg cccgcaccga tcgcccttcc caacagttgc gcagcctgaa tggcgaatgg   6120
acgcgccctg tagcggcgca ttaagcgcgg cgggtgtggt ggttacgcgc agcgtgaccg   6180
ctacacttgc cagcgcccta gcgcccgctc ctttcgcttt cttcccttcc tttctcgcca   6240
cgttcgccgg ctttccccgt caagctctaa atcgggggct ccctttaggg ttccgattta   6300
gagctttacg gcacctcgac cgcaaaaaac ttgatttggg tgatggttca cgtagtgggc   6360
catcgccctg atagacggtt tttcgccctt tgacgttgga gtccacgttc tttaatagtg   6420
gactcttgtt ccaaactgga acaacactca accctatctc ggtctattct tttgatttat   6480
aagggatttt gccgatttcg gcctattggt taaaaaatga gctgatttaa caaatattta   6540
acgcgaattt taacaaaata ttaacgttta caatttcgcc tgatgcggta ttttctcctt   6600
acgcatctgt gcggtatttc acaccgcata cgcggatctg cgcagcacca tggcctgaaa   6660
taacctctga aagaggaact tggttaggta ccttctgagg cggaaagaac cagctgtgga   6720
atgtgtgtca gttagggtgt ggaaagtccc caggctcccc agcaggcaga agtatgcaaa   6780
gcatgcatct caattagtca gcaaccaggt gtggaaagtc cccaggctcc ccagcaggca   6840
gaagtatgca aagcatgcat ctcaattagt cagcaaccat agtcccgccc ctaactccgc   6900
ccatcccgcc cctaactccg cccagttccg cccattctcc gccccatggc tgactaattt   6960
tttttattta tgcagaggcc gaggccgcct cggcctctga gctattccag aagtagtgag   7020
gaggcttttt tggaggccta ggcttttgca aaaagcttga ttcttctgac acaacagtct   7080
cgaacttaag gctagagcca ccatgattga acaagatgga ttgcacgcag gttctccggc   7140
cgcttgggtg gagaggctat tcggctatga ctgggcacaa cagacaatcg gctgctctga   7200
tgccgccgtg ttccggctgt cagcgcaggg gcgcccggtt ctttttgtca agaccgacct   7260
gtccggtgcc ctgaatgaac tgcaggacga ggcagcgcgg ctatcgtggc tggccacgac   7320
gggcgttcct tgcgcagctg tgctcgacgt tgtcactgaa gcgggaaggg actggctgct   7380
attgggcgaa gtgccggggc aggatctcct gtcatctcac cttgctcctg ccgagaaagt   7440
atccatcatg gctgatgcaa tgcggcggct gcatacgctt gatccggcta cctgcccatt   7500
cgaccaccaa gcgaaacatc gcatcgagcg agcacgtact cggatggaag ccggtcttgt   7560
cgatcaggat gatctggacg aagagcatca ggggctcgcg ccagccgaac tgttcgccag   7620
```

-continued gctcaaggcg cgcatgcccg acggcgagga tctcgtcgtg acccatggcg atgcctgctt 7680
gccgaatatc atggtggaaa atggccgctt ttctggattc atcgactgtg gccggctggg 7740
tgtggcggac cgctatcagg acatagcgtt ggctacccgt gatattgctg aagagcttgg 7800
cggcgaatgg gctgaccgct tcctcgtgct ttacggtatc gccgctcccg attcgcagcg 7860
catcgccttc tatcgccttc ttgacgagtt cttctgagcg ggactctggg gttcgaaatg 7920
accgaccaag cgacgcccaa cctgccatca cgatggccgc aataaaatat ctttattttc 7980
attacatctg tgtgttggtt ttttgtgtga atcgatagcg ataaggatcc gcgtatggtg 8040
cactctcagt acaatctgct ctgatgccgc atagttaagc cagccccgac acccgccaac 8100
acccgctgac gcgccctgac gggcttgtct gctcccggca tccgcttaca gacaagctgt 8160
gaccgtctcc gggagctgca tgtgtcagag gttttcaccg tcatcaccga aacgcgcgag 8220
acgaaagggc ctcgtgatac gcctattttt ataggttaat gtcatgataa taatggtttc 8280
ttagacgtca ggtggcactt ttcggggaaa tgtgcgcgga acccctattt gtttattttt 8340
ctaaatacat tcaaatatgt atccgctcat gagacaataa ccctgataaa tgcttcaata 8400
atattgaaaa aggaagagta tgagtattca acatttccgt gtcgccctta ttcccttttt 8460
tgcggcattt tgccttcctg tttttgctca cccagaaacg ctggtgaaag taaaagatgc 8520
tgaagatcag ttgggtgcac gagtgggtta catcgaactg gatctcaaca gcggtaagat 8580
ccttgagagt tttcgccccg aagaacgttt tccaatgatg agcactttta aagttctgct 8640
atgtggcgcg gtattatccc gtattgacgc cgggcaagag caactcggtc gccgcataca 8700
ctattctcag aatgacttgg ttgagtactc accagtcaca gaaaagcatc ttacggatgg 8760
catgacagta agagaattat gcagtgctgc cataaccatg agtgataaca ctgcggccaa 8820
cttacttctg acaacgatcg gaggaccgaa ggagctaacc gcttttttgc acaacatggg 8880
ggatcatgta actcgccttg atcgttggga accggagctg aatgaagcca taccaaacga 8940
cgagcgtgac accacgatgc ctgtagcaat ggcaacaacg ttgcgcaaac tattaactgg 9000
cgaactactt actctagctt cccggcaaca attaatagac tggatggagg cggataaagt 9060
tgcaggacca cttctgcgct cggcccttcc ggctggctgg tttattgctg ataaatctgg 9120
agccggtgag cgtgggtctc gcggtatcat tgcagcactg gggccagatg gtaagccctc 9180
ccgtatcgta gttatctaca cgacggggag tcaggcaact atggatgaac gaaatagaca 9240
gatcgctgag ataggtgcct cactgattaa gcattggtaa ctgtcagacc aagtttactc 9300
atatatactt tagattgatt taaaacttca tttttaattt aaaaggatct aggtgaagat 9360
cctttttgat aatctcatga ccaaaatccc ttaacgtgag ttttcgttcc actgagcgtc 9420
agaccccgta gaaaagatca aaggatcttc ttgagatcct ttttttctgc gcgtaatctg 9480
ctgcttgcaa acaaaaaaac caccgctacc agcggtggtt tgtttgccgg atcaagagct 9540
accaactctt tttccgaagg taactggctt cagcagagcg cagataccaa atactgtcct 9600
tctagtgtag ccgtagttag gccaccactt caagaactct gtagcaccgc ctacatacct 9660
cgctctgcta atcctgttac cagtggctgc tgccagtggc gataagtcgt gtcttaccgg 9720
gttggactca agacgatagt taccggataa ggcgcagcgg tcgggctgaa cggggggttc 9780
gtgcacacag cccagcttgg agcgaacgac ctacaccgaa ctgagatacc tacagcgtga 9840
gctatgagaa agcgccacgc ttcccgaagg gagaaaggcg gacaggtatc cggtaagcgg 9900
cagggtcgga acaggagagc gcacgaggga gcttccaggg ggaaacgcct ggtatcttta 9960
tagtcctgtc gggtttcgcc acctctgact tgagcgtcga tttttgtgat gctcgtcagg 10020

-continued

```
ggggcggagc ctatggaaaa acgccagcaa cgcggccttt ttacggttcc tggccttttg  10080

ctggcctttt gctcacatgg ctcgacagat ct                                10112
```

<210> SEQ ID NO 7
<211> LENGTH: 5993
<212> TYPE: DNA
<213> ORGANISM: Artificial Sequence
<220> FEATURE:
<223> OTHER INFORMATION: Description of Artificial Sequence: Synthetic nucleic acid pClneoERev, EIAV Rev expression plasmid

<400> SEQUENCE: 7

```
tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480

gcagtacatc tacgtattag tcatcgctat taccatggtg atgcggtttt ggcagtacac    540

caatgggcgt ggatagcggt ttgactcacg gggatttcca agtctccacc ccattgacgt    600

caatgggagt ttgttttggc accaaaatca acgggacttt ccaaaatgtc gtaacaactg    660

cgatcgcccg ccccgttgac gcaaatgggc ggtaggcgtg tacggtggga ggtctatata    720

agcagagctc gtttagtgaa ccgtcagatc actagaagct ttattgcggt agtttatcac    780

agttaaattg ctaacgcagt cagtgcttct gacacaacag tctcgaactt aagctgcagt    840

gactctctta aggtagcctt gcagaagttg gtcgtgaggc actgggcagg taagtatcaa    900

ggttacaaga caggtttaag gagaccaata gaaactgggc ttgtcgagac agagaagact    960

cttgcgtttc tgataggcac ctattggtct tactgacatc cactttgcct ttctctccac   1020

aggtgtccac tcccagttca attacagctc ttaaggctag agtacttaat acgactcact   1080

ataggctagt aacggccgcc agtgtgctgg aattcggctt atggcagaat cgaaggaagc   1140

aagagaccaa gaaatgaacc tgaaagaaga atctaaagaa gaaaaaagaa gaaatgactg   1200

gtggaaaata gatcctcagg gccctctgga aggtgaccag tggtgcaggg tcctccggca   1260

gtcgttacct gaagaaaaaa ttccatcaca aacatgcatc gcgagaagac acctgggacc   1320

aggcccaaca caacatacac ctagcaggcg tgaccggtgg atcaggggac aaatactaca   1380

agcagaagta ctccaggaac gactggaatg gagaatcaga ggagtacaac aggcggccaa   1440

agagctgggt gaagtcaatc gaggcatttg gagagagcta tatttccgag aagaccaaag   1500

gggagatttc tcagcctggg gcggctatca acgagcacaa gaacggctct gggggggaaca   1560

atcctcacca agggtcctta gacctggaga ttcgaagcga aggaggaaac atttatgaag   1620

ccgaattctg cagatatcca tcacactggc ggccgcttcc ctttagtgag ggttaatgct   1680

tcgagcagac atgataagat acattgatga gtttggacaa accacaacta gaatgcagtg   1740

aaaaaaatgc tttatttgtg aaatttgtga tgctattgct ttatttgtaa ccattataag   1800

ctgcaataaa caagttaaca acaacaattg cattcatttt atgtttcagg ttcaggggga   1860
```

-continued gatgtgggag gttttttaaa gcaagtaaaa cctctacaaa tgtggtaaaa tccgataagg 1920
atcgatccgg gctggcgtaa tagcgaagag gcccgcaccg atcgcccttc ccaacagttg 1980
cgcagcctga atggcgaatg gacgcgccct gtagcggcgc attaagcgcg gcgggtgtgg 2040
tggttacgcg cagcgtgacc gctacacttg ccagcgccct agcgcccgct cctttcgctt 2100
tcttcccttc ctttctcgcc acgttcgccg gctttccccg tcaagctcta aatcgggggc 2160
tccctttagg gttccgattt agagctttac ggcacctcga ccgcaaaaaa cttgatttgg 2220
gtgatggttc acgtagtggg ccatcgccct gatagacggt ttttcgccct ttgacgttgg 2280
agtccacgtt ctttaatagt ggactcttgt tccaaactgg aacaacactc aaccctatct 2340
cggtctattc ttttgattta taagggattt tgccgatttc ggcctattgg ttaaaaaatg 2400
agctgattta acaaatattt aacgcgaatt ttaacaaaat attaacgttt acaatttcgc 2460
ctgatgcggt attttctcct tacgcatctg tgcggtattt cacaccgcat acgcggatct 2520
gcgcagcacc atggcctgaa ataacctctg aaagaggaac ttggttaggt accttctgag 2580
gcggaaagaa ccagctgtgg aatgtgtgtc agttagggtg tggaaagtcc ccaggctccc 2640
cagcaggcag aagtatgcaa agcatgcatc tcaattagtc agcaaccagg tgtggaaagt 2700
ccccaggctc cccagcaggc agaagtatgc aaagcatgca tctcaattag tcagcaacca 2760
tagtcccgcc cctaactccg cccatcccgc ccctaactcc gcccagttcc gcccattctc 2820
cgccccatgg ctgactaatt ttttttattt atgcagaggc cgaggccgcc tcggcctctg 2880
agctattcca gaagtagtga ggaggctttt ttggaggcct aggcttttgc aaaaagcttg 2940
attcttctga cacaacagtc tcgaacttaa ggctagagcc accatgattg aacaagatgg 3000
attgcacgca ggttctccgg ccgcttgggt ggagaggcta ttcggctatg actgggcaca 3060
acagacaatc ggctgctctg atgccgccgt gttccggctg tcagcgcagg ggcgcccggt 3120
tctttttgtc aagaccgacc tgtccggtgc cctgaatgaa ctgcaggacg aggcagcgcg 3180
gctatcgtgg ctggccacga cgggcgttcc ttgcgcagct gtgctcgacg ttgtcactga 3240
agcgggaagg gactggctgc tattgggcga agtgccgggg caggatctcc tgtcatctca 3300
ccttgctcct gccgagaaag tatccatcat ggctgatgca atgcggcggc tgcatacgct 3360
tgatccggct acctgcccat tcgaccacca agcgaaacat cgcatcgagc gagcacgtac 3420
tcggatggaa gccggtcttg tcgatcagga tgatctggac gaagagcatc aggggctcgc 3480
gccagccgaa ctgttcgcca ggctcaaggc gcgcatgccc gacggcgagg atctcgtcgt 3540
gacccatggc gatgcctgct tgccgaatat catggtggaa aatggccgct tttctggatt 3600
catcgactgt ggccggctgg gtgtggcgga ccgctatcag gacatagcgt tggctacccg 3660
tgatattgct gaagagcttg gcggcgaatg ggctgaccgc ttcctcgtgc tttacggtat 3720
cgccgctccc gattcgcagc gcatcgcctt ctatcgcctt cttgacgagt tcttctgagc 3780
gggactctgg ggttcgaaat gaccgaccaa gcgacgccca acctgccatc acgatggccg 3840
caataaaata tctttatttt cattacatct gtgtgttggt tttttgtgtg aatcgatagc 3900
gataaggatc cgcgtatggt gcactctcag tacaatctgc tctgatgccg catagttaag 3960
ccagccccga cacccgccaa cacccgctga cgcgccctga cgggcttgtc tgctcccggc 4020
atccgcttac agacaagctg tgaccgtctc cgggagctgc atgtgtcaga ggttttcacc 4080
gtcatcaccg aaacgcgcga gacgaaaggg cctcgtgata cgcctatttt tataggttaa 4140
tgtcatgata ataatggttt cttagacgtc aggtggcact tttcggggaa atgtgcgcgg 4200
aacccctatt tgtttatttt tctaaataca ttcaaatatg tatccgctca tgagacaata 4260

```
accctgataa atgcttcaat aatattgaaa aaggaagagt atgagtattc aacatttccg   4320

tgtcgccctt attccctttt ttgcggcatt ttgccttcct gtttttgctc acccagaaac   4380

gctggtgaaa gtaaaagatg ctgaagatca gttgggtgca cgagtgggtt acatcgaact   4440

ggatctcaac agcggtaaga tccttgagag ttttcgcccc gaagaacgtt ttccaatgat   4500

gagcactttt aaagttctgc tatgtggcgc ggtattatcc cgtattgacg ccgggcaaga   4560

gcaactcggt cgccgcatac actattctca gaatgacttg gttgagtact caccagtcac   4620

agaaaagcat cttacggatg gcatgacagt aagagaatta tgcagtgctg ccataaccat   4680

gagtgataac actgcggcca acttacttct gacaacgatc ggaggaccga aggagctaac   4740

cgcttttttg cacaacatgg gggatcatgt aactcgcctt gatcgttggg aaccggagct   4800

gaatgaagcc ataccaaacg acgagcgtga caccacgatg cctgtagcaa tggcaacaac   4860

gttgcgcaaa ctattaactg gcgaactact tactctagct tcccggcaac aattaataga   4920

ctggatggag gcggataaag ttgcaggacc acttctgcgc tcggcccttc cggctggctg   4980

gtttattgct gataaatctg gagccggtga gcgtgggtct cgcggtatca ttgcagcact   5040

ggggccagat ggtaagccct cccgtatcgt agttatctac acgacgggga gtcaggcaac   5100

tatggatgaa cgaaatagac agatcgctga gataggtgcc tcactgatta agcattggta   5160

actgtcagac caagtttact catatatact ttagattgat ttaaaacttc atttttaatt   5220

taaaaggatc taggtgaaga tcctttttga taatctcatg accaaaatcc cttaacgtga   5280

gttttcgttc cactgagcgt cagaccccgt agaaaagatc aaaggatctt cttgagatcc   5340

tttttttctg cgcgtaatct gctgcttgca aacaaaaaaa ccaccgctac cagcggtggt   5400

ttgtttgccg gatcaagagc taccaactct ttttccgaag gtaactggct tcagcagagc   5460

gcagatacca aatactgtcc ttctagtgta gccgtagtta ggccaccact tcaagaactc   5520

tgtagcaccg cctacatacc tcgctctgct aatcctgtta ccagtggctg ctgccagtgg   5580

cgataagtcg tgtcttaccg ggttggactc aagacgatag ttaccggata aggcgcagcg   5640

gtcgggctga acggggggtt cgtgcacaca gcccagcttg gagcgaacga cctacaccga   5700

actgagatac ctacagcgtg agctatgaga aagcgccacg cttcccgaag ggagaaaggc   5760

ggacaggtat ccggtaagcg gcagggtcgg aacaggagag cgcacgaggg agcttccagg   5820

gggaaacgcc tggtatcttt atagtcctgt cgggtttcgc cacctctgac ttgagcgtcg   5880

atttttgtga tgctcgtcag gggggcggag cctatggaaa aacgccagca acgcggcctt   5940

tttacggttc ctggcctttt gctggccttt tgctcacatg gctcgacaga tct          5993
```

<210> SEQ ID NO 8
<211> LENGTH: 5961
<212> TYPE: DNA
<213> ORGANISM: Artificial Sequence
<220> FEATURE:
<223> OTHER INFORMATION: Description of Artificial Sequence: Synthetic
      nucleic acid pESYNREV, codon-optimized EIAV
      Rev expression plasmid

<400> SEQUENCE: 8

```
tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240
```

-continued

```
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg ccccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc ctcgagaatt cgccaccatg gctgagagca aggaggccag ggatcaagag   1140
atgaacctca aggaagagag caaagaggag aagcgccgca acgactggtg gaagatcgac   1200
ccacaaggcc ccctggaggg ggaccagtgg tgccgcgtgc tgagacagtc cctgcccgag   1260
gagaagattc ctagccagac ctgcatcgcc agaagacacc tcggccccgg tcccacccag   1320
cacacaccct ccagaaggga taggtggatt aggggccaga ttttgcaagc cgaggtcctc   1380
caagaaaggc tggaatggag aattaggggc gtgcaacaag ccgctaaaga gctgggagag   1440
gtgaatcgcg gcatctggag ggagctctac ttccgcgagg accagagggg cgatttctcc   1500
gcatggggag gctaccagag ggcacaagaa aggctgtggg gcgagcagag cagccccccgc   1560
gtcttgaggc ccggagactc caaaagacgc cgcaaacacc tgtgaagtcg acccgggcgg   1620
ccgcttccct ttagtgaggg ttaatgcttc gagcagacat gataagatac attgatgagt   1680
ttggacaaac cacaactaga atgcagtgaa aaaaatgctt tatttgtgaa atttgtgatg   1740
ctattgcttt atttgtaacc attataagct gcaataaaca agttaacaac aacaattgca   1800
ttcattttat gtttcaggtt cagggggaga tgtgggaggt tttttaaagc aagtaaaacc   1860
tctacaaatg tggtaaaatc cgataaggat cgatccgggc tggcgtaata gcgaagaggc   1920
ccgcaccgat cgcccttccc aacagttgcg cagcctgaat ggcgaatgga cgcgccctgt   1980
agcggcgcat taagcgcggc gggtgtggtg gttacgcgca gcgtgaccgc tacacttgcc   2040
agcgccctag cgcccgctcc tttcgctttc ttcccttcct ttctcgccac gttcgccggc   2100
tttccccgtc aagctctaaa tcgggggctc cctttagggt tccgatttag agctttacgg   2160
cacctcgacc gcaaaaaact tgatttgggt gatggttcac gtagtgggcc atcgccctga   2220
tagacggttt ttcgcccttt gacgttggag tccacgttct ttaatagtgg actcttgttc   2280
caaactggaa caacactcaa ccctatctcg gtctattctt ttgatttata agggattttg   2340
ccgatttcgg cctattggtt aaaaaatgag ctgatttaac aaatatttaa cgcgaatttt   2400
aacaaaatat taacgtttac aatttcgcct gatgcggtat tttctcctta cgcatctgtg   2460
cggtatttca caccgcatac gcggatctgc gcagcaccat ggcctgaaat aacctctgaa   2520
agaggaactt ggttaggtac cttctgaggc ggaaagaacc agctgtggaa tgtgtgtcag   2580
ttagggtgtg gaaagtcccc aggctcccca gcaggcagaa gtatgcaaag catgcatctc   2640
```

-continued

```
aattagtcag caaccaggtg tggaaagtcc ccaggctccc cagcaggcag aagtatgcaa   2700
agcatgcatc tcaattagtc agcaaccata gtcccgcccc taactccgcc catcccgccc   2760
ctaactccgc ccagttccgc ccattctccg ccccatggct gactaatttt ttttatttat   2820
gcagaggccg aggccgcctc ggcctctgag ctattccaga agtagtgagg aggctttttt   2880
ggaggcctag gcttttgcaa aaagcttgat tcttctgaca caacagtctc gaacttaagg   2940
ctagagccac catgattgaa caagatggat tgcacgcagg ttctccggcc gcttgggtgg   3000
agaggctatt cggctatgac tgggcacaac agacaatcgg ctgctctgat gccgccgtgt   3060
tccggctgtc agcgcagggg cgcccggttc tttttgtcaa gaccgacctg tccggtgccc   3120
tgaatgaact gcaggacgag gcagcgcggc tatcgtggct ggccacgacg ggcgttcctt   3180
gcgcagctgt gctcgacgtt gtcactgaag cgggaaggga ctggctgcta ttgggcgaag   3240
tgccggggca ggatctcctg tcatctcacc ttgctcctgc cgagaaagta tccatcatgg   3300
ctgatgcaat gcggcggctg catacgcttg atccggctac ctgcccattc gaccaccaag   3360
cgaaacatcg catcgagcga gcacgtactc ggatggaagc cggtcttgtc gatcaggatg   3420
atctggacga agagcatcag gggctcgcgc cagccgaact gttcgccagg ctcaaggcgc   3480
gcatgcccga cggcgaggat ctcgtcgtga cccatggcga tgcctgcttg ccgaatatca   3540
tggtggaaaa tggccgcttt tctggattca tcgactgtgg ccggctgggt gtggcggacc   3600
gctatcagga catagcgttg gctacccgtg atattgctga agagcttggc ggcgaatggg   3660
ctgaccgctt cctcgtgctt tacggtatcg ccgctcccga ttcgcagcgc atcgccttct   3720
atcgccttct tgacgagttc ttctgagcgg gactctgggg ttcgaaatga ccgaccaagc   3780
gacgcccaac ctgccatcac gatggccgca ataaaatatc tttattttca ttacatctgt   3840
gtgttggttt tttgtgtgaa tcgatagcga taaggatccg cgtatggtgc actctcagta   3900
caatctgctc tgatgccgca tagttaagcc agccccgaca cccgccaaca cccgctgacg   3960
cgccctgacg ggcttgtctg ctcccggcat ccgcttacag acaagctgtg accgtctccg   4020
ggagctgcat gtgtcagagg ttttcaccgt catcaccgaa acgcgcgaga cgaaagggcc   4080
tcgtgatacg cctattttta taggttaatg tcatgataat aatggtttct tagacgtcag   4140
gtggcacttt tcggggaaat gtgcgcggaa cccctatttg tttatttttc taaatacatt   4200
caaatatgta tccgctcatg agacaataac cctgataaat gcttcaataa tattgaaaaa   4260
ggaagagtat gagtattcaa catttccgtg tcgcccttat tccctttttt gcggcatttt   4320
gccttcctgt ttttgctcac ccagaaacgc tggtgaaagt aaaagatgct gaagatcagt   4380
tgggtgcacg agtgggttac atcgaactgg atctcaacag cggtaagatc cttgagagtt   4440
ttcgccccga agaacgtttt ccaatgatga gcacttttaa agttctgcta tgtggcgcgg   4500
tattatcccg tattgacgcc gggcaagagc aactcggtcg ccgcatacac tattctcaga   4560
atgacttggt tgagtactca ccagtcacag aaaagcatct tacggatggc atgacagtaa   4620
gagaattatg cagtgctgcc ataaccatga gtgataacac tgcggccaac ttacttctga   4680
caacgatcgg aggaccgaag gagctaaccg cttttttgca caacatgggg gatcatgtaa   4740
ctcgccttga tcgttgggaa ccggagctga atgaagccat accaaacgac gagcgtgaca   4800
ccacgatgcc tgtagcaatg gcaacaacgt tgcgcaaact attaactggc gaactactta   4860
ctctagcttc ccggcaacaa ttaatagact ggatggaggc ggataaagtt gcaggaccac   4920
ttctgcgctc ggcccttccg gctggctggt ttattgctga taaatctgga gccggtgagc   4980
```

-continued gtgggtctcg cggtatcatt gcagcactgg ggccagatgg taagccctcc cgtatcgtag 5040
ttatctacac gacggggagt caggcaacta tggatgaacg aaatagacag atcgctgaga 5100
taggtgcctc actgattaag cattggtaac tgtcagacca agtttactca tatatacttt 5160
agattgattt aaaacttcat ttttaattta aaaggatcta ggtgaagatc ctttttgata 5220
atctcatgac caaaatccct taacgtgagt tttcgttcca ctgagcgtca gaccccgtag 5280
aaaagatcaa aggatcttct tgagatcctt tttttctgcg cgtaatctgc tgcttgcaaa 5340
caaaaaaacc accgctacca gcggtggttt gtttgccgga tcaagagcta ccaactcttt 5400
ttccgaaggt aactggcttc agcagagcgc agataccaaa tactgtcctt ctagtgtagc 5460
cgtagttagg ccaccacttc aagaactctg tagcaccgcc tacatacctc gctctgctaa 5520
tcctgttacc agtggctgct gccagtggcg ataagtcgtg tcttaccggg ttggactcaa 5580
gacgatagtt accggataag gcgcagcggt cgggctgaac ggggggttcg tgcacacagc 5640
ccagcttgga gcgaacgacc tacaccgaac tgagatacct acagcgtgag ctatgagaaa 5700
gcgccacgct tcccgaaggg agaaaggcgg acaggtatcc ggtaagcggc agggtcggaa 5760
caggagagcg cacgagggag cttccagggg gaaacgcctg gtatctttat agtcctgtcg 5820
ggtttcgcca cctctgactt gagcgtcgat ttttgtgatg ctcgtcaggg gggcggagcc 5880
tatggaaaaa cgccagcaac gcggcctttt tacggttcct ggccttttgc tggccttttg 5940
ctcacatggc tcgacagatc t 5961

<210> SEQ ID NO 9
<211> LENGTH: 12481
<212> TYPE: DNA
<213> ORGANISM: Artificial Sequence
<220> FEATURE:
<223> OTHER INFORMATION: Description of Artificial Sequence: Synthetic
nucleic acid pONY3.1, EIAV gag/pol expression
plasmid

<400> SEQUENCE: 9
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtccg ccccctattg acgtcaatga 420
cggtaaatgg cccgcctggc attatgccca gtacatgacc ttacgggact ttcctacttg 480
gcagtacatc tacgtattag tcatcgctat taccatggtg atgcggtttt ggcagtacac 540
caatgggcgt ggatagcggt ttgactcacg gggatttcca agtctccacc ccattgacgt 600
caatgggagt ttgttttggc accaaaatca acgggacttt ccaaaatgtc gtaacaactg 660
cgatcgcccg ccccgttgac gcaaatgggc ggtaggcgtg tacggtggga ggtctatata 720
agcagagctc gtttagtgaa ccgtcagatc actagaagct ttattgcggt agtttatcac 780
agttaaattg ctaacgcagt cagtgcttct gacacaacag tctcgaactt aagctgcagt 840
gactctctta aggtagcctt gcagaagttg gtcgtgaggc actgggcagg taagtatcaa 900
ggttacaaga caggtttaag gagaccaata gaaactgggc ttgtcgagac agagaagact 960
cttgcgtttc tgataggcac ctattggtct tactgacatc cactttgcct ttctctccac 1020

-continued

```
aggtgtccac tcccagttca attacagctc ttaaggctag agtacttaat acgactcact   1080
ataggctagc ctcgaggtcg acggtatcgc ccgaacaggg acctgagagg ggcgcagacc   1140
ctacctgttg aacctggctg atcgtaggat ccccgggaca gcagaggaga acttacagaa   1200
gtcttctgga ggtgttcctg gccagaacac aggaggacag gtaagatggg agaccctttg   1260
acatggagca aggcgctcaa gaagttagag aaggtgacgg tacaagggtc tcagaaatta   1320
actactggta actgtaattg ggcgctaagt ctagtagact tatttcatga taccaacttt   1380
gtaaaagaaa aggactggca gctgagggat gtcattccat tgctggaaga tgtaactcag   1440
acgctgtcag gacaagaaag agaggccttt gaaagaacat ggtgggcaat ttctgctgta   1500
aagatgggcc tccagattaa taatgtagta gatggaaagg catcattcca gctcctaaga   1560
gcgaaatatg aaaagaagac tgctaataaa aagcagtctg agccctctga agaatatcca   1620
atcatgatag atggggctgg aaacagaaat tttagacctc taacacctag aggatatact   1680
acttgggtga ataccataca gacaaatggt ctattaaatg aagctagtca aaacttattt   1740
gggatattat cagtagactg tacttctgaa gaaatgaatg catttttgga tgtggtacct   1800
ggccaggcag gacaaaagca gatattactt gatgcaattg ataagatagc agatgattgg   1860
gataatagac atccattacc gaatgctcca ctggtggcac caccacaagg gcctattccc   1920
atgacagcaa ggtttattag aggtttagga gtacctagag aaagacagat ggagcctgct   1980
tttgatcagt ttaggcagac atatagacaa tggataatag aagccatgtc agaaggcatc   2040
aaagtgatga ttggaaaacc taaagctcaa aatattaggc aaggagctaa ggaaccttac   2100
ccagaatttg tagacagact attatcccaa ataaaaagtg agggacatcc acaagagatt   2160
tcaaaattct tgactgatac actgactatt cagaacgcaa atgaggaatg tagaaatgct   2220
atgagacatt taagaccaga ggatacatta gaagagaaaa tgtatgcttg cagagacatt   2280
ggaactacaa aacaaaagat gatgttattg gcaaaagcac ttcagactgg tcttgcgggc   2340
ccatttaaag gtggagcctt gaaaggaggg ccactaaagg cagcacaaac atgttataac   2400
tgtgggaagc caggacattt atctagtcaa tgtagagcac ctaaagtctg ttttaaatgt   2460
aaacagcctg gacatttctc aaagcaatgc agaagtgttc caaaaaacgg gaagcaaggg   2520
gctcaaggga ggccccagaa acaaactttc ccgatacaac agaagagtca gcacaacaaa   2580
tctgttgtac aagagactcc tcagactcaa aatctgtacc cagatctgag cgaaataaaa   2640
aaggaataca atgtcaagga gaaggatcaa gtagaggatc tcaacctgga cagtttgtgg   2700
gagtaacata taatctagag aaaaggccta ctacaatagt attaattaat gatactccct   2760
taaatgtact gttagacaca ggagcagata cttcagtgtt gactactgca cattataata   2820
ggttaaaata tagagggaga aaatatcaag ggacgggaat aataggagtg ggaggaaatg   2880
tggaaacatt ttctacgcct gtgactataa agaaaaaggg tagacacatt aagacaagaa   2940
tgctagtggc agatattcca gtgactattt tgggacgaga tattcttcag gacttaggtg   3000
caaaattggt tttggcacag ctctccaagg aaataaaatt tagaaaaata gagttaaaag   3060
agggcacaat ggggccaaaa attcctcaat ggccactcac taaggagaaa ctagaagggg   3120
ccaaagagat agtccaaaga ctattgtcag agggaaaaat atcagaagct agtgacaata   3180
atccttataa ttcacccata tttgtaataa aaaagaggtc tggcaaatgg aggttattac   3240
aagatctgag agaattaaac aaaacagtac aagtaggaac ggaaatatcc agaggattgc   3300
ctcacccggg aggattaatt aaatgtaaac acatgactgt attagatatt ggagatgcat   3360
```

-continued

```
atttcactat acccttagat ccagagttta gaccatatac agctttcact attccctcca   3420
ttaatcatca agaaccagat aaaagatatg tgtggaaatg tttaccacaa ggattcgtgt   3480
tgagcccata tatatatcag aaaacattac aggaaatttt acaacctttt agggaaagat   3540
atcctgaagt acaattgtat caatatatgg atgatttgtt catgggaagt aatggttcta   3600
aaaaacaaca caaagagtta atcatagaat taagggcgat cttactggaa aagggttttg   3660
agacaccaga tgataaatta caagaagtgc caccttatag ctggctaggt tatcaacttt   3720
gtcctgaaaa ttggaaagta caaaaaatgc aattagacat ggtaaagaat ccaaccctta   3780
atgatgtgca aaaattaatg gggaatataa catggatgag ctcagggatc ccagggttga   3840
cagtaaaaca cattgcagct actactaagg gatgtttaga gttgaatcaa aaagtaattt   3900
ggacggaaga ggcacaaaaa gagttagaag aaaataatga gaagattaaa aatgctcaag   3960
ggttacaata ttataatcca gaagaagaaa tgttatgtga ggttgaaatt acaaaaaatt   4020
atgaggcaac ttatgttata aaacaatcac aaggaatcct atgggcaggt aaaaagatta   4080
tgaaggctaa taagggatgg tcaacagtaa aaaatttaat gttattgttg caacatgtgg   4140
caacagaaag tattactaga gtaggaaaat gtccaacgtt taaggtacca tttaccaaag   4200
agcaagtaat gtgggaaatg caaaaaggat ggtattattc ttggctccca gaaatagtat   4260
atacacatca agtagttcat gatgattgga gaatgaaatt ggtagaagaa cctacatcag   4320
gaataacaat atacactgat gggggaaaac aaaatggaga aggaatagca gcttatgtga   4380
ccagtaatgg gagaactaaa cagaaaaggt taggacctgt cactcatcaa gttgctgaaa   4440
gaatggcaat acaaatggca ttagaggata ccagagataa acaagtaaat atagtaactg   4500
atagttatta ttgttggaaa aatattacag aaggattagg tttagaagga ccacaaagtc   4560
cttggtggcc tataatacaa aatatacgag aaaaagagat agtttatttt gcttgggtac   4620
ctggtcacaa agggatatat ggtaatcaat tggcagatga agccgcaaaa ataaaagaag   4680
aaatcatgct agcataccaa ggcacacaaa ttaaagagaa aagagatgaa gatgcagggt   4740
ttgacttatg tgttccttat gacatcatga tacctgtatc tgacacaaaa atcataccca   4800
cagatgtaaa aattcaagtt cctcctaata gctttggatg ggtcactggg aaatcatcaa   4860
tggcaaaaca ggggttatta attaatggag gaataattga tgaaggatat acaggagaaa   4920
tacaagtgat atgtactaat attggaaaaa gtaatattaa attaatagag ggacaaaaat   4980
ttgcacaatt aattatacta cagcatcact caaattccag acagccttgg gatgaaaata   5040
aaatatctca gagaggggat aaaggatttg gaagtacagg agtattctgg gtagaaaata   5100
ttcaggaagc acaagatgaa catgagaatt ggcatacatc accaaagata ttggcaagaa   5160
attataagat accattgact gtagcaaaac agataactca agaatgtcct cattgcacta   5220
agcaaggatc aggacctgca ggttgtgtca tgagatctcc taatcattgg caggcagatt   5280
gcacacattt ggacaataag ataatattga cttttgtaga gtcaaattca ggatacatac   5340
atgctacatt attgtcaaaa gaaaatgcat tatgtacttc attggctatt ttagaatggg   5400
caagattgtt ttcaccaaag tccttacaca cagataacgg cactaatttt gtggcagaac   5460
cagttgtaaa tttgttgaag ttcctaaaga tagcacatac cacaggaata ccatatcatc   5520
cagaaagtca gggtattgta gaaagggcaa ataggacctt gaaagagaag attcaaagtc   5580
atagagacaa cactcaaaca ctggaggcag ctttacaact tgctctcatt acttgtaaca   5640
aagggaggga aagtatggga ggacagacac catgggaagt atttatcact aatcaagcac   5700
aagtaataca tgagaaactt ttactacagc aagcacaatc ctccaaaaaa ttttgttttt   5760
```

-continued

```
acaaaatccc tggtgaacat gattggaagg gacctactag ggtgctgtgg aagggtgatg   5820
gtgcagtagt agttaatgat gaaggaaagg gaataattgc tgtaccatta accaggacta   5880
agttactaat aaaaccaaat tgagtattgt tgcaggaagc aagacccaac taccattgtc   5940
agctgtgttt cctgaggtct ctaggaattg attacctcga tgcttcatta aggaagaaga   6000
ataaacaaag actgaaggca atccaacaag gaagacaacc tcaatatttg ttataaggtt   6060
tgatatatgg gagtatttgg taaaggggta acatggtcag catcgcattc tatgggggaa   6120
tcccaggggg aatctcaacc cctattaccc aacagtcaga aaaatctaag tgtgaggaga   6180
acacaatgtt tcaaccttat tgttataata atgacagtaa gaacagcatg gcagaatcga   6240
aggaagcaag agaccaagaa atgaacctga aagaagaatc taaagaagaa aaaagaagaa   6300
atgactggtg gaaaataggt atgtttctgt tatgcttagc aggaactact ggaggaatac   6360
tttggtggta tgaaggactc ccacagcaac attatatagg gttggtggcg atagggggaa   6420
gattaaacgg atctggccaa tcaaatgcta tagaatgctg ggttccttc ccggggtgta    6480
gaccatttca aaattacttc agttatgaga ccaatagaag catgcatatg gataataata   6540
ctgctacatt attagaagct ttaaccaata taactgctct ataaataaca aaacagaatt   6600
agaaacatgg aagttagtaa agacttctgg cataactcct ttacctattt cttctgaagc   6660
taacactgga ctaattagac ataagagaga ttttggtata agtgcaatag tggcagctat   6720
tgtagccgct actgctattg ctgctagcgc tactatgtct tatgttgctc taactgaggt   6780
taacaaaata atggaagtac aaaatcatac ttttgaggta gaaaatagta ctctaaatgg   6840
tatggattta atagaacgac aaataaagat attatatgct atgattcttc aaacacatgc   6900
agatgttcaa ctgttaaagg aaagacaaca ggtagaggag acatttaatt taattggatg   6960
tatagaaaga acacatgtat tttgtcatac tggtcatccc tggaatatgt catggggaca   7020
tttaaatgag tcaacacaat gggatgactg ggtaagcaaa atggaagatt taaatcaaga   7080
gatactaact acacttcatg gagccaggaa caatttggca caatccatga taacattcaa   7140
tacaccagat agtatagctc aatttggaaa agacctttgg agtcatattg gaaattggat   7200
tcctggattg ggagcttcca ttataaaata tatagtgatg tttttgctta tttatttgtt   7260
actaacctct tcgcctaaga tcctcagggc cctctggaag gtgaccagtg gtgcagggtc   7320
ctccggcagt cgttacctga agaaaaaatt ccatcacaaa catgcatcgc gagaagacac   7380
ctgggaccag gcccaacaca acatacacct agcaggcgtg accggtggat caggggacaa   7440
atactacaag cagaagtact ccaggaacga ctggaatgga gaatcagagg agtacaacag   7500
gcggccaaag agctgggtga agtcaatcga ggcatttgga gagagctata tttccgagaa   7560
gaccaaaggg gagatttctc agcctggggc ggctatcaac gagcacaaga acggctctgg   7620
ggggaacaat cctcaccaag ggtccttaga cctggagatt cgaagcgaag gaggaaacat   7680
ttatgactgt tgcattaaag cccaagaagg aactctcgct atcccttgct gtggatttcc   7740
cttatggcta ttttggggac tagtaattat agtaggacgc atagcaggct atggattacg   7800
tggactcgct gttataataa ggatttgtat tagaggctta aatttgatat ttgaaataat   7860
cagaaaaatg cttgattata ttggaagagc tttaaatcct ggcacatctc atgtatcaat   7920
gcctcagtat gtttagaaaa acaagggggg aactgtgggg tttttatgag gggttttata   7980
aatgattata agagtaaaaa gaaagttgct gatgctctca taaccttgta taacccaaag   8040
gactagctca tgttgctagg caactaaacc gcaataaccg catttgtgac gcgagttccc   8100
```

-continued

```
cattggtgac gcgtggtacc tctagagtcg acccgggcgg ccgcttccct ttagtgaggg   8160
ttaatgcttc gagcagacat gataagatac attgatgagt ttggacaaac cacaactaga   8220
atgcagtgaa aaaaatgctt tatttgtgaa atttgtgatg ctattgcttt atttgtaacc   8280
attataagct gcaataaaca agttaacaac aacaattgca ttcattttat gtttcaggtt   8340
caggggggaga tgtgggaggt tttttaaagc aagtaaaacc tctacaaatg tggtaaaatc   8400
cgataaggat cgatccgggc tggcgtaata gcgaagaggc ccgcaccgat cgcccttccc   8460
aacagttgcg cagcctgaat ggcgaatgga cgcgccctgt agcggcgcat taagcgcggc   8520
gggtgtggtg gttacgcgca gcgtgaccgc tacacttgcc agcgccctag cgcccgctcc   8580
tttcgctttc ttcccttcct ttctcgccac gttcgccggc tttccccgtc aagctctaaa   8640
tcgggggctc cctttagggt tccgatttag agctttacgg cacctcgacc gcaaaaaact   8700
tgatttgggt gatggttcac gtagtgggcc atcgccctga tagacggttt ttcgcccttt   8760
gacgttggag tccacgttct ttaatagtgg actcttgttc caaactggaa caacactcaa   8820
ccctatctcg gtctattctt ttgatttata agggattttg ccgatttcgg cctattggtt   8880
aaaaaatgag ctgatttaac aaatatttaa cgcgaatttt aacaaaatat taacgtttac   8940
aatttcgcct gatgcggtat tttctcctta cgcatctgtg cggtatttca caccgcatac   9000
gcggatctgc gcagcaccat ggcctgaaat aacctctgaa agaggaactt ggttaggtac   9060
cttctgaggc ggaaagaacc agctgtggaa tgtgtgtcag ttagggtgtg gaaagtcccc   9120
aggctcccca gcaggcagaa gtatgcaaag catgcatctc aattagtcag caaccaggtg   9180
tggaaagtcc ccaggctccc cagcaggcag aagtatgcaa agcatgcatc tcaattagtc   9240
agcaaccata gtcccgcccc taactccgcc catcccgccc ctaactccgc ccagttccgc   9300
ccattctccg ccccatggct gactaatttt ttttatttat gcagaggccg aggccgcctc   9360
ggcctctgag ctattccaga agtagtgagg aggctttttt ggaggcctag gcttttgcaa   9420
aaagcttgat tcttctgaca caacagtctc gaacttaagg ctagagccac catgattgaa   9480
caagatggat tgcacgcagg ttctccggcc gcttgggtgg agaggctatt cggctatgac   9540
tgggcacaac agacaatcgg ctgctctgat gccgccgtgt tccggctgtc agcgcagggg   9600
cgcccggttc tttttgtcaa gaccgacctg tccggtgccc tgaatgaact gcaggacgag   9660
gcagcgcggc tatcgtggct ggccacgacg ggcgttcctt gcgcagctgt gctcgacgtt   9720
gtcactgaag cgggaaggga ctggctgcta ttgggcgaag tgccggggca ggatctcctg   9780
tcatctcacc ttgctcctgc cgagaaagta tccatcatgg ctgatgcaat gcggcggctg   9840
catacgcttg atccggctac ctgcccattc gaccaccaag cgaaacatcg catcgagcga   9900
gcacgtactc ggatggaagc cggtcttgtc gatcaggatg atctggacga agagcatcag   9960
gggctcgcgc cagccgaact gttcgccagg ctcaaggcgc gcatgcccga cggcgaggat  10020
ctcgtcgtga cccatggcga tgcctgcttg ccgaatatca tggtggaaaa tggccgcttt  10080
tctggattca tcgactgtgg ccggctgggt gtggcggacc gctatcagga catagcgttg  10140
gctacccgtg atattgctga agagcttggc ggcgaatggg ctgaccgctt cctcgtgctt  10200
tacggtatcg ccgctcccga ttcgcagcgc atcgccttct atcgccttct tgacgagttc  10260
ttctgagcgg gactctgggg ttcgaaatga ccgaccaagc gacgcccaac ctgccatcac  10320
gatggccgca ataaaatatc tttattttca ttacatctgt gtgttggttt tttgtgtgaa  10380
tcgatagcga taaggatccg cgtatggtgc actctcagta caatctgctc tgatgccgca  10440
tagttaagcc agccccgaca cccgccaaca cccgctgacg cgccctgacg ggcttgtctg  10500
```

-continued

```
ctcccggcat ccgcttacag acaagctgtg accgtctccg ggagctgcat gtgtcagagg  10560
ttttcaccgt catcaccgaa acgcgcgaga cgaaagggcc tcgtgatacg cctattttta  10620
taggttaatg tcatgataat aatggtttct tagacgtcag gtggcacttt tcggggaaat  10680
gtgcgcggaa cccctatttg tttatttttc taaatacatt caaatatgta tccgctcatg  10740
agacaataac cctgataaat gcttcaataa tattgaaaaa ggaagagtat gagtattcaa  10800
catttccgtg tcgcccttat tccctttttt gcggcatttt gccttcctgt ttttgctcac  10860
ccagaaacgc tggtgaaagt aaaagatgct gaagatcagt tgggtgcacg agtgggttac  10920
atcgaactgg atctcaacag cggtaagatc cttgagagtt ttcgccccga agaacgtttt  10980
ccaatgatga gcacttttaa agttctgcta tgtggcgcgg tattatcccg tattgacgcc  11040
gggcaagagc aactcggtcg ccgcatacac tattctcaga atgacttggt tgagtactca  11100
ccagtcacag aaaagcatct tacggatggc atgacagtaa gagaattatg cagtgctgcc  11160
ataaccatga gtgataacac tgcggccaac ttacttctga caacgatcgg aggaccgaag  11220
gagctaaccg cttttttgca caacatgggg gatcatgtaa ctcgccttga tcgttgggaa  11280
ccggagctga atgaagccat accaaacgac gagcgtgaca ccacgatgcc tgtagcaatg  11340
gcaacaacgt tgcgcaaact attaactggc gaactactta ctctagcttc ccggcaacaa  11400
ttaatagact ggatggaggc ggataaagtt gcaggaccac ttctgcgctc ggcccttccg  11460
gctggctggt ttattgctga taaatctgga gccggtgagc gtgggtctcg cggtatcatt  11520
gcagcactgg ggccagatgg taagccctcc cgtatcgtag ttatctacac gacggggagt  11580
caggcaacta tggatgaacg aaatagacag atcgctgaga taggtgcctc actgattaag  11640
cattggtaac tgtcagacca agtttactca tatatacttt agattgattt aaaacttcat  11700
ttttaattta aaaggatcta ggtgaagatc ctttttgata atctcatgac caaaatccct  11760
taacgtgagt tttcgttcca ctgagcgtca gaccccgtag aaaagatcaa aggatcttct  11820
tgagatcctt tttttctgcg cgtaatctgc tgcttgcaaa caaaaaaacc accgctacca  11880
gcggtggttt gtttgccgga tcaagagcta ccaactcttt ttccgaaggt aactggcttc  11940
agcagagcgc agataccaaa tactgtcctt ctagtgtagc cgtagttagg ccaccacttc  12000
aagaactctg tagcaccgcc tacatacctc gctctgctaa tcctgttacc agtggctgct  12060
gccagtggcg ataagtcgtg tcttaccggg ttggactcaa gacgatagtt accggataag  12120
gcgcagcggt cgggctgaac ggggggttcg tgcacacagc ccagcttgga gcgaacgacc  12180
tacaccgaac tgagatacct acagcgtgag ctatgagaaa gcgccacgct tcccgaaggg  12240
agaaaggcgg acaggtatcc ggtaagcggc agggtcggaa caggagagcg cacgagggag  12300
cttccagggg gaaacgcctg gtatctttat agtcctgtcg ggtttcgcca cctctgactt  12360
gagcgtcgat ttttgtgatg ctcgtcaggg gggcggagcc tatggaaaaa cgccagcaac  12420
gcggcctttt tacggttcct ggccttttgc tggccttttg ctcacatggc tcgacagatc  12480
t                                                                  12481
```

<210> SEQ ID NO 10
<211> LENGTH: 10815
<212> TYPE: DNA
<213> ORGANISM: Artificial Sequence
<220> FEATURE:
<223> OTHER INFORMATION: Description of Artificial Sequence: Synthetic
nucleic acid pESYNGPRRE, codon-optimized EIAV
gag/pol expression plasmid -continued

<400> SEQUENCE: 10
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtccg ccccctattg acgtcaatga 420
cggtaaatgg cccgcctggc attatgccca gtacatgacc ttacgggact ttcctacttg 480
gcagtacatc tacgtattag tcatcgctat taccatggtg atgcggtttt ggcagtacac 540
caatgggcgt ggatagcggt ttgactcacg gggatttcca agtctccacc ccattgacgt 600
caatgggagt ttgttttggc accaaaatca acgggacttt ccaaaatgtc gtaacaactg 660
cgatcgcccg ccccgttgac gcaaatgggc ggtaggcgtg tacggtggga ggtctatata 720
agcagagctc gtttagtgaa ccgtcagatc actagaagct ttattgcggt agtttatcac 780
agttaaattg ctaacgcagt cagtgcttct gacacaacag tctcgaactt aagctgcagt 840
gactctctta aggtagcctt gcagaagttg gtcgtgaggc actgggcagg taagtatcaa 900
ggttacaaga caggtttaag gagaccaata gaaactgggc ttgtcgagac agagaagact 960
cttgcgtttc tgataggcac ctattggtct tactgacatc cactttgcct ttctctccac 1020
aggtgtccac tcccagttca attacagctc ttaaggctag agtacttaat acgactcact 1080
ataggctaga gaattcgcca ccatgggcga tcccctcacc tggtccaaag ccctgaagaa 1140
actggaaaaa gtcaccgttc agggtagcca aaagcttacc acaggcaatt gcaactgggc 1200
attgtccctg gtggatcttt tccacgacac taatttcgtt aaggagaaag attggcaact 1260
cagagacgtg atcccccctct tggaggacgt gacccaaaca ttgtctgggc aggagcgcga 1320
agctttcgag cgcacctggt gggccatcag cgcagtcaaa atggggctgc aaatcaacaa 1380
cgtggttgac ggtaaagcta gctttcaact gctccgcgct aagtacgaga agaaaaccgc 1440
caacaagaaa caatccgaac ctagcgagga gtacccaatt atgatcgacg gcgccggcaa 1500
taggaacttc cgcccactga ctcccagggg ctataccacc tgggtcaaca ccatccagac 1560
aaacggactt ttgaacgaag cctcccagaa cctgttcggc atcctgtctg tggactgcac 1620
ctccgaagaa atgaatgctt ttctcgacgt ggtgccagga caggctggac agaaacagat 1680
cctgctcgat gccattgaca agatcgccga cgactgggat aatcgccacc ccctgccaaa 1740
cgcccctctg gtggctcccc cacaggggcc tatccctatg accgctaggt tcattagggg 1800
actggggggtg ccccgcgaac gccagatgga gccagcattt gaccaattta ggcagaccta 1860
cagacagtgg atcatcgaag ccatgagcga ggggattaaa gtcatgatcg gaaagcccaa 1920
ggcacagaac atcaggcagg gggccaagga accataccct gagtttgtcg acaggcttct 1980
gtcccagatt aaatccgaag gccaccctca ggagatctcc aagttcttga cagacacact 2040
gactatccaa aatgcaaatg aagagtgcag aaacgccatg aggcacctca gacctgaaga 2100
taccctggag gagaaaatgt acgcatgtcg cgacattggc actaccaagc aaaagatgat 2160
gctgctcgcc aaggctctgc aaaccggcct ggctggtcca ttcaaaggag gagcactgaa 2220
gggaggtcca ttgaaagctg cacaaacatg ttataattgt gggaagccag gacatttatc 2280
tagtcaatgt agagcaccta aagtctgttt taaatgtaaa cagcctggac atttctcaaa 2340

-continued

```
gcaatgcaga agtgttccaa aaaacgggaa gcaaggggct caagggaggc cccagaaaca   2400
aactttcccg atacaacaga agagtcagca caacaaatct gttgtacaag agactcctca   2460
gactcaaaat ctgtacccag atctgagcga aataaaaaag gaatacaatg tcaaggagaa   2520
ggatcaagta gaggatctca acctggacag tttgtgggag taacatacaa tctcgagaag   2580
aggcccacta ccatcgtcct gatcaatgac accccctctta atgtgctgct ggacaccgga   2640
gccgacacca gcgttctcac tactgctcac tataacagac tgaaatacag aggaaggaaa   2700
taccagggca caggcatcat cggcgttgga ggcaacgtcg aaacctttc cactcctgtc   2760
accatcaaaa agaaggggag acacattaaa accagaatgc tggtcgccga catccccgtc   2820
accatccttg gcagagacat tctccaggac ctgggcgcta aactcgtgct ggcacaactg   2880
tctaaggaaa tcaagttccg caagatcgag ctgaaagagg gcacaatggg tccaaaaatc   2940
ccccagtggc cctgaccaa agagaagctt gagggcgcta aggaaatcgt gcagcgcctg   3000
ctttctgagg gcaagattag cgaggccagc gacaataacc cttacaacag ccccatcttt   3060
gtgattaaga aaaggagcgg caaatggaga ctcctgcagg acctgaggga actcaacaag   3120
accgtccagg tcggaactga gatctctcgc ggactgcctc accccggcgg cctgattaaa   3180
tgcaagcaca tgacagtcct tgacattgga gacgcttatt ttaccatccc cctcgatcct   3240
gaatttcgcc cctatactgc ttttaccatc cccagcatca atcaccagga gcccgataaa   3300
cgctatgtgt ggaagtgcct cccccaggga tttgtgctta gcccctacat ttaccagaag   3360
acacttcaag agatcctcca acctttccgc gaaagatacc cagaggttca actctaccaa   3420
tatatggacg acctgttcat ggggtccaac gggtctaaga agcagcacaa ggaactcatc   3480
atcgaactga gggcaatcct cctggagaaa ggcttcgaga cacccgacga caagctgcaa   3540
gaagttcctc catatagctg gctgggctac cagctttgcc ctgaaaactg gaaagtccag   3600
aagatgcagt tggatatggt caagaaccca acactgaacg acgtccagaa gctcatgggc   3660
aatattacct ggatgagctc cggaatccct gggcttaccg ttaagcacat tgccgcaact   3720
acaaaaggat gcctggagtt gaaccagaag gtcatttgga cagaggaagc tcagaaggaa   3780
ctggaggaga ataatgaaaa gattaagaat gctcaagggc tccaatacta caatcccgaa   3840
gaagaaatgt tgtgcgaggt cgaaatcact aagaactacg aagccaccta tgtcatcaaa   3900
cagtcccaag gcatcttgtg ggccggaaag aaaatcatga aggccaacaa aggctggtcc   3960
accgttaaaa atctgatgct cctgctccag cacgtcgcca ccgagtctat cacccgcgtc   4020
ggcaagtgcc ccaccttcaa agttcccttc actaaggagc aggtgatgtg ggagatgcaa   4080
aaaggctggt actactcttg gcttcccgag atcgtctaca cccaccaagt ggtgcacgac   4140
gactggagaa tgaagcttgt cgaggagccc actagcggaa ttacaatcta taccgacggc   4200
ggaaagcaaa acggagaggg aatcgctgca tacgtcacat ctaacggccg caccaagcaa   4260
aagaggctcg gccctgtcac tcaccaggtg gctgagagga tggctatcca gatggccctt   4320
gaggacacta gagacaagca ggtgaacatt gtgactgaca gctactactg ctggaaaaac   4380
atcacagagg gccttggcct ggagggaccc cagtctccct ggtggcctat catccagaat   4440
atccgcgaaa aggaaattgt ctatttcgcc tgggtgcctg gacacaaagg aatttacggc   4500
aaccaactcg ccgatgaagc cgccaaaatt aaagaggaaa tcatgcttgc ctaccagggc   4560
acacagatta aggagaagag agacgaggac gctggctttg acctgtgtgt gccatacgac   4620
atcatgattc ccgttagcga cacaaagatc attccaaccg atgtcaagat ccaggtgcca   4680
```

-continued

```
cccaattcat ttggttgggt gaccggaaag tccagcatgg ctaagcaggg tcttctgatt   4740
aacgggggaa tcattgatga aggatacacc ggcgaaatcc aggtgatctg cacaaatatc   4800
ggcaaaagca atattaagct tatcgaaggg cagaagttcg ctcaactcat catcctccag   4860
caccacagca attcaagaca accttgggac gaaaacaaga ttagccagag aggtgacaag   4920
ggcttcggca gcacaggtgt gttctgggtg gagaacatcc aggaagcaca ggacgagcac   4980
gagaattggc acacctcccc taagattttg gcccgcaatt acaagatccc actgactgtg   5040
gctaagcaga tcacacagga atgcccccac tgcaccaaac aaggttctgg ccccgccggc   5100
tgcgtgatga ggtcccccaa tcactggcag gcagattgca cccacctcga caacaaaatt   5160
atcctgacct tcgtggagag caattccggc tacatccacg caacactcct ctccaaggaa   5220
aatgcattgt gcacctccct cgcaattctg gaatgggcca ggctgttctc tccaaaatcc   5280
ctgcacaccg acaacggcac caactttgtg gctgaacctg tggtgaatct gctgaagttc   5340
ctgaaaatcg cccacaccac tggcattccc tatcaccctg aaagccaggg cattgtcgag   5400
agggccaaca gaactctgaa agaaaagatc caatctcaca gagacaatac acagacattg   5460
gaggccgcac ttcagctcgc ccttatcacc tgcaacaaag gaagagaaag catgggcggc   5520
cagacccccct gggaggtctt catcactaac caggcccagg tcatccatga aaagctgctc   5580
ttgcagcagg cccagtcctc caaaaagttc tgcttttata agatccccgg tgagcacgac   5640
tggaaaggtc ctacaagagt tttgtggaaa ggagacggcg cagttgtggt gaacgatgag   5700
ggcaagggga tcatcgctgt gcccctgaca cgcaccaagc ttctcatcaa gccaaactga   5760
acccgacgaa tcccaggggg aatctcaacc cctattaccc aacagtcaga aaaatctaag   5820
tgtgaggaga acacaatgtt tcaaccttat tgttataata atgacagtaa gaacagcatg   5880
gcagaatcga aggaagcaag agaccaagaa atgaacctga aagaagaatc taaagaagaa   5940
aaaagaagaa atgactggtg gaaaataggt atgtttctgt tatgcttagc cagggccctc   6000
tggaaggtga ccagtggtgc agggtcctcc ggcagtcgtt acctgaagaa aaaattccat   6060
cacaaacatg catcgcgaga agacacctgg gaccaggccc aacacaacat acacctagca   6120
ggcgtgaccg gtggatcagg ggacaaatac tacaagcaga agtactccag gaacgactgg   6180
aatggagaat cagaggagta caacaggcgg ccaaagagct gggtgaagtc aatcgaggca   6240
tttggagaga gctatatttc cgagaagacc aaaggggaga tttctcagcc tggggcggct   6300
atcaacgagc acaagaacgg ctctgggggg aacaatcctc accaagggtc cttagacctg   6360
gagattcgaa gcgaaggagg aaacatttat gactgttgca ttaaagccca agaaggaact   6420
ctcgctatcc cttgctgtgg atttccctta tggctatttt gggggtcggg gcggccgctt   6480
ccctttagtg agggttaatg cttcgagcag acatgataag atacattgat gagtttggac   6540
aaaccacaac tagaatgcag tgaaaaaaat gctttatttg tgaaatttgt gatgctattg   6600
ctttatttgt aaccattata agctgcaata aacaagttaa caacaacaat tgcattcatt   6660
ttatgtttca ggttcagggg gagatgtggg aggtttttta aagcaagtaa aacctctaca   6720
aatgtggtaa aatccgataa ggatcgatcc gggctggcgt aatagcgaag aggcccgcac   6780
cgatcgccct tcccaacagt tgcgcagcct gaatggcgaa tggacgcgcc ctgtagcggc   6840
gcattaagcg cggcgggtgt ggtggttacg cgcagcgtga ccgctacact tgccagcgcc   6900
ctagcgcccg ctcctttcgc tttcttccct tcctttctcg ccacgttcgc cggctttccc   6960
cgtcaagctc taaatcgggg gctcccttta gggttccgat ttagagcttt acggcacctc   7020
gaccgcaaaa aacttgattt gggtgatggt tcacgtagtg ggccatcgcc ctgatagacg   7080
```

-continued

```
gtttttcgcc ctttgacgtt ggagtccacg ttctttaata gtggactctt gttccaaact   7140
ggaacaacac tcaaccctat ctcggtctat tcttttgatt tataagggat tttgccgatt   7200
tcggcctatt ggttaaaaaa tgagctgatt taacaaatat ttaacgcgaa ttttaacaaa   7260
atattaacgt ttacaatttc gcctgatgcg gtattttctc cttacgcatc tgtgcggtat   7320
ttcacaccgc atacgcggat ctgcgcagca ccatggcctg aaataacctc tgaaagagga   7380
acttggttag gtaccttctg aggcggaaag aaccagctgt ggaatgtgtg tcagttaggg   7440
tgtggaaagt ccccaggctc cccagcaggc agaagtatgc aaagcatgca tctcaattag   7500
tcagcaacca ggtgtggaaa gtccccaggc tccccagcag gcagaagtat gcaaagcatg   7560
catctcaatt agtcagcaac catagtcccg cccctaactc cgcccatccc gcccctaact   7620
ccgcccagtt ccgcccattc tccgccccat ggctgactaa ttttttttat ttatgcagag   7680
gccgaggccg cctcggcctc tgagctattc cagaagtagt gaggaggctt ttttggaggc   7740
ctaggctttt gcaaaaagct tgattcttct gacacaacag tctcgaactt aaggctagag   7800
ccaccatgat tgaacaagat ggattgcacg caggttctcc ggccgcttgg gtggagaggc   7860
tattcggcta tgactgggca caacagacaa tcggctgctc tgatgccgcc gtgttccggc   7920
tgtcagcgca ggggcgcccg gttctttttg tcaagaccga cctgtccggt gccctgaatg   7980
aactgcagga cgaggcagcg cggctatcgt ggctggccac gacgggcgtt ccttgcgcag   8040
ctgtgctcga cgttgtcact gaagcgggaa gggactggct gctattgggc gaagtgccgg   8100
ggcaggatct cctgtcatct caccttgctc ctgccgagaa agtatccatc atggctgatg   8160
caatgcggcg gctgcatacg cttgatccgg ctacctgccc attcgaccac caagcgaaac   8220
atcgcatcga gcgagcacgt actcggatgg aagccggtct tgtcgatcag gatgatctgg   8280
acgaagagca tcaggggctc gcgccagccg aactgttcgc caggctcaag gcgcgcatgc   8340
ccgacggcga ggatctcgtc gtgacccatg gcgatgcctg cttgccgaat atcatggtgg   8400
aaaatggccg cttttctgga ttcatcgact gtggccggct gggtgtggcg gaccgctatc   8460
aggacatagc gttggctacc cgtgatattg ctgaagagct tggcggcgaa tgggctgacc   8520
gcttcctcgt gctttacggt atcgccgctc ccgattcgca gcgcatcgcc ttctatcgcc   8580
ttcttgacga gttcttctga gcgggactct ggggttcgaa atgaccgacc aagcgacgcc   8640
caacctgcca tcacgatggc cgcaataaaa tatctttatt ttcattacat ctgtgtgttg   8700
gttttttgtg tgaatcgata gcgataagga tccgcgtatg gtgcactctc agtacaatct   8760
gctctgatgc cgcatagtta agccagcccc gacacccgcc aacacccgct gacgcgccct   8820
gacgggcttg tctgctcccg gcatccgctt acagacaagc tgtgaccgtc tccgggagct   8880
gcatgtgtca gaggttttca ccgtcatcac cgaaacgcgc gagacgaaag ggcctcgtga   8940
tacgcctatt tttataggtt aatgtcatga taataatggt ttcttagacg tcaggtggca   9000
cttttcgggg aaatgtgcgc ggaaccccta tttgtttatt tttctaaata cattcaaata   9060
tgtatccgct catgagacaa taaccctgat aaatgcttca ataatattga aaaaggaaga   9120
gtatgagtat tcaacatttc cgtgtcgccc ttattccctt ttttgcggca ttttgccttc   9180
ctgtttttgc tcacccagaa acgctggtga aagtaaaaga tgctgaagat cagttgggtg   9240
cacgagtggg ttacatcgaa ctggatctca acagcggtaa gatccttgag agttttcgcc   9300
ccgaagaacg ttttccaatg atgagcactt ttaaagttct gctatgtggc gcggtattat   9360
cccgtattga cgccgggcaa gagcaactcg gtcgccgcat acactattct cagaatgact   9420
```

-continued

```
tggttgagta ctcaccagtc acagaaaagc atcttacgga tggcatgaca gtaagagaat   9480

tatgcagtgc tgccataacc atgagtgata acactgcggc caacttactt ctgacaacga   9540

tcggaggacc gaaggagcta accgcttttt tgcacaacat gggggatcat gtaactcgcc   9600

ttgatcgttg ggaaccggag ctgaatgaag ccataccaaa cgacgagcgt gacaccacga   9660

tgcctgtagc aatggcaaca acgttgcgca aactattaac tggcgaacta cttactctag   9720

cttcccggca acaattaata gactggatgg aggcggataa agttgcagga ccacttctgc   9780

gctcggccct tccggctggc tggtttattg ctgataaatc tggagccggt gagcgtgggt   9840

ctcgcggtat cattgcagca ctggggccag atggtaagcc ctcccgtatc gtagttatct   9900

acacgacggg gagtcaggca actatggatg aacgaaatag acagatcgct gagataggtg   9960

cctcactgat taagcattgg taactgtcag accaagttta ctcatatata ctttagattg  10020

atttaaaact tcatttttaa tttaaaagga tctaggtgaa gatccttttt gataatctca  10080

tgaccaaaat cccttaacgt gagttttcgt tccactgagc gtcagacccc gtagaaaaga  10140

tcaaaggatc ttcttgagat cctttttttc tgcgcgtaat ctgctgcttg caaacaaaaa  10200

aaccaccgct accagcggtg gtttgtttgc cggatcaaga gctaccaact ctttttccga  10260

aggtaactgg cttcagcaga gcgcagatac caaatactgt ccttctagtg tagccgtagt  10320

taggccacca cttcaagaac tctgtagcac cgcctacata cctcgctctg ctaatcctgt  10380

taccagtggc tgctgccagt ggcgataagt cgtgtcttac cgggttggac tcaagacgat  10440

agttaccgga taaggcgcag cggtcgggct gaacgggggg ttcgtgcaca cagcccagct  10500

tggagcgaac gacctacacc gaactgagat acctacagcg tgagctatga gaaagcgcca  10560

cgcttcccga agggagaaag gcggacaggt atccggtaag cggcagggtc ggaacaggag  10620

agcgcacgag ggagcttcca gggggaaacg cctggtatct ttatagtcct gtcgggtttc  10680

gccacctctg acttgagcgt cgatttttgt gatgctcgtc aggggggcgg agcctatgga  10740

aaaacgccag caacgcggcc tttttacggt tcctggcctt ttgctggcct tttgctcaca  10800

tggctcgaca gatct                                                    10815
```

<210> SEQ ID NO 11
<211> LENGTH: 385
<212> TYPE: DNA
<213> ORGANISM: Artificial Sequence
<220> FEATURE:
<223> OTHER INFORMATION: Description of Artificial Sequence: Synthetic nucleic acid pONY3.1 (nt1246-1606)

<400> SEQUENCE: 11

```
atgggagacc ctttgacatg gagcaaggcg ctcaagaagt tagagaaggt gacggtacaa     60

gggtctcaga aattaactac tggtaactgt aattgggcgc taagtctagt agacttattt    120

catgatacca actttgtaaa agaaaaggac tggcagctga gggatgtcat tccattgctg    180

gaagatgtaa ctcagacgct gtcaggacaa gaaagagagg cctttgaaag aacatggtgg    240

gcaatttctg ctgtaaagat gggcctccag attaataatg tagtagatgg aaaggcatca    300

ttccagctcc taagagcgaa atatgaaaag aagactgcta ataaaaagca gtctgagccc    360

tctgaagaat atccaatcat gatag                                          385
```

<210> SEQ ID NO 12
<211> LENGTH: 385
<212> TYPE: DNA
<213> ORGANISM: Artificial Sequence
<220> FEATURE:

-continued

<223> OTHER INFORMATION: Description of Artificial Sequence: Synthetic
      nucleic acid pONY3.2opti (nt366-726)

<400> SEQUENCE: 12

```
atgggcgatc ccctcacctg gtccaaagcc ctgaaaaaac tggaaaaagt caccgttcag     60

ggtagccaaa agcttaccac aggcaattgc aactgggcat tgtccctggt ggatcttttc    120

cacgacacta atttcgttaa ggagaaagat tggcaactca gagacgtgat ccccctcttg    180

gaggacgtga cccaaacatt gtctgggcag gagcgcgaag ctttcgagcg cacctggtgg    240

gccatcagcg cagtcaaaat ggggctgcaa atcaacaacg tggttgacgg taaagctagc    300

tttcaactgc tccgcgctaa gtacgagaaa aaaaccgcca acaagaaaca atccgaacct    360

agcgaggagt acccaatcat gatag                                          385
```

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 13

```
aaactcgagc aaagcatgcc tgcaggaatt cg                                   32
```

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 14

```
aaactcgagt ttataaaacc cctcataaaa accccac                              37
```

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 15

```
aaacccgggt cgagtgtttt tacagtatat aagtgcttgt attc                      44
```

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 16

```
aaacccgggg agcgcagcga gtcagtgagc gag                                  33
```

<210> SEQ ID NO 17
<211> LENGTH: 990
<212> TYPE: DNA
<213> ORGANISM: Artificial Sequence
<220> FEATURE:
<223> OTHER INFORMATION: Description of Artificial Sequence: Synthetic
      nucleic acid EIAV-TRE hybrid LTR

<400> SEQUENCE: 17

-continued

```
ctcgagcaaa gcatgcctgc aggaattcga tatcaagctt atcgataccg tcgaattgga     60

agagctttaa atcctggcac atctcatgta tcaatgcctc agtatgttta gaaaaacaag    120

gggggaactg tggggttttt atgaggggtt ttataaactc gagtttacca ctccctatca    180

gtgatagaga aaagtgaaag tcgagtttac cactccctat cagtgataga gaaaagtgaa    240

agtcgagttt accactccct atcagtgata gagaaaagtg aaagtcgagt ttaccactcc    300

ctatcagtga tagagaaaag tgaaagtcga gtttaccact ccctatcagt gatagagaaa    360

agtgaaagtc gagtttacca ctccctatca gtgatagaga aaagtgaaag tcgagtttac    420

cactccctat cagtgataga gaaaagtgaa agtcgagctc ggtacccggg tcgagtgttt    480

ttacagtata taagtgcttg tattctgaca attgggcact cagattctgc ggtctgagtc    540

ccttctctgc tgggctgaaa aggcctttgt aataaatata attctctact cagtccctgt    600

ctctagtttg tctgttcgag atcctacaga gctcatgcct tggcgtaatc atggtcatag    660

ctgtttcctg tgtgaaattg ttatccgctc acaattccac acaacatacg agccggaagc    720

ataaagtgta aagcctgggg tgcctaatga gtgagctaac tcacattaat tgcgttgcgc    780

tcactgcccg ctttccagtc gggaaacctg tcgtgccagc tgcattaatg aatcggccaa    840

cgcgcgggga gaggcggttt gcgtattggg cgctcttccg cttcctcgct cactgactcg    900

ctgcgctccc cggggatcct ctagtcagct gacgcgtgct agcgcggccg catcgataag    960

cttgtcgacg atatctctag agctgagaac                                     990


<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 18

tttggcgcgc caggtaagat gggagaccct ttgac                                35


<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 19

ctacttgatc cttctccttg ac                                              22


<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

caggtaagat g                                                          11


<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 21

tacggaagat ctaaatgagt cttcggacct                                    30


<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 22

ctcaacgcta gcgtactcta gccttaagag ctg                                33


<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 23

gaattggtac cgccaccatg attgaacaag atggattgca cgc                     43


<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 24

gaattggcta gctcagaaga actcgtcaag aaggcgatag aaggcg                  46


<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: 6x His tag

<400> SEQUENCE: 25

His His His His His His
  1               5
```